(12) United States Patent
Cyr

(10) Patent No.: US 9,364,508 B2
(45) Date of Patent: Jun. 14, 2016

(54) INHIBITORS OF EXTRACELLULAR PROTEASES

(71) Applicant: LUCAS MEYER COSMETICS CANADA INC., Quebec (CA)

(72) Inventor: Benoit Cyr, St. Augustin de Desmaures (CA)

(73) Assignee: LUCAS MEYER COSMETICS CANADA INC., Quebec (CA)

(*) Notice: Subject to any disclaimer, the term of this patent is extended or adjusted under 35 U.S.C. 154(b) by 0 days.

(21) Appl. No.: 14/220,432

(22) Filed: Mar. 20, 2014

(65) Prior Publication Data

US 2014/0205686 A1 Jul. 24, 2014

Related U.S. Application Data

(60) Division of application No. 12/871,097, filed on Aug. 30, 2010, now abandoned, which is a continuation of application No. 11/878,978, filed on Jul. 30, 2007, now abandoned, which is a continuation of application No. 10/469,402, filed as application No. PCT/CA02/00285 on Mar. 4, 2002, now abandoned.

(30) Foreign Application Priority Data

Mar. 2, 2001 (CA) ...................................... 2339081

(51) Int. Cl.
| | |
|---|---|
| *A61K 36/704* | (2006.01) |
| *A61K 36/185* | (2006.01) |
| *A61K 8/97* | (2006.01) |
| *A61K 36/00* | (2006.01) |
| *A61Q 19/08* | (2006.01) |
| *C12N 9/99* | (2006.01) |

(52) U.S. Cl.
CPC ................. *A61K 36/185* (2013.01); *A61K 8/97* (2013.01); *A61K 36/00* (2013.01); *A61K 36/704* (2013.01); *A61Q 19/08* (2013.01); *C12N 9/99* (2013.01); *A61K 2800/782* (2013.01)

(58) Field of Classification Search
None
See application file for complete search history.

(56) References Cited

FOREIGN PATENT DOCUMENTS

| CN | 1174661 A | * | 3/1998 |
| RU | 2139722 C1 | * | 10/1999 |
| RU | 2157177 C2 | * | 10/2000 |
| RU | 2163132 C1 | * | 2/2001 |

OTHER PUBLICATIONS

Revilla et al. (J. Agric. Food Chem. (1998), vol. 46, pp. 4592-4597).*

* cited by examiner

*Primary Examiner* — Susan Hoffman
(74) *Attorney, Agent, or Firm* — Sutherland Asbill & Brennan LLP

(57) ABSTRACT

Provided is a plant derived extract including inhibitory activity against one or more extracellular proteases which degrade human tissue matrix. Moreover, the amount of inhibitory activity in an extract can be increased by stressing the plant prior to forming an extract. These extracts are each prepared by a process and demonstrate the ability to inhibit one or more extracellular proteases which degrade human tissue matrix. Libraries of extracts can be prepared from stressed and non-stressed plants, where each of the extracts demonstrate inhibitory activity against on or more extracellular protease inhibitors. Alternatively, semi-purified and purified inhibitory compounds can be isolated from the extracts. In one aspect, these extracts with inhibitory activity can be used during protein purification to minimize degradation due to extracellular proteases.

Figure 1:
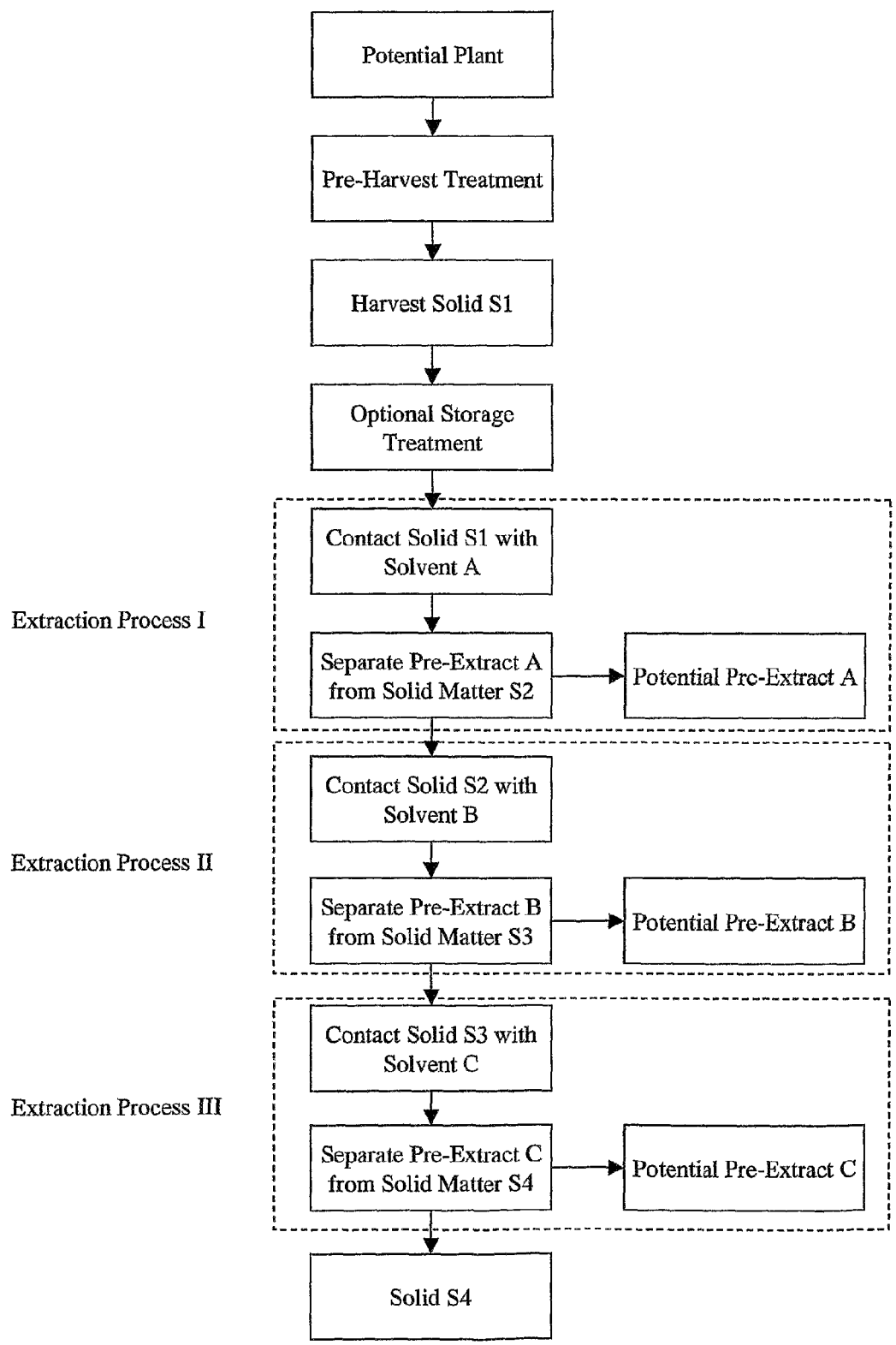

3 Claims, 3 Drawing Sheets

INHIBITORS OF EXTRACELLULAR PROTEASES

CROSS REFERENCES TO RELATED APPLICATIONS

This is a Divisional application of U.S. patent application Ser. No. 12/871,097, filed Aug. 30, 2010, now abandoned, which was a Continuation application of U.S. patent application Ser. No. 11/878,978, filed Jul. 30, 2007, now abandoned, which was a Continuation application of U.S. patent application Ser. No. 10/469,402, filed Mar. 25, 2004, now abandoned, and which is a National Stage Entry Under USC 371 of International Application No. PCT/CA02/00285 filed Mar. 4, 2002, claims benefit of Canadian Application No. 2339081, filed Mar. 2, 2001, the contents of each of which are hereby incorporated by reference in their entirety.

FIELD OF INVENTION

The invention pertains to the field of protease inhibitors, specifically inhibitors of extracellular proteases.

BACKGROUND OF THE INVENTION

The cells of tissues are generally in contact with a network of large extracellular macromolecules that occupies the spaces in a tissue between the component cells and also occupies the space between adjacent tissues. This extracellular matrix functions as a scaffolding on which the cells and tissue are supported and is involved actively in regulating interaction of the cells that contact it. The principal macromolecules of the extracellular matrix include the collagens (the most abundant proteins in the body) and glycosaminoglycans (complex polysaccharides which are usually bonded also to protein and then termed proteoglycans). The macromolecules that comprise the extracellular matrix are produced typically by the cells in contact therewith, for example, epithelial cells in contact with a basement membrane and fibroblasts embedded in connective tissue.

The glycosaminoglycan (proteoglycan) molecules form a highly hydrated matrix (a gel) in which elastic or fibrous proteins (such as collagen fibers) are embedded. The aqueous nature of the gel permits diffusion of metabolically required substances between the cells of a tissue and between tissues. Additional proteins that may be found in extracellular matrix include elastin, fibronectin and laminin.

The term "connective tissue" refers to extracellular matrix plus specialised cells such as, for example, fibroblasts, chondrocytes, osteoblasts, macrophages and mast cells found therein. The term "interstitial tissue" is best reserved for an extracellular matrix that stabilizes a tissue internally, filling the gaps between the cells thereof. There are also specialized forms of extracellular matrix (connective tissue) that have additional functional roles—cornea, cartilage and tendon, and when calcified, the bones and teeth.

A structural form of extracellular matrix is the basal lamina (basement membrane). Basal laminae are thin zones of extracellular matrix that are found under epithelium or surrounding, for example, muscle cells or the cells that electrically insulate nerve fibres. Generally speaking, basal laminae separate cell layers from underlying zones of connective tissue or serve as a boundary between two cell layers wherein a basal lamina can serve as a pathway for invading cells associated with pathologic processes, or for structural organisation associated with tissue repair (i.e. as a blueprint from which to regenerate original tissue architecture and morphology).

The regulated turnover of extracellular matrix macromolecules is critical to a variety of important biological processes. Localised degradation of matrix components is required when cells migrate through a basal lamina, as when white blood cells migrate across the vascular basal lamina into tissues in response to infection or injury, or when cancer cells migrate from their site of origin to distant organs via the bloodstream or lymphatic vessels, during metastasis. In normal tissues, the activity of extracellular proteases is tightly regulated and the breakdown/production of connective tissue is in dynamic equilibrium, such that there is a slow and continual turnover due to degradation and resynthesis in the extracellular matrix of adult animals.

In each of these cases, matrix components are degraded by extracellular proteolytic enzymes that are secreted locally by cells. These proteases belong to one of four general classes: many are metalloproteinases, which depend on bound $Ca^{2+}$ or $Zn^{2+}$ for activity, while the others are serine, aspartic and cysteine proteases, which have a highly reactive serine, aspartate or cysteine residue in their respective active site (Vincenti et al., (1994) Arthritis and Rheumatism, 37: 1115-1126). Together, metalloproteinases, serine, aspartate and cysteine proteases cooperate to degrade matrix proteins such as collagen, laminin, and fibronectin.

Several mechanisms operate to ensure that the degradation of matrix components is tightly controlled. First, many proteases are secreted as inactive precursors that can be activated locally. Second, the action of proteases is confined to specific areas by various secreted protease inhibitors, such as the tissue inhibitors of metalloproteases and the serine protease inhibitors known as serpins. These inhibitors are specific for particular proteases and bind tightly to the activated enzyme to block its activity. Third, many cells have receptors on their surface that bind proteases, thereby confining the enzyme to where it is needed.

Many pathogenic bacteria produce extracellular metalloproteases, of which many are zinc containing proteases that can be classified into two families, the thermolysin (neutral) proteases and the serralysin (alkaline) proteases.

A number of patents and publications report the inhibition of one or more extracellular proteases by compounds extracted from plants. For example, Sun et al., (1996) Phytotherapy Res., 10: 194-197, reports the inhibition in vitro of stromelysin (MMP-3) and collagenase by betulinic acid extracted from *Doliocarpus verruculosis*. Sazuka et al, (1997).

Biosci. Biotechnol. Biochem., 61: 1504-1506, reports the inhibition of gelatinases (MMP-2 and MMP-9) and metastasis by compounds isolated from green and black teas. Kumagai et al, JP 08104628 A2, Apr. 1, 1996 (CA 125: 67741) reports the use of flavones and anthocyanines isolated from *Scutellaris baicanlensis* roots to inhibit collagenase. Gervasi et al., (1996) Biochem. Biophys. Res. Comm., 228: 530-538, reports the regulation of MMP-2 by some plant lectins and other saccharides. Dubois et al., (1998) FEBS Lett., 427: 275-278, reports the increased secretion of deleterious gelatinase-B (MMP-9) by some plant lectins. Nagase et al., (1998) Planta Med., 64: 216-219, reports the weak inhibition of collagenase (MMPs) by delphinidin, a flavonoid isolated from *Solanum melongena*.

Other reports discuss the use of extracts to inhibit extracellular proteases. For example, Asano et al., (1998) Immunopharmacology, 39: 117-126, reports the inhibition of TNF-a production using Tripteggium wilfordii Hook F. extracts. Maheu et al., (1998) Arthritis Rheumatol., 41: 81-91, reports the use of avocado/soy bean non-saponifiable extracts in the treatment of arthritis. Makimura et al., (1993). J. Periodontol., 64: 630-636, also reports the use of green tea extracts to inhibit collagenases in vitro. Obayashi et al., (1998) Nippon Keshonin Gijutsusha Kaishi, 32: 272-279 (CA 130: 92196) reports the inhibition of collagenase-I (MMP-1) from human fibroblast and neutrophil elastase by plant extract from *Eucalyptus* and Elder.

When a plant is stressed, several biochemical processes are activated and many new chemicals, in addition to those constitutively expressed, are synthesised as a response. These chemicals include enzymes, enzyme inhibitors (especially protease inhibitors), lectins, alkaloids, terpenes, oligosaccharides, and antibiotics. The biosynthesis of these defense chemicals and secondary metabolites is not yet fully understood. The most studied system is the production of protease inhibitors following pest attack or mechanical wounding. On the other hand, several inducible chemicals are the products of complex biochemical pathways which require several biosynthetic enzymes to be activated.

It has been shown that many chemicals can be used to "stress" plants and to artificially stimulate biosynthesis of several new and constitutive defense chemicals. Also, different types of stress can activate distinct metabolic defense pathways, thereby leading to production of a variety of chemicals. Although the various biosynthetic defense pathways share some similarities, these pathways are characteristic of specific plant species. Therefore, treating many plants with many types of stress can lead to a vast number of collections of diverse chemicals from plant origin.

In addition to pests, fungi, and other pathogenic attacks, stressors include drought, heat, water and mechanical wounding. Furthermore, many chemicals can act as stressors that activate gene expression; these include: hydrogen peroxide, ozone, sodium chloride, jasmonic acid and derivatives, .alpha.-linoleic acid, '.gamma.-linoleic acid, salicylic acid, abscesic acid, volicitin, small oligopeptides, among others.

The use of abiotic stressors on plants has been the focus of intense studies in plant science. Artificial stresses have been used to stimulate the production of natural plant protease inhibitors for insect digestive proteases, in order to enhance crop protection against certain pests and herbivores. They have proven useful in combination with plants genetically modified to express other protease inhibitor genes. Finally, in the area of molecular farming, stresses have been used to stimulate gene expression in plants genetically modified to include an inducible coding sequence for a protein of nutraceutical and/or medicinal interest (Ryan and Farmer, U.S. Pat. No. 5,935,809).

Likewise, the use of gene activators or elicitors have been described to enhance the production of volatile chemicals in plant cell cultures. These elicitors have been demonstrated to induce the activity of several enzymes such as for example phenylalanine ammonia lyase, therefore leading to an increase in the production of plant volatile components.

No one has used stress to improve or modify plants human protease inhibitor content.

BRIEF DESCRIPTION OF THE FIGURES AND TABLES

FIG. 1 presents an overview of one standard procedure that is followed in order to generate the extracts of the invention each of which is derived from the solid plant material. Solvent A, B and C generally represent separate classes of solvents, for example, aqueous, alcoholic and organic. They are generally applied in a polar to non-polar order. They can be applied in a non-polar to polar order, however, in each case the solid matter must be dried prior to contacting the solid matter with the subsequent solvent.

Figure 2:
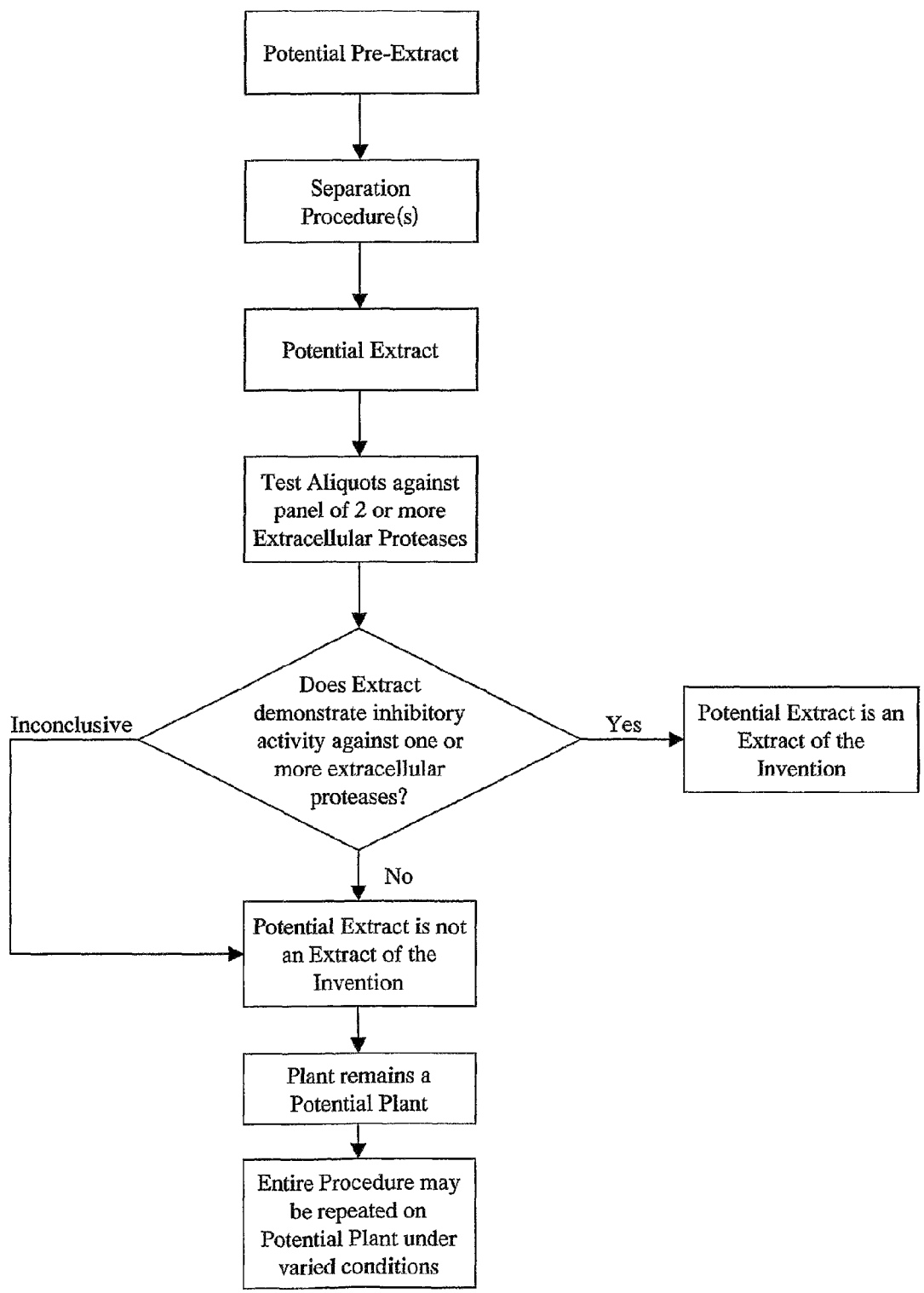

FIG. 2 describes in further detail, one standard procedure that is followed in order to generate the extracts of the invention.

Figure 3:
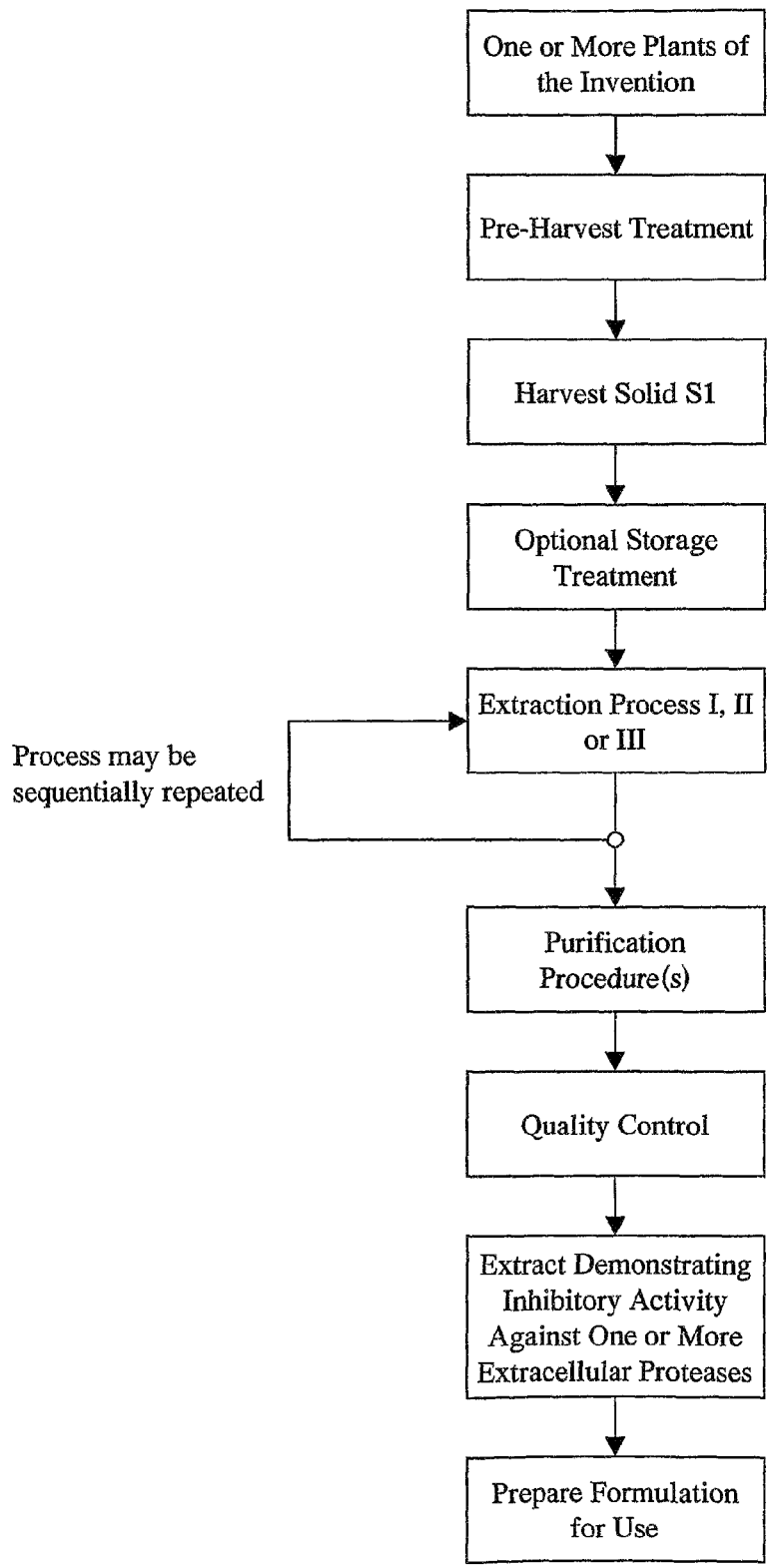

FIG. 3 presents an overview of one example of a commercial procedure that could be followed to prepare extracts of the invention.

Table 1 reports the inhibition of human MMP-1 by aqueous (A), ethanolic (R) and organic (S) 25 extracts for exemplary stressed and non-stressed plant sources.

Table 2 reports the inhibition of human MMP-2 by aqueous (A), ethanolic (R) and organic (S) extracts for exemplary stressed and non-stressed plant sources.

Table 4 reports the inhibition of human MMP-9 by aqueous (A), ethanolic (R) and organic (S) extracts for exemplary stressed and non-stressed plant sources.

Table 5 reports the inhibition of human Cathepsin B by aqueous (A), ethanolic (R) and organic (S) extracts for exemplary stressed and non-stressed plant sources.

Table 6 reports the inhibition of human Cathepsin D by aqueous (A), ethanolic (R) and organic (S) extracts for exemplary stressed and non-stressed plant sources.

Table 7 reports the inhibition of human Cathepsin G by aqueous (A), ethanolic (R) and organic (S) extracts for exemplary stressed and non-stressed plant sources.

Table 8 reports the inhibition of human Cathepsin L by aqueous (A), ethanolic (R) and organic (S) extracts for exemplary stressed and non-stressed plant sources.

Table 9 reports the inhibition of human Cathepsin K by aqueous (A), ethanolic (R) and organic (S) extracts for exemplary stressed and non-stressed plant sources.

Table 10 reports the inhibition of FILE by aqueous (A), ethanolic (R) and organic (S) extracts for 20 exemplary stressed and non-stressed plant sources.

Table 11 reports the inhibition of bacteria Clostripain by aqueous (A), ethanolic (R) and organic (S) extracts for exemplary stressed and non-stressed plant sources.

Table 12 reports the inhibition of bacteria subtilisin by aqueous (A), ethanolic (R) and organic (S) extracts for exemplary stressed and non-stressed plant sources.

SUMMARY OF THE INVENTION

In one aspect the invention provides n extract from a plant, which inhibits the activity of one or more extracellular proteases, wherein the extract has been prepared by the steps of harvesting plant material, treating plant material with a solvent, separating the resulting extract from the solid material. testing an aliquot of the extract against a panel of extracellular proteases, and retaining the extract if it inhibits the activity of one or more extracellular proteases an extract.

In one aspect the invention provides a library of extracts from plants wherein each extract inhibits the activity of one or more extracellular proteases.

In another aspect the invention provides a library of plant extracts formed by a process comprising: contacting plant material with either an aqueous, ethanolic, or an organic solvent; isolating an extract from said plant material; analysing said extract for the presence of one or more inhibitory activities against an extracellular protease; and collected together, so as to form a library of plant extracts wherein each extract inhibits one or more extracellular proteases.

In one aspect the invention provides an extract from a plant, which inhibits the activity of one or more extracellular proteases, wherein said plant has been stressed prior to generating the extract.

In a further aspect the invention provides a library of extracts derived from plants wherein each extract inhibits the activity of one or more extracellular proteases and wherein said 20 plants have been stressed prior to generating the extract.

In yet a further aspect provides an extracellular protease inhibitor derived from a plant comprising the steps of: contacting plant material with either an aqueous, ethanolic, or an organic solvent; isolating an extract from said plant material; analysing said extract for the presence of one or more inhibitory activities against a panel of extracellular proteases; further purifying a compound from said extract if said extract demonstrates the inhibition of one or more extracellular proteases greater than about 20%.

In another aspect the invention provides a method for increasing the levels of extracellular 30 protease inhibitors in plants comprising the step of stressing the plant prior to forming a plant extract.

In another aspect the invention provides for the use of such extracts during protein purification to minimize the degradation due to extracellular proteases.

DETAILED DESCRIPTION OF THE INVENTION

Definitions

Unless defined otherwise, all technical and scientific terms used herein have the same meaning as commonly understood by one of ordinary skill in the art to which this invention belongs.

"Extracellular protease" means enzymes which degrade proteins (proteases) secreted outside the cell. Included MMPs, cathepsins, elastase, plasmin, TPA, uPA, kallikrein, ADAMS family members, neprilysin, gingipain, clostripain, thermolysin, serralysin, and other bacterial and viral enzymes.

"Extract of the invention," means a composition prepared by contacting a solvent with plant material, produced following the procedures of the invention, which demonstrates inhibitory activity against one or more extracellular proteases. In one embodiment an extract of the invention demonstrates inhibitory activity against two or more extracellular proteases. In one embodiment an extract of the invention demonstrates inhibitory activity against three or more extracellular proteases. In one embodiment, an extract of the invention demonstrates inhibitory activity against four or more extracellular proteases. The solvent may be evaporated leaving a solid embodiment of the extract. In one embodiment, the inhibitory activity is greater than about 20% when measured according to one of the assays as described herein. In one embodiment a panel of extracellular proteases can be used to test the inhibitory activity of the extract.

"Panel of Extracellular Proteases" means the array of distinct extracellular proteases that are used to perform routine assays to monitor the presence or absence of inhibitory activity throughout the extraction process of the invention. In one embodiment, inhibitory activity against one or more extracellular proteases is monitored; in one embodiment, inhibitory activity against two or more extracellular proteases is monitored; in one embodiment inhibitory activity against three or more extracellular proteases is monitored; in one embodiment inhibitory activity against four or more extracellular proteases is monitored; in one embodiment inhibitory activity against five or more extracellular proteases is monitored. One skilled in the art would appreciate that as high throughput screening techniques develop, one could routinely assay the fractions of the extracts with as many extracellular proteases as the technology permits. In general, the more enzymes that can be routinely tested the more information that can be generated during this process that will be useful for defining extracts useful to inhibit extracellular proteases.

"Potential plants" includes all species of the Kingdom Plantae, including plants under the Division Chlorophyta, Division Rhodophora, Division Paeophyta, Division Bryophyta and Division Tracheophyta; Subdivision Lycopsida, Subdivision Sphenopsida, Subdivision Pteropsida and Subdivision Spermopsida; Class Gymnospermae, Class Angiospermae, Subclass Dicotyledonidae and Subclass Monocotyledonidae. In general terms, all plants, herbs, and lower plants such as fungi and algae. Potential plants are those plants that can be subjected to the methodology of the invention in order to generate an extract which can then be tested against a panel of extracellular proteases. Those plants which yield an extract demonstrating inhibitory activity against an extracellular protease are considered to be plants and extracts comprising the subject matter of the invention.

"Potential Pre-Extract" means an extract which has not yet been determined to possess inhibitory activity against one or more extracellular proteases.

"Plant material" means any part of a plant taken individually or in group, could include but not restricted to leafs, flowers, roots, seeds, stems, and other part of a plant, wherein a plant may be terrestrial, aquatic or other.

"Protease inhibitor" as used herein, refers to any compound that attenuates the proteolytic activity of proteases. "Protease inhibitor" may or may not be proteinaceous.

"Stressor" as used herein, refers to any physical stress, chemical compound, or a biological agent used to elicit production of extracellular protease inhibitors as a result of activation of a defence response in a plant. Elicitors and inducers are also considered to be stressors. Any material of a plant may be contacted with a stressor, elicitor, or inducer, which is a chemical compound, for example organic and inorganic acids, fatty acids, glycerides, phospholipids, glycolipids, organic solvents, amino acids, and peptides, monosaccharides, oligosaccharides, polysaccharides and lipopolysaccharides, phenolics, alkaloids, terpenes and terpenoids, antibiotics, detergents, polyamines, peroxides, ionophores, etc., or subjected to a physical treatment, such as ultraviolet radiation, low and high temperature stress, osmotic stress induced by salt or sugars, nutritional stress defined as depriving the plant of essential nutrients (N, P, or K), in order to induce or elicit increased production of one or more chemicals. Such chemical compound or physical treatment may be applied continuously or intermittently to the plant or plant part. In one embodiment, such treatment may be accomplished by contacting the plant material with a solution containing the elicitor or by irradiating the plant material or exposing the plant material to other environmental stresses such as temperature stresses.

The term "substantially purified" or "substantially pure" or "isolated," when used in reference to a molecule having protease inhibitor activity, means that the molecule is in a form that is relatively free of proteins, nucleic acids, lipids, carbohydrates or other materials with which it is naturally associated in a plant. As disclosed herein, a plant extract of the invention is considered to be substantially purified. In addition, the molecules having protease inhibitor activity can be further purified using routine and well known methods as provided herein. As such, a substantially pure protease inhibitor of the invention can constitute at least about one or a few percent of a sample, for example, at least about five percent of a sample, generally at least about twenty percent of a sample, and can be further purified to constitute at least about fifty percent of a sample, generally at least about eighty percent of a sample, and particularly about ninety percent or ninety-five percent or more of a sample. A determination that a protease inhibitor of the invention is substantially pure can be made using methods as disclosed herein or otherwise known in the art, for example, by performing electrophoresis and identifying the particular molecule as a relatively discrete band.

Other chemistry terms herein are used according to conventional usage in the art, as exemplified by The McGraw-Hill Dictionary of Chemical Terms (ed. Parker, S., 1985), 30 McGraw-Hill, San Francisco, incorporated herein by reference).

The subject invention involves extracts from the tissues of plant species which provide inhibitory activity against extracellular proteases. In one embodiment, the present invention relates to the use of plants to produce extracts or semi-purified/purified compounds, compositions and formulations demonstrating an inhibitory activity against one or more proteases involved in the proteolytic degradation of human extracellular matrix. Such extracts, compounds, compositions and formulations derived from plant sources, optionally from water, ethanol or organic extracts prepared from said plant tissues, and fractions separable from said extracts by chromatography or centrifugal ultra-filtration or other means. In one aspect, these extracts with inhibitory activity can be used during protein purification to minimize the degradation due to extracellular proteases.

With reference to FIG. 1, the process for producing an extract of the invention begins with choosing a plant species. Then a pre-harvest treatment is selected, wherein either treatment with water, or water in addition to any combination of a stress, wherein the stress can be applied separately from the water (if the stress is drought, then the water would not be provided for the period in which the plant is to be stressed); followed by choosing whether the treated plant will be treated for storage and stored prior to contacting plant material with the first solvent. The plant material is treated with the first solvent and then the liquid is separated from the solid material (solid S2), wherein the liquid becomes Fraction F1 or Pre-Extract A. The solid S2 is treated with the second solvent and then the liquid is separated from the solid material (Solid S3), wherein the liquid becomes Fraction F2 or Pre-Extract B. The solid S3 is treated with the third solvent and then the liquid is separated from the solid material (Solid S4).

Plant Material

In one embodiment, plants that may be employed in the invention comprise: Abelmoschus esculentus; Abies balsamea; Abies lasiocarpa; Achillea millefolium; Achillea tomentosa; Aconitum napellus; Aconitum spp.; Acorus calamus; Actaea racemosa; Actinidia arguta; Actinidia chinensis; Adiantum pedatum; Adiantum tenerum; Aesculus hippocastanum; Aframomum melegueta; Agaricus bisporus; Agastache foeniculum; Ageratum conyzoides; Agrimonia eupatoria; Agropyron cristatum; Agropyron repens; Agrostis alba; Agrostis stolonifera; Alcea rosea; Alchemilla twills; Alkanna tinctoria; Allium ampeloprasum; Allium cepa; Allium fistulosum; Allium grande; Allium porrum; Allium sativum; Allium schoenoprasum; Allium tuberosum; Allium victorialis; Aloe vera; Alpinia officinarum; Althaea officinalis; Amaranthus caudatus; Amaranthus retroflexus; Amaranthus tricolor; Ambrosia artemisiifolia; Amelanchier alnifolia; Amelanchier canadensis; Amelanchier sanguinea; Amelanchier sanguinea.times.A. laevis; Amsonia tabernaemontana; Ananas comosus; Anaphalis margaritacea; Anethum graveolens; Angelica archangelica; Angelica dahurica; Angelica sinensis; Anthemis tinctoria; Anthoxanthum odoratum; Anthriscus cerefolium; Anthurium guildingii; Apium graveolens; Apocynum cannabinum; Arachis hypogaea; Aralia cordata; Aralia nudicaulis; Arctium lappa; Arctium minus; Arctostaphylos uva-ursi; Armoracia rusticana; Aronia melanocarpa; Aronia.times.prunifolia; Arrhenatherum elatius; Artemisia abrotanum; Artemisia absinthium; Artemisia dracunculus; Artemisia ludoviciana; Artemisia vulgaris; Asarum europaeum; Asclepias incarnata; Asclepias tuberosa; Asparagus officinalis; Aster spp.; Astilbe.times.arendsii; Astilboides tabularis; Athyrium asperum; Atriplex hortensis; Atropa belladonna; Avena sativa; Averrhoa carambola; Baptisia tinctoria; Beckmannia eruciformis; Begonia convolvulacea; Begonia eminii; Begonia glabra; Begonia mannii; Begonia polygonoides; Bellis perennis; Berberis vulgaris; Beta vulgaris; Betula alleghaniensis; Betula glandulosa; Boesenbergia rotunda; Boletus edulis; Borago officinalis; Brassica cepticepa; Brassica juncea; Brassica napus; Brassica nigra; Brassica oleracea; Brassica rapa; Bromus inermis; Buddleja davidii; Bupleurum falcatum; Butomus umbellatus; Caladium spp.; Calamagrostis arundiflora; Calamintha nepeta; Calendula officinalis; Camellia sinensis; Campanula rapunculus; Canna indica; Cantharellus cibarius; Capsella bursa-pastoris; Capsicum annuum; Capsicum frutescens; Carex morrowii; Carica papaya; Carthamus tinctorius; Carum carvi; Carya cordiformis; Castanea spp.; Centaurea solstitialis; Cerastium tomentosum; Chaerophyllum bulbosum; Chamaemelum nobile; Chelidonium majus; Chenopodium album; Chenopodium bonus-henricus; Chenopodium quinoa; Chrysanthemum coronarium; Cicer arietinum; Cichorium endivia subsp. endivia; Cichorium intybus; Cinnamomum verum; Cirsium arvense; Cissus discolor; Citrullus colocynthis; Citrullus lanatus; Citrus limettoides; Citrus limon; Citrus reticulata; Citrus sinensis; Citrus.times.paradisi; Clematis armandii; Clematis chiisanensis; Coccoloba caracasana; Cocos nucifera; Coix lacrymajobi; Colocasia spp.; Convallaria majalis; Conyza canadensis; Corchorus olitorius; Coriandrum sativum; Cornus canadensis; Cornus mas; Cosmos sulphureus; Cotinus coggygria; Crataegus sanguinea; Crataegus spp.; Crataegus submollis; Crithmum maritimum; Cryptotaenia canadensis; Cucumis anguria; Cucumis melo; Cucumis metuliferus; Cucumis sativus; Cucurbita maxima; Cucurbita moschata; Cucurbita pepo; Cullen corylifolium; Cuminum cyminum; Curcuma longa; Curcuma zedoaria; Cydonia oblonga; Cymbopogon citratus; Cymbopogon martinii; Cynara cardunculus subsp. cardunculus; Cyperus esculentus; Dactylis glomerata; Datisca cannabina; Datura metel; Datura stramonium; Daucus carota; Digitalis purpurea; Dimocarpus longan; Dioscorea batatas; Diospyros kaki; Dipsacus sativus; Dirca palustris; Dolichos lablab; Dryopteris filix-mas; Echinacea purpurea; Echinochloa frumentacea; Eleusine coracana; Equisetum hyemale; Erigeron speciosus; Eriobotrya japonica; Eruca vesicaria; Erysimum perofskianum; Eschscholzia californica; Fagopyrum esculentum; Fagopyrum tataricum; Festuca rubra; Filipendula rubra; Filipendula ulmaria; Filipendula vulgaris; Foeniculum vulgare; Forsythia.times.intermedia; Fortunella spp.; Fragaria.times.ananassa; Frangula alnus; Fucus vesiculosus; Fumaria officinalis; Galinsoga quadriradiata; Galium odoratum; Gaultheria hispidula; Gaultheria procumbens; Genista multibracteata; Gentiana lutea; Gentiana macrophylla; Geum rivale; Ginkgo biloba; Glechoma hederacea; Glyceria maxima; Glycine max; Glycyrrhiza glabra; Gossypium herbaceum; Guizotia abyssinica; Hamamelis virginiana; Hedeoma pulegioides; Hedychium spp.; Helianthus annuus; Helianthus strumosus; Helianthus tuberosus; Helichrysum angustifolium; Helichrysum thianschanicum; Heliotropium arborescens; Helleborus niger; Herba schizonepetae; Hibiscus cannabinus; Hordeum hexastichon; Hordeum vulgare; Hordeum vulgare subsp. vulgare; Houttuynia cordata; Humulus lupulus; Hydrastis canadensis; Hylotelephium spp.; Hymenoxys hoopesii; Hyoscyamus niger; Hypericum henryi; Hypericum perforatum; Hypericum spp.; Hypomyces lactifluorum; Hyssopus officinalis; Iberis amara; Iberis sempervirens; Inula helenium; Ipomoea batatas; Iris versicolor; Isatis tinctoria; Jeffersonia diphylla; Juglans nigra; Juniperus communis; Kochia scoparia; Koeleria glauca; Kolkwitzia amabilis; Krameria lappacea; Lactuca sativa; Lactuca serriola; Laportea canadensis; Laserpitium latifolium; Lathyrus sativus; Lathyrus sylvestris; Laurus nobilis; Lavandula angustifolia; Lavandula latifolia; Ledum groenlandicum; Lens culinaris subsp. culinaris; Lentinus edodes; Leonurus cardiaca; Lepidium sativum; Leucanthemum vulgare; Levisticum officinale; Ligularia dentata; Ligustrum vulgare; Linaria vulgaris; Lindera benzoin; Linum usitatissimum; Litchi chinensis; Lolium multiflorum; Lolium perenne; Lonicera ramosissima; Lonicera syringantha; Lotus corniculatus; Lotus tetragonolobus; Lunaria annua; Lupinus polyphyllus; Luzula sylvatica; Lychnis chalcedonica; Lycopersicon esculentum; Lycopersicon pimpinellifolium; Lysimachia clethroides; Lythrum salicaria; Madia sativa; Magnolia stellata; Malus hupehensis; Malus prunifolia; Malus spp.; Malva moschata; Malva sylvestris; Mangifera indica; Manihot esculenta; Marrubium vulare; Matricaria recutita; Matricaria spp.; Medicago sativa; Melaleuca alternifolia; Melilotus albus; Melilotus officinalis; Melissa officinalis; Mentha arvensis; Mentha pulegium; Mentha spicata; Mentha suaveolens; Mentha.times.piperita; Menyanthes trifoliata; Microlepia platyphylla; Miscanthus sacchariflorus; Miscanthus sinensis; Momordica charantia; Monarda didyma; Monarda fistulosa; Monarda spp.; Musa.times.paradisiaca; Myrica pensylvanica; Nasturtium officinale; Nepeta cataria; Nicotiana rustica; Nicotiana tabacum; Nigella sativa; Ocimum Basilicum; Oenothera biennis; Onobrychis viciifolia; Ophiopogon japonicus; Opuntia spp.; Origanum majorana; Origanum vulgare; Oryza sativa; Oxalis deppei; Oxyria digyna; Paeonia rubra; Paeonia spp.; Panax quinquefolius; Panicum miliaceum; Passiflora caerulea; Passiflora spp.; Pastinaca sativa; Pennisetum alopecuroides; Perilla frutescens; Persea americana; Petasites japonicus; Petroselinum crispum; Peucedanum cervaria; Peucedanum oreaselinum; Pfaffia paniculata; Phacelia tanacetifolia; Phalaris arundinacea; Phalaris canariensis; Phaseolus acutifolius; Phaseolus coccineus; Phaseolus vulgaris; Philadelphus coronarius; Phleum pratense; Phlox paniculata; Phoenix dactylifera; Physalis grisea; Physalis philadelphica; Physalis spp.; Physostegia virginiana; Phytolacca americana; Pimpinella anisum; Pisum sativum; Plantago coronopus; Plantago major; Plectranthus fruticosus; Plectranthus spp.; Pleurotus spp.; Plumbago zeylanica; Poa compressa; Poa pratensis; Podophyllum peltatum; Polygonatum odoratum; Polygonum aviculare; Polygonum chinense; Polygonum pensylvanicum; Polygonum persicaria; Pongamia pinnata; Pontederia cordata; Populus incrassata; Populus tremula; Populus.times.petrowskyana; Portulaca oleracea; Potentilla anserina; Poterium sanguisorba; Primula veris; Prunella vulgaris; Prunus armeniaca; Prunus cerasus; Prunus persica; Prunus spp.; Prunus tomentosa; Psathyrostachys juncea; Psidium guajava; Psidium spp.; Pteridium aquilinum; Pulmonaria officinalis; Pulmonaria saccharata; Punica granatum; Pyrus communis; Pyrus pyrifolia; Raphanus raphanistrum; Raphanus sativus; Rehmannia glutinosa; Reseda luteola; Reseda odorata; Rheum officinale; Rheum palmatum; Rheum.times.hybridum; Rhus aromatica; Rhus trilobata; Ribes grossularia; Ribes nigrum; Ribes rubrum; Ribes sylvestre; Ribes uva-crispa; Ribes.times.nidigrolaria; Ricinus communis; Rosa rugosa; Rosmarinus officinalis; Rubus allegheniensis; Rubus canadensis; Rubus idaeus; Rubus occidentalis; Rubus thibetanus; Rumex acetosa; Rumex acetosella; Rumex crispus; Rumex patientia; Rumex scutatus; Ruta graveolens; Saccharum officinarum; Salix purpurea; Salvia elegans; Salvia officinalis; Salvia sclarea; Salvia sylvestris; Sambucus canadensis; Sambucus ebulus; Sambucus nigra; Sanguisorba minor; Sanguisorba officinalis; Santolina chamaecyparissus; Saponaria officinalis; Satureja hortensis; Satureja montana; Satureja repanda; Scolymus hispanicus; Scorzonera hispanica; Scrophularia nodosa; Scutellaria lateriflora; Secale cereale; Sechium edule; Senecio vulgaris; Serenoa repens; Serratula tinctoria; Sesamum indicum; Setaria italica; Sidalcea spp.; Silene vulgaris; Silybum marianum; Sinapis alba subsp. alba; Sium sisarum; Solanum dulcamara; Solanum melongena; Solanum scabrum; Solanum tuberosum; Solidago canadensis; Solidago spp.; Solidago virgaurea; Solidago.times.hybrida; Sonchus oleraceus; Sorghum bicolor; Sorghum.times.drummondii; Spinacia oleracea; Stachys affinis; Stachys byzantina; Stachys macrantha; Stellaria graminea; Stellaria media; Stipa capillata; Symphytum officinale; Tamarindus indica; Tanacetum balsamita; Tanacetum balsamita subsp. balsamita; Tanacetum cinerariifolium; Tanacetum parthenium; Tanacetum vulgare; Taraxacum officinale; Tetradenia riparia; Teucrium chamaedrys; Thalictrum aquilegiifolium; Thlaspi arvense; Thuja occidentalis; Thymus fragantissimus; Thymus herba-barona; Thymus praecox subsp. arcticus; Thymus pseudolanuginosus; Thymus serpyllum; Thymus vulgaris; Thymus.times.citriodorus; Tiarella cordifolia; Tiarella spp.; Tragopogon porrifolius; Tragopogon spp.; Trichosanthes kirilowii; Trifolium hybridum; Trifolium incamatum; Trifolium pannonicum; Trifolium pratense; Trifolium repens; Trigonella foenum-graecum; Triticum aestivum; Triticum aestivum subsp. spelta; Triticum turgidum; Trollius.times.cultorum; Tropaeolum majus; Tsuga canadensis; Tsuga diversifolia; Tsuga mertensiana; Tussilago farfara; Typha latifolia; Ulmus americana; Urtica dioica; Uvularia perfoliata; Vaccinium angustifolium; Vaccinium corymbosum; Vaccinium macrocarpon; Valeriana officinalis; Valerianella locusta; Veratrum viride; Verbascum thapsus; Verbena officinalis; Veronica officinalis; Viburnum opulus; Vicia faba; Vicia sativa; Vicia villosa; Vigna angularis; Vigna mungo; Vigna unguiculata; Vinca minor; Vitis spp.; Weigela coraeensis; Weigela hortensis; Withania somnifera; .times.Triticosecale spp.; Xanthium sibiricum; Xanthium strumarium; Yucca filamentosa; Zea mays; Zingiber officinale; Achillea ptarmica; Ajuga reptans; Aster spp; Astilbe chinensis; Bergenia.times.schmidtii; Brassica chinensis; Butomus umbellatus; Buxus microphylla; Carpinus caroliniana; Centaurea dealbata; Chaenomeles.times.superba; Clematis alpina; Coreopsis verticillata; Corpus alba; Corpus sericea; Corylus maxima; Crambe cordifolia; Cyperus alternifolius; Dahlia spp.; Euphorbia amygdaloides; Fuchsia spp.; Fuchsia magellanica; Galium aparine; Geranium sanguineum; Geranium phaeum; Geranium pratense; Geranium sanguineum; Geranium.times.cantabrigiense; Glaux Maritima; Hamamelis mollis; Hedychium coronarium; Helenium spp.; Herba Schizonepetae; Hosta sieboldiana; Hydrangea quercifolia; Ipomoea aquatica; Lamiastrum galeobdolon; Magnolia.times.loebneri; Malva verticillata; Matteuccia pensylvanica; *Microbiata decussata; Montia perfoliata; Ocimum tenuiflorum; Oenothera fruticosa* subsp *fruticosa; Onoclea sensibilis; paeonia suffruticosa; Penstemon digitalis; Petasites japonicus; Physalis alkekengi; Pinus cembra; Pinus mugo; Potentilla fruticosa; Rhododendron* spp.; *ribes americanum; Rodgersia* spp.; *Rodgersia podophylla; Rubus arcticus; Rubus phoenicolasius; Rubus pubescens; Rudbeckia maxima; Sempervivum tectorum; Soleirolia soleirolii; Solidago caesia; Staphylea trifolia; Stephanandra incisa; Stewartia pseudocamellia; Strelitzia reginae; Symphoricarpos orbiculatus; Symphoricarpos albus; Taxus*.times.*media; Vernonia gigantea; Veronica austriaca* ssp *teucrium; Veronica beccabunga; Viburnum plicatum.*

It is further contemplated by this invention that any plant may be employed in the method as a potential plant. For example, plants belonging to the following classifications may optionally be employed in order to prepare an extract of the invention when such extracts are demonstrated to possess inhibitory activities against extracellular proteases: Superdivision Spermatophyta—Seed plants Division Coniferophyta—Conifers Class Pinopsida Order Finales Family Araucariaceae *Araucaria* family Family Cephalotaxaceae—Plum Yew family Family Cupressaceae—Cypress family Family Pinaceae—Pine family Family Podocarpaceae Podocarpus family Family Taxodiaceae—Redwood family Order Taxales Family Taxaceae—Yew family Division Cycadophyta Cycads Class Cycadopsida Order Cycadales Family Cycadaceae Cycad family Family Zamiaceae Sago-palm family Division Ginkgophyta—*Ginkgo* Class Ginkgoopsida Order Ginkgoales Family Ginkgoaceae—*Ginkgo* family Division Gnetophyta—Mormon tea and other gnetophytes Class Gnetopsida Order Ephedrales Family Ephedraceae—Mormontea family Order Gnetales Family Gnetaceae Gnetum family Division Magnoliophyta—Flowering plants Class Liliopsida—Monocotyledons Subclass Alismatidae Order Alismatales Family Alismataceae—Water-plantain family Family Butomaceae—Flowering Rush family Family Limnocharitaceae—Water-poppy family Order Hydrocharitales Family Hydrocharitaceae—Tape-grass family Order Najadales Family Aponogetonaceae—Cape-pondweed family Family Cymodoceaceae—Manatee-grass family Family Juncaginaceae—Arrow-grass family Family Najadaceae—Water-nymph family Family Posidoniaceae—Posidonia family Family Potamogetonaceae—Pondweed family Family Ruppiaceae—Ditch-grass family Family Scheuchzeriaceae—Scheuchzeria family Family Zannichelliaceae—Horned pondweed family Family Zosteraceae—Eel-grass family Subclass Arecidae Order Arales Family Acoraceae—Calamus family Family Araceae—*Arum* family Family Lemnaceae—Duckweed family Order Arecales Family Arecaceae—Palm family Order Cyclanthales Family Cyclanthaceae—Panama Hat family Order Pandanales Family Pandanaceae—Screw-pine family Subclass Commelimidae Order Commelinales Family Commelinaceae—Spiderwort family Family Mayacaceae—Mayaca family Family Xyridaceae—Yellow-eyed Grass family Order Cyperales Family Cyperaceae—Sedge family Family Poaceae—Grass family Order Eriocaulales Family Eriocaulaceae—Pipewort family Order Juncales Family Juncaceae—Rush family Order Restionales Family Joinvilleaceae—Joinvillea family Order Typhales Family Sparganiaceae—Bur-reed family Family Typhaceae—Cat-tail family Subclass Liliidae Order Liliales Family Agavaceae—Century-plant family Family Aloeaceae—*Aloe* family Family Dioscoreaceae—Yam family Family Haemodoraceae—Bloodwort family Family Hanguanaceae—Hanguana family Family Iridaceae—*Iris* family Family Liliaceae—Lily family Family Phylydraceae—Philydraceae family Family Pontederiaceae—Water-Hyacinth family Family Smilacaceae—Catbrier family Family Stemonaceae—Stemona family Family Taccaceae—Tacca family Order Orchidales Family Burmanniaceae—Burmannia family Family Orchidaceae—Orchid family Subclass Zingiberidae Order Bromeliales Family Bromeliaceae—Bromeliad family Order Zingiberales Family Cannaceae—*Canna* family Family Costaceae—Costus family Family Heliconiaceae—*Heliconia* family Family Marantaceae—Prayer-Plant family Family Musaceae—Banana family Family Zingiberaceae—Ginger family Class Magnoliopsida—Dicotyledons Subclass Asteridae Order Asterales Family Asteraceae—Aster family Order Callitrichales Family Callitrichaceae—Water-starwort family Family Hippuridaceae—Mare's-tail family Order Calycerales Family Calyceraceae—Calycera family Order Campanulales Family Campanulaceae—Bellflower family Family Goodeniaceae—Goodenia family Family Sphenocleaceae—Spenoclea family Order Dipsacales Family Adoxaceae—Moschatel family Family Caprifoliaceae—Honeysuckle family Family Dipsacaceae—Teasel family Family Valerianaceae—Valerian family Order Gentianales Family Apocynaceae—Dogbane family Family Asclepiadaceae—Milkweed family Family Gentianaceae—Gentian family Family Loganiaceae—Logania family Order Lamiales Family Boraginaceae—Borage family Family Lamiaceae—Mint family Family Lennoaceae—Lennoa family Family Verbenaceae—*Verbena* family Order Plantaginales Family Plantaginaceae—Plantain family Order Rubiales Family Rubiaceae—Madder family Order Scrophulariales Family Acanthaceae—Acanthus family Family Bignoniaceae—Trumpet-creeper family Family Buddlejaceae—Butterfly-bush family Family Gesneriaceae—Gesneriad family Family Lentibulariaceae—Bladderwort family Family Myoporaceae—*Myoporum* family Family Oleaceae—Olive family Family Orobanchaceae—Broom-rape family Family Pedaliaceae—Sesame family Family Scrophulariaceae—Figwort family Order Solanales Family Convolvulaceae—Morning-glory family Family Cuscutaceae—Dodder family Family Fouquieriaceae—Ocotillo family Family Hydrophyllaceae—Waterleaf family Family Menyanthaceae—Buckbean family Family Polemoniaceae—*Phlox* family Family Solanaceae—Potato family Subclass Caryophyllidae Order Caryophyllales Family Achatocarpaceae—Achatocarpus family Family Aizoaceae—Fig-marigold family Family Amaranthaceae—Amaranth family Family Basellaceae—Basella family Family Cactaceae—*Cactus* family Family Caryophyllaceae—Pink family Family Chenopodiaceae—Goosefoot family Family Molluginaceae—Carpet-weed family Family Nyctaginaceae—Four o'clock family Family Phytolaccaceae—Pokeweed family Family Portulacaceae—Purslane family Order Plumbaginales Family Plumbaginaceae—Leadwort family Order Polygonales Family Polygonaceae—Buckwheat family Subclass Dilleniidae Order Batales Family Bataceae—Saltwort family Order Capparales Family Brassicaceae—Mustard family Family Capparaceae—Caper family Family Moringaceae—Horse-radish tree family Family Resedaceae—Mignonette family Order Diapensiales Family Diapensiaceae—Diapensia family Order Dilleniales Family Dilleniaceae—Dillenia family Family Paeoniaceae—Peony family Order Ebenales Family Ebenaceae—Ebony family Family Sapotaceae—Sapodilla family Family Styracaceae—Storax family Family Symplocaceae—Sweetleaf family Order Ericales Family Clethraceae—Clethra family Family Cyrillaceae—Cyrilla family Family Empetraceae—Crowberry family Family Epacridaceae—Epacris family Family Ericaceae—Heath family Family Monotropaceae—Indian Pipe family Family Pyrolaceae—Shinleaf family Order Lecythidales Family Lecythidaceae—Brazil-nut family Order Malvales Family Bombacaceae—Kapok-tree family Family Elaeocarpaceae—Elaeocarpus family Family Malvaceae—Mallow family Family Sterculiaceae—Cacao family Family Tiliaceae—Linden family Order Nepenthales Family Droseraceae—Sundew family Family Nepenthaceae—East Indian Pitcher-plant family Family Sarraceniaceae—Pitcher-plant family Order Primulales Family Myrsinaceae—Myrsine family Family Primulaceae—Primrose family Family Theophrastaceae—Theophrasta family Order Salicales Family Salicaceae—Willow family Order Theales Family Actinidiaceae—Chinese Gooseberry family Family Caryocaraceae—Souari family Family Clusiaceae—Mangosteen family Family Dipterocarpaceae—Meranti family Family Elatinaceae—Waterwort family Family Marcgraviaceae—Shingle Plant family Family Ochnaceae—Ochna family Family Theaceae—Tea family Order Violales Family Begoniaceae—*Begonia* family Family Bixaceae—Lipstick-tree family Family Caricaceae—*Papaya* family Family Cistaceae—Rock-rose family Family Cucurbitaceae—Cucumber family Family Datiscaceae—*Datisca* family Family Flacourtiaceae—Flacourtia family Family Frankeniaceae—Frankenia family Family Loasaceae—Loasa family Family Passifloraceae—Passion-flower family Family Tamaricaceae—*Tamarix* family Family Tumeraceae—Turnera family Family Violaceae—Violet family Subclass Hamamelidae Order Casuarinales Family Casuarinaceae—She-oak family Order Fagales Family Betulaceae—Birch family Family Fagaceae—Beech family Order Hamamelidales Family Cercidiphyllaceae—Katsura-tree family Family Hamamelidaceae—Witch-hazel family Family Platanaceae—Planetree family Order Juglandales Family Juglandaceae—Walnut family Order Leitneriales Family Leitneriaceae—Corkwood family Order Myricales Family Myricaceae—Bayberry family Order Urticales Family Cannabaceae—Hemp family Family Cecropiaceae—Cecropia family Family Moraceae—Mulberry family Family Ulmaceae—Elm family Family Urticaceae—Nettle family Subclass Magnoliidae Order Aristolochiales Family Aristolochiaceae—Birthwort family Order Illiciales Family Illiciaceae—Star-anise family Family Schisandraceae—*Schisandra* family Order Laurales Family Calycanthaceae—Strawberry-shrub family Family Hernandiaceae—Hernandia family Family Lauraceae—Laurel family Family Monimiaceae—Monimia family Order Magnoliales Family Annonaceae—Custard-apple family Family Canellaceae—Canella family Family Magnoliaceae—*Magnolia* family Family Myristicaceae—Nutmeg family Family Sonneratiaceae—Sonneratia family Family Winteraceae—Wintera family Order Nymphaeales Family Cabombaceae—Water-shield family Family Ceratophyllaceae—Hornwort family Family Nelumbonaceae—*Lotus*-lily family Family Nymphaeaceae—Water-lily family Order Papaverales Family Fumariaceae—Fumitory family Family Papaveraceae—Poppy family Order Piperales Family Chloranthaceae—Chloranthus family Family Piperaceae—Pepper family Family Saururaceae—Lizard's-tail family Order Ranunculales Family Berberidaceae—Barberry family Family Lardizabalaceae—Lardizabala family Family Menispermaceae—Moonseed family Family Ranunculaceae—Buttercup family Family Sabiaceae—Sabia family Subclass Rosidae Order Apiales Family Apiaceae—Carrot family Family Araliaceae—*Ginseng* family Order Celastrales Family Aquifoliaceae—Holly family Family Celastraceae—Bittersweet family Family Corynocarpaceae—Karaka family Family Hippocrateaceae—Hippocratea family Family Icacinaceae—Icacina family Family Stackhousiaceae—Stackhousia family Order Comales Family Cornaceae—Dogwood family Family Garryaceae—Silk Tassel family Family Nyssaceae—Sour Gum family Order Euphorbiales Family Buxaceae—Boxwood family Family Euphorbiaceae—Spurge family Family Simmondsiaceae—Jojoba family Order Fabales Family Fabaceae—Pea family Order Geraniales Family Balsaminaceae—Touch-me-not family Family Geraniaceae—Geranium family Family Limnanthaceae—Meadow-Foam family Family Oxalidaceae—Wood-Sorrel family Family Tropaeolaceae—*Nasturtium* family Order Haloragales Family Gunneraceae—Gunnera family Family Haloragaceae—Water Milfoil family Order Linales Family Erythroxylaceae—Coca family Family Linaceae—Flax family Order Myrtales Family Combretaceae—Indian Almond family Family Lythraceae—Loosestrife family Family Melastomataceae—Melastome family Family Myrtaceae—Myrtle family Family Onagraceae—Evening Primrose family Family Punicaceae—Pomegranate family Family Thymelaeaceae—Mezereum family Family Trapaceae—Water Chestnut family Order Podostemales Family Podostemaceae—River-weed family Order Polygalales Family Krameriaceae—*Krameria* family Family Malpighiaceae—Barbados Cherry family Family Polygalaceae—Milkwort family Order Proteales Family Proteaceae—Protea family Order Rafflesiales Family Rafflesiaceae—Rafflesia family Order Rhamnales Family Elaeagnaceae—*Oleaster* family Family Rhamnaceae—Buckthorn family Family Vitaceae—Grape family Order Rhizophorales Family Rhizophoraceae—Red Mangrove family Order Rosales Family Brunelliaceae—Bruneilia family Family Chrysobalanaceae—Cocoa-plum family Family Connaraceae—Cannarus family Family Crassulaceae—Stonecrop family Family Crossosomataceae—Crossosoma family Family Cunoniaceae—Cunonia family Family Gros sulariaceae—Currant family Family Hydrangeaceae—*Hydrangea* family Family Pittosporaceae—*Pittosporum* family Family Rosaceae—Rose family Family Saxifragaceae—Saxifrage family Family Surianaceae—Suriana family Order Santalales Family Balanophoraceae—Balanophora family Family Eremolepidaceae—Catkin-mistletoe family Family Loranthaceae—Showy Mistletoe family Family Olacaceae—Olax family Family Santalaceae—Sandalwood family Family Viscaceae—Christmas Mistletoe family Order Sapindales Family Aceraceae—Maple family Family Anacardiaceae—Sumac family Family Burseraceae—Frankincense family Family Hippocastanaceae—Horse-chestnut family Family Meliaceae—Mahogany family Family Rutaceae—Rue family Family Sapindaceae—Soapberry family Family Simaroubaceae—Quassia family Family Staphyleaceae—Bladdernut family Family Zygophyllaceae—Creosote-bush family.

In one embodiment, potential plants comprise: *Atropa Belladonna, Erythrinia glabeliferus, Ipomea tricolor, Erythrinia crista, Celosia cristata, Gallium sporium, Laurus nobilis, Vitis labrissa, Gratiola officinalis, Symphitium officinalis, Hosta fortuna, Casia hebecarpa, Thalictum flavum, Scutellarian altissima, Portulaca oleacea, Scutellaria certicola, Physalis creticola, Geum fanieri, Gentiana tibetica, Linium hirsutum, Aconitum napellus, Podophyllum amodii, Thymus cretaceus, Hosta fortunaea, Carlina acaulis, Charnaechrista fasciculata, Pinus pinea, Pegamun hamalis, Tamarindus india, Carica papaya, Cistus incanus, Capparis spinosa inemis, Cupress lusitanica, Diopiros kaka, Erungium campestre, Aesculus woerlitzenis, Aesculus hippocastanum, Cupressus sempervirens, Celtis occidentalis, Polygonum cuspidatum, Eleagnus angustifolia, Eleagnus cemutata, Gentiana macrophilla, Brassica napa, Sesbania exaltata, Sesbania*

*speciosa, Spartina potentiflora, Brassica juncea, Helianthus annus, Puansetia* sp., *Pelargonium zonale, Sundapsis* spp., *Leontopodium alpinum, Lupinus luteaus, Buxus microphilla "japonica", Liatris spinata, Rimula japonica, Betula nigra, Filipendula vulgrais, Lobelia siphitica, Gravilia robusta, Reseda luteola, Gentiana littorala, Campanula carpatica, Aesculus hypocastanum, Aesculus waertilensis, Ageratum conizoides, Psidium guajava, Ailantus altissima, Buxus microphylla "japonica", Hydrocotile asiatica, Gravilea robusta, Brugmansia suaveolens, Thymus puliglodes, Thymus lemabarona, Thymus serphylum* (wild), *Gaultheria procumbens, Thymus serphylum, Thymus camosus, Thymus thrasicus, Calicatus floridus, Zingiber officinalis, Lapia dulcis, Thymus vulgaris "argenteus", Thymus praecox "arcticus", Thymus puleglodes "lemons", Thymus speciosa, Thymus camosus, Thymus pseudolamginosus, Thymus praecox, Thymus vulgaris "oregano", Ficus religiosa, Forsithsia suspensa, Chelidonium majus, Thymus wooly, Thymus portugalense, Nicotiana tabacum, Thymus cytridorus "aureus", Thymus vulgaris, Cactus officinalis, Lal lab purpurea, Juglands regia, Actinidia chinensis, Hernerocalis* spp., *Betula pendula, Gardenia jasminoides, Taxodium dixticum, Magnolia loebheril, Crataegus praegophyrum, Larix dedidua, Tuja orientalis "eligantissima", Tula ocidentalis "columbia", Xeupressocyparis deylandii, Pseudotsuga menzisia, Abies firma, Fautenousus qualiqualia, Alium cernum* (wild), *Juniperus* "blue pacific", *Taraxacum officinalis, Juca* sp., *Ilex agnifolium, Tsuga canadensis "penola", Ilex cornuta, Taxus hiksii, Taxus media, Metasequoia glyptotrobioldes, Pinus bungiana, Boxus sempervirens, Stevartia coreana, Prunus xocane, Betula daurica, Plantago minor, Acer palmatum "burgundy", Acer campestre, Cotynus cogygria, Quercus robur "fastigiate", Acer truncatum, Archirantus bidentata, Alum japonica, Carum capsicum, Agastache mexuicana, Prunella vulgaris, Tagetes minuta, Nepeta cataria, Ratibiunda columnus-Fera, Aster-Nova anglicae, Mirica certifera, Pittisporum tibica, Taxodium dixticum* (H.sub.20), *Taxodium dixticum* (Acetic acid), *Plantago major,* Scotch pine, *Asorum canadensis, Pieras japonica, Pinus sirtrobus, Trifolium pratense, Prunus serotica, Darura stramonium, Geranium maculata, Hydrocotile asiatica, Astragulus sinicus, Centauria maculata, Ruschia indurata, Myrthus comunis, Platanus acidentalis, Liclum barbatum, Lavandula officinalis, Gravilea robusta, Hyppoach rhamnoides, Filipendula ulmaria, Betula pendula, Polygonium odoratum, Brugmansi graveolens* (calf), *Rhus toxicodenta, Armoraica ristica, Ficus benjaminii, Sluffera* sp., *Pelagonium zonale, Allium* sp., *Asimina triloba, Lippa dulcis, Epilobium augustifolium, Brugmansia suaveolens* (old), *Brugmansia suaveolens* (young), *Xanthosoma sagittifolium* (leaf), *Xanthosoma sagittifolium* (stem), *Monstera deliciosa, Aglaonema commutatus, Dieffenbachia leopoldii, Anthurium andreanum, Syngoniurn podophyllum, Dracaena fragrans, Ananas comosus, Strelitzia reglinae, Dieffenbachia segiunae, Syngoniurn aurutum, Dracaena* sp., *Haemanthus katharina, Anthurium altersianum, Spathiphyllum grandiflorum, Spathiphyllum cochlearispaturn, Monstera pertusa, Anthurium magnificurn, Anthurium hookeri, Anthurium elegans, Calathea zebrina, Yucca elephantipes, Bromelia balansae, Musa textilis* (Leaf), *Musa textilis* (Stem), *Myrthus communis, Olea olcaster, Olea europaea, Verium oleander, Cocculus laurifolius, Microsorium punctatum, Ficus* sp., *Senseviera* sp., *Adansonia digitata, Boechimeria boloba, Piper nigrum, Phymatosorus scolopendria, Tumera ulmifolia, Nicodemia diversifolia, Tapeinochilos spectabilis, Rauwolfia tetraphylla, Ficus elastica, Cycas cirinalis, Caryota ureus, Cynnamonum zeylonicum, Aechmea luddemoniana, Foenix zeulonica, Ficus benjamina, Ficus pumila, Murraya exotica, Trevesia sungaica, Clerodendrurn speciossicum, Actinidi colonicta, Paeonia lactiflora, Paeonia suffructicisa, Quercus imbricaria, Iris alida, Portulaca olleracea, Poligonum aviculare, Iris pseudocarpus, Allium nutans, Allium fistulosum, Antericum ramosum, Veratrum nigrum, Poligornun latifolia, Hosta lancefolia, Hosta zibalda, Echinops sphae, Paeonia daurica, Inula hilenium, Trambe pontica, Digitalis lutea, Bactisia australis, Austolachia australis, Hissopus zeraucharicus, Feucrium hamedris, Sedum album, Heraclelum pubescens, Origanurn vulgare, Cachris alpina, Haser trilobum, Matteucia strutiontoris, Sedum telchium, Bocconia cordata, Hiuga rentans, Talictrum minus, Anemona japonica, Clematis rectae, Talictrum* sp., *Alchemilla* sp., *Potentilla alba, Poterium sangiusorba, Minispermum dauricum, Oxobachus nictogenea, Armoracea rusticana, Cramble cardifolia, Agrimonia eupatora, Uschusa* sp., *Polymonium ceruleum, Valeriana officinalis, Pulmonaria molissima, Stachis lanata, Coronolla varia, Platicada grandiflora, Lavandula officinalis, Vincetocsicum officinalis, Acolypha hispida, Gnetum guemon, Psychotria nigropunctata, Psychotria metbacteriodomasica, Cobiaeum varilarturn, Phyllanthus grandifolium, Pterigota alata, Pachyra affinis, Sterulia data, Phylidendron speciosus, Pithecelobium unguis, Sanchezia nobilis, Oreopanax capitata, Ficus triangularis, Pigelia pennata, Piper chaba, Laurus nobilis, Erythrinia caffra, Metrosideros excelsa, Osmanthus* spp., *Cupressus sempervirens, Jacobinia* sp., *Senecio platifilla, Livistona fragrans, Tetraclinis articulata hinensis, Eucaliptus rudis, Podocarpus spinulosus, Eriobotria japonica, Gingko biloba, Rhododendron* spp., *Thuja occidentalis, Fagopyrum suffruticosum, Geum macrophyllum, Magnolia cobus, Vinca minor, Convalaria majalis, Corylus avelana, Barbaric* sp., *Rosa multiflora, Ostrea carpinifolia, Ostrea connote, Quercus rubra,* Tulip tree, *Sorbus aucuparia, Betula nigra* (leaf), *Betula nigra* (flower), *Castanea sativa, Bergenia crassifolia, Artemisia dracunculus, Ruta graveolens, Quercus nigra, Schisandra chinensis, Betula alba, Sambucus niora, Gentiana cruciata, Encephalaris horridum, Phebodium aureum, Microlepia platphylla, Ceratoramia mexicana, Stepochlaena tenuifolia, Adianthum trapezieformis, Adianthum radiatum, Lycodium japonicum, Aessopteria crasifolia, Asplenium australasicum, Agatis robusta, Osmunda regalis, Osmundastrum claytonionum, Phyllitis scolopendrium, Polyschium braunii, Crytomium fortunei, Dryopteris filis-max, Equisetum variegatum, Anthyrium nopponicum, Anthyrium filis-femina, Parthenosicus tricuspidata, Ligustum vulgare, Charnaeciparis pisifera, Rosa cocanica, Citinis coggriaria, Pinus strobus, Celtis occidentalis, Picea schrenkiana, Cydonia oblonga, Ulmus pumila, Euonomus verrucosa, Deutria scabra, Mespilus germanica, Quercus castanufolia, Euonomus europea, Seruginea suffruticisa, Keyleiteria paniculata, Sering a josiceae, Zelcova, carpinifolia, Abies cephalonica, Taccus bacata, Taxus cuspidata, Salis babilonics, Thuja occidentalis, Actinidia colomicta, Magonia agrifolia, Aralis mandshurica, Luglands nigra, Euonimus elata, Princepia* sp., *Forsitsia europea, Sorbocotoneaster* sp., *Morus alba, Crategus macrophyllum, Eucomia ulurifolia, Sorbus cominicta, Philodendron amurense, Comus mass, Korria japonica, Parrotia persica, Jasminum frutocarus, Sulda sanganea, Pentaphylloides fruticosa, Sibirea altaiensis, Cerasus japonica, Kolkwitzia amabilis, Amigdalus nana, Acer mandshurica, Salix tamarisifolia, Amelanchier spicata, Cerasus maghabab, Prunus cerasifera. Coryllus ayelana, Acer tataricum, Viburnum opulus, Siringa vulgaris, Fraxinus exelsior, Quercus trojana, Chaernomelis superba, Pinus salinifolia, Berberis vulgaris, Cotoneaster horisontalis, Cotoneaster fangianus, Fagus silvatica, Pinus pumila, Pinus silvestris* and *Berberis thungergi.*

Another interesting group of plants that can be considered as plants and/or potential plants of the invention comprise the plants that are indigenous to arid regions, for example, those located between 35° north latitude and 35° south latitude. In accordance with the present invention potential extracts and extracts of the invention can be obtained from plants selected from the group comprising: the agave, Agavaceae, family including such members as: *Yucca elata, Y. breviflora, Agave deserti, A. chrysantha, Dasylirion wheeleri*; the buckwheat, Polygonaceae, family, such as *Eriogonum fasciculatum*; the crowfoot, Ranunculaceae, family, such as *Delphinium scaposum, Anemone tuberosa* and *D. parishii*; the poppy, Papaveraceae, family, including *Platystemon californicus, Argemone pleiacantha, Corydalis aurea, Eschschoizia californica* and *Ar. corymbosa*; members of the mustard, Cruciferae, family, such as *Dithyrea californica, Streptanthus carinatus* and *Lesquerella gordoni*; members of the legume, Leguminosae, family, such as *Acacia greggii, Prosopis velutina, A. constrica, Senna covesii, Cercidium floridum, C. microphyllum, Lotus huminstratus, Krameria parvifolia, Parkinsonia aculeata, Calliendia eriophylla, Lupinus arizonicus, Olyneya tesota, Astragalus lentiginosus, Psorothamunus spinosus* and *Lupinus sparsiflorus;* members of the loasa family, Loasaceae, including *Mentzelia involucrata, M. pumila* and *Mohavea Confertiflora*; members of the cactus, Cactaceae, family, such as *Carnegiea gigantia, Opuntia leptocaulis, Ferocactus wislizenii, O. bigelovii, O. pheacantha, O. versicolor, O. fulgida, Echinocereus engelmannii, Mammillaria microcarpa, O. basilaris, Stenocereins thurberi, O. violacea, M. tetrancistra, O. ramosissima, O. acanthocarpa, E. pectinatins* and *O. arbuscula*; members of the evening primrose, Onagraceae, family, such as *Oenothera deltoides, Camissonia claviformis* and *Oe. primiveris*; members of the milkweed, Asclepiadaceae, family, including *Asclepias erosa, A. sublata* and *Sarcostemma cynanchoides*; members of the borage, Boraginaceae, family, such as *Cryptantha augusti* folia and *Amsinckia intermedia*; members of the sunflower, Compositae, family, including *Baccharis sarothroides, Monoptiilon belloides, Erieron divergens, Zinnia acerosa, Melampodium leucanthan, Chaenactis fremontii, Calycoseris wrightii, Malacothrix californica, Helianthus annus, H. niveus, Geraea canescens, Hymenothrix wislizenii, Encelia farinosa Psilostrophe cooperi, Baileva multiradiata, Bebbia iuncea, Senecio douglasii, Trixis californica, Machaeranthera tephrodes, Xylorhiza tortifolia, Cirsiinm neomexicanum, Antennaria parviflora* and *Ch. douglasii*; members of the caltrop, Zygophyllaceae, family, including *Lama tridentata* and *Kallstroemia grandiflora*; members of the mallow, Malvaceae, family, including *Hibiscus coulteri, H. denudatus* and *Sphaeralcea ambigua*; members of the phlox, Polemoniaceae, family, such as *Luanthus aureus*; members of the unicorn plant, Martyniac eae, family, such as *Proboscidiea altheaefolia*; members of the gourd, Cucurbitaceae, family, such as *Cucurbita digitata*; members of the lily, Lilaceae, family, including *Calochortus kennedyi, Dichelostemma pulchellum, Allium macropetalum* and *Hesperocallis indulata*; members of the ocotillo, Fouquieriaceae, family, including *Fouquieria splendens*; members of the figwort, Scrophulariaceae, family, such as *Castilleja* sp., *Penstemon parryi* and *Orthocarpus purpurascens*; members of the acanthus, Acanthaceae, family, including *Anisacanthus thurberi, Justicia californica* and *Ruellia nudiflora*; members of the four o'clock, Nyctaginaceae, family, such as *Allionia incarnate, Abronia villosa* and *Mirabilis multiflora*; members of the geranium, Geraniaceae, family, including *Erodium cicutarium*; members of the waterleaf, Hydrophyllaceae, family, such as *Nama demissum, Phacelia bombycina* and *Ph. distans*; members of the bignonia, Bignoniaceae, family, such as *Chilopsis linearis*; members of the vervain, Verbenaceae, family, including *Glandularia gooddugii* and *Verbena neomexicana*; members of the mint, Labiatae, family, such as *Hyptis emoryi* and *Salvia columbariae*; members of the broomrape, Orobanchaceae, family, such as *Orobanche cooperi*; members of the portulaca, Portulaceae, family, such as *Talinum auriantiacum*; members of the carpet-weed, Aizoaceae, family, such as *Sesuvium verrucosum*; members of the flax, Linaceae, family, such as *Linum lewisii*; members of the potato, Solanaceae, family, including *Nicotiana trigonophylla* and *Physalis lobata*; and members of the cochlospermum, Cochlospermaceae, family, such as *Amoreuxia palmatifida*.

Pre-Harvest Treatment

Once a potential plant is selected, a pre-harvest treatment is selected, wherein the treatment can be water or water in combination with a stressor, elicitor, or inducor. One skilled in the art would appreciate to perform the procedure with water and then with a series of stressors in order to determine whether the potential plant becomes an extract of the invention which demonstrates inhibitory activity against one or more extracellular proteases.

In one embodiment, this invention relates to altering the amount and/or composition of extracellular protease inhibitory activity by stressing a plant by chemical elicitors which act as stressor agent and activated defence plants pathways as mechanical wounding, drought, heat, or cold before tissue collection and extraction.

In one embodiment, stress involves exposing plants to a solution of one or more chemical elicitors to induce defense metabolic pathways and secondary metabolites prior to collection of plant tissues. Known chemical elicitors reported in the literature include ozone, hydrogen peroxide, jasmonic acid and its derivatives, arachidonic acid, salicylic acid and ester derivatives, alpha- and gamma-linoleic acids, volicitin, peptides, oligopeptides, saccharides, oligosaccharides such as chitosan, and synthetic chemicals such as Benzo-1,2,3-thiadiazole-7-carbathioic acid S-methyl ester (BTH).

A stressor may be one or more organic compounds. Some exemplary compounds that may be used as a stressor include Jasmonic acid, Jamonic acid lower alkyl esters, .alpha.-linoleic acid, .alpha.-linoleic acid lower alkyl esters, .gamma.-linoleic acid, .gamma.-linoleic acid lower alkyl esters, Arachidonic acid, Arachidonic acid lower alkyl esters, salicylic acid.

A stressor may be able to induce abiotic stresses in plants. Thus, for example, plants can be treated with one or more chemical or mechanical stresses prior to tissue collection. Mechanical stress can be performed twelve hours to ten days prior to tissue collection. In one embodiment, mechanical stress can be performed one day to three days prior to tissue collection. In one embodiment, mechanical stress can be performed three to six days prior to tissue collection. In one embodiment, mechanical stress can be performed four to eight days prior to tissue collection. In one embodiment, mechanical stress can be performed six to ten days prior to tissue collection.

Chemical stress can be induced by spraying plant material once or more than once with an aqueous or alcoholic solution of the chemical elicitor one hour to 10 days prior to tissue collection. In one embodiment, chemical stress can be induced one day to three days prior to harvesting the plant tissue; in one embodiment, chemical stress can be induced two to four days prior to harvesting the plant tissue; in one embodiment, chemical stress can be induced five to ten days prior to harvesting the plant tissue.

A chemical stress can be added by feeding a plant with an aqueous or alcoholic solution of the chemical. Likewise, the plants can be stressed by airborne transport of the chemical agents one hour to ten days prior tissue collection. In one embodiment, plants can be treated by spray one day before collection. In one embodiment, such chemical stress can be induced one hour to three days prior to harvesting the plant tissue; in one embodiment, such chemical stress can be induced two to eight days prior to harvesting the plant tissue; in one embodiment, such chemical stress can be induced five to ten days prior to harvesting the plant tissue.

Any combination of the above-mentioned stressors and treatment regiemes can be employed to induce the production or enhanced production of one or more extracellular proteases. One skilled in the art would be able to determine from the results of the assay against the panel of extracellular proteases whether it is desirable to follow one or more of the stressor regiemes.

Harvesting the Plant Material for Extraction and Optional Storage Treatment

The plant material may be used immediately after pre-harvest treatment, or it may be desirable to store the plant material for a period of time, prior to performing the extraction procedure(s). In one embodiment, the plant material could be treated prior to storage. In such cases, the treatment could include drying, freezing, lyophilisizing, or some combination thereof.

Following treatment to prepare the plant material for storage, the plant material may be stored for an extended period of time, prior to contacting the plant material with the first solvent. In one embodiment the plant material is stored less than one week. In one embodiment the plant material is stored from one week to one month. In one embodiment the plant material is stored from one month to six months. In one embodiment the plant material is stored from four months to one year. In one embodiment the plant material is stored longer than one year.

The Extraction Process

As depicted in FIG. 1, there are generally three basic extraction processes which can be performed in sequence to generate potential pre-extracts. The procedure for each Extraction process entails contacting the solid plant material with a solvent with adequate mixing and for an amount of time to ensure adequate exposure of the solid material to the solvent to enable inhibitory activity to be taken up by the solvent. Solvent A, B and C generally represent separate classes of solvents, for example, aqueous, alcoholic and organic. They are generally applied in a polar to non-polar order. They can be applied in a non-polar to polar order, however, in each case the solid matter must be dried prior to contacting the solid matter with the subsequent solvent. The liquid is then separated from the solid (insoluble) matter by a process known to those skilled in the art, to generate two fractions: the liquid fraction which is a potential pre-extract and a solid fraction.

The term "liquid" is used to denote a distinction from the solid, insoluble matter. Thus, a liquid, which may be converted to a gas or function in a gaseous form, as in the case with steam, for example can serve as a solvent. Likewise, other non-solid solvents may be used such as highly viscous liquids or other gaseous solvents, some of which can then be converted into a liquid phase.

A liquid solvent may also indicate a composition or a mixture of solvents. Common examples include a buffered aqueous solution, such as a TRIS-HCl buffer, or an ethanol/methanol combination.

In one embodiment, selected parts of a plant (which can be fresh, dried or frozen) can be crushed either mechanically, using a grinder or any device to break plant parts into small particles, or by freezing them in liquid nitrogen. In another embodiment, plant particles can be extracted with an aqueous TRIS-HCl buffer at pH 6-8, in one embodiment pH 7, from 30 minutes to 8 hours, in one embodiment 30 min to 2 hours, at a temperature between 4 to 50° C., in one embodiment 4 to 25° C.; in one embodiment, 4-10° C. In one embodiment, extraction can be performed at 4° C. for 30 minutes.

The solid material can be separated from the solvent by centrifugation, filtration or any other means known to those of skill in the art to separate solids from a solution, to yield aqueous, alcoholic or organic extract, a potential pre-extract. These potential pre-extracts can be tested directly by a panel of extracellular proteases for the ability to inhibit extracellular protease activity, and/or subjected to further separation procedures to generate a potential extract as The remaining solid can be contacted with a second solvent, such as an alcoholic solvent and a cosolvent, methanol or water In one embodiment, ethanol is used as alcoholic solvent, wherein the range of ethanol:methanol, ranges from 50:50 to 85:15, and 10 minute to one hour, in one embodiment 15 to 30 minute extraction time, at a temperature range of 4 to 25° C. in one embodiment, 4 to 10° C. in one embodiment, and 4° C. in another embodiment. Adequate contact of the solvent with the plant material can be encouraged by shaking the solid suspension for 15 min to 24 hour at a temperature ranging from 4 to 50° C.

The alcoholic extract is recovered and separated from the solids by centrifugation (the material which is insoluble in alcohol is used for organic extraction(s)). The potential pre-extract can be dried using a lyophilizer, a speed vac, a rotary evaporator, or a vacuum pump and dried under vacuum in order to remove the solvent. The dried extract can be dissolved in Tris-HCl buffer wherein the pH is between pH 6 to pH 8, in one embodiment and at pH 7 in one embodiment, and assayed against the panel of extracellular proteases for its bioactivity or, as in the case of the aqueous extract, the alcoholic extract can be treated to obtain purified extracts, as described below.

The organic extract can be obtained by shaking the residual solid for one to twenty-four hours in one embodiment, for one to fifteen hours in one embodiment, one to eight in one embodiment, one to four in one embodiment, with an organic solvent such as diethylether, hexane, dichloromethane, or ethylacetate. The solid can be separated by centrifugation or by filtration (regular or suction) and the organic solvent removed by distillation or by using a rotating evaporator. The organic extract can be dissolved in an aqueous buffer, or a mixture of an aqueous buffer and a suitable solvent (such as dimethylsulfoxide), to evaluate its bioactivity. In one embodiment the organic extracts are prepared using dichloromethane as the solvent of extraction, and the extraction is performed at room temperature for 2 hours.

Are included in the invention extracts prepared by all known large, medium and small-scale 30 methods to prepare extracts.

Determination of Extracellular Protease Inhibitory Activity in an Extract

In order to prepare various embodiments of the invention, (i.e., extracts, compositions and formulations with extracellular protease inhibitory activity) one requires techniques for measuring qualitatively and/or quantitatively the presence of such inhibitory activity. One skilled in the art would appreciate that there are numerous methods and techniques for measuring such activity, that can be used to determine, for example, which extracts are of interest and to follow the processing of the active ingredient(s) giving rise to such activity.

Currently, there are several assays to measure MMP, elastase andcathepsins activity (for a review of these methods, see Murphy and Crabbe, In Barrett (ed.) Methods in Enzymology. Proteolytic Enzymes: Aspartic Acid and Metallopeptidases (New York: Academic Press, 1995)-248: 470. One method, the gelatinolytic assay, is based on the degradation of radio-labelled type I collagen. Although this method is relatively sensitive, it requires the use of radio-labelled specific substrates.

Another widely-used technique is the zymography assay. In this assay, MMP, elastase and cathepsins activity is detected by the presence of negatively-stained bands following electrophoresis in substrate-impregnated SDS polyacrylamide gels. The zymography assay is a sensitive and quantitative method for the detection of various MMPs, elastase, cathepsins and TACE in biological samples; nonetheless, it is labour intensive and has a low dynamic range. Zymography, moreover, is not suitable to measure the intrinsic net activity in biological samples: SDS dissociates MMP-TIMP complexes and activates latent enzyme forms. This is particularly important since matrix degradation ultimately depends on the ratio of free active gelatinase to latent proenzyme or TIMP-complexed forms.

A microtitreplate assay has been developed recently (Pacmen et al., (1996) Biochem. Pharm. 52: 105-111). This assay provides measurement of net biological enzymatic activity of MMP, does not require a radioisotope safety environment, and could be used efficiently for routine measurement of inhibitory activity of MMP; however, it is not likely to be highly efficient as a diagnostic test since the incubation times are long and the sensitivity is much lower than that obtained by standard zymography and radio-labelled substrate assays.

Other methods used auto-quenched fluorogenic substrates. Many fluorogenic substrates have been designed for the quantification of MMPs, elastase, and cathepsins activity throught fluorescent level variation measuring (reviewed by Nagase and Fields (1996) Biopolymers 40: 399-416).

Fluorescence polarization assays were based on the principle that when fluorescent molecules are excited with plane polarized light, they will emit light in the same polarized plane provided that the molecule remains stationary throughout the excited state. However, if the excited molecule rotates or tumbles during the excited state, then light is emitted in a plane different from the excitation plane. If vertically polarized light is used to excite the fluorophore, the emission light intensity can be monitored in both the original vertical plane and also the horizontal plane. The degree to which the emission intensity moves from the vertical to horizontal plane is related to the mobility of the fluorescently labeled molecule. If fluorescently labeled molecules are very large, they move very little during the excited state interval, and the emitted light remains highly polarized with respect to the excitation plane. If fluorescently labeled molecules are small, they rotate or tumble faster, and the resulting emitted light is depolarized relative to the excitation plane. Therefore, FP can be used to follow any biochemical reaction which results in a change in molecular size of a fluorescently labeled molecule (e.g. protein-DNA interactions; immunoassays; receptor-ligand interactions; degradation reactions). (Adapted from Bolger R, Checovich W. (1994) Biotechniques 17(3):585-9).

Another method uses the fluorescent activated substrate conversion (FASO) assay described in Canadian Patent No. 2,189,486 (1996) and in St-Pierre et al., (1996) Cytometry 25: 374-380.

The Commercial Process for Preparing Extracts of the Invention

Extracts of the invention can be prepared on a commercial scale by repeating the extraction process that results in an optimal composition of extracts demonstrating an inhibitory activity of interest. As demonstrated in FIG. 3, one would simply scale-up the procedure and include steps of quality control to ensure reproducible results for the resulting extracts.

Methods of Purifting or Fractionating Active Ingredients from Plant Extracts

There are a number of techniques well known in the art for isolating protease inhibitors from natural sources. For example, For example, purifications can be performed using centrifugation, ultracentrifugation, filtration, liquid or gas phase chromatography (including size exclusion, affinity, etc.) with or without high pressure, lyophylisation, evaporation, precipitation with various "carriers" (PVPP, carbon, antibody, etc.), or any combination thereof. One skilled in the art, would appreciate how to use the following options, in a sequential fashion, in order to enrich each successive fraction in the activity of interest by following its activity throughout the purification procedure, using one of the assays for the inhibitory activity against an extracellular protease of interest, as defined above.

The present invention also includes compounds, chemicals, active principles, and purified or concentrated extracts that could be obtained by purification, partial purification, and/or fractionation of plant extracts that are subject of the invention. Purification, partial purification, and/or fractionation can be achieved by any methods known by those skilled in the art. These methods include, but are not limited to: solid-liquid extraction, liquid-liquid extraction, solid-phase extraction (SPE), membrane and ultrafiltration, dialysis, chromatography, selective precipitation, electrophoresis, and solvent concentration.

Solid-liquid extraction means include the use of all possible solvents known from those in the art, and covers the use of supercritical solvents, soxhlet extractors, vortex shaker, ultrasounds and any other means to enhance extraction, as well as recovery by filtration, centrifugation and any related methods as described in the literature (R. J. P. Carmen, Natural Products Isolation, Humana Press, 1998). The solvent is selected from the group consisting of, but not limited to, hydrocarbon, chlorinated solvents, organic esters, organic ethers, alcohols, water, and mixtures thereof. In the case of supercritical fluid extraction, the invention also covers the use of modifiers as described in V. H. Bright, Ee Pe McNally, Supercritical Fluid Technology, ACS Symp. Ser. Vol. 488, ch. 22, 1999.

Liquid-liquid extraction means include the use of any mixture of solvents known from those in the art, including solvents under supercritical conditions. Typical solvents include, but are not limited to, hydrocarbon, chlorinated solvents, organic esters, organic ethers, alcohols, water, and all possible aqueous solutions. The liquid-liquid extraction can be effected manually, semi-automated or completely automated, and the solvent can be removed or concentrated by any usual techniques known from those in the art (S. Ahuja. Handbook of Bioseparations, Academic Press, 2000).

Solid-phase extraction (SPE) means include techniques using cartridges, columns or any other devices used in this technique and known in the art. The sorbents that may be used with this method include but are not limited to silica gel (normal phase), reverse phase silica gel (modified silica gel), ion-exchange resins, and fluorisil. The invention also includes the use of scavenger resins or any others trapping reagents attached to solid supports derived from organic or inorganic macromolecular materials to remove selectively active ingredients or any constituents from said extracts.

Membrane, reverse osmosis and ultrafiltration means include the use of all types of membranes known from those in the art, as well as the use of pressure, vacuum, centrifugal force, and/or any other means that can be utilized in membrane and ultrafiltration processes (S. Ahuja, Handbook of Bioseparations, Academic Press, 2000).

Dialysis means include membranes having molecular weight cut-offs varying from less than 0.5 KDa to larger than 50 KDa. The invention also covers the recovery of purified and/or fractionated extracts from either the dialysate or the retentate by any means known in the art including but not limited to evaporation, reduced pressure evaporation, distillation, vacuum distillation, and lyophilization.

Chromatographic means include all means of carrying out chromatography known by those skilled in the art and described in G. Sofer, L. Hagel, Handbook of Process Chromatography, Academic Press, 1997. Fractionation, partial purification, and/or purification can be carried out by but not limited to regular column chromatography, flash chromatography, high performance liquid chromatography (HPLC), medium pressure liquid chromatography (MPLC), supercritical fluid chromatography (SFC), countercurrent chromatography (CCC), moving bed chromatography, simulated moving bed chromatography, expanded bed chromatography, and planar chromatography. With every chromatographic methods, sorbents that may be used include but is not limited to silica gel, alumina, fluorisil, cellulose and modified celluloses, all possible modified silica gels, all types of ion-exchange resins, all types of size exclusion gels and any other sorbents known from those skilled in the art and described in T. Hanai. HPLC: A Practical Guide. RSC Press, U K 1999. The present invention also includes the use of two or more solvent gradients to effect the fractionation, partial purification, and/or purification of said active extracts in any chromatographic methods. The solvents that may be utilized include but are not limited to hexanes, pentane, petroleum ethers, cyclohexane, heptane, diethyl ether, methanol, ethanol, isopropanol, propanol, butanol, isobutanol, tert-butanol, water, dichloromethane, dichloroethane, ethyl acetate, tetrahydrofurane, dioxane, tert-butyl methyl ether, acetone, and 2-butanone. When water or and aqueous phase is used, it may contains certain amounts of iorganic or organic salts and the pH may be adjusted to different values with an acid or a base to enhance fractionation and/or purification.

In the case of planar chromatography, the present invention includes the use of all variants of this type of chromatography including but not limited to one- and two dimension thin-layer chromatography (1D- and 2D-TLC), high performance thin-layer chromatography (HPTLC), and centrifugal thin-layer chromatography (centrifugal TLC).

In the case of countercurrent chromatography (CCC), the present invention includes the use of manual, semi-automated, and automated systems, and the use of all possible solvents and solvent combinations necessary to effect fractionation and/or purification of said active extracts as described in W. D. Conway, R. J. Petroski, Modem Countercurrent Chromatography, ACS Symp. Ser. Vol. 593, 1995. Solvent removal and/or concentration can be effected by any means known by those skilled in the art, including but not limited to reduced pressure evaporation, evaporation, reduced pressure distillation, distillation, and lyophilization.

The present invention includes the fractionation, partial purification, and purification of said active plant extracts by expanded bed chromatography, moving and simulated moving bed chromatography, and any other related methods known by those skilled in the art and described in G. Sofer, L. Hagel, Handbook of Process Chromatography, Academic Press, 1997 and S. Ahuja, Handbook of Bioseparations, Academic Press, 2000.

Selective precipitation means includes the use of all possible solvents and solvent combinations, the use of temperature changes, the addition of precipitent and/or modifiers, and/or modifying the pH by adding a base or an acid to effect a selective preceipation of active principles or any other constituents.

Further, the present invention covers the fractionation, partial purification, and purification of said active plant extracts by electrophoresis and other related techniques known to those skilled in the art.

The invention also includes the fractionation, partial purification, and/or purification of said active plant extracts by steam distillation, hydrodistillation, or any other related methods of distillation known from those in the art (L. M. Harwood, C. J. Moody, Experimental Organic Chemistry, Blackwell Scientific Publications, U K, 1989).

The process of purifying the active component(s) also includes the concentration of purified or partially purified chemicals, active ingredients, active principles by solvent removal of said plant extracts and/or fractionated plant extracts, and/or purified plant extracts. The techniques of solvent removal are known to those skilled in the art and include but are not limited to rotary evaporation, distillation (normal and reduced pressure), centrifugal vacuum evaporation (speed-vac), and lyophilization.

One embodiment of the invention includes the concentration of chemicals, active ingredients, active principles by solvent removal of said plant extracts and/or fractionated plant extracts, and/or purified plant extracts. The techniques of solvent removal are known to those skilled in the art and include but are not limited to rotary evaporation, distillation (normal and reduced pressure), centrifugal vacuum evaporation (speed-vac), and lyophilization.

To get a better understanding of the invention described herein, the following examples are set forth. It should be understood that these examples are for illustrative purposes only. Therefore, they should not limit the scope of this invention in any way.

EXAMPLES

Example I

Preparation of Stressed and Non-Stressed Plant Extracts

Pre-Harvest Treatment Aerian parts of a living plant are sprayed with an aqueous solution of gamma linolenic acid (6,9,12-Octadecatrienoic acid, Sigma L-2378) (stress G) or arachidonic acid (5,8,11,14-Eicosatetraenoic acid, Sigma A-3925) (stress A) (400. mu.M in water with 0.125% (v/v) Triton X-100) to completely cover the leaves.
Harvest Solid SI and Optional Storage Treatment Twenty to twenty-four hours after the stress, more than 4 grams of leaves, stems, fruit, flowers, seeds or other plant parts are harvested and frozen immediately in dry ice, then transferred as soon as possible to a −20° C. freezer until use. Plant materials may be stored at −20° C. for a long period of time, more than a year, without losing inhibitory activity.
Temperature is Monitored to Ensure a Constant Condition.

Stressed and non-stressed plant specimens are collected as wet samples and stored at −20° C. for various periods of time, and are submitted to a process which generats 3 subfractions: aqueous, ethanolic and organic fractions. Complete extraction process are performed in a continuous cycle using the following steps. An initial 5 g of plant specimen is homogenized in liquid nitrogen with a blender. The resulting powder is weighed.

Extraction Process I: Aqueous Extraction

To each 4.5 grams of plant powder, 12 ml of a cold solution of 100 mM Tris, pH 7.0 is added. The mixture is thoroughly vortexed for 2 minutes. The mixture is kept on ice for 30 minutes and vortexed after each 10 minute period of time. The sample is centrifuged in a Corex™ 30 ml tube for 5 minutes at 4500 rpm. The resulting supernatant is decanted in a 15 ml tube after filtration with a Miracloth™ filter. This extract is therefore referred as the Potential Pre-Extract A. The pellet, referred as Solid S2, is kept for ethanolic extraction.

The aqueous extract (Potential Pre-Extract A) is further purified in order to determine its extracellular protease inhibition capability. The Potential Pre-Extract A is purified by size-exclusion chromatography, wherein the aqueous extract is chromatographed on a calibrated Sephadex G-25 column (1.times.10 cm) using a 20 mM Tris-HCl, 150 mM NaCl, pH 7.5 buffer as eluant. Fractions corresponding to compounds that seem to have molecular weight (MW) less than 1500 daltons (D) are pooled to constitute the purified aqueous extract that is tested for inhibitory activity in an assay as described in Example II.

Prior to this analysis, the extract is treated with 10% gelatin-Sepharose (Pharmacia Biotech, Uppsala, Sw.) in order to remove unspecific enzyme ligands. To 1 mL of extract, 100 .mu.L of gelatin-Sepharose resin is added in a microassay tube, the solution in the tube is mixed, kept on ice for 30 minutes, and then centrifuged 5 minutes at 5,000 rpm. The supernatant is removed and used directly for assays.

Extraction Process II: Alcoholic Extraction

To the pellet, Solid S2, collected from the previous aqueous extraction, 12 ml of cold ethanol:methanol (85:15) is added and the mixture is thoroughly vortexed for 2 minutes. The mixture is kept on ice for 30 minutes and vortexed every 10 minutes. The sample is centrifuged in a Corex™ 30 ml tube for 5 minutes at 4,500 rpm. The resulting supernatant is decanted in a 15 ml tube after filtration with a Miracloth™ filter. The pellet, referred as Solid S3 is kept for the subsequent organic extraction. This extract is therefore referred as the Potential Pre-Extract B.

The ethanolic extract, Potential Pre-Extract B, is purified by liquid/liquid extraction prior to analysis by enzymatic assay. For this purpose, 1 ml of ethanolic extract is evaporated under vacuum, dissolved in 150 .mu.l of dimethylsulfoxide (DMSO), and completed to a final volume of 1.5 ml with Tris buffer (final concentration: Tris-HCl 20 mM; pH 7.5). Four ml of hexane is added to the Tris phase in a glass tube and the tube is thoroughly vortexed, then allowed to form a biphasic liquid. The organic phase is removed and the extract is submitted to a second round of liquid/liquid extraction. The aqueous phase is removed and treated with 10% gelatin-Sepharose (Pharmacia Biotech, Uppsala, Sw.) to remove unspecific enzyme ligands prior to conducting subsequent assays. To 1 ml of extract, 100 .mu.l of gelatin-Sepharose resin is added in a microassay tube, the tube is mixed, kept on ice for 30 minutes, and then centrifuged 5 minutes at 5,000 rpm. Supernatant is removed and used directly for assays as described in Example II.

Extraction Process III: Organic Extraction

To the pellet, Solid S3, collected from previous ethanolic extraction, 12 ml of cold dichloromethane is added and the mixture is thoroughly vortexed for 2 minutes. The mixture is kept on ice for 30 minutes and vortexed after each 10 minutes period. The sample is centrifuged in a Corex™ 30 ml tube for 5 minutes at 4,500 rpm. The resulting supernatant is decanted in a 15 ml glass tube after filtration with a Miracloth™ filter. The final pellet is discarded. The organic solvent is evaporated under vacuum and the phase is dissolved with dimethylsulfoxide (DMSO). This extract is therefore referred as the Potential Pre-Extract C, which was further purified by solid phase extraction prior to analysis by enzymatic assay.

In order to assay the Potential Pre-Extract C, the organic extract is diluted 1:10 in a solution of DMSO:Methanol:Tris (20 mM, pH 7.5) (10:50:40) (Solution A), ie, 220 of extract is added to 2.0 ml of solution A. After 10 seconds of vigorous vortex, the mix is sonicated for 10 seconds. Dissolved extracts are subsequently applied to a solid phase extraction plate (Discovery SPE-96, Sigma Chemical Co, St-Louis, Mo.). After initial conditioning of the columns with 1 ml of methanol, columns are equilibrated with solution A, and extract samples are deposited on the columns. Elution is completed with solution A (final volume of 2 ml) and this fraction is used directly in assays as described in Example II.

Example II

In Vitro Enzyme Inhibition Assays

The inhibitory activity of sample compositions towards human MMP-1, human MMP-2, human MMP-3, human MMP-9, human cathepsin-B, human cathepsin-D, human cathepsin-G, human cathepsin-L, human cathepsin-K, human leukocyte elastase (HLE), bacteria clostripain and bacteria subtilisin can be determined using either fluorogenic substrates or the FASC assay.

Measurement of Human MMP-1, -2, -3 and -9 Activity with Fluorogenic Peptidic Substrates MMP-1, -2, -9 are purified from natural sources (human immortalized cell lines: 8505C (Deutsche Sammlung von Mikroorganismen und Zellkulturen GmbH) for MMP-1, HT-1080 (ATCC, Manassas, Va.) for MMP-2 and THP-1 (ATCC, Manassas, Va.) for MMP-9) as described in literature and based on protocols found in I. M. Clark: <<Matrix metalloproteinases protocols>>, Humana Press (2001). Recombinant human MMP-3 is overexpressed in *E. Coli* and purified according to Windsor L J, Steele D L (2001), Methods Mol Biol 151:191-205. Proteolytic activity of these proteases is evaluated with the assay based on the cleavage of autoquenched peptide substrate: (MCA-Pro-Leu-Gly-Leu-Dpa-Ala-Arg-NH.sub.2. TFA [Dpa=N-3-(2,4-dinitrophenyl)-L-2,3-diaminopropionyl]) for MMP-1, -2, and -9; and, MCA-Arg-Pro-Lys-Pro-Val-Glu-Nva-Trp-Arg-Lys (DNP)-NH.sub.2 (DNP=2,4-dinitrophenyl; Nva=L-norvaline) for MMP-3 (Calbiochem, San Diego, Calif.). In the intact peptide, Dpa or DNP quenches the MCA fluorescence. Cleavage of the peptide causes release of the fluorescent MCA group which is then quantitated on a fluorometer (Gemini XS, Molecular Devices, Sunnyvale, Calif.). The assay is performed in TNCZ assay buffer (20 mM Tris-HCl; NaCl 150 mM; CaCL.sub.2 5 mM; ZnCl.sub.2 0.5 mM; pH 7.5) with human purified proteases (I. M. Clark: <<Matrix metalloproteinases protocols>>, Humana Press (2001). The substrate, primarily dissolved in DMSO is then redissolved in TNCZ buffer for the assay. In a typical assay, 10 .mu.l of purified enzyme (1-50 ng) and 5 .mu.l of dissolved substrate (final concentration of 10 .mu.M) is mixed in a final volume of 75 .mu.l (completed with TNCZ). All assays were performed in 96 well plate and the reaction is started by the addition of substrate. Assays are measured (excitation 325 nm, emission 392 nm) for 20, 40 and 60 minutes.

Measurement of Human Cathepsin L and K Activity with Fluorogenic Peptidic Substrate.

Human recombinant cathepsins L and K are overexpressed in *P. Pastoris* according to Krupa J C, Mort J S. (2000), Anal Biochem 283(1):99-103. The assay is similar to the previous except for the auto-quenched peptidic substrate: Z-Arg-Phe-AMC, 2HCl (Bachem California, Torrance, Calif.) and reaction buffer. Assays for Cathepsin L are performed in 20 mM acetate pH 5.5, 1 mM EDTA buffer and assays for Cathepsin K in 20 mM acetate pH 4.2, 1 mM EDTA. Assays are monitored with fluorometer settled at excitation 380 nm/emission 460 nm wavelengths (Krupa J C, Mort J S. (2000), Anal Biochem 283(1):99-103).

Measurement of Human MMP-9, Cathepsin B, Cathepsin G, and Human Leukocyte Elastase (HLE) Activity Using the FASC Assay Human Cathepsin B and G and human leukocyte elastase are obtained from Calbiochem (San Diego, Calif.). Human MMP-9 is purified as previously described. The assay is based on the method described in Canadian Patent No. 2,189,486 (1996) and in St-Pierre et al., (1996) Cytometry 25:374-380. For the assay, 5 .mu.l of the purified enzyme (1-100 ng), 5 .mu.l of concentrated buffer solution (20 mM Tris-HCl; NaCl 150 mM; CaCL.sub.2 5 mM; ZnCl.sub.2 0.5 mM; pH 7.5), and 5 .mu.l of gelatin-FITC beads are typically used in a final volume of 100 .mu.l. The assay is performed by incubation of the reaction mixture for 90 minutes at 37° C. The reaction is stopped by the transfer of the mix in 0.5 ml of 20 mM Tris, 150 mM NaCl; pH 9.5 buffer. This tube is analyzed in a flow cytometer (Epics MCL, Beckman Coulter, Mississauga, Ontario) as described in Canadian Patent No. 2,189,486 (1996).

Measurement of Human Cathepsin D, Cathepsin B, Cathepsin G and HLE Activity with a Fluorogenic Proteic Substrate Cathepsin D is purified from human MCF-7 cells according to Stewart A J, Piggott N H, May F E, Westley B R. (1994), Int J Cancer 57(5):715-8. Cathepsin B, Cathepsin G and HLE are obtained as previously described. The activities of Cathepsin D, Cathepsin B, Cathepsin G and HLE are measured by an assay based on the increase of fluorescence of a proteic substrate (Haemoglobin in the case of Cathepsin D and B and beta-casein in the case of Cathepsin G and HLE) heavily labelled with Alexa-488 dye (Molecular Probes, Eugene, Or). The substrate, when highly labelled with the dye, will almost quench the dye fluorescence. Cleavage of the substrate will result in an increase of the fluorescence which can be measured with a spectrofluorometer, and which is proportional to protease activity. Typically, 10 .mu.l of purified human Cathepsin D, Cathepsin B, Cathepsin G or HLE (10-50 ng) and 10 .mu.l of Hemoglobin-Alexa488 or beta-casein-Alexa488 (100 ng) are assayed in final volume of 75 .mu.l adjusted with 20 mM citrate pH 3.3 buffer in the case of Cathepsins D and B or TNCZ buffer in the case of Cathepsin G and HLE. The reaction is performed as already described except that the fluorescence is read at excitation 488 nm/emission 525 nm wavelengths.

Subtilisin Assay

Subtilisin (isolated from *B. Subtilisis*) is purchased from Fluka. Assays are performed with a fluorogenic peptide (Z-Gly-Gly-Leu-AMC, Bachem California, Torrance, Calif.) as already described for MMPs with the following modification: the assay is buffered with 20 mM Tris, 150 mM NaCl; pH 7.5 and the results are read at excitation 380 nrn/emission 460 nm wavelengths.

Clostripain Assay

Clostripain from *Clostridium histolyticum* (Worthington Lakewood, N.J.) is prepared and activated as described by manufacturer's protocol. The activity is determined by using Z-Arg-Arg-AMC, 2HCl (Calbiochem, San Diego, Calif.) as a fluorogenic peptidic substrate and the incubation buffer is 75 mM phosphate, pH 7.6. The reaction is performed as already described except that the fluorescence is read at excitation 380 nm/emission 460 nm wavelengths.

Extract Inhibition Assay

Before a typical assay, aqueous extracts prepared extracts prepared as described in Example I are preincubated with 1:10 of gelatin-Sepharose 4B™ for 30 minutes to remove fluorescence quenching. For the ethanolic extract, an initial hexane extraction is performed and samples are treated with 1:10 of gelatin-Sepharose 4B™ to remove quenching.

In a typical fluorescent assay, 10 .mu.l of purified enzyme at concentrations previously mentioned for the enzymatic assay, 5 .mu.l of dissolved fluorogenic peptide or 10 .mu.l of dissolved fluorescent proteic substrate (final concentration of 10 pM) and 40 .mu.L, of the aqueous, ethanolic or organic extract to be tested and prepared as described in Example I are mixed in a final volume of 75 .mu.l (completed with TNCZ for fluorogenic peptide substrate assay or 20 mM citrate pH 3.3 buffer for fluorescent protein substrate assay). All assays are performed in 96 well plate and the reaction is started by the addition of substrate. Assays are measured (excitation 325 nm, emission 392 nm for peptide and excitation 488 nm/emission 525 nm wavelengths for protein) for 20, 40 and 60 minutes. Activity and inhibition values are determined from the increase in fluorescence.

For the FASC assay, 35 .mu.l of the treated extract prepared as described in Example I, 5 .mu.l of the purified enzyme prepared as described previously, 5 .mu.l of concentrated buffer solution (TNCZ), and 5 .mu.l of gelatin-FITC beads are typically used. The initial step of the assay is the incubation of the reaction without beads for a 30 minutes period on ice to allow the binding of inhibitors to enzyme. Fluorescent beads are added and the reaction mix is incubated for 90 minutes at 37° C. The reaction is stopped is stopped by transfer of the mix in 0.5 ml of 20 mM Tris, 150 mM NaCl; pH 9.5 buffer. This tube is analyzed in the flow cytometer (Epics MCL, Beckman Coulter, Mississauga, Ontario) as described in Canadian Patent Application No. 2,189,486 (1996).

Results of the inhibition studies are shown in Tables 1-12. Table 1 reports the inhibition of human MMP-1 by aqueous (A), ethanolic (R) and organic (S) extracts for exemplary stressed (A and G) and non-stressed (T) plant sources. Table 2 reports the inhibition of human MMP-2 by aqueous (A), ethanolic (R) and organic (S) extracts for exemplary stressed (A and G) and non-stressed (T) plant sources. Table 3 reports the inhibition of human MMP-3 by aqueous (A), ethanolic (R) and organic (S) extracts for exemplary stressed (A and G) and non-stressed (T) plant sources. Table 4 reports the inhibition of human MMP-9 by aqueous (A), ethanolic (R) and organic (S) extracts for exemplary stressed (A and G) and non-stressed (T) plant sources. Table 5 reports the inhibition of human Cathepsin B by aqueous (A), ethanolic (R) and organic (S) extracts for exemplary stressed (A and G) and non-stressed (T) plant sources. Table 6 reports the inhibition of human Cathepsin D by aqueous (A), ethanolic (R) and organic (S) extracts for exemplary stressed (A and G) and non-stressed (T) plant sources. Table 7 reports the inhibition of human Cathepsin G by aqueous (A), ethanolic (D) and organic (S) extracts for exemplary stressed (A and G) and non-stressed (T) plant sources. Table 8 reports the inhibition of human Cathepsin L by aqueous (A), ethanolic (R) and organic (S) extracts for exemplary stressed (A and G) and non-stressed (T) plant sources. Table 9 reports the inhibition of human Cathepsin K by aqueous (A), ethanolic (R) and organic (S) extracts for exemplary stressed (A and G) and non-stressed (T) plant sources. Table 10 reports the inhibition of HLE by aqueous (A), ethanolic (R) and organic (S) extracts for exemplary stressed (A and G) and non-stressed (T) plant sources. Table 12 reports the inhibition of bacteria subtilisin by aqueous (A), ethanolic (R) and organic (S) extracts for exemplary stressed (A and G) and non-stressed (T) plant sources. Table 11 reports the inhibition of bacterial clostripain by aqueous (A), ethanolic (R) and organic (S) extracts for exemplary stressed (A and G) and non-stressed (T) plant sources. The inhibition is reported as percentage (%) of inhibition of substrate degradation as compared with the degradation without extract.

Example III

Exemplary Purification of Inhibitory Activity Found in an Extract

Extracts were separated by HPLC on an Agilent 1100 system (San Fernando, Calif.). Briefly, 100 .mu.l of a crude extract prepared as described in Example I was applied on a C18 reverse-phase column (Purospher RP-18 5 .mu.m, 4.0.times.125 mm (HP), Agilent, San Fernando, Calif.). Elution of compounds was achieved with a linear gradient of 10-85% acetonitrile. Fractions were collected, evaporated, resuspended in aqueous buffer and then reanalysed for their inhibition activity on specific enzymes as already described. Fractions of interest (demonstrating a biological activity) where then reisolated at a larger scale for further analysis and characterization.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

| | | MMP-1 Inhibition | | | | |
|---|---|---|---|---|---|---|
| Nom latin | Stress | extrait | Inhibition (%) | Nom latin | Stress | extrait | Inhibition (%) |
| Achillea millefolium | A | O | 22.2 | Filipendula rubra | A | O | 51.7 |
| Acorus calamus | A | O | 100.0 | Foeniculum vulgare | A | O | 86.2 |
| Actinidia arguta | A | O | 56.4 | Fragaria x ananassa | A | O | 23.7 |
| Agastache foeniculum | A | S | 30.4 | Fragaria x ananassa | A | S | 40.6 |
| Alchemilla mollis | A | 4 | 36.4 | Fragaria x ananassa | A | R | 28.3 |
| Allium cepa | A | O | 61.4 | Galinsoga ciliata | A | R | 29.7 |
| Allium grande | A | R | 46.5 | Gallium odoratum | A | 6 | 48.8 |
| Allium porrum | A | R | 25.0 | Gaultheria hispidula | A | R | 23.9 |
| Allium porrum | A | O | 98.9 | Glycine max | A | R | 24.7 |
| Allium sativum | A | O | 42.5 | Glycine max | A | S | 29.6 |
| Allium sativum | A | R | 98.7 | Glycine max | A | O | 100.0 |
| Allium schoenoprasum | A | R | 22.3 | Guizotia abyssinica | A | S | 39.4 |
| Allium Tuberosum | A | R | 29.9 | Hamamelis virginiana | A | R | 49.1 |
| Allium Tuberosum | A | O | 100.0 | Helianthus Tuberosus | A | O | 95.9 |
| Althaea officinalis | A | S | 21.6 | Heliotropium arborescens | A | R | 25.0 |
| Angelica archangelica | A | S | 45.9 | Hordeum hexastichon | A | O | 100.0 |
| Anthemis nobilis | A | R | 34.5 | Hordeum vulgare | A | O | 46.2 |
| Aralia nudicaulis | A | O | 100.0 | Vulgare | A | O | 43.8 |
| Armoracia rusticana | A | O | 31.2 | Inula helenium | A | O | 25.8 |
| Armoracia rusticana | A | S | 39.7 | Lathyrus sativus | A | O | 27.1 |
| Aronia melanocarpa | A | R | 39.8 | Leonurus cardiaca | A | O | 34.4 |
| Aster sp | A | O | 67.6 | Levisticum officinale | A | R | 31.7 |
| Beckmannia eruciformis | A | O | 24.1 | Lolium multiflorum | A | O | 39.0 |
| Beta vulgaris | A | R | 41.2 | Lotus corniculatus | A | O | 100.0 |
| Beta vulgaris spp. Maritima | A | O | 44.1 | Malva sylvestris | A | R | 22.8 |
| Brassica napus | A | O | 26.3 | Matricaria recutita | A | O | 25.1 |
| Brassica oleracea | A | S | 28.6 | Matteucia pensylvanica | A | R | 48.1 |
| Brassica oleracea | A | R | 33.8 | Medicago sativa | A | R | 25.1 |

TABLE 1-continued

MMP-1 Inhibition

| Nom latin | Stress | extrait | Inhibition (%) | Nom latin | Stress | extrait | Inhibition (%) |
|---|---|---|---|---|---|---|---|
| Brassica Oleracea | A | O | 100.0 | Melissa officinalis | A | O | 100.0 |
| Brassica rapa | A | R | 61.4 | Mentha piperita | A | O | 60.1 |
| Calamintha nepeta | A | R | 40.2 | Mentha suaveolens | A | O | 35.1 |
| Camellia sinensis | A | O | 39.3 | Nepeta cataria | A | O | 100.0 |
| Capsicum annuum | A | R | 34.3 | Nicotiana rustica | A | R | 20.7 |
| Capsicum annuum | A | O | 88.3 | Origanum vulgare | A | R | 60.5 |
| Capsicum frutescens | A | R | 39.4 | Origanum vulgare | A | O | 73.2 |
| Chenopodium bonus-henricus | A | O | 100.0 | Perilla frutescens | A | R | 74.4 |
| Chenopodium bonus-henricus | A | R | 37.3 | Perilla frutescens | A | O | 92.4 |
| Chenopodium quinoa | A | O | 66.3 | Petroselinum crispum | A | R | 77.4 |
| Chrysanthenum coronarium | A | R | 37.4 | Phacelia tanacetifolia | A | R | 52.8 |
| Cichorium intybus | A | R | 22.0 | Phaseolus coccineus | A | R | 20.9 |
| Cichorium intybus | A | S | 66.9 | Phaseolus coccineus | A | S | 34.2 |
| Citrullus lanatus | A | O | 41.9 | Phaseolus Vulgaris | A | S | 29.2 |
| Comus canadensis | A | S | 73.0 | Phaseolus vulgaris | A | R | 56.1 |
| Crataegus sp | A | O | 100.0 | Phaseolus Vulgaris | A | R | 60.0 |
| Cucumis Anguria | A | S | 34.2 | Phaseolus Vulgaris | A | O | 100.0 |
| Cucurbita moschata | A | O | 27.3 | Phlox paniculata | A | O | 100.0 |
| Cucurbita pepo | A | O | 84.9 | Pimpinella anisum | A | S | 100.0 |
| Cymbopogn citratus | A | O | 100.0 | Pimpinella anisum | A | R | 72.2 |
| Cymbopogon citratus | A | R | 22.1 | Plantago coronopus | A | R | 23.7 |
| Cyperus esculentus | A | R | 25.8 | Plectranthus sp. | A | O | 25.0 |
| Cyperus esculentus | A | O | 28.1 | Poa compressa | A | O | 31.5 |
| Dactylis glomerata | A | O | 25.5 | Potentilla anserina | A | R | 71.2 |
| Daucus carota | A | O | 43.4 | Pysalis ixocarpa | A | R | 32.1 |
| Daucus carota | A | R | 100.0 | Raphanus raphanistrum | A | O | 31.5 |
| Dipsacus sativus | A | O | 35.3 | Raphanus sativus | A | O | 100.0 |
| Dirca palustris | A | S | 47.9 | Raphanus sativus | A | O | 30.2 |
| Eruca vesicaria | A | R | 33.7 | Rheum officinale | A | O | 79.1 |
| Eschscholzia californica | A | O | 61.1 | Rheum rhabarbarum | A | R | 22.9 |
| Eschscholzia californica | A | R | 74.1 | Rheum rhabarbarum | A | R | 32.8 |
|  |  |  |  | Ribes nigrum | A | O | 100.0 |
|  |  |  |  | Ribes nigrum | A | R | 100.0 |
|  |  |  |  | Ribes salivum | A | R | 48.6 |
|  |  |  |  | Ribes sylvestre | A | S | 26.5 |
|  |  |  |  | Ribes uva-crispa | A | R | 100.0 |
|  |  |  |  | Rubus canadensis | A | R | 46.1 |
|  |  |  |  | Rubus canadensis | A | R | 53.1 |
|  |  |  |  | Rubus idaeus | A | R | 100.0 |
|  |  |  |  | Salvia officianalis | A | O | 100.0 |
|  |  |  |  | Salvia sclarea | A | S | 43.8 |
|  |  |  |  | Satureja montana | A | R | 100.0 |
|  |  |  |  | Solanum dulcamara | A | S | 43.8 |
|  |  |  |  | Solanum melanocerasum | A | R | 37.2 |

TABLE 1-continued

| Nom latin | Stress | extrait | Inhibition (%) | Nom latin | Stress | extrait | Inhibition (%) |
|---|---|---|---|---|---|---|---|
| Solatium tuberosum | A | R | 100.0 | | | | |
| | | | | Cucurbita Pepo | G | O | 40.2 |
| | | | | Cuminum cyminum | G | R | 25.5 |
| Sorghum dochna | A | O | 100.0 | | | | |
| Stachys byzantina | A | S | 28.9 | Cymbopogon citratus | G | R | 33.7 |
| Stellaria media | A | S | 33.1 | Datura stramonium | G | O | 73.5 |
| Tanacetum parthenium | A | O | 28.9 | Daucus carota | G | O | 86.0 |
| Tanacetum vulgare | A | R | 76.0 | Daucus carota | G | O | 27.9 |
| Taraxacum officinale | A | O | 65.7 | Diyopteris filix-mas | G | O | 21.9 |
| Thymus praecox subsp arcticus | A | O | 64.2 | Erysimum perofskianum | G | O | 24.4 |
| Thymus praecox subsp arcticus | A | R | 88.2 | Fagopyrum esculentum | G | O | 100.0 |
| Thymus vulgaris | A | R | 42.7 | Foeniculum vulgare | G | O | 28.0 |
| Thymus x citriodorus | A | O | 34.7 | Foeniculum vulgare | G | R | 57.3 |
| Trichosanthes kirilowii | A | R | 31.8 | Gaultheria hispidula | G | O | 44.2 |
| Trifolium hybridum | A | R | 96.0 | Gaultheria procumbens | G | R | 94.8 |
| Trifolium incarnatum | A | R | 100.0 | Glechoma hederacea | G | O | 25.5 |
| Trifolium pannonicum | A | R | 27.7 | Glycine max | G | S | 100.0 |
| Trifolium repens | A | R | 79.5 | Glycyrrhiza glabra | G | O | 24.9 |
| Vaccinum augustifolium | A | R | 52.5 | Guizotia abyssinica | G | R | 30.3 |
| Vaccinum macrocarpon | A | O | 64.5 | Helenium hoopesii | G | O | 28.6 |
| Vicia sativa | A | O | 60.8 | Helianthus annuus | G | O | 33.6 |
| | | | | Helianthus tuberosus | G | O | 54.4 |
| Vicia sativa | A | R | 28.6 | | | | |
| | | | | Hordeum vulgare | G | O | 28.8 |
| Vicia villosa | A | R | 64.7 | | | | |
| Vicia villosa | A | O | 57.3 | Vulgare | G | R | 28.1 |
| Vigna sesquipedalis | A | O | 33.0 | Hypericum henryl | G | R | 80.0 |
| Vigna sesquipedalis | A | R | 24.4 | Iberis amara | G | O | 44.6 |
| Vigna unguiculata | A | R | 20.6 | Lactuca sativa | G | R | 25.3 |
| Vitia spp | A | R | 72.6 | Lathyrus sylvestris | G | O | 90.2 |
| Vitia spp | A | O | 100.0 | Lavandula angustifolia | G | R | 22.5 |
| Zea Mays | A | R | 99.2 | Lepidium Sativum | G | S | 29.5 |
| Zea Mays | A | O | 100.0 | Levisticum officinale | G | O | 100.0 |
| Abelmochus esculentus | G | R | 37.6 | Lolium multiflorum | G | O | 24.9 |
| Aconitum napellus | G | O | 100.0 | Lolium multiflorum | G | R | 27.1 |
| Allium ampeloprasum | G | R | 33.4 | Lotus corniculatus | G | O | 52.2 |
| Allium ascalonicum | G | R | 31.5 | Lycopersicon esculentum | G | R | 24.4 |
| Allium cepa | G | O | 34.4 | Lycopersicon pimpinellifolium | G | R | 30.3 |
| Allium cepa | G | R | 36.4 | Malus hupehensis | G | R | 65.8 |
| Allium sativum | G | R | 53.2 | Malva verticillata | G | R | 43.1 |
| | | | | Matricaria recutita | G | S | 100.0 |
| Allium tuberosum | G | R | 68.3 | | | | |
| Althaea officianalis | G | O | 47.7 | Matteucia pensylvanica | G | R | 57.5 |
| Althaea officinalis | G | S | 30.7 | Melissa officinalis | G | O | 28.5 |

TABLE 1-continued

| MMP-1 Inhibition | | | | | | | |
|---|---|---|---|---|---|---|---|
| Nom latin | Stress | extrait | Inhibition (%) | Nom latin | Stress | extrait | Inhibition (%) |
| Althaea officinalis | G | S | 44.3 | Mentha piperita | G | O | 36.0 |
| Althea officinalis | G | R | 83.6 | Mentha spicata | G | S | 20.3 |
| Anethum graveolens | G | S | 44.3 | Mentha spicata | G | S | 26.0 |
| Apium graveolens | G | R | 27.7 | Mentha suaveolens | G | O | 60.5 |
| Armoracia rusticana | G | O | 51.8 | Nepeta cataria | G | O | 24.1 |
| Armoracia rusticana | G | S | 47.1 | Nicotiana rustica | G | R | 28.1 |
| Aronia melanocarpa | G | S | 66.5 | Nicotiana tabacum | G | R | 40.6 |
| Artemisia dracunculus | G | S | 79.0 | Oenothera biennis | G | R | 28.4 |
| Artemisia dracunculus | G | R | 50.3 | Oenothera biennis | G | O | 100.0 |
| Asparagus officinalis | G | O | 96.4 | Origanum vulgare | G | S | 100.0 |
| Beilis perennis | G | R | 44.1 | Origanum vulgare | G | O | 20.1 |
| Beta vulgaris spp. Maritima | G | R | 43.7 | Origanum vulgare | G | O | 85.4 |
| Beta vulgaris spp. Maritima | G | O | 34.9 | Oryza Sativa | G | R | 53.3 |
| Betula glandulosa | G | S | 40.8 | Panax quinquefolius | G | S | 100.0 |
| Borago officinalis | G | O | 30.3 | Panicum miliaceum | G | S | 100.0 |
| Borago officinalis | G | R | 29.7 | Passiflora caerula | G | O | 20.9 |
| Brassica cepticepa | G | R | 21.9 | Pastinaca sativa | G | R | 68.4 |
| Brassica oleracea | G | O | 33.6 | Pastinaca sativa | G | O | 100.0 |
| Brassica oleracea | G | O | 100.0 | Pennisetum alopecuroides | G | R | 100.0 |
| Brassica rapa | G | O | 42.5 | Petroselinum crispum | G | R | 73.0 |
| Brassica rapa | G | R | 40.2 | Phalaris canariensis | G | O | 100.0 |
| Calamintha nepeta | G | O | 28.7 | Phaseolus coccineus | G | R | 29.9 |
| Calendula officinalis L. | G | O | 100.0 | Phaseolus coccineus | G | R | 67.6 |
| Camellia sinensis | G | O | 46.4 | Phaseolus coccineus | G | O | 32.4 |
| Campanula rapunculus | G | R | 27.2 | Phaseolus vulgaris | G | R | 33.4 |
| Capsella bursa-pastoris | G | R | 24.1 | Phaseolus vulgaris | G | R | 60.2 |
| Capsicum annum | G | O | 36.0 | Phaseolus vulgaris | G | R | 22.3 |
| Chaerophyllum bulbosum | G | R | 38.9 | Phaseolus vulgaris | G | O | 87.7 |
| Chenopodium quinoa | G | O | 100.0 | Phlox paniculata | G | O | 89.3 |
| Cichorium intybus | G | S | 44.6 | Physalis pruinosa | G | O | 37.0 |
| Circium arvense | G | R | 30.3 | Plantago coronopus | G | R | 48.1 |
| Citrullus lanatus | G | R | 21.2 | Plantago major | G | O | 47.0 |
| Cucurbita pepo | G | O | 59.5 | Plectranthus sp. | G | O | 97.2 |
| Potentilla anserina | G | R | 22.0 | Ananas comosus | T | O | 100.0 |
| Prunella vulgaris | G | O | 21.2 | Anthemis nobilis | T | O | 22.7 |
| Raphanus Raphanistrum | G | O | 95.9 | Anthriscus cerefolium | T | O | 56.8 |
| Raphanus sativus | G | O | 67.7 | Apium graveolens | T | R | 29.8 |
| Reseda odorata | G | O | 40.6 | Aralia nudicaulis | T | O | 100.0 |
| | | | | Armoracia rusticana | T | O | 58.9 |
| Rheum officinale | G | O | 82.1 | | | | |
| Rheum rhabarbarum | G | R | 48.1 | Artemisia dracunculus | T | O | 100.0 |
| | | | | Asparagus officinalis | T | R | 25.2 |
| Ribes Nigrum | G | R | 100.0 | | | | |

TABLE 1-continued

| MMP-1 Inhibition | | | | | | | |
|---|---|---|---|---|---|---|---|
| Nom latin | Stress | extrait | Inhibition (%) | Nom latin | Stress | extrait | Inhibition (%) |
| Ribes Sylvestre | G | O | 42.9 | Atriplex hortensis | T | R | 44.7 |
| Ricinus communis | G | O | 73.5 | Beilis perennis | T | R | 58.1 |
| Rubus Phoenicalasius | G | R | 31.4 | Beta vulgaris | T | R | 37.3 |
| Ruta graveolens | G | R | 100.0 | Betula glandulosa | T | O | 23.5 |
| Salvia officinalis | G | R | 100.0 | Boletus edulis | T | S | 64.2 |
| Santolina | G | R | 28.1 | Brassica juncea | T | R | 35.6 |
| Satureja hortensis | G | R | 100.0 | Brassica napus | T | O | 100.0 |
| Satureja repandra | G | O | 57.1 | Brassica oleracea | T | R | 33.2 |
| Scrophularia nodosa | G | R | 41.6 | Brassica oleracea | T | O | 49.7 |
| Scutelaria lateriflora | G | S | 72.1 | Camellia sinensis | T | O | 24.7 |
| Slum sisarum | G | O | 99.7 | Camellia sinensis | T | R | 45.7 |
| Solanum dulcamara | G | R | 65.4 | Canna edulis | T | R | 26.2 |
| Solanum melanocerasum | G | R | 32.4 | Carum carvi | T | O | 100.0 |
| Solanum melorgena | G | O | 100.0 | Chaerophyllum bulbosum | T | R | 40.9 |
| Solanum tuberosum | G | S | 46.4 | Chrysanthemun coronarium (Chp suey) | T | R | 48.1 |
| Sorghum caffrorum | G | R | 100.0 | Chrysanthenum coronarium | T | R | 29.9 |
| Sorghum dochna | G | R | 51.4 | Chrysanthenum coronarium | T | R | 100.0 |
| Sorghum dochna | G | R | 39.6 | Cichorium endivia | T | R | 20.5 |
| Sorghum sudanense | G | O | 97.4 | Cichorium endivia | T | R | 21.9 |
| | | | | Cichorium intybus | T | S | 50.6 |
| Stachys byzantina | G | O | 41.4 | | | | |
| Stellaria media | G | O | 33.8 | Cichorium intybus | T | R | 31.7 |
| Symphytum officinale | G | O | 52.0 | Cichorium intybus | T | R | 52.9 |
| Tanacetum parthenium | G | O | 79.1 | Citrullus lanatus | T | O | 100.0 |
| Tanacetum vulgare | G | O | 100.0 | Citrus paradisi | T | O | 40.6 |
| Taraxacum officinale | G | S | 25.9 | Cocos nucifera | T | O | 27.2 |
| Teucrium chamaedrys | G | O | 100.0 | Comus canadensis | T | S | 44.9 |
| Teucrium chamaedrys | G | R | 48.0 | Crithmum maritimum | T | R | 32.3 |
| arcticus | G | R | 73.1 | Cucumis anguria | T | O | 22.6 |
| Thymus x citriodorus | G | O | 52.2 | Cucurbita moschata | T | O | 33.5 |
| | | | | Cucurbita moschata (Early Butternut) | T | R | 32.3 |
| Trichosanthes kirilowil | G | O | 35.9 | | | | |
| Trifolium hybridum | G | R | 76.0 | Cucurbita pepo | T | O | 89.0 |
| Trifolium incarnatum | G | R | 73.4 | Cuminum cyminum | T | R | 54.3 |
| Trifolium pannonicum | G | R | 24.8 | Curcuma zedoaria | T | S | 100.0 |
| Trifolium repens | G | R | 48.5 | Cymbopogon citratus | T | O | 42.6 |
| Triticosecale spp. | G | R | 48.5 | Datura metel | T | O | 24.8 |
| Triticum spelta | G | R | 22.9 | Datura metel | T | R | 25.5 |
| Tropaeolum majus | G | S | 23.4 | Dioscorea batatas | T | R | 100.0 |
| Urtica dioica | G | O | 96.4 | Dipsacus sativus | T | O | 85.0 |
| Vaccinium corymbosum | G | S | 60.7 | Diyopteris filix-mas | T | O | 46.4 |
| Vaccinium corymbosum | G | R | 61.4 | Erigeron canadensis | T | O | 100.0 |

TABLE 1-continued

| MMP-1 Inhibition | | | | | | | |
|---|---|---|---|---|---|---|---|
| Nom latin | Stress | extrait | Inhibition (%) | Nom latin | Stress | extrait | Inhibition (%) |
| Vaccinum angustifolium | G | R | 54.7 | Eruca vesicaria | T | R | 30.9 |
| Vicia sativa | G | R | 68.8 | Erysimum perofskianum | T | O | 23.0 |
| Vicia sativa | G | O | 31.5 | Eschscholzia califomica | T | O | 37.8 |
| | | | | Eschscholzia califomica | T | R | 20.8 |
| Vicia villosa | G | O | 100.0 | Fagopyrum esculentum | T | O | 100.0 |
| Vicia villosa | G | R | 35.5 | | | | |
| Vigna sesquipedalis | G | R | 23.0 | Fagopyrum tartaricum | T | R | 78.5 |
| | | | | Foeniculum vulgare | T | O | 63.4 |
| Vitia spp | G | R | 36.9 | | | | |
| Withanla somnifera | G | O | 44.0 | Foeniculum vulgare | T | O | 27.2 |
| Xanthium strumarium | G | R | 37.6 | Forsythia x intermedia | T | S | 32.0 |
| Zea mays | G | O | 100.0 | Fragaria x ananassa | T | S | 33.0 |
| Aconitum napellus | T | R | 100.0 | Galinsoga ciliata | T | R | 25.8 |
| Agaricus bisporus | T | R | 58.9 | Gaultheria procumbens | T | O | 46.8 |
| Agaricus bisporus | T | O | 100.0 | Hedeoma pulegioides | T | O | 73.6 |
| Allium ampeloprasum | T | R | 43.3 | Helianthus tuberosus | T | O | 39.3 |
| Allium ascalonicum | T | R | 34.5 | Hordeum vulgare | T | O | 32.4 |
| Allium cepa | T | R | 53.5 | Humulus lupulus | T | O | 21.1 |
| Allium cepa | T | O | 45.8 | Hypericum henryi | T | R | 29.3 |
| Allium grande | T | R | 43.2 | Hypericum perforatum | T | R | 42.7 |
| Allium schoenoprasum | T | R | 47.1 | Iberis amara | T | O | 29.5 |
| Allium tuberosum | T | R | 74.6 | Ipomea aquatica | T | R | 22.9 |
| Allium tuberosum | T | O | 33.6 | Lathyrus Sativus | T | R | 69.4 |
| Aloe vera | T | R | 34.1 | Taurus nobilis | T | O | 70.2 |
| | | | | Lavandula latifolia | T | O | 100.0 |
| Althaea officinalis | T | S | 47.8 | | | | |
| Amelanchier alnitolia | T | R | 59.1 | Culinaris | T | O | 70.2 |
| Lepidium sativum | T | O | 100.0 | Ribes nigrum | T | R | 30.0 |
| Levisticum officinale | T | O | 100.0 | Ribes Sativum | T | R | 61.7 |
| Lolium multiflorum | T | O | 35.1 | Ribes Sylvestre | T | R | 75.4 |
| Lunaria annua | T | O | 100.0 | Ricinus communis | T | S | 100.0 |
| | | | | Rosmarinus officinalis | T | R | 29.0 |
| pimpinellifolium | T | R | 24.4 | | | | |
| Malus hupehensis | T | R | 73.1 | Rubus canadensis | T | R | 86.1 |
| Malus sp. | T | R | 80.9 | Sabal serrulata | T | R | 100.0 |
| Malva sylvestris | T | R | 34.7 | Salvia officinalis | T | O | 100.0 |
| Malva sylvestris | T | O | 100.0 | Sambuous canadensis | T | O | 24.8 |
| | | | | Satureja montana | T | R | 100.0 |
| Manihot esculenta | T | R | 33.0 | | | | |
| Melissa officinalis | T | O | 100.0 | Satureja repandra | T | S | 27.2 |
| Melissa officinalis | T | O | 100.0 | Satureja repandra | T | O | 36.4 |
| Mentha suaveolens | T | S | 39.7 | Satureja repandra | T | R | 42.0 |
| Nigella sativa | T | R | 58.9 | Scrophularia nodosa | T | R | 68.8 |
| Nigella sativa | T | R | 100.0 | Secale cereale | T | O | 100.0 |
| Ocimum Basilicum | T | R | 100.0 | Setaria italica | T | R | 23.2 |
| Origanum majorana | T | O | 41.5 | Silybum marianum | T | O | 73.5 |

TABLE 1-continued

| MMP-1 Inhibition | | | | | | | |
|---|---|---|---|---|---|---|---|
| Nom latin | Stress | extrait | Inhibition (%) | Nom latin | Stress | extrait | Inhibition (%) |
| *Origanum vulgare* | T | O | 29.8 | *Solanum melongena* | T | R | 20.1 |
| *Origanum vulgare* | T | R | 33.1 | *Solanum tuberosum* | T | S | 24.4 |
| *Panax quinquefolius* | T | R | 75.2 | *Solidago virgaurea* | T | R | 71.4 |
| *Passiflora* spp. | T | S | 32.0 | *Sorghum dochna* | T | O | 22.5 |
| *Pastinaca sativa* | T | R | 20.8 | *Stachys byzantina* | T | O | 39.2 |
| *Perroselinum crispum* | T | R | 55.4 | *Stellaria media* | T | O | 43.3 |
| *Petroselinum crispum* | T | R | 76.1 | *Symphytum officinale* | T | O | 58.7 |
| *Petroselinum crispum* | T | O | 24.1 | *Tanacetum parthenium* | T | O | 100.0 |
| *Peucedanum oreaselinum* | T | O | 21.0 | *Tanacetum vulgare* | T | O | 32.5 |
| *Phacelia tanacetifolia* | T | R | 48.6 | *Taraxacum officinale* | T | S | 27.8 |
| *Phalaris canariensis* | T | O | 56.4 | *Teucrium chamaedrys* | T | R | 62.9 |
| *Phaseolus coccineus* | T | R | 22.7 | *Teucrium chamaedrys* | T | O | 100.0 |
| *Phaseolus mungo* | T | R | 47.4 | *Thalpsi arvense* | T | O | 21.2 |
| *Phaseolus vulgaris* | T | R | 40.0 | *Thymus praecox* subsp *arcticus* | T | R | 60.9 |
| *Phaseolus vulgaris* | T | O | 29.4 | *Tragopogon porrifolium* | T | R | 24.6 |
| *Phoenix dactylifera* | T | R | 46.3 | *Trifolium incarnatum* | T | R | 33.7 |
| pourpre | T | R | 28.9 | *Trifolium pannonicum* | T | R | 72.4 |
| *Phytolacca americana* | T | O | 100.0 | *Trifolium repens* | T | R | 72.4 |
| | | | | *Triticosecale* spp. | T | R | 33.7 |
| *Plectranthus* sp. | T | O | 73.8 | *Tropaeolum majus* | T | R | 100.0 |
| *Pleurotus* spp. | T | O | 100.0 | | | | |
| *Poa compressa* | T | O | 22.3 | *Tropaeolum majus* | T | O | 31.5 |
| | | | | *Vaccinium angustifolium* | T | O | 100.0 |
| *Poa pratensis* | T | O | 73.1 | | | | |
| | | | | *Vaccinium angustifolium* | T | S | 42.1 |
| *Populus Tremula* | T | O | 100.0 | | | | |
| *Prunella vulgaris* | T | O | 38.0 | *Vaccinium macrocarpon* | T | S | 30.9 |
| *Psoralea corylifolia* | T | S | 96.4 | | | | |
| *Psoralea corylifolia* | T | R | 100.0 | *Vicia villosa sesquipedalis* | T | R | 35.5 |
| *Raphanus raphanistrum* | T | O | 100.0 | | | | |
| *Raphanus sativus* | T | R | 33.7 | *Vigna unguiculata* | T | R | 31.6 |
| *Raphanus sativus* | T | R | 28.0 | *Vinca minor* | T | O | 28.7 |
| *Raphanus sativus* | T | O | 100.0 | *Withania somnifera* | T | O | 26.9 |
| *Reseda luteola* | T | S | 69.6 | *Xanthium strumarium* | T | O | 30.9 |
| *Reseda odorata* | T | O | 51.8 | *Zea mays* | T | R | 20.1 |
| *Rheum officinale* | T | O | 46.7 | *Zea mays* | T | O | 32.2 |
| *Rheum officinale* | T | S | 100.0 | | | | |

TABLE 2

| MMP-2 | | | | | | | |
|---|---|---|---|---|---|---|---|
| Nom latin | Stress | extrait | Inhibition (%) | Nom latin | Stress | extrait | Inhibition (%) |
| *Achillea millefolium* | A | S | 21.9 | *Capsicum annuum* | A | R | 100.0 |
| *Achillea millefolium* | A | O | 63.0 | *Capsicum frutescens* | A | S | 66.6 |
| *Achillea millefolium* | A | R | 100.0 | *Capsicum frutescens* | A | R | 100.0 |
| *Aconitum napellus* | A | R | 71.0 | *Carthamus tinctorius* | A | R | 21.3 |

TABLE 2-continued

| MMP-2 | | | | | | | |
|---|---|---|---|---|---|---|---|
| Nom latin | Stress | extrait | Inhibition (%) | Nom latin | Stress | extrait | Inhibition (%) |
| *Alcea rosea* | A | R | 67.9 | *Carthamus tinctorius* | A | R | 21.5 |
| *Alchemilla mollis* | A | O | 64.4 | *Chaerophyllum bulbosom* | A | R | 57.2 |
| *Allium ascalonicum* | A | R | 20.9 | *Chelidonium majus* | A | S | 34.4 |
| *Allium cepa* | A | R | 84.3 | *Chenopodium bonus-henricus* | A | R | 43.5 |
| *Allium grande* | A | R | 36.7 | *Chenopodium bonus-henricus* | A | O | 100.0 |
| *Allium porrum* | A | O | 100.0 | *Chenopodium bonus-henricus* | A | R | 76.4 |
| *Allium porum* | A | S | 51.9 | *Chenopodium quinoa* | A | O | 92.0 |
| *Allium porum* | A | R | 66.7 | *Chrysanthemum coronarium* | A | S | 48.6 |
| *Allium sativum* | A | R | 100.0 | *Chrysanthemum coronarium* | A | O | 49.7 |
| *Allium schoenoprasum* | A | R | 73.5 | *Chrysanthemun coronarium* | A | R | 47.3 |
| *Allium Tuberosum* | A | S | 24.3 | *Chrysanthenum coronarium* | A | R | 26.7 |
| *Allium Tuberosum* | A | O | 83.6 | *Cicer arietinum* | A | S | 22.0 |
| *Allium Tuberosum* | A | R | 89.3 | *Cicer arietinum* | A | O | 23.6 |
| *Aloe vera* | A | R | 69.7 | *Cichorium intybus* | A | S | 21.1 |
| *Althaea officinalis* | A | S | 27.6 | *Cichorium intybus* | A | R | 100.0 |
| *Althaea officinalis* | A | R | 64.7 | *Citrullus lanatus* | A | S | 65.5 |
| *Amaranthus gangeticus* | A | S | 29.4 | *Citrullus lanatus* | A | R | 96.3 |
| *Anethum graveolens* | A | O | 100.0 | *Citrullus lanatus* | A | O | 100.0 |
| *Apium graveolens* | A | S | 25.1 | *Coix Lacryma-Jobi* | A | O | 32.2 |
| *Apium graveolens* | A | R | 52.1 | *Cornus canadensis* | A | S | 52.8 |
| *Aralia cordata* | A | S | 66.4 | *Cosmos sulphureus* | A | R | 72.5 |
| *Aralia cordata* | A | R | 92.2 | *Crataegus* spp | A | O | 100.0 |
| *Aralia nudicaulis* | A | O | 29.4 | *Cryptotaenia canadensis* | A | R | 50.6 |
| *Arctium minus* | A | S | 28.4 | *Cryptotaenia canadensis* | A | O | 51.3 |
| *Armoracia rusticana* | A | S | 20.2 | *Cucumis anguria* | A | S | 53.4 |
| *Armoracia rusticana* | A | O | 55.0 | *Cucumis Anguria* | A | R | 84.9 |
| *Arrhenatherum elatius* | A | S | 40.2 | *Cucumis melo* | A | R | 91.7 |
| *Artemisia dracunculus* | A | S | 39.7 | *Cucurbita Maxima* | A | S | 34.9 |
| *Asparagus officinalis* | A | S | 29.3 | *Cucurbita Maxima* | A | R | 41.7 |
| *Atnpiex hortensis* | A | R | 33.6 | *Cucurbita moschata* | A | R | 36.8 |
| *Avena sativa* | A | R | 37.2 | *Cucurbita moschata* | A | S | 37.4 |
| *Beta vulgaris* | A | S | 45.4 | *Cucurbita pepo* | A | S | 48.1 |
| *Beta vulgaris* | A | R | 95.9 | *Cucurbita pepo* | A | R | 85.7 |
| *Beta vulgaris* spp. *Maritima* | A | R | 100.0 | *Curcuma zedoaria* | A | S | 21.0 |
| *Brassica chinensis* | A | R | 49.6 | *Curcuma zedoaria* | A | R | 32.1 |
| *Brassica napus* | A | O | 28.5 | *Curcurbita maxima* | A | S | 27.0 |
| *Brassica Napus* | A | S | 52.4 | *Cymbopogon citratus* | A | R | 34.5 |
| *Brassica Napus* | A | R | 82.4 | *Cymbopogon citratus* | A | O | 100.0 |
| *Brassica nigra* | A | O | 29.2 | *Cymbopogon martinii* | A | S | 47.4 |
| *Brassica oleracea* | A | R | 31.2 | *Dactylis glomerata* | A | S | 20.6 |
| *Brassica Oleracea* | A | R | 31.4 | *Dactylis glomerata* | A | O | 75.0 |
| *Brassica oleracea* | A | R | 64.0 | *Daucus carota* | A | S | 44.5 |
| *Brassica oleracea* | A | S | 68.7 | *Daucus carota* | A | R | 70.5 |
| *Brassica oleracea* | A | R | 75.3 | *Dipsacus sativus* | A | O | 40.4 |
| *Brassica oleracea* | A | O | 100.0 | *Dirca palustris* | A | S | 27.2 |
| *Brassica rapa* | A | S | 27.6 | *Dolichos Lablab* | A | S | 54.2 |
| *Brassica rapa* | A | R | 33.4 | *Dryopteris filix-mas* | A | R | 76.3 |
| *Brassica rapa* | A | O | 57.6 | *Echinacea purpurea* | A | R | 42.9 |
| *Brassica rapa* | A | R | 58.1 | *Eleusine coracana* | A | S | 37.5 |
| *Brassica rapa* | A | R | 84.5 | *Eleusine coracana* | A | O | 100.0 |
| *Calamintba nepeta* | A | O | 65.0 | *Erigeron canadensis* | A | O | 45.7 |
| *Camellia sinensis* | A | S | 21.9 | *Eruca vesicaria* | A | R | 80.2 |
| *Camellia sinensis* | A | R | 26.5 | *Eschscholzia californica* | A | S | 42.4 |
| *Camellia sinensis* | A | O | 79.0 | *Eschscholzia californica* | A | O | 75.0 |
| *Cana edulis* | A | R | 45.5 | *Eschscholzia californica* | A | R | 88.8 |
| *Canna edulis* | A | S | 20.2 | *Fagopyrum esculentum* | A | O | 100.0 |
| *Capsella bursa-pastoris* | A | S | 35.5 | *Fagopyrum tartaricum* | A | R | 38.6 |
| *capsicum annuum* | A | S | 61.5 | *Fagopyrum tartaricum* | A | S | 40.3 |
| *Capsicum annuum* | A | O | 89.8 | *Nicotiana tabacum* | A | S | 42.5 |
| *Fagopyrum tartaricum* | A | O | 71.0 | *Nicotiana tabacum* | A | R | 61.1 |
| *Filipendula rubra* | A | R | 36.3 | *Nigella sativa* | A | R | 81.7 |
| *Foeniculum vulgare* | A | R | 41.6 | *Ocimum tenuiflorum* | A | R | 23.1 |
| *Foeniculum vulgare* | A | S | 84.4 | *Oenothera biennis* | A | R | 28.6 |
| *Foeniculum vulgare* | A | O | 100.0 | *Origanum majorana* | A | O | 52.9 |
| *Forsythia intermedia* | A | R | 35.8 | *Origanum majorana* | A | R | 100.0 |
| *Fragaria x ananassa* | A | R | 97.2 | *Origanum vulgare* | A | O | 66.8 |
| *Galinsoga ciliata* | A | R | 54.0 | *Panax quinquefolius* | A | S | 31.8 |
| *Galium odoratum* | A | O | 34.3 | *Pastinaca sativa* | A | S | 27.7 |
| *Galium odoratum* | A | O | 100.0 | *Pastinaca sativa* | A | R | 33.8 |
| *Gaultheria hispidula* | A | S | 35.8 | *Petasites japonicus* | A | S | 26.2 |
| *Gaultheria hispidula* | A | R | 100.0 | *Petroselinum crispum* | A | R | 69.1 |
| *Glaux maritima* | A | R | 46.5 | *Phalaris canariensis* | A | S | 28.4 |
| *Glycine max* | A | S | 27.0 | *Phalaris canariensis* | A | R | 29.7 |
| *Glycine Max* | A | R | 43.1 | *Phalaris canariensis* | A | O | 94.3 |
| *Glycine max* | A | O | 100.0 | *Phaseolus coccineus* | A | S | 30.8 |

TABLE 2-continued

MMP-2

| Nom latin | Stress | extrait | Inhibition (%) | Nom latin | Stress | extrait | Inhibition (%) |
|---|---|---|---|---|---|---|---|
| *Guizotia abyssinica* | A | S | 29.8 | *Phaseolus coccineus* | A | R | 79.5 |
| *Guizotia abyssinica* | A | R | 32.5 | *Phaseolus coccineus* | A | O | 80.9 |
| *Hamamelis virginiana* | A | R | 75.7 | *Phaseolus mungo* | A | R | 59.8 |
| *Helianthus annuus* | A | R | 69.0 | *Phaseolus vulgaris* | A | S | 47.3 |
| *Helianthus Tuberosus* | A | R | 22.2 | *Phaseolus Vulgaris* | A | R | 74.4 |
| *Helianthus tuberosus* | A | R | 69.7 | *Phaseolus vulgaris* | A | R | 83.2 |
| *Heliantbus Tuberosus* | A | O | 100.0 | *Phaseolus Vulgaris* | A | O | 100.0 |
| *Hordeum hexastichon* | A | R | 22.3 | *Phlox paniculata* | A | O | 23.7 |
| *Hordeum hexastichon* | A | R | 34.9 | *Phlox paniculata* | A | R | 81.7 |
| *Hordeum hexastichon* | A | O | 86.9 | *Physalis alkekengi* | A | R | 23.5 |
| *Hordeum vulgare* | A | O | 74.8 | *Physalis Ixocarpa* | A | O | 85.8 |
| *Hordeum vulgare* subsp. *Vulgare* | A | S | 34.5 | *Physalis ixocarpa* | A | R | 91.5 |
| *Hordeum vulgare* subsp. *Vulgare* | A | O | 74.2 | *Physalis Pruinosa* | A | R | 25.7 |
| *Hyssopus officinalis* | A | O | 57.5 | *Physalis Pruinosa* | A | O | 83.5 |
| *Inula helenium* | A | S | 26.8 | *Phytolacca decandra* | A | O | 31.5 |
| *Ipomoea Batatas* | A | S | 20.1 | *Phytolacca decandra* | A | S | 38.5 |
| *Lathyrus sativus* | A | S | 28.7 | *Pimpinella anisum* | A | S | 100.0 |
| *Lathyrus sativus* | A | O | 100.0 | *Pimpinella anisum* | A | R | 100.0 |
| *Lathyrus sylvestris* | A | R | 42.4 | *Plantago coronopus* | A | R | 36.0 |
| *Lavandula latifolia* | A | O | 39.1 | *Plantago coronopus* | A | R | 38.4 |
| *Lepidium sativum* | A | O | 20.1 | *Plantago coronopus* | A | O | 53.6 |
| *Lepidium sativum* | A | S | 49.0 | *Plantago major* | A | R | 65.3 |
| *Levisticum officinale* | A | S | 23.0 | *Plectranthus* sp. | A | O | 74.2 |
| *Levisticum officinale* | A | O | 29.8 | *Poa compressa* | A | S | 37.3 |
| *Linum usitatissimum* | A | R | 56.9 | *Poa compressa* | A | R | 49.8 |
| *Lolium multiflorum* | A | S | 41.5 | *Poa compressa* | A | O | 100.0 |
| *Lolium multiflorum* | A | O | 92.3 | *Polygonum pensylvanicum* | A | R | 63.5 |
| *Lotus comiculatus* | A | O | 95.5 | *Polygonum pensylvanicum* | A | O | 72.9 |
| *Lotus tetragonolobus* | A | R | 76.7 | *Polygonum persicaria* | A | S | 27.5 |
| *Lycopersicon esculentum* | A | S | 35.3 | *Polygonum persicaria* | A | O | 43.0 |
| *Lycopersicon esculentum* | A | R | 78.1 | *Poterium sanguisorba* | A | R | 100.0 |
| *Lycopersicon esculentum* | A | R | 85.6 | *Poterium Sanquisorba* | A | O | 84.2 |
| *Lycopersicon pimpinollifolium* | A | R | 74.9 | *Pteridium aquilinum* | A | O | 45.1 |
| *Malva moschata* | A | S | 21.5 | *Pteridium aquilinum* | A | R | 100.0 |
| *Malva moschata* | A | O | 44.5 | *Pysalis ixocarpa* | A | R | 87.3 |
| *Malva verticillata* | A | R | 22.0 | *Raphanus raphanistrum* | A | S | 32.2 |
| *Matricaria recutita* | A | S | 40.9 | *Raphanus sativus* | A | R | 25.3 |
| *Matricaria recutita* | A | O | 67.3 | *Raphanus sativus* | A | S | 47.5 |
| *Melaleuca alternifolia* | A | O | 65.0 | *Raphanus sativus* | A | R | 83.5 |
| *Melilotus albus* | A | S | 50.7 | *Raphanus sativus* | A | R | 84.7 |
| *Melilotus albus* | A | O | 100.0 | *Raphanus Sativus* | A | O | 100.0 |
| *Melissa officinalis* | A | O | 42.4 | *Rheum officinale* | A | O | 44.0 |
| *Mentha pulegium* | A | O | 88.3 | *Ribes nigrum* | A | O | 100.0 |
| *Mentha spicata* | A | O | 94.8 | *Ribes nigrum* | A | R | 100.0 |
| *Mentha suaveotens* | A | O | 82.9 | *Ricinus communis* | A | O | 100.0 |
| *Nepeta cataria* | A | O | 100.0 | *Rosa rugosa* | A | R | 25.2 |
| *Nicotiana rustica* | A | S | 24.0 | *Rosa rugosa* | A | S | 26.6 |
| *Nicotiana rustica* | A | R | 100.0 | *Triticum spelta* | A | R | 26.4 |
| *Rosa rugosa* | A | O | 83.2 | *Triticum spelta* | A | S | 36.7 |
| *Rosmarinus officinalis* | A | R | 68.2 | *Triticum spelta* | A | O | 51.9 |
| *Rubus idaeus* | A | O | 81.9 | *Tropaeolum majus* | A | R | 25.8 |
| *Rubus ideaus* | A | R | 73.4 | *Urtica dioica* | A | O | 22.9 |
| *Rumex Acetosa* | A | S | 24.2 | *Urtica dioica* | A | S | 30.6 |
| *Rumex Acetosa* | A | R | 85.5 | *Vaccinium Corymbosum* | A | R | 100.0 |
| *Rumex Acetosa* | A | O | 100.0 | *Veratrum viride* | A | R | 33.2 |
| *Rumex crispus* | A | O | 46.7 | *Verbascum thapsus* | A | S | 22.9 |
| *Rumex crispus* | A | R | 100.0 | *Veronica beccabunga* | A | R | 52.8 |
| *Ruta graveolens* | A | O | 100.0 | *Veronica officinalis* | A | O | 84.2 |
| *Saccharum officinarum* | A | R | 80.8 | *Vicia sativa* | A | R | 100.0 |
| *Salix purpurea* | A | S | 56.7 | *Vicia villosa* | A | S | 32.9 |
| *Salvia officinalis* | A | S | 24.1 | *Vicia villosa* | A | R | 100.0 |
| *Salvia officinalis* | A | O | 91.8 | *Vigna angularis* | A | R | 54.0 |
| *Salvia sclarea* | A | O | 99.7 | *Vigna sesquipedalis* | A | S | 48.3 |
| *Santolina chamaecyparissus* | A | O | 83.8 | *Vigna sesquipedalis* | A | R | 73.0 |
| *Satureja hortensis* | A | O | 79.1 | *Vigna sesquipedalis* | A | O | 96.6 |
| *Satureja hortensis* | A | R | 100.0 | *Vigna unguiculata* | A | R | 70.7 |
| *Satureja montana* | A | R | 60.4 | *Vinca minor* | A | S | 22.1 |
| *Satureja montana* | A | O | 76.1 | *Vinca minor* | A | R | 88.4 |
| *Scorzonera hispanica* | A | S | 22.1 | *Vitis* sp. | A | S | 20.9 |
| *Secale cereale* | A | R | 47.2 | *Vitis* sp. | A | R | 30.4 |
| *Secale cereale* | A | O | 67.2 | *Xanthium sibiricum* | A | S | 39.2 |
| *Senecio vulgaris* | A | S | 23.2 | *Xanthium sibiricum* | A | R | 47.8 |
| *Senecio vulgaris* | A | R | 76.6 | *Xanthium sibiricum* | A | O | 70.1 |
| *Sesamum indicum* | A | R | 100.0 | *Zea mays* | A | R | 100.0 |
| *Sesamum indicum* | A | S | 100.0 | *Zea Mays* | A | O | 100.0 |

TABLE 2-continued

| MMP-2 | | | | | | | |
|---|---|---|---|---|---|---|---|
| Nom latin | Stress | extrait | Inhibition (%) | Nom latin | Stress | extrait | Inhibition (%) |
| *Solanum dulcamara* | A | R | 54.5 | *Abelmochus esculentus* | G | S | 21.6 |
| *Solanum melanocerasum* | A | S | 45.4 | *Abelmochus esculentus* | G | R | 79.3 |
| *Solanum melanocerasum* | A | R | 85.2 | *Achillea millefolium* | G | O | 62.7 |
| *Solanum melanocerasum* | A | O | 88.7 | *Aconitum napellus* | G | O | 82.0 |
| *Soianum melongena* | A | S | 42.5 | *Acorus calamus* | G | S | 100.0 |
| *Solanum melongena* | A | R | 85.9 | *Ageratum conyzoides* | G | S | 49.3 |
| *Sonchus oleraceus* | A | R | 25.6 | *Alcea rosea* | G | R | 64.4 |
| *Sorghum caffrorum* | A | R | 39.6 | *Alchemilla mollis* | G | S | 21.5 |
| *Sorghum dochna* | A | S | 30.0 | *Alchemilla mollis* | G | R | 30.2 |
| *Sorghum dochna* | A | R | 48.0 | *Alchemilla mollis* | G | O | 55.7 |
| *Sorghum dochna* | A | O | 62.0 | *Allium ampeloprasum* | G | O | 36.1 |
| *Sorghum durra* | A | R | 72.1 | *Allium ampeloprasum* | G | R | 52.8 |
| *Sorghum durra* | A | O | 94.6 | *Allium ascalonicum* | G | O | 68.9 |
| *Sorghum sudanense* | A | O | 100.0 | *Allium cepa* | G | S | 40.2 |
| *Spinacia oleracea* | A | S | 23.6 | *Allium cepa* | G | R | 66.4 |
| *Stachys affinis* | A | R | 74.4 | *Allium cepa* | G | O | 100.0 |
| *Stachys byzantina* | A | R | 48.4 | *Allium grande* | G | R | 36.4 |
| *Stachys byzantina* | A | O | 100.0 | *Allium sativum* | G | S | 29.5 |
| *Stellaria graminea* | A | S | 20.8 | *Allium sativum* | G | R | 68.4 |
| *Stellaria graminea* | A | R | 37.5 | *Allium sativum* | G | O | 100.0 |
| *Stellaria media* | A | R | 49.0 | *Allium schoenoprasum* | G | S | 47.1 |
| *Stellaria media* | A | S | 50.7 | *Allium schoenoprasum* | G | R | 61.7 |
| *Symphytum officinale* | A | R | 44.2 | *Allium tuberosum* | G | S | 23.8 |
| *Tanacetum cinerariifolium* | A | R | 100.0 | *Allium tuberosum* | G | O | 54.5 |
| *Tanacetum parthenium* | A | S | 30.4 | *Allium tuberosum* | G | R | 85.9 |
| *Tanacetum vulgare* | A | S | 28.6 | *Aloe vera* | G | R | 53.6 |
| *Tanacetum vulgare* | A | R | 100.0 | *Althaea officinalis* | G | S | 37.4 |
| *Taraxacum officinale* | A | R | 59.1 | *Althaea officinalis* | G | S | 42.4 |
| *Thymus praecox* subsp *arcticus* | A | R | 43.5 | *Amaranthus caudathus* | G | S | 30.9 |
| *Thymus vulgaris* | A | S | 30.1 | *Amaranthus caudathus* | G | O | 56.7 |
| *Thymus x citriodorus* | A | R | 100.0 | *Amaranthus gangeticus* | G | S | 23.1 |
| *Trichosanthes kirilowii* | A | S | 29.2 | *Anethum graveolens* | G | S | 23.9 |
| *Trichosanthes kirilowii* | A | O | 42.1 | *Angelica archangelica* | G | S | 22.0 |
| *Thgonetta foenumgraecum* | A | O | 53.4 | *Angelica archangelica* | G | S | 24.9 |
| *Triticosecal* spp. | A | R | 44.8 | *Apium graveolens* | G | O | 33.0 |
| *Triticum aestivum* | A | R | 65.5 | *Apium graveolens* | G | R | 44.8 |
| *Triticum durum* | A | O | 53.9 | *Cosmos sulphureus* | G | S | 79.4 |
| *Apium graveolens* | G | S | 54.1 | *Cucumis sativus* | G | S | 39.9 |
| *Apium graveolens* | G | R | 84.1 | *Cucumis sativus* | G | S | 39.9 |
| *Aralia nudicaulis* | G | R | 51.8 | *Cucurbita maxima* | G | S | 33.9 |
| *Arctium minus* | G | S | 25.4 | *Cucurbita maxima* | G | R | 43.4 |
| *Armoracia rusticana* | G | O | 52.1 | *Cucurbita maxima* | G | O | 100.0 |
| *Aronia melanocarpa* | G | S | 22.5 | *Cucurbita moschata* | G | S | 41.3 |
| *Aronia melanocarpa* | G | R | 82.3 | *Cucurbita pepo* | G | S | 42.8 |
| *Artemisia dracunculus* | G | R | 53.6 | *Cucurbita pepo* | G | S | 45.4 |
| *Artemisia dracunculus* | G | R | 58.8 | *Cucurbita Pepo* | G | R | 83.0 |
| *Artemisia dracunculus* | G | S | 100.0 | *Cuminum cyminum* | G | O | 66.2 |
| *Artemisia dracunculus* | G | O | 100.0 | *Curcuma zedoaria* | G | R | 33.9 |
| *Asclepias incarnata* | G | S | 26.9 | *Cymbopogon citratus* | G | R | 65.8 |
| *Asparagus officinalis* | G | S | 24.0 | *Cymbopogon martinii motia* | G | S | 41.4 |
| *Asparagus officinalis* | G | R | 65.9 | *Cymbopogon martinii motia* | G | O | 60.5 |
| *Asparagus officinalis* | G | O | 95.0 | *Dactylis glomerata* | G | S | 21.9 |
| *Aster* spp | G | O | 48.4 | *Dactylis glomerata* | G | O | 61.2 |
| *Beckmannia eruciformis* | G | O | 24.8 | *Datura stramonium* | G | S | 27.0 |
| *Bellis perennis* | G | O | 52.6 | *Daucus carota* | G | O | 21.3 |
| *Beta vulgaris* | G | S | 45.3 | *Daucus carota* | G | S | 31.0 |
| *Beta vulgaris* | G | R | 100.0 | *Daucus carota* | G | R | 100.0 |
| *Beta vulgaris* spp. *Maritima* | G | R | 100.0 | *Digitalis purpurea* | G | S | 30.9 |
| *Brassica cepticepa* | G | R | 52.9 | *Dipsacus sativus* | G | O | 63.6 |
| *Brassica chinensis* | G | R | 41.9 | *Dirca palustris* | G | O | 23.1 |
| *Brassica juncea* | G | R | 22.8 | *Dolichos Lablab* | G | S | 33.0 |
| *Brassica Napus* | G | S | 22.9 | *Dryopteris filix-mas* | G | R | 100.0 |
| *Brassica oleracea* | G | R | 45.5 | *Echinacea purpurea* | G | R | 93.4 |
| *Brassica oleracea* | G | R | 47.1 | *Eleusine coracana* | G | S | 30.0 |
| *Brassica oleracea* | G | S | 62.9 | *Erigeron speciosus* | G | S | 28.9 |
| *Brassica oleracea* | G | R | 77.9 | *Errhenatherum elatius* | G | S | 55.6 |
| *Brassica oleracea* | G | O | 100.0 | *Eruca vesicaria* | G | R | 54.7 |
| *Brassica rapa* | G | S | 26.5 | *Eschscholzia carlifornica* | G | S | 47.9 |
| *Brassica rapa* | G | R | 38.9 | *Eschscholzia californica* | G | O | 75.9 |
| *Brassica Rapa* | G | R | 53.6 | *Fagopyrum tartaricum* | G | O | 41.1 |
| *Calamintba nepeta* | G | S | 20.4 | *Filipendula rubra* | G | R | 38.5 |
| *Calamintba nepeta* | G | O | 78.0 | *Foeniculum vulgare* | G | R | 70.0 |
| *Cameilia sinensis* | G | O | 100.0 | *Foeniculum Vulgare* | G | S | 100.0 |
| *Campanula rapunculus* | G | R | 60.6 | *Galinsoga ciliata* | G | S | 34.6 |
| *Canna edutis* | G | O | 78.1 | *Galinsoga ciliata* | G | R | 48.2 |

TABLE 2-continued

MMP-2

| Nom latin | Stress | extrait | Inhibition (%) | Nom latin | Stress | extrait | Inhibition (%) |
|---|---|---|---|---|---|---|---|
| Capsella bursa-pastoris | G | S | 30.7 | Gaultheria hispidula | G | R | 60.5 |
| Capsella bursa-pastoris | G | R | 60.6 | Gaultheria hispidula | G | O | 100.0 |
| Capsicum annuum | G | S | 70.8 | Gaultheria hispidula | G | S | 100.0 |
| Capsicum annuum | G | O | 80.0 | Glaux maritima | G | R | 59.3 |
| Capsicum annuum | G | R | 100.0 | Glycine max | G | R | 21.1 |
| Capsicum frutescens | G | S | 63.2 | Glycine max | G | S | 24.4 |
| Capsicum frutescens | G | R | 100.0 | Glycine max | G | O | 28.1 |
| Carthamus tinctorius | G | R | 100.0 | Guizotia abyssinica | G | S | 26.0 |
| Centaurea solstilialis | G | S | 46.4 | Guizotia abyssinica | G | R | 36.8 |
| Cerastium tomentosum | G | R | 52.3 | Guizotia abyssinica | G | O | 100.0 |
| Chenopodium bonus-benricus | G | S | 22.0 | Hedeoma pulegioides | G | O | 94.6 |
| Chenopodium quinoa | G | S | 31.0 | Helianthus annuus | G | S | 35.5 |
| Chenopodium quinoa | G | O | 53.4 | Helianthus annuus | G | O | 75.0 |
| Chrysanthemun coronarium | G | R | 76.2 | Helianthus annuus | G | R | 79.9 |
| Chrysanthenum coronarium | G | R | 54.2 | Helianthus strumosus | G | O | 100.0 |
| Cicer arietinum | G | S | 23.1 | Helianthus tuberosus | G | R | 64.2 |
| Cichorium endivia subsp endivia | G | S | 28.7 | Helichrysum thianschanicum | G | O | 61.1 |
| Cichorium endivia subsp endivia | G | O | 68.7 | Helleborus niger | G | R | 48.0 |
| Cichorium intybus | G | S | 41.4 | Hordeum hexastichon | G | S | 26.8 |
| Cichorium intybus | G | O | 62.1 | Hordeum vulgare | G | O | 65.4 |
| Circium arvense | G | S | 25.3 | Hordeum vulgare subsp. Vulgare | G | O | 75.8 |
| Circium arvense | G | R | 59.3 | Humulus lupulus | G | S | 26.0 |
| Citrullus lanatus | G | S | 24.8 | Hypericum henryi | G | R | 20.2 |
| Citrullus lanatus | G | R | 41.1 | Hypericum henryi | G | O | 71.1 |
| Citrullus lanatus | G | R | 100.0 | Hyssopus officinalis | G | O | 100.0 |
| Cosmos sulphureus | G | R | 77.9 | Pastinaca sativa | G | S | 24.3 |
| Ibens amara | G | S | 21.0 | Pastinaca sativa | G | R | 90.2 |
| Inula helenium | G | S | 24.3 | Petroselinum crispum | G | R | 87.6 |
| Lactuca sativa | G | R | 100.0 | Petroselinum crispum | G | O | 100.0 |
| Lactuca serriola | G | R | 69.3 | Phalaris canariensis | G | R | 100.0 |
| Laportea canadensis | G | R | 100.0 | Phalaris canariensis | G | O | 100.0 |
| Lathyrus sylvestris | G | O | 39.6 | Phaseolus acutifolius | G | R | 79.6 |
| Lavandula angustifolia | G | O | 70.0 | Phaseolus coccineus | G | S | 28.3 |
| Lavandula latifolia | G | S | 22.7 | Phaseolus coccineus | G | R | 80.4 |
| Lepidium Sativum | G | R | 30.6 | Phaseolus mungo | G | R | 37.2 |
| Lepidium sativum | G | S | 53.3 | Phaseolus vulgaris | G | R | 54.3 |
| Levisticum officinale | G | O | 80.7 | Phaseolus vulgaris | G | S | 59.0 |
| Lolium multiflorum | G | O | 34.5 | Phaseolus vulgaris | G | O | 73.7 |
| Lotus corniculatus | G | S | 32.9 | Phaseolus vulgaris | G | R | 100.0 |
| Lotus corniculatus | G | O | 100.0 | Phlox paniculata | G | R | 37.7 |
| Lotus tetragonolobus | G | R | 79.9 | Phlox paniculata | G | O | 77.0 |
| Lycopersicon esculentum | G | S | 28.2 | Phlox paniculata | G | R | 80.8 |
| Lycopersicon esculentum | G | R | 75.4 | Physalis ixocarpa | G | S | 30.5 |
| Lycopersicon pimpinellifolium | G | R | 81.4 | Physalis ixocarpa | G | R | 78.3 |
| Malus hupehensis | G | R | 32.5 | Physalis ixocarpa | G | R | 80.9 |
| Malus hupehensis | G | S | 41.2 | Physalis pruinosa | G | O | 63.2 |
| Malva moschata | G | O | 47.1 | Phytolacca americana | G | S | 36.1 |
| Malva sylvestris | G | S | 23.1 | Phytolacca americana | G | O | 100.0 |
| Malva verticillata | G | R | 39.9 | Pimpinella anisum | G | S | 26.1 |
| Matricaria recutita | G | O | 30.0 | Pimpinella anisum | G | R | 30.0 |
| Matricaria recutita | G | S | 71.3 | Pisum sativum | G | S | 28.4 |
| Melaleuca alternifolia | G | O | 58.3 | Plantago coronopus | G | R | 27.8 |
| Melilotus alba | G | S | 41.1 | Plantago coronopus | G | O | 51.1 |
| Melilotus albus | G | O | 88.8 | Plantago coronopus | G | R | 67.5 |
| Melilotus albus | G | R | 100.0 | Plantago major | G | S | 30.3 |
| Melissa officinalis | G | O | 47.8 | Plantago major | G | O | 64.6 |
| Mentha arvensis | G | R | 33.9 | Poa compressa | G | O | 63.0 |
| Mentha arvensis | G | O | 63.3 | Poa compressa | G | S | 67.4 |
| Mentha piperita | G | S | 32.3 | Poa compressa | G | R | 89.0 |
| Mentha piperita | G | O | 85.9 | Poa pratensis | G | S | 28.2 |
| Mentha piperita | G | R | 100.0 | Polygonum aviculare | G | R | 100.0 |
| Mentha spicata | G | S | 28.9 | Polygonum pensylvanicum | G | S | 27.7 |
| Mentha spicata | G | R | 37.5 | Polygonum pensylvanicum | G | O | 54.1 |
| Mentha suaveotens | G | R | 25.6 | Polygonum persicaria | G | S | 32.0 |
| Mentha suaveotens | G | O | 70.3 | Polygonum persicaria | G | O | 35.7 |
| Momordica charantia | G | R | 52.9 | Polygonum persicaria | G | R | 100.0 |
| Monarda didyma | G | S | 22.0 | Portulaca oleracera | G | R | 51.5 |
| Monarda didyma | G | O | 100.0 | Poterium sanguisorba | G | O | 89.9 |
| Monarda fistulosa | G | O | 26.0 | Poterium sanguisorba | G | R | 100.0 |
| Nepeta cataria | G | S | 23.4 | Poterium sanguisorba | G | S | 23.7 |
| Nicotiana tabacum | G | S | 45.2 | Prunella vulgaris | G | S | 26.7 |
| Nigella sativa | G | R | 94.7 | Prunus cerasifera | G | R | 95.3 |
| Ocimum basilicum | G | S | 23.0 | Raphanus Raphanistrum | G | R | 41.7 |
| Ocimum basilicum | G | O | 100.0 | Raphanus Raphanistrum | G | S | 43.5 |
| Ocimum tenuifiorum | G | R | 45.3 | Raphanus sativus | G | R | 41.0 |

TABLE 2-continued

MMP-2

| Nom latin | Stress | extrait | Inhibition (%) | Nom latin | Stress | extrait | Inhibition (%) |
|---|---|---|---|---|---|---|---|
| *Oerothera biennis* | G | R | 54.3 | *Raphanus sativus* | G | S | 44.6 |
| *Origanum majorana* | G | O | 100.0 | *Raphanus sativus* | G | R | 50.5 |
| *Origanum majorana* | G | R | 100.0 | *Raphanus sativus* | G | R | 86.1 |
| *Origanum vulgare* | G | R | 93.3 | *Raphanus sativus* | G | O | 100.0 |
| *Origanum vulgare* | G | O | 93.5 | *Reseda odorata* | G | O | 58.3 |
| *Origanum vulgare* | G | S | 97.4 | *Rheum officinale* | G | O | 30.7 |
| *Oxalis Deppei* | G | S | 28.7 | *Ribes nigrum* | G | O | 54.3 |
| *Oxalis Deppei* | G | R | 87.2 | *Ribes nigrum* | G | R | 63.8 |
| *Oxalis Deppei* | G | O | 100.0 | *Ribes Sylvestre* | G | R | 100.0 |
| *Oxyria digyna* | G | R | 54.5 | *Ricinus communis* | G | R | 41.5 |
| *Panicum miliaceum* | G | O | 71.1 | *Ricinus communis* | G | O | 100.0 |
| *Panicum miliaceum* | G | R | 100.0 | *Rosmarinus officinalis* | G | R | 90.0 |
| *Panicum miliaceum* | G | S | 100.0 | *Rubus idaeus* | G | S | 37.1 |
| *Passiflora caerula* | G | S | 26.3 | *Rubus ideaus* | G | R | 26.6 |
| *Passiflora caerula* | G | R | 72.1 | *Thymus vulgaris* | G | S | 23.3 |
| *Rubus occidentalis* | G | R | 35.1 | *Thymus vulgaris* | G | R | 86.4 |
| *Rumex crispus* | G | R | 30.3 | *Thymus x citriodorus* | G | R | 97.6 |
| *Rumex crispus* | G | S | 100.0 | *Tragopogon porrifolius* | G | R | 76.2 |
| *Rumex patientia* | G | R | 41.0 | *Trichosanthes kirilowii* | G | O | 87.7 |
| *Rumex patientia* | G | S | 41.9 | *Trigonella foenumgraecum* | G | S | 31.0 |
| *Ruta graveolens* | G | S | 47.9 | *Trigonella foenumgraecum* | G | O | 84.0 |
| *Ruta graveolens* | G | R | 82.1 | *Triticosecale* spp | G | S | 26.5 |
| *Saccharum officinarum* | G | R | 100.0 | *Triticosecale* spp | G | O | 73.5 |
| *Salvia elegens* | G | O | 100.0 | *Triticum aestivum* | G | R | 62.4 |
| *Salvia officinalis* | G | S | 35.3 | *Triticum durum* | G | O | 51.9 |
| *Salvia officinalis* | G | O | 100.0 | *Triticum spelta* | G | S | 24.5 |
| *Salvia officinalis* | G | R | 100.0 | *Triticum spelta* | G | O | 32.9 |
| *Sambucus ebulus* | G | R | 53.9 | *Triticum turgidum* | G | O | 25.1 |
| *Santolina chamaecyparissus* | G | S | 36.4 | *Tropaeolum majus* | G | S | 21.3 |
| *Santolina chamaecyparissus* | G | O | 69.5 | *Tropaeolum majus* | G | R | 45.6 |
| *Santolina chamaecyparissus* | G | R | 100.0 | *Urtica dioica* | G | S | 21.3 |
| *Saponaria officinalis* | G | S | 29.8 | *Urtica dioica* | G | O | 100.0 |
| *Satureja hortensis* | G | O | 97.4 | *Valerianella locusta* | G | O | 32.2 |
| *Satureja hortensis* | G | R | 100.0 | *Veratrum viride* | G | R | 77.7 |
| *Satureja montana* | G | O | 59.2 | *Verbascum thapsus* | G | S | 34.0 |
| *Satureja repandra* | G | S | 35.3 | *Veronica beccabunga* | G | R | 44.1 |
| *Satureja repandra* | G | O | 66.2 | *Veronica officinalis* | G | S | 38.8 |
| *Scorzonera hispanica* | G | S | 24.5 | *Veronica officinalis* | G | R | 87.5 |
| *Scrophularia nodosa* | G | S | 24.5 | *Viburnum trilobum* | G | O | 62.6 |
| *Scrophularia nodosa* | G | O | 30.0 | *Vicia faba* | G | S | 22.2 |
| *Scrophularia nodosa* | G | R | 55.6 | *Vicia sativa* | G | 0 | 74.8 |
| *Scutellaria lateriflora* | G | S | 20.3 | *Vicia sativa* | G | R | 100.0 |
| *Scutellaria lateriflora* | G | R | 83.1 | *Vicia villosa* | G | R | 100.0 |
| *Secale cereale* | G | O | 51.1 | *Vigna angularis* | G | R | 65.2 |
| *Senecio vulgaris* | G | R | 42.5 | *Vigna sesquipedalis* | G | S | 35.1 |
| *Sesamum indicum* | G | S | 34.3 | *Vigna sesquipedalis* | G | R | 73.8 |
| *Sesamum indicum* | G | R | 44.5 | *Vigna sesquipedalis* | G | O | 100.0 |
| *Silene vulgaris* | G | S | 34.1 | *Vigna unguiculata* | G | S | 65.9 |
| *Sium sisarum* | G | O | 100.0 | *Vigna unguiculata* | G | R | 84.5 |
| *Solanum melanocerasum* | G | S | 40.6 | *Vinca minor* | G | S | 22.1 |
| *Solanum melanocerasum* | G | R | 85.4 | *Vitis* sp. | G | R | 40.1 |
| *solanum melongena* | G | S | 58.2 | *Vitis* sp. | G | O | 74.7 |
| *solanum melongena* | G | O | 83.0 | *Withania somnifera* | G | S | 37.3 |
| *solanum melongena* | G | R | 85.2 | *Withania somnifera* | G | O | 91.0 |
| *Solanum tuberosum* | G | O | 40.2 | *Xanthium sibiricum* | G | S | 38.4 |
| *Sonchus oleraceus* | G | R | 41.1 | *Xanthium sibiricum* | G | O | 100.0 |
| *Sorghum dochna* | G | S | 25.0 | *Xanthium strumarium* | G | S | 37.7 |
| *Sorghum dochna* | G | O | 64.3 | *Xanthium strumarium* | G | O | 39.6 |
| *Sorghum dochna* | G | R | 100.0 | *Xanthium strumarium* | G | R | 40.0 |
| *sorghum durra* | G | R | 60.1 | *Zea mays* | G | S | 43.3 |
| *Sorghum durra* | G | O | 100.0 | *Zea mays* | G | O | 64.4 |
| *Sorghum sudanense* | G | O | 98.0 | *Zea mays* | G | R | 68.3 |
| *Spinacia oleracea* | G | S | 24.9 | *Perilla frutescens* | T | R | 100.0 |
| *Spinacia oleracea* | G | O | 100.0 | *Abies lasiocarpa* | T | S | 20.2 |
| *Stachys byzantina* | G | R | 78.8 | *Abies lasiocarpa* | T | R | 59.1 |
| *Stellaria graminea* | G | S | 29.3 | *Achillea millefollum* | T | O | 84.7 |
| *Stellaria media* | G | S | 33.4 | *Aconitum napellus* | T | O | 22.0 |
| *Stellaria media* | G | R | 45.4 | *Aconitum napellus* | T | R | 100.0 |
| *Symphytum officinale* | G | O | 57.5 | *Adiantum pedatum* | T | R | 100.0 |
| *Tanacetum cinerariifolium* | G | R | 100.0 | *Agaricus bisporus* | T | R | 52.1 |
| *Tanacetum parthenium* | G | R | 28.2 | *Agaricus bisporus* | T | R | 65.5 |
| *Tanacetum vulgare* | G | S | 25.2 | *Ageratum conyzoides* | T | S | 26.7 |
| *Tanacetum vulgare* | G | R | 39.3 | *Agropyron repens* | T | S | 30.2 |
| *Tanacetum vulgare* | G | O | 81.2 | *Agrostis Stolonifera* | T | O | 100.0 |
| *Taraxacum officinale* | G | R | 51.1 | *Alces rosea* | T | R | 63.7 |

TABLE 2-continued

MMP-2

| Nom latin | Stress | extrait | Inhibition (%) | Nom latin | Stress | extrait | Inhibition (%) |
|---|---|---|---|---|---|---|---|
| *Thymus fragantissimus* | G | S | 29.9 | *Alchemilla mollis* | T | R | 28.6 |
| *Thymus fragantissimus* | G | O | 55.3 | *Allium ampeloprasum* | T | R | 55.9 |
| *Thymus praecox* subsp *arcticus* | G | S | 27.7 | *Allium ampeloprasum* | T | O | 60.4 |
| *Thymus serpyllum* | G | R | 74.9 | *Camellia sinensis* | T | R | 43.8 |
| *Allium ascalonicum* | T | S | 20.4 | *Camellia sinensis* | T | O | 66.2 |
| *Allium ascalonicum* | T | O | 73.4 | *Canna edulis* | T | O | 100.0 |
| *Allium cepa* | T | S | 33.8 | *Cantharellus cibarias* | T | S | 26.0 |
| *Allium cepa* | T | S | 35.6 | *Capsicum annuum* | T | S | 54.6 |
| *Allium cepa* | T | R | 48.0 | *Capsicum annuum* | T | R | 100.0 |
| *Allium cepa* | T | R | 78.6 | *Capsicum frutescens* | T | S | 60.9 |
| *Allium grande* | T | R | 32.4 | *Capsicum frutescens* | T | R | 100.0 |
| *Allium schoenoprasum* | T | R | 67.7 | *Carex morrowii* | T | R | 24.4 |
| *Allium tuberosum* | T | S | 38.8 | *Carica papaya* | T | S | 20.8 |
| *Allium tuberosum* | T | O | 82.5 | *Carthamus tinctorius* | T | R | 39.6 |
| *Allium tuberosum* | T | R | 85.2 | *Carya cordiformis* | T | R | 100.0 |
| *Aloe vera* | T | R | 74.6 | *Cerastium tomentosum* | T | R | 54.8 |
| *Althaea officinalis* | T | S | 37.7 | *Chaerophyllum bulbosum* | T | S | 42.2 |
| *Althaea officinalis* | T | O | 55.3 | *Chaerophyllum bulbosum* | T | R | 74.3 |
| *Althaea officinalis* | T | R | 72.3 | *Chelidonium majus* | T | S | 20.3 |
| *Amaranthus caudathus* | T | O | 53.5 | *Chenopodium quinoa* | T | O | 76.0 |
| *Amaranthus gangeticus* | T | S | 28.1 | *Chrysanthemum coronarium* | T | S | 30.6 |
| *Ananas comosus* | T | R | 37.9 | *Chrysanthemum parthenium* | T | R | 57.2 |
| *Ananas comosus* | T | O | 100.0 | *chrysanthemun coronarium* | T | R | 56.5 |
| *angelica archangelica* | T | R | 41.3 | *Chrysanthenum coronarium* | T | R | 81.6 |
| *Anthemis nobilis* | T | O | 100.0 | *Cicer arietinum* | T | O | 32.2 |
| *Anthemis nobilis* | T | R | 100.0 | *Cichorium endivia* subsp *endivia* | T | R | 27.1 |
| *Anthriscus cerefolium* | T | S | 21.9 | *Cichorium endivia* subsp. *Endivia* | T | S | 26.9 |
| *Anthriscus cerefolium* | T | O | 67.1 | *Cichorium endivia* subsp. *Endivia* | T | O | 64.5 |
| *Apium graveolens* | T | R | 35.5 | *Cichorium intybus* | T | S | 22.7 |
| *Apium graveolens* | T | R | 52.1 | *Cichorium intybus* | T | R | 53.5 |
| *Aralia cordata* | T | R | 100.0 | *Cimicifuga racemosa* | T | S | 41.1 |
| *Aralia nudicaulis* | T | R | 31.2 | *Cimicifuga racemosa* | T | R | 68.4 |
| *Arctium minus* | T | S | 31.3 | *Circium arvense* | T | S | 42.5 |
| *Arctium minus* | T | O | 73.7 | *Circium arvense* | T | R | 64.5 |
| *Armoracia rusticana* | T | O | 49.9 | *Citrullus lanatus* | T | S | 72.4 |
| *Arrhenatherum elatius* | T | O | 100.0 | *Citrullus lanatus* | T | O | 92.2 |
| *Artemisia dracunculus* | T | S | 100.0 | *Citrullus lanatus* | T | R | 100.0 |
| *Asclepias incarnata* | T | S | 32.3 | *Citrus limettoides* | T | O | 77.1 |
| *Asparagus officinalis* | T | S | 48.2 | *Citrus limon* | T | R | 43.6 |
| *Atriplex hortensis* | T | R | 28.4 | *Citrus paradisi* | T | S | 21.8 |
| *Avena sativa* | T | R | 31.3 | *Citrus paradisi* | T | R | 90.9 |
| *Avena sativa* | T | O | 70.6 | *Citrus sinensis* | T | R | 46.7 |
| *Avena sativa* | T | R | 100.0 | *Colocasia* sp | T | R | 43.4 |
| *Averrhoa carambola* | T | R | 44.0 | *Colocasia* sp | T | O | 84.3 |
| *Bellis perennis* | T | R | 82.0 | *Corchorus olitorius* | T | R | 22.7 |
| *Beta vulgaris* | T | S | 33.7 | *Corlandrum sativum* | T | S | 20.4 |
| *Beta vulgaris* | T | R | 100.0 | *Cornus canadensis* | T | S | 66.0 |
| *Betula glandulosa* | T | O | 53.5 | *Cosmos sulphureus* | T | R | 47.1 |
| *Boletus edulis* | T | S | 21.8 | *Crataegus submollis* | T | S | 21.2 |
| *Borago officinalis* | T | S | 42.3 | *Crataegus submollis* | T | O | 94.3 |
| *Borago officinalis* | T | R | 78.5 | *Cucumis anguria* | T | S | 49.4 |
| *Brassica hirta* | T | R | 53.1 | *Cucumis anguria* | T | R | 84.1 |
| *Brassica hirta* | T | O | 68.9 | *Cucumis melo* | T | S | 56.6 |
| *Brassica Napus* | T | S | 45.1 | *Cucumis melo* | T | R | 92.4 |
| *Brassica Napus* | T | R | 82.9 | *Cucumis melo* | T | O | 100.0 |
| *Brassica oleracea* | T | R | 38.8 | *Cucumis metuliferus* | T | S | 29.5 |
| *Brassica oleracea* | T | R | 49.7 | *Cucumis sativus* | T | S | 28.3 |
| *Brassica oleracea* | T | O | 75.5 | *Cucurbita maxima* | T | S | 26.7 |
| *Brassica oleracea* | T | R | 77.0 | *Cucurbita maxima* | T | O | 34.7 |
| *Brassica oleracea* | T | S | 77.2 | *Cucurbita maxima* | T | R | 62.1 |
| *Brassica rapa* | T | R | 25.4 | *Cucurbita moschata* | T | R | 30.7 |
| *Brassica rapa* | T | O | 37.9 | *Cucurbita moschata* | T | S | 33.4 |
| *Brassica rapa* | T | S | 47.7 | *Cucurbita moschata* | T | S | 48.3 |
| *Brassica rapa* | T | R | 64.7 | *Cucurbita moschata* | T | R | 98.8 |
| *Brassica rapa* | T | R | 81.8 | *Cucurbita moschata* | T | O | 100.0 |
| *Calamintha nepeta* | T | O | 57.6 | *Cucurbita pepo* | T | S | 45.8 |
| *Calendula officinalis* | T | S | 32.6 | *Cucurbita pepo* | T | R | 80.2 |
| *Camellia sinensis* | T | S | 21.0 | *Helleborus niger* | T | R | 23.0 |
| *Cucurbita pepo* | T | O | 98.9 | *Hibiscus cannabinus* | T | R | 37.9 |
| *Cuminum cyminum* | T | O | 54.0 | *Hordeum vulgare* | T | O | 75.9 |
| *Curcuma zedoaria* | T | S | 100.0 | *Hordeum vulgare* supsp *vulgare* | T | S | 20.5 |
| *Cymbopogon citratus* | T | S | 21.0 | *Hordeum vulgare* supsp *vulgare* | T | O | 62.3 |
| *Cymbopogon martinii motia* | T | S | 27.5 | *Humulus lupulus* | T | S | 44.7 |
| *Cynara scoiymus* | T | S | 23.1 | *Humulus lupulus* | T | O | 70.6 |
| *Cynara scoiymus* | T | O | 83.4 | *Hypericum henryl* | T | O | 76.8 |

TABLE 2-continued

MMP-2

| Nom latin | Stress | extrait | Inhibition (%) | Nom latin | Stress | extrait | Inhibition (%) |
|---|---|---|---|---|---|---|---|
| *Cyperus esculentus* | T | R | 100.0 | *Hypericum henryl* | T | R | 99.8 |
| *Dactilis Glomerata* | T | S | 30.8 | *Hypericum perforatum* | T | R | 38.8 |
| *Dactilis Glomerata* | T | O | 34.5 | *Hyssopus officinalis* | T | O | 100.0 |
| *Daucus carota* | T | S | 27.1 | *Iberis amara* | T | O | 100.0 |
| *Daucus carota* | T | R | 56.8 | *Juniperus communis* | T | S | 100.0 |
| *Daucus Carota* | T | O | 100.0 | *Kochia scoparia* | T | S | 25.2 |
| *Digitalis purpurea* | T | S | 38.4 | *Koeleria glauca* | T | S | 23.1 |
| *Dirca palustris* | T | S | 45.9 | *Lactuca sativa* | T | R | 70.5 |
| *Dolichos lablab* | T | S | 46.6 | *Lactuca serriola* | T | R | 34.1 |
| *Dryopteris filix-mas* | T | O | 29.5 | *Laportea canadensis* | T | R | 61.3 |
| *Dryopteris filix-mas* | T | R | 100.0 | *Lathyrus sylvestris* | T | R | 48.6 |
| *Echinacea purpurea* | T | R | 59.3 | *Laurus nobilis* | T | O | 73.6 |
| *Echinacea purpurea* | T | O | 87.8 | *Lavandula angustifolia* | T | R | 35.0 |
| *Eleusine coracana* | T | S | 28.6 | *Lavandula angustifolia* | T | O | 100.0 |
| *Eleusine coracana* | T | R | 80.0 | *Lavandula latifolia* | T | O | 77.1 |
| *Erigeron canadensis* | T | O | 100.0 | *Lepidium sativum* | T | S | 35.2 |
| *Eruca vesicaria* | T | R | 60.5 | *Lepidium sativum* | T | R | 48.1 |
| *Erysimum perofskianum* | T | S | 28.2 | *Lepidium sativum* | T | O | 72.9 |
| *Erysimum perofskianum* | T | R | 85.2 | *Levisticum officinale* | T | S | 38.7 |
| *Eschscholzia califomica* | T | S | 49.9 | *Levisticum officinale* | T | O | 60.3 |
| *Eschscholzia califomica* | T | O | 74.5 | *Linum usitatissimum* | T | R | 24.7 |
| *Fagopyrum esculentum* | T | O | 52.9 | *Lolium multiflorum* | T | S | 39.8 |
| *Fagopyrum tartaricum* | T | S | 25.6 | *Lolium multiflorum* | T | O | 74.1 |
| *Fagopyrum tartaricum* | T | R | 68.4 | *Lonicera ramosissima* | T | S | 34.4 |
| *Fagopyrum tartaricum* | T | O | 100.0 | *Lonicera ramosissima* | T | O | 80.5 |
| *Festuca rubra* | T | O | 51.6 | *Lonicera syringantha* | T | R | 58.4 |
| *Festuca rubra* | T | S | 56.6 | *Lotus cornioulatus* | T | S | 36.0 |
| *Festuca rubra* | T | R | 71.7 | *Lotus corniculatus* | T | O | 100.0 |
| *Foeniculum vulgare* | T | S | 36.5 | *Lotus tetragonolobus* | T | R | 76.1 |
| *Foeniculum vulgare* | T | R | 41.4 | *Lunaria annua* | T | R | 47.4 |
| *Foeniculum vulgare* | T | O | 100.0 | *Lycopersicon esculentum* | T | R | 69.7 |
| *Fortunella* spp | T | R | 53.9 | *Lycopersicon pimpinellifolium* | T | R | 58.7 |
| *Fragaria xananassa* | T | R | 28.1 | *Malus hupehensis* | T | R | 53.1 |
| *Galinsoga ciliata* | T | S | 43.2 | *Malus hupehensis* | T | S | 100.0 |
| *Galinsoga ciliata* | T | R | 73.3 | *Malus* sp. | T | R | 72.6 |
| *Galium odoratum* | T | S | 42.0 | *Malva moschata* | T | O | 96.7 |
| *Galium odoratum* | T | O | 94.2 | *Malva verticilata* | T | R | 35.8 |
| *Glaux Maritima* | T | R | 24.8 | *Manihot esculenta* | T | R | 53.7 |
| *Glycine max* | T | R | 37.2 | *Melaleuca altemifolia* | T | S | 21.5 |
| *Glycine max* | T | O | 100.0 | *Melaleuca altemifolia* | T | O | 78.7 |
| *Glycine max* | T | R | 100.0 | *Melilotus albus* | T | R | 79.7 |
| *Glycine max* | T | S | 100.0 | *Melilotus officinalis* | T | S | 34.6 |
| *Gossypium herbaceum* | T | R | 48.7 | *Melilotus officinalis* | T | R | 100.0 |
| *Guizotia abyssinica* | T | S | 26.8 | *Melissa officinalis* | T | O | 100.0 |
| *Guizotia abyssinica* | T | R | 100.0 | *Mentha piperita* | T | S | 24.5 |
| *Hedeoma pulegioides* | T | R | 20.3 | *Mentha pulegium* | T | O | 100 |
| *Hedeoma pulegioides* | T | O | 72.7 | *Mentha suaveolens* | T | O | 20.9 |
| *Heliantbus annuus* | T | R | 56.1 | *Miscanthus sinensis Andress* | T | S | 69.1 |
| *Heliantbus strumosus* | T | O | 100.0 | *Momordica charantia* | T | R | 54.9 |
| *Heliantbus tuberosus* | T | S | 25.3 | *Monarda didyma* | T | S | 31.3 |
| *Heliantbus tuberosus* | T | R | 28.1 | *Monarda fistulosa* | T | S | 21.3 |
| *Heliantbus tuberosus* | T | O | 78.6 | *Monarda fistulosa* | T | O | 100.0 |
| *Heliantbus tuberosus* | T | R | 91.5 | *Montia perfoliata* | T | R | 67.2 |
| *Helichrysum angustifolium* | T | R | 83.4 | *Musa paradisiaca* | T | R | 47.3 |
| *Helichrysum angustifolium* | T | S | 88.3 | *nasturtium officinale* | T | S | 55.7 |
| *Helichrysum thianschanicum* | T | O | 26.0 | *Nepeta cataria* | T | S | 20.7 |
| *Heliotropium arborescens* | T | R | 100.0 | *Plantago major* | T | S | 22.3 |
| *Nepeta cataria* | T | S | 69.0 | *Plectranthus* sp. | T | S | 59.2 |
| *Nepeta cataria* | T | O | 100.0 | *Pleurotus* spp | T | R | 26.6 |
| *Nicotiana rustica* | T | S | 52.8 | *Poa compressa* | T | S | 33.4 |
| *Nicotiana rustica* | T | R | 88.1 | *Poa compressa* | T | R | 75.7 |
| *Nicotiana tabacum* | T | S | 50.3 | *Poa compressa* | T | O | 100.0 |
| *Nicotians tabacum* | T | R | 91.5 | *Poa pratensis* | T | S | 25.4 |
| *Nigella sativa* | T | R | 34.2 | *Polygonum pensylvanicum* | T | O | 66.8 |
| *Nigella sativa* | T | R | 90.3 | *Polygonum pensylvanicum* | T | R | 73.3 |
| *Nigella sativa* | T | R | 100.0 | *Polygonum persicaria* | T | S | 27.1 |
| *Ocimum Basilicum* | T | S | 21.6 | *Polygonum persicaria* | T | O | 50.8 |
| *Ocimum Basilicum* | T | O | 100.0 | *Populus inerassata* | T | O | 74.3 |
| *Ocimum tenuiflorum* | T | R | 44.5 | *Populus incrassata* | T | S | 100.0 |
| *Oenothera biennis* | T | R | 48.2 | *Prunus armeniaca* | T | R | 55.0 |
| *Onobrychis vicHfolia* | T | S | 34.4 | *Prunus cerasus* | T | O | 100.0 |
| *Onobrychis vicHfolia* | T | O | 35.6 | *Prunus persica* | T | S | 26.0 |
| *Opunlia* sp. | T | S | 23.5 | *Prunus persica* | T | R | 46.2 |
| *Origanum vulgare* | T | S | 20.7 | *Psoralea corylifolia* | T | S | 47.4 |
| *Origanum vulgare* | T | R | 76.7 | *Pteridium aquilnum* | T | R | 100.0 |

TABLE 2-continued

| MMP-2 | | | | | | |
|---|---|---|---|---|---|---|
| Nom latin | Stress | extrait | Inhibition (%) | Nom latin | Stress | extrait | Inhibition (%) |
| Origanum vulgare | T | O | 100.0 | Pyrus communis | T | R | 42.9 |
| Oryza sativa | T | R | 60.8 | Raphanus raphanistrum | T | S | 24.4 |
| Oxalis Deppei | T | S | 22.2 | Raphanus raphanistrum | T | R | 56.9 |
| Oxalis Deppei | T | R | 81.4 | Raphanus raphanistrum | T | O | 62.1 |
| Passiflora caerulea | T | S | 36.9 | Raphanus raphanistrum | T | O | 100.0 |
| Passiflora caerulea | T | R | 87.0 | Raphanus sativus | T | R | 48.9 |
| Passiflora spp | T | R | 54.6 | Raphanus sativus | T | S | 59.8 |
| Pastinaca sativa | T | S | 24.8 | Raphanus sativus | T | R | 81.6 |
| Pastinaca sativa | T | R | 74.7 | Reseda odorata | T | O | 71.3 |
| Perroselinum crispum | T | R | 85.2 | Rhamnus frangula | T | O | 44.6 |
| Perroselinum crispum | T | O | 100.0 | Rhamnus frangula | T | R | 74.4 |
| Persea americana | T | R | 43.1 | Rheum officinale | T | O | 73.9 |
| Petasites Japonious | T | S | 21.9 | Rheum officinale | T | S | 100.0 |
| Petroselinum crispum | T | R | 52.8 | Ricinus communis | T | O | 100.0 |
| Peucedanum oreaselinum | T | R | 41.9 | Rosmarinus officinalis | T | O | 100.0 |
| Phalaris canariensis | T | R | 41.1 | Rosmarinus officinalis | T | R | 100.0 |
| Phalaris canariensis | T | O | 100.0 | Rubus ideaus | T | R | 78.1 |
| Phaseotus acutifollus | T | R | 88.2 | Rumex acetosella | T | R | 42.2 |
| Phaseolus coccineus | T | S | 22.2 | Rumex crispus | T | 0 | 73.1 |
| Phaseolus coccineus | T | R | 36.4 | Rumex patientia | T | S | 52.0 |
| Phaseolus coccineus | T | R | 86.7 | Ruta graveolens | T | S | 34.7 |
| Phaseolus coccineus | T | O | 100.0 | Ruta graveolens | T | 0 | 100.0 |
| Phaseolus mungo | T | S | 43.0 | Saccharum officinarum | T | S | 59.6 |
| Phaseolus vulgaris | T | S | 62.9 | Saccharum officinarum | T | R | 66.1 |
| Phaseolus vulgaris | T | R | 71.9 | Salvia elegans | T | S | 36.3 |
| Phaseolus vulgaris | T | R | 73.0 | Salvia elegans | T | O | 44.3 |
| Phaseolus vulgaris | T | O | 100.0 | Salvia officinalis | T | S | 28.2 |
| Phlox paniculata | T | R | 23.1 | Salvia officinalis | T | O | 100.0 |
| Phlox paniculata | T | R | 92.8 | Salvia sclarea | T | R | 38.6 |
| Physalis alkekengi | T | R | 39.5 | Sambucus canadensis | T | S | 36.3 |
| Physalis ixocarpa | T | R | 36.7 | Sambucus canadensis | T | R | 64.5 |
| Physalis ixocarpa | T | R | 75.9 | Sambucus canadensis | T | O | 100.0 |
| Physalis pruinosa | T | R | 65.6 | Sanguisorba minor | T | O | 73.1 |
| Physalis pruinosa | T | R | 71.0 | Sanguisorba minor | T | R | 100.0 |
| Physalis pruinosa | T | O | 100.0 | Santolina chamaecyparissus | T | 0 | 27.7 |
| Physalis pruinosa | T | O | 100.0 | Santolina chamaecyparissus | T | R | 100.0 |
| Phytolacca decandra | T | S | 39.3 | Saponaria officinalis | T | R | 100.0 |
| Phytolacca decandra | T | O | 42.0 | Satureja hortensis | T | O | 62.2 |
| Pimpinella anisum | T | S | 27.9 | Satureja hortensis | T | R | 100.0 |
| Pimpinella anisum | T | R | 35.8 | Satureja montana | T | S | 34.7 |
| Pimpinella anisum | T | O | 49.9 | Satureja montana | T | O | 36.3 |
| Pimpinella anisum | T | R | 55.5 | Satureja montana | T | R | 100.0 |
| Pisum sativum | T | S | 22.3 | Satureja repandra | T | O | 47.0 |
| Plantago coronopus | T | R | 35.2 | Satureja repandra | T | S | 47.6 |
| Plantago coronopus | T | R | 46.0 | Satureja repandra | T | R | 84.6 |
| Plantago coronopus | T | O | 73.5 | Typha latifolia | T | S | 29.2 |
| Scolymus hispanicus | T | R | 35.8 | Urtica diolca | T | S | 29.5 |
| Scorzorera hipanica | T | R | 99.4 | Vaccinium angustifolium | T | R | 59.4 |
| Scrophularia nodosa | T | S | 29.1 | Vaccinium angustifolium | T | R | 100.0 |
| Scrophularia nodosa | T | R | 90.1 | Vaccinium macrocarpon | T | S | 51.1 |
| Scrophularia nodosa | T | O | 100.0 | Vaccinium macrocarpon | T | O | 64.7 |
| Scutellaria lateriflora | T | S | 30.9 | Valerianella locusta | T | S | 22.7 |
| Scutellaria lateriflora | T | R | 63.9 | Valerianella locusta | T | O | 24.8 |
| Secaie cereale | T | O | 100.0 | Veronica beccabunga | T | R | 33.3 |
| Senecio vulgaris | T | S | 24.7 | Veronica officinalis | T | R | 59.2 |
| Senecio vulgaris | T | R | 32.2 | Veronica officinalis | T | O | 100.0 |
| Sesamum indicum | T | R | 100.0 | Vibumum trilobum | T | O | 71.2 |
| Silene vulgaris | T | S | 25.6 | Vicia faba | T | S | 25.5 |
| Sium sisarum | T | O | 81.4 | Vicia faba | T | R | 27.0 |
| Sium sisarum | T | O | 100.0 | Vicia sativa | T | O | 56.6 |
| Solanum melanocerasum | T | s | 28.0 | Vicia villosa | T | R | 100.0 |
| Solanum melanocerasum | T | R | 78.8 | Vigna angularis | T | R | 49.2 |
| Solanum melanocerasum | T | R | 99.6 | Vigna sesquipedalis | T | R | 77.4 |
| Solanum melongena | T | S | 70.5 | Vigna sesquipedalis | T | O | 100.0 |
| Sorghum caffrorum | T | S | 28.1 | Vigna unguiculata | T | S | 27.2 |
| Sorghum dochna | T | R | 40.6 | Vigna unguiculata | T | R | 59.0 |
| Sorghum dochna | T | O | 100.0 | Vinca minor | T | R | 39.2 |
| Sorghum durra | T | R | 29.7 | Vitis sp. | T | R | 31.9 |
| Sorghum durra | T | O | 78.9 | Vitis sp. | T | S | 36.3 |
| Sorghum sudanense | T | R | 74.6 | Vitis sp. | T | O | 72.2 |
| Sorghum sudanense | T | O | 100.0 | Weigela coraeensis | T | S | 32.9 |
| Spinacia oleracea | T | S | 28.5 | Weigela coraeensis | T | R | 61.5 |
| Spinacia oleracea | T | O | 62.7 | Withania somnifera | T | S | 36.1 |
| Stachys byzantina | T | R | 66.9 | Withania somnifera | T | O | 83.3 |
| Stachys byzantina | T | O | 100.0 | Xanthium sibiricum | T | S | 32.1 |

TABLE 2-continued

MMP-2

| Nom latin | Stress | extrait | Inhibition (%) | Nom latin | Stress | extrait | Inhibition (%) |
|---|---|---|---|---|---|---|---|
| Stellaria media | T | S | 21.4 | Xanthium sibiricum | T | R | 33.2 |
| Stellaria media | T | R | 87.1 | Xanthium sibiricum | T | O | 62.4 |
| Stipa capillata | T | R | 37.5 | Xanthium strumarium | T | S | 47.2 |
| Symphytum officinale | T | O | 58.5 | Xanthium strumarium | T | O | 74.3 |
| Tanacetum cinerariifolium | T | O | 100.0 | Zea mays | T | R | 55.7 |
| Tanacetum cinerariifolium | T | R | 100.0 | Zea mays | T | O | 100.0 |
| Tanacetum parthenium | T | R | 100.0 | Zingiber officinale | T | R | 79.0 |
| Tanacetum vulgare | T | R | 20.8 | | | | |
| Taraxacum officinale | T | R | 76.3 | | | | |
| Teucrium chamaedrys | T | O | 75.6 | | | | |
| Thalpsi arvense | T | O | 64.1 | | | | |
| Thymus fragantissimus | T | S | 21.4 | | | | |
| Thymus praecox subsp arcticus | T | S | 36.4 | | | | |
| Thymus pseudolanuginosus | T | S | 21.1 | | | | |
| Thymus pseudolanuginosus | T | O | 75.4 | | | | |
| Thymus serpyllum | T | O | 64.2 | | | | |
| Thymus vulgaris | T | R | 71.5 | | | | |
| Thymus x citriodorus | T | S | 27.6 | | | | |
| Tragopogon porrifolium | T | S | 44.8 | | | | |
| Tragopogon porrifolius | T | O | 39.1 | | | | |
| Tragopogon porrifolius | T | R | 57.9 | | | | |
| Tragopogon sp. | T | R | 20.0 | | | | |
| Trifolium repens | T | R | 79.7 | | | | |
| Trigonella foenum graecum | T | O | 28.4 | | | | |
| Trigonella foenum graecum | T | S | 34.8 | | | | |
| Triticosecale spp | T | S | 28.5 | | | | |
| Triticosecale spp | T | O | 100.0 | | | | |
| Triticum aestivum | T | R | 32.9 | | | | |
| Triticum aestivum | T | O | 67.7 | | | | |
| Triticum durum | T | O | 47.7 | | | | |
| Triticum spelta | T | O | 37.1 | | | | |
| Triticum turgidumm | T | O | 41.2 | | | | |
| Tropaeolum majus | T | S | 42.7 | | | | |
| Tropaeolum majus | T | R | 77.6 | | | | |
| Tsuga diversifolia | T | R | 53.4 | | | | |

TABLE 3

MMP-3

| Nom latin | Stress | extrait | Inhibition (%) | Nom latin | Stress | extrait | Inhibition (%) |
|---|---|---|---|---|---|---|---|
| Achillea millefolium | A | O | 21.4 | Hypericum perforatum | A | R | 31.7 |
| Allium Tuberosum | A | S | 32.5 | Hyssopus officinalis | A | R | 21.6 |
| Anethum graveolens | A | S | 26.0 | Iris versicolor | A | R | 53.6 |
| Anthemis nobilis | A | R | 20.3 | Isatis tinctoria | A | S | 32.9 |
| Anthemis tinctoria | A | R | 58.0 | Levisticum officinale | A | O | 46.7 |
| Apium graveolens | A | R | 34.1 | Lotus tetragonolobus | A | R | 26.2 |
| Arctium minus | A | R | 53.9 | Matricaria recutita | A | S | 43.5 |
| Arctium minus | A | O | 100.0 | Matteucia pensylvanica | A | R | 24.7 |
| Arctostaphylos uva-ursi | A | S | 58.6 | Melissa officinalis | A | S | 30.3 |
| Aronia melanocarpa | A | R | 32.2 | Mentha suaveolens | A | R | 91.7 |
| Artemisia Absinthium | A | O | 100.0 | Nepeta cataria | A | S | 30.3 |
| Artemisia dracunculus | A | R | 23.4 | Nigella sativa | A | O | 26.0 |
| Artemisia dracunculus | A | S | 63.0 | Ocinum tenuiflorum | A | O | 33.0 |
| Aster sp | A | O | 42.4 | Ocinum tenuiflorum | A | R | 49.8 |
| Atropa belladonna | A | O | 23.8 | Perilla frutescens | A | R | 34.8 |
| Beta vulgaris | A | S | 24.1 | Petasites japonicus | A | R | 38.0 |
| Beta vulgaris | A | O | 42.9 | Phaseolus mungo | A | O | 62.6 |
| Beta vulgaris | A | O | 94.3 | Phaseolus vulgaris | A | S | 21.2 |
| Beta vulgaris | A | R | 97.9 | Phaseolus vulgaris | A | O | 50.6 |
| Beta vulgaris var. condivata | A | O | 21.2 | Phaseolus Vulgaris | A | R | 100.0 |
| Brassica napus | A | S | 25.0 | Phlox paniculata | A | S | 46.4 |
| Brassica napus | A | O | 100.0 | Physalis alkekengi | A | O | 37.5 |
| Brassica oleracea | A | S | 39.9 | Plantago major | A | O | 27.3 |
| Canna edulis | A | S | 39.6 | Polygonum aviculare linne | A | S | 24.8 |
| Capsicum annuum | A | S | 35.4 | Polygonum persicaria | A | S | 59.1 |
| Capsicum frutesoens | A | S | 27.2 | Potentilla anserina | A | R | 40.1 |
| Cichorium intybus | A | O | 20.2 | Poterium sanguisorba | A | R | 75.7 |
| Cichorium intybus | A | R | 26.5 | Prunus cerasifera | A | R | 80.0 |
| Cichorium intybus | A | S | 28.2 | Ptaridium aquilinus | A | R | 39.6 |

TABLE 3-continued

MMP-3

| Nom latin | Stress | extrait | Inhibition (%) | Nom latin | Stress | extrait | Inhibition (%) |
|---|---|---|---|---|---|---|---|
| *Citrullus lanatus* | A | S | 21.7 | *Raphanus raphanistrum* | A | S | 28.2 |
| *Citrullus lanatus* | A | O | 27.8 | *Raphanus sativus* | A | S | 64.4 |
| *Citrullus lanatus* | A | R | 34.4 | *Ribes nigrum* | A | O | 47.6 |
| *Coix Lacryma-Jobi* | A | S | 37.3 | *ribes uva-crispa* | A | R | 21.0 |
| *Coix Lacryma-Jobi* | A | O | 78.1 | *ribes uva-crispa* | A | O | 100.0 |
| *Cosmos sulphureus* | A | R | 26.8 | *Rosa rugosa* | A | S | 21.4 |
| *Crataegus submollis* | A | S | 22.3 | *Rosmarinus officinalis* | A | R | 27.3 |
| *Crataegus submollis* | A | R | 61.6 | *Rubus allegheniensis* | A | R | 81.0 |
| *Cucumis anguria* | A | S | 27.8 | *Rubus arcticus* | A | R | 51.0 |
| *Cucurbita Maxima* | A | S | 28.9 | *Rubus canadensis* | A | R | 48.8 |
| *Cucurbita moschata* | A | S | 32.9 | *Rubus idaeus* | A | S | 28.5 |
| *Cucurbita pepo* | A | S | 50.9 | *Rubus idaeus* | A | R | 35.1 |
| *Datisca cannabina* | A | R | 43.3 | *Rubus pubescens* | A | O | 50.4 |
| *Datisca cannabina* | A | S | 100.0 | *Rubus thibetanus* | A | O | 39.1 |
| *Digitalis purpurea* | A | R | 20.0 | *Rumex patientia* | A | S | 24.8 |
| *Dipsacus sativus* | A | R | 64.8 | *Ruta graveolens* | A | O | 56.1 |
| *Dirca palustris* | A | S | 29.6 | *Salvia officinalis* | A | R | 43.2 |
| *Diyopteris filix-mas* | A | R | 22.0 | *Santolina chamaecyparissus* | A | R | 27.0 |
| *Diyopteris filix-mas* | A | O | 32.8 | *Scutellaria lateriflora* | A | R | 53.5 |
| *Echinacea purpurea* | A | O | 100.0 | *Solanum melongena* | A | S | 21.8 |
| *Fagopyrum tataricum* | A | R | 28.3 | *Solidago canadensis* | A | S | 27.4 |
| *Fagopyrum tataricum* | A | O | 29.7 | *Stachys affinis* | A | S | 100.0 |
| *Filipendula rubra* | A | S | 43.7 | *Stellaria media* | A | O | 24.4 |
| *Filipendula rubra* | A | R | 63.2 | *Tanacetum vulgare* | A | R | 62.1 |
| *Fragaria x ananassa* | A | R | 41.5 | *Thymus praecox* subsp *arcticus* | A | S | 28.4 |
| *Fragaria x ananassa* | A | S | 67.1 | *Thymus praecox* subsp *arcticus* | A | O | 31.8 |
| *Fragaria x ananassa* | A | O | 99.6 | *Trichosanthes kirilowii* | A | S | 23.2 |
| *Fragaria x ananassa* | A | R | 31.7 | *Vaccinium Corymbosum* | A | R | 100.0 |
| *Gaultheria hispidula* | A | R | 50.5 | *Vaccinium macrocarpon* | A | S | 48.6 |
| *Glycyrrhiza glabra* | A | R | 56.2 | *Vaccinum augustifolium* | A | R | 56.6 |
| *Hedeoma pulegioides* | A | O | 51.7 | *Vigna angularia* | A | O | 23.1 |
| *Helianthus tuberosus* | A | O | 22.9 | *Vigna sesquipedalis* | A | O | 37.8 |
| *Hordeum vulgare* subsp *vulgare* | A | S | 36.0 | *Vigna unguiculata* | A | S | 52.5 |
| *Hyperioum henryi* | A | R | 67.2 | *Vinca minor* | A | O | 23.2 |
| *Vitis sp.* | A | S | 20.8 | *Iris versicolor* | G | R | 47.0 |
| *Vitis sp.* | A | O | 21.5 | *Isatis tinctoria* | G | S | 32.1 |
| *Vitis sp.* | A | R | 33.6 | *Lavandula angustifolia* | G | S | 43.9 |
| *Xanthium sibiricum* | A | S | 27.3 | *Levisticum officinale* | G | O | 51.4 |
| *Aconitum napellus* | G | O | 59.0 | *Malus hupehensis* | G | S | 24.2 |
| *Agropyron repens* | G | O | 69.4 | *Malus hupehensis* | G | R | 37.2 |
| *Alchemilla mollis* | G | S | 30.6 | *Malva sylvestris* | G | O | 73.7 |
| *Alchemilla mollis* | G | O | 73.3 | *Matricaria recutita* | G | S | 31.5 |
| *Allium grande* | G | O | 33.4 | *Melaleuca alternifolia* | G | S | 21.5 |
| *Anethum graveolens* | G | S | 40.5 | *Melissa officinalis* | G | S | 32.8 |
| *Aronia melanocarpa* | G | O | 100.0 | *Melissa officinalis* | G | R | 44.8 |
| *Artemisia absinthium* | G | S | 31.3 | *Melissa officinalis* | G | O | 82.4 |
| *Artemisia absinthium* | G | O | 67.9 | *Mentha piperita* | G | F | 77.3 |
| *Artemisia dracunculus* | G | S | 100.0 | *Mentha pulegium* | G | R | 41.1 |
| *Atropa belladonna* | G | S | 41.2 | *Monarda didyma* | G | S | 31.8 |
| *Bellis perennis* | G | S | 48.4 | *Nepeta cataria* | G | R | 25.8 |
| *Brassica oleracea* | G | S | 26.4 | *Nepeta cataria* | G | O | 84.9 |
| *Brassica oleracea* | G | O | 40.6 | *Nigella sativa* | G | O | 44.9 |
| *Brassica rapa* | G | S | 21.4 | *Ocinum tenuiflorum* | G | R | 23.7 |
| *Capsicum annuum* | G | S | 35.0 | *Oenothera biennis* | G | S | 25.6 |
| *Capsicum annuum* | G | S | 35.7 | *Origanum vulgare* | G | S | 28.6 |
| *Capsicum frutescens* | G | S | 27.5 | *Origanum vulgare* | G | R | 31.2 |
| *Chelidonium majus* | G | O | 34.7 | *Pennisetum alopecuroides* | G | S | 49.9 |
| *Cichorium intybus* | G | R | 34.4 | *Petroselinum crispum* | G | S | 31.5 |
| *Coix Lacryma-Jobi* | G | S | 20.2 | *Peucedanum oreaselinum* | G | R | 68.3 |
| *Cosmos sulphureus* | G | O | 32.9 | *Phaseolus acutifolius* | G | R | 25.4 |
| *Crataegus submollis* | G | S | 25.6 | *Phaseolus acutifolius* | G | O | 61.8 |
| *Crataegus submollis* | G | R | 28.6 | *Phaseolus vulgaris* | G | O | 24.4 |
| *Cucumis anguria* | G | S | 33.6 | *Phaseolus vulgaris* | G | S | 35.6 |
| *Cucurbita maxima* | G | S | 44.6 | *Phiox paniculata* | G | S | 27.2 |
| *Cucurbita moschata* | G | S | 33.4 | *Physalis alkekengi* | G | R | 26.1 |
| *Cucurbita pepo* | G | S | 25.3 | *Physalis alkekengi* | G | O | 54.9 |
| *Cymbopogon citratus* | G | S | 30.3 | *Plantago major* | G | O | 55.9 |
| *Cymbopogon martinii* | G | S | 61.1 | *Plectranthus sp.* | G | R | 23.0 |
| *Daucus carota* | G | O | 30.0 | *Polygonum persicaria* | G | S | 41.1 |
| *Diyopteris filix-mas* | G | S | 26.0 | *Potentilla anserina* | G | R | 55.4 |
| *Diyopteris filix-mas* | G | R | 45.3 | *Poterium sanguisorba* | G | R | 76.4 |
| *Echinacea purpurea* | G | O | 51.8 | *Prunus cerasifera* | G | R | 55.3 |
| *Echinochloa frumentacea* | G | S | 30.3 | *Ptaridium aquilinus* | G | R | 44.5 |

TABLE 3-continued

MMP-3

| Nom latin | Stress | extrait | Inhibition (%) | Nom latin | Stress | extrait | Inhibition (%) |
|---|---|---|---|---|---|---|---|
| *Fagopyrum esculentum* | G | R | 50.9 | *Rhaphanus sativus* | G | O | 98.1 |
| *Fagopyrum tartaricum* | G | O | 44.0 | *Rheum x cultorum* | G | R | 27.0 |
| *Fagopyrum tartaricum* | G | R | 46.0 | *Ribes nidigrolaria* | G | R | 22.0 |
| *Filipendula rubra* | G | S | 53.1 | *Ribes Silvestris* | G | R | 88.8 |
| *Filipendula rubra* | G | R | 58.7 | *Rosmarinus officinalis* | G | R | 39.4 |
| *Forsythi aintermedia* | G | O | 52.9 | *Rubus idaeus* | G | S | 100.0 |
| *Fragaria x ananassa* | G | R | 40.7 | *Rubus ideaus* | G | O | 37.0 |
| *Fragaria x ananassa* | G | R | 28.1 | *Rubus Phoenicalasius* | G | R | 24.9 |
| *Gaultheria hispidula* | G | R | 72.8 | *Rubus pubescens* | G | O | 23.0 |
| *Gaultheria hispidula* | G | O | 100.0 | *Rubus thibetanus* | G | O | 41.2 |
| *Gaultheria procumbens* | G | R | 24.1 | *Rumex patientia* | G | S | 36.2 |
| *Glycine max* | G | S | 31.2 | *Salvia officinalis* | G | O | 34.5 |
| *Glycyrrhiza glabra* | G | R | 37.1 | *Salvia officinalis* | G | R | 89.5 |
| *Gulzotia abyssinica* | G | R | 35.4 | *Sanguisorba officinalis* | G | S | 48.8 |
| *Hamamelis virginiana* | G | S | 29.1 | *Santolina chamaecyparissus* | G | R | 33.7 |
| *Hamamelis virginiana* | G | R | 67.1 | *Secale cereals* | G | S | 24.4 |
| *Helenium hoopesii* | G | R | 39.8 | *Senecio vulgaris* | G | R | 37.6 |
| *Helianthus tuberosus* | G | O | 32.8 | *Solanum melongena* | G | S | 21.1 |
| *Hordeum hexastichon* | G | S | 60.9 | *Solanum tuberosum* | G | S | 27.6 |
| *Humulus lupulus* | G | R | 61.2 | *Sorghum dochna* | G | S | 23.7 |
| *Humulus lupulus* | G | S | 90.5 | *Sorghum dochna* | G | R | 56.3 |
| *Hypericum henryi* | G | R | 100.0 | *Symphytum officinale* | G | S | 25.2 |
| *Hypericum perforalum* | G | R | 43.4 | *Teucrium chamaedrys* | G | S | 75.4 |
| *Hyssopus officinalis* | G | S | 25.1 | *Thymus praecox* subsp *arcticus* | G | S | 28.4 |
| *Hyssopus officinalis* | G | O | 48.2 | *Thymus praecox* subsp *arcticus* | G | O | 52.1 |
| *Thymus x citriodorus* | G | R | 25.3 | *Carya cordiformis* | T | R | 27.5 |
| *Triticum durum* | G | S | 21.9 | *Chaerophyllum bulbosum* | T | S | 27.1 |
| *Triticum turgidum* | G | O | 80.2 | *Chaerophyllum bulbosum* | T | O | 100.0 |
| *Vaccinium angustifolium* | G | R | 47.6 | *Chelidonium majus* | T | O | 54.0 |
| *Vaccinium angustifolium* | G | R | 48.1 | *Chrysanthemum parthenium* | T | S | 50.4 |
| *Vaccinium angustifolium* | G | R | 71.0 | *Chrysanthemum coronarium* | T | S | 25.8 |
| *Vaccinium corymbosum* | G | R | 60.6 | *Cichorium intybus* | T | R | 23.9 |
| *Vaccinium corymbosum* | G | R | 61.7 | *Citrullus lanatus* | T | S | 33.2 |
| *Vaccinium corymbosum* | G | O | 99.4 | *Citrullus lanatus* (Garden baby) | T | S | 21.4 |
| *Vaccinium macrocarpon* | G | R | 100.0 | *Citrus limettoides* | T | O | 39.2 |
| *Vaccinum angustifolium* | G | O | 24.4 | *Citrus limon* | T | O | 60.4 |
| *Vaccinum angustifolium* | G | R | 41.5 | *Corchorus olitorius* | T | S | 28.6 |
| *Valeriana officinalis* | G | R | 33.5 | *Cornus canadensis* L. | T | O | 50.0 |
| *Veronica officinalis* | G | S | 27.0 | *Cornus canadensis* L. | T | R | 80.6 |
| *Vicia faba* | G | O | 31.2 | *Cosmos sulphureus* | T | R | 20.6 |
| *Vicia faba* | G | R | 44.7 | *Cosmos sulphureus* | T | S | 27.0 |
| *Vigna angularia* | G | O | 40.8 | *Crataegus sp* | T | S | 43.9 |
| *Vigna angularis* | G | S | 39.4 | *Crataegus submollis* | T | O | 24.2 |
| *Vigna unguiculata* | G | O | 26.1 | *Crataegus submollis* | T | R | 55.1 |
| *Vitis sp.* | G | R | 62.4 | *Cucumis anguria* | T | S | 33.2 |
| *Vitis sp.* | G | S | 63.3 | *Cucumis sativus* Fanfare | T | S | 35.4 |
| *Vitis sp.* | G | O | 82.0 | *Cucurbita moschata* | T | S | 30.4 |
| *Withania somnifera* | G | S | 22.4 | *Cucurbita pepo* | T | R | 23.8 |
| *Xanthium strumarium* | G | S | 20.7 | *Cucurbita pepo* | T | S | 46.6 |
| *Zea mays* | G | S | 26.1 | *Cuminum cyminum* | T | S | 23.1 |
| *Zea mays* | G | R | 67.5 | *Curcuma zedoaria* | T | S | 20.8 |
| *Abies lasiocarpa* | T | R | 46.2 | *Cymbopogon citratus* | T | S | 39.7 |
| *Acorus calamus* | T | R | 21.8 | *Dolichus lablab* | T | S | 25.8 |
| *Actinidia arguta* | T | R | 64.6 | *Diyopteris filix-mas* | T | O | 54.0 |
| *Agropyron repens* | T | O | 48.3 | *Echinacea purpurea* | T | S | 20.4 |
| *Alchemilla mollis* | T | R | 100.0 | *Eriobotrya japonica* | T | O | 34.8 |
| *Alchemilla mollis* | T | O | 100.0 | *Eriobotrya japonica* | T | S | 42.9 |
| *Allium cepa* | T | R | 39.8 | *Foericulum vulgare* | T | O | 33.1 |
| *Allium cepa* | T | O | 45.2 | *Fragaria x ananassa* | T | S | 20.3 |
| *Allium tuberosum* | T | R | 28.2 | *Fragaria x ananassa* | T | R | 42.8 |
| *Allium tuberosum* | T | S | 28.8 | *Glycine max* | T | S | 26.3 |
| *Alpinia officinarum* | T | S | 26.4 | *Glycine max* | T | O | 30.5 |
| *Amelanchier alnitolia* | T | R | 78.3 | *Gossypium herbaceum* | T | R | 22.5 |
| *Amelanchier sanguinea* xA. *laevis* | T | R | 66.5 | *Guizotia abyssinica* | T | R | 46.6 |
| *angelica archangelica* | T | S | 25.2 | *Hamamelis virginiana* | T | S | 33.1 |
| *Apium graveolens* | T | R | 43.3 | *Hamamelis virginiana* | T | S | 33.1 |
| *Aralia cordata* | T | S | 31.5 | *Hamamelis virginiana* | T | R | 44.8 |
| *Aralia nudicaulis* | T | S | 37.7 | *Hedeoma pulegiodes* | T | O | 46.8 |
| *Aralia nudicaulis* | T | R | 48.5 | *Helenium hoopesii* | T | R | 27.9 |
| *Aronia melanocarpa* | T | S | 26.0 | *Helianthus annus* | T | S | 22.7 |
| *Aronia melanocarpa* | T | O | 53.3 | *Helianthus strumosus* | T | O | 30.0 |
| *Aronia prunifolia* | T | R | 79.2 | *Heliotropium arborescens* | T | O | 53.7 |
| *Artemisia absinthium* | T | O | 100.0 | *Helleborus niger* | T | S | 40.5 |
| *Artemisia dracunlus* | T | S | 42.0 | *Hibiscus cannabinus* | T | O | 34.0 |
| *Ayperus esculentus* | T | O | 67.8 | *Hordeum vulgare* subsp. *Vulgare* | T | O | 100.0 |

TABLE 3-continued

MMP-3

| Nom latin | Stress | extrait | Inhibition (%) | Nom latin | Stress | extrait | Inhibition (%) |
|---|---|---|---|---|---|---|---|
| Beta vulgaris | T | R | 27.9 | Humulus lupulus | T | S | 24.9 |
| Beta vulgaris | T | S | 33.2 | Humulus lupulus | T | R | 55.1 |
| Beta vulgaris | T | O | 53.0 | Humulus lupulus | T | R | 77.6 |
| Borago officinalis | T | O | 55.7 | Humulus lupulus | T | S | 79.1 |
| Brassica Napus | T | O | 71.9 | Humulus lupulus | T | S | 100.0 |
| Brassica oleracea | T | O | 37.0 | Humulus lupulus | T | R | 100.0 |
| Brassica oleracea | T | S | 46.9 | Humulus lupulus | T | S | 100.0 |
| Brassica rapa | T | S | 36.7 | Hypericum henryl | T | R | 100.0 |
| Bromus inermis | T | R | 42.8 | Hypericum perforatum | T | O | 99.3 |
| Calendula officinalis L. | T | S | 28.4 | Hypomyces lactillorum | T | O | 20.5 |
| Camellia sinensis syn. Thea sinensis | T | R | 86.4 | Iris versicolor | T | R | 48.5 |
| Capsicum annus | T | S | 29.7 | Juniperus communis | T | R | 33.8 |
| Capsicum annus | T | R | 43.7 | Lactuca serriola | T | R | 21.5 |
| Capsicum frutescens (tabasco) | T | S | 22.0 | Laportea canadensis | T | S | 37.7 |
| Lavendula angustifolia | T | S | 91.7 | Rosmarinum officinalis | T | R | 48.2 |
| Lepidium sativum | T | R | 24.7 | Rubus arotious | T | R | 59.1 |
| Levisticum officinale | T | O | 24.9 | Rubus ideaus | T | O | 21.5 |
| Lolium perenne | T | S | 22.3 | Rubus pubescens | T | O | 51.8 |
| Lonicera ramosissima | T | R | 42.5 | Rubus thibetanus | T | O | 33.7 |
| Lonicera syringantha | T | R | 21.1 | Rumex patientia | T | S | 34.4 |
| Malus | T | O | 53.1 | Ruta graveolens | T | O | 24.3 |
| Malus hupehensis (Pamp.) Rehd. | T | R | 76.5 | Salvia (elegens) | T | O | 37.2 |
| Malus sp. | T | R | 39.8 | Salvia (elegens) | T | R | 42.9 |
| Malus sp. | T | R | 45.7 | Salvia officinalis | T | R | 67.3 |
| Malva moschata | T | S | 22.8 | Sambucus canadensis | T | S | 30.2 |
| Malva sylvestris | T | O | 57.6 | Sanguisorba minor | T | R | 21.0 |
| Matteucia pensylvanica | T | R | 20.1 | Sanguisorba minor | T | R | 29.9 |
| Melissa officinalis | T | O | 55.0 | Sanguisorba minor | T | R | 30.8 |
| Mentha piperita | T | R | 35.5 | Sanguisorba minor | T | R | 44.5 |
| Mentha piperita | T | 0 | 43.9 | Santolina | T | R | 43.8 |
| Mentha piperita | T | R | 56.6 | Sarratula tinctoria | T | S | 37.7 |
| Mentha pulegium | T | O | 33.3 | Satureja montana | T | R | 45.0 |
| Mentha pulegium | T | R | 56.2 | Satureja repandra | T | S | 46.3 |
| Mentha spicata hipanica | T | O | 43.4 | Scorzorera | T | R | 25.7 |
| Mentha spicata | T | O | 58.0 | Scuttellaria lateriflora | T | S | 41.2 |
| Nicotiana tabacum | T | R | 27.3 | Setaria italica | T | S | 33.4 |
| Nigella sativa | T | R | 25.1 | Solidago canadensis | T | S | 78.5 |
| Ocimum Basilicum | T | R | 20.2 | Stachys affinis | T | S | 100.0 |
| Oenothera bienris | T | S | 37.8 | Stachys byzantina | T | O | 100.0 |
| Origanum marjonara | T | R | 45.2 | Stellaria media (linne) Cyrillo | T | O | 51.2 |
| Origanum vulgare | T | S | 21.3 | Tanacetum vulgare | T | R | 30.5 |
| Origanum vulgare | T | O | 23.3 | Tepary | T | R | 31.7 |
| Origanum vulgare | T | R | 23.6 | Tepary | T | O | 39.7 |
| Origanum vulgare | T | O | 37.2 | Thymus serpyllum | T | O | 29.9 |
| Panicum miliaceum | T | S | 20.6 | Thymus serpyllum | T | R | 32.6 |
| Panicum miliaceum | T | S | 30.7 | Thymus x citriodorus | T | S | 22.1 |
| Pastinaca saliva | T | R | 26.1 | Tiarella cordifolia | T | R | 46.8 |
| Pastinaca sativa | T | O | 100.0 | Tragopogon porrifolium | T | R | 26.3 |
| Peucedanum oreaselinum | T | S | 39.6 | Tragopogon porrifolium | T | R | 29.8 |
| Peucedanum oreaselinum | T | R | 53.4 | Tragopogon porrifolium | T | O | 58.0 |
| Phaseolus vulgaris | T | S | 21.8 | Triticale sp. | T | O | 25.3 |
| Phaseolus vulgaris | T | O | 23.6 | Tropaeolum majus | T | O | 46.9 |
| Phaseolus vulgaris | T | O | 59.8 | Tropaeolum majus | T | O | 55.8 |
| Physalis alkekengi | T | O | 55.5 | Tropaeolum majus | T | R | 64.7 |
| Physalis pruinosa | T | S | 24.8 | Tsuga canOadensis | T | R | 39.2 |
| Plantago major | T | O | 77.1 | Vaccinium angustifolium | T | R | 28.0 |
| Poa compressa | T | R | 54.4 | Vaccinium angustifolium | T | S | 29.6 |
| Polygonium chinense | T | O | 36.3 | Vaccinium angustifolium | T | R | 33.3 |
| Polygonium chinense | T | R | 61.4 | Vaccinium angustifolium Ait. | T | R | 100.0 |
| Polygonium persicaria | T | S | 21.3 | Vaccinium macrocarpon | T | S | 25.1 |
| Populus incrassata | T | S | 50.7 | Vaccinium macrocarpon | T | R | 27.4 |
| Populus incrassata | T | S | 50.7 | Vaccinium macrocarpon | T | O | 35.4 |
| Populus x petrowskyana | T | R | 66.7 | Vaccinium macrocarpon | T | R | 80.5 |
| Prunus cerasifera | T | O | 26.1 | Vaccinium macrocarpon | T | O | 90.5 |
| Prunus cerasifera | T | R | 64.2 | Valeriana officinalis | T | 0 | 33.0 |
| Psidium guajaba | T | S | 22.9 | Veratrum viride | T | S | 46.8 |
| Ptaridium aquilinus | T | R | 43.0 | Verbascum thapsus | T | O | 33.4 |
| Pyrus pyrifolia | T | S | 28.2 | Vicia faba | T | R | 26.6 |
| Rahmnus frangula | T | R | 25.9 | Vicia faba | T | O | 35.8 |
| Raphanus sativus | T | R | 21.4 | Vigna angularia | T | S | 29.3 |
| Raphanus sativus | T | O | 36.9 | Vigna angularia | T | O | 54.0 |
| Rhamnus frangula | T | O | 43.2 | Vigna sesquipedalis | T | O | 100.0 |
| Rheum rhabarbarum | T | O | 28.5 | Vigna ungulculata | T | S | 49.5 |
| Rheum x cultorum | T | R | 28.2 | Vitia sp. | T | O | 99.6 |
| Rianus communis | T | S | 32.4 | Vitis sp | T | R | 50.9 |

TABLE 3-continued

MMP-3

| Nom latin | Stress | extrait | Inhibition (%) | Nom latin | Stress | extrait | Inhibition (%) |
|---|---|---|---|---|---|---|---|
| *Ribes nidigrolaria* | T | S | 28.5 | *Vitis* sp. | T | R | 75.8 |
| *Ribes nigrum* | T | R | 49.9 | *Weigela coracensis* | T | S | 22.8 |
| *Rosa rugosa* | T | S | 29.1 | *Weigela coracensis* | T | S | 22.8 |
| *Weigela hortensis* | T | R | 54.9 | | | | |
| *Zea mays* | T | O | 74.3 | | | | |

TABLE 4

MMP-9

| Nom latin | Stress | extrait | Inhibition (%) | Nom latin | Stress | extrait | Inhibition (%) |
|---|---|---|---|---|---|---|---|
| *Abelmochus esculentus* | A | S | 26.8 | *Brassica napus* | A | R | 53.1 |
| *Achillea millefolium* | A | S | 41.6 | *Brassica napus* | A | O | 100.0 |
| *Aconitum napellus* | A | O | 47.7 | *Brassica nigra* | A | S | 24.2 |
| *Acorus calamus* | A | O | 83.2 | *Brassica oleracea* | A | R | 33.0 |
| *Actinidia arguta* | A | S | 26.8 | *Brassica oleracea* | A | R | 36.0 |
| *Adiantum pedatum* | A | O | 20.7 | *Brassica oleracea* | A | W | 36.2 |
| *Agastache foeniculum* | A | S | 100.0 | *Brassica oleracea* | A | S | 73.1 |
| *Agrimonia eupatoria* | A | W | 21.4 | *Brassica Oleracea* | A | O | 100.0 |
| *Agropyron cristatum* | A | R | 51.4 | *Brassica rapa* | A | R | 31.0 |
| *Agropyron repens* | A | S | 27.3 | *Brassica rapa* | A | W | 38.6 |
| *Agrostis alba* | A | R | 40.6 | *Brassica rapa* | A | V | 42.8 |
| *Agrostis Stofonifera* | A | R | 35.4 | *Brassica rapa* | A | R | 48.8 |
| *Alcea rosea* | A | S | 45.8 | *Brassica rapa* | A | S | 68.2 |
| *Alkanna tinctoria* | A | S | 42.5 | *Brassica rapa* | A | O | 89.2 |
| *Allium cepa* | A | O | 49.7 | *Bromus inermis* | A | R | 51.4 |
| *Allium grande* | A | R | 71.4 | *Campanula rapunculus* | A | O | 25.1 |
| *Allium porrum* | A | S | 28.0 | *Canna edulis* | A | S | 31.1 |
| *Allium porrum* | A | O | 82.0 | *Canna edulis* | A | O | 47.6 |
| *Allium sativum* | A | S | 23.7 | *Canna edulis* | A | R | 68.9 |
| *Allium schoenoprasum* | A | O | 45.5 | *Capsella bursa-pastoris* | A | R | 32.5 |
| *Allium tuberosum* | A | V | 20.1 | *Capsicum annuum* | A | O | 22.0 |
| *Allium Tuberosum* | A | O | 91.5 | *Capsicum annuum* | A | R | 24.0 |
| *Althaea officinalis* | A | S | 29.6 | *capsicum annuum* | A | S | 55.7 |
| *Amaranthus gangeticus* | A | O | 25.1 | *Capsicum frutescens* | A | S | 30.3 |
| *Amaranthus gangeticus* | A | R | 31.1 | *Capsicum frutescens* | A | O | 34.7 |
| *Amaranthus gangeticus* | A | S | 73.2 | *Carthamus tinctorius* | A | R | 28.5 |
| *Amaranthus retroflexus* | A | S | 20.4 | *Carum carvi* | A | S | 38.6 |
| *Ambrosia artemisiifolia* | A | R | 50.1 | *Chelidonium majus* | A | O | 27.9 |
| *Amelanchier sanguinea* | A | W | 37.6 | *Chenopodium bonus-henricus* | A | R | 47.4 |
| *Anthemis nobilis* | A | O | 40.4 | *Chenopodium bonus-henricus* | A | O | 20.7 |
| *Anthemis nobilis* | A | R | 66.7 | *Chenopodium bonus-henricus* | A | W | 23.2 |
| *Anthemis tinctorium* | A | S | 30.3 | *chenopodium bonus-henricus* | A | S | 62.8 |
| *Apium graveolens* | A | R | 71.2 | *Chenopodium quinoa* | A | V | 23.1 |
| *Arachis hypogaea* | A | V | 23.5 | *Chenopodium quinoa* | A | W | 34.7 |
| *Aralia cordata* | A | S | 21.2 | *Chrysanthemum leucanthemum* | A | O | 20.6 |
| *Aralia cordata* | A | S | 56.3 | *Chrysanthemum leucanthemum* | A | R | 30.9 |
| *Arctium minus* | A | R | 31.1 | *Chrysanthemun coronarium* (Chp Suey) | A | R | 26.4 |
| *Arctostaphylos uva-ursi* | A | S | 31.2 | *Chrysanthemum coronarium* | A | S | 66.6 |
| *Arctostaphylos uva-ursi* | A | O | 31.2 | *Cichorium intybus* | A | S | 44.7 |
| *Arctostaphylos uva-ursi* | A | R | 59.7 | *Citrullus lanatus* | A | S | 62.1 |
| *Armoracia rusticana* | A | W | 25.1 | *Citrullus lanatus* | A | O | 70.6 |
| *Armoracia rusticana* | A | S | 56.2 | *Cornus canadensis* | A | S | 48.5 |
| *Aronia melanocarpa* | A | S | 26.8 | *Cosmos sulphureus* | A | S | 23.4 |
| *Aronia melanocarpa* | A | S | 41.3 | *Cosmos sulphureus* | A | O | 37.0 |
| *Aronia melanocarpa* | A | O | 44.8 | *Crataegus sp* | A | V | 32.4 |
| *Aronia melanocarpa* | A | W | 47.7 | *Crataegus sp* | A | S | 45.5 |
| *Aronia melanocarpa* | A | R | 55.7 | *Crataegus sp* | A | R | 100.0 |
| *Aronia melanocarpa* | A | V | 100.0 | *Crataegus submollis* | A | S | 45.5 |
| *Arrhenatherum elatius* | A | R | 40.4 | *Cryptotaenia canadensis* | A | W | 26.4 |
| *Artemisia dracunculus* | A | S | 51.1 | *Cucumis Anguria* | A | R | 27.2 |
| *Asparagus officinalis* | A | S | 20.9 | *Cucumis anguria* | A | S | 36.6 |
| *Asparagus officinalis* | A | S | 32.6 | *Cucumis anguria* | A | O | 38.5 |
| *Aster sp* | A | O | 29.5 | *Cucumis melo* | A | O | 59.2 |
| *Aster sp* | A | R | 80.0 | *Cucumis sativus* | A | R | 39.8 |
| *Atropa belladonna* | A | S | 47.4 | *Cucumis sativus* | A | O | 49.4 |
| *Beta vulgaris* | A | S | 25.3 | *Cucumis sativus* | A | S | 54.4 |
| *Beta vulgaris* | A | R | 26.6 | *Cucurbita Maxima* | A | O | 46.7 |
| *Beta vulgaris* | A | W | 34.0 | *Cucurbita moschata* | A | S | 32.1 |

TABLE 4-continued

| | | | MMP-9 | | | | |
|---|---|---|---|---|---|---|---|
| Nom latin | Stress | extrait | Inhibition (%) | Nom latin | Stress | extrait | Inhibition (%) |
| *Beta vulgaris* | A | O | 42.0 | *Cucurbita pepo* | A | O | 37.0 |
| *Beta vulgaris* | A | V | 44.0 | *Curburbita pepo* | A | R | 41.0 |
| *Beta vulgaris* spp. Maritima | A | R | 44.0 | *Curburbita pepo* | A | S | 43.9 |
| *Beta vulgaris* var. condivata | A | R | 35.4 | *Curcuma zedoaria* | A | S | 67.6 |
| *Brassica napus* | A | S | 24.6 | *Levisticum officinale* | A | O | 44.9 |
| *Curcurbita maxima* | A | S | 25.8 | *Linaria vulgaris miller* | A | O | 23.6 |
| *Cymbopogon citratus* | A | O | 26.7 | *Linum usitatissimum* | A | R | 33.3 |
| *Dactylis glomerata* | A | R | 27.2 | *Lolium multiflorum* | A | S | 29.0 |
| *Datisca cannabina* | A | S | 26.9 | *Lolium perenne* | A | R | 52.0 |
| *Datisca cannabina* | A | O | 38.0 | *Lotus corniculatus* | A | R | 62.9 |
| *Daucus carota* | A | R | 30.8 | *Lotus tetragonolobus* | A | S | 62.9 |
| *Daucus carota* | A | O | 31.9 | *Lycopersicon esculentum* | A | S | 26.1 |
| *Dirca palustris* | A | O | 27.3 | *Lycopersicon esculentum* | A | W | 33.0 |
| *Dirca palustris* | A | S | 34.2 | *Malva moschata* | A | S | 31.8 |
| *Dolicos Lablab* | A | S | 22.0 | *Malva sylvestris* | A | S | 21.4 |
| *Dolicos Lablab* | A | R | 25.3 | *Malva verticillata* | A | R | 43.4 |
| *Diyopteris filix-mas* | A | S | 24.9 | *Matteucia pensylvanica* | A | R | 26.9 |
| *Diyopteris filix-mas* | A | R | 40.6 | *Medicago sativa* | A | V | 20.4 |
| *Eleusine coracana* | A | S | 20.2 | *Melilotus albus* | A | R | 53.9 |
| *Eleusine coracana* | A | R | 20.9 | *Melissa officinalis* | A | S | 21.4 |
| *Eleusine coracana* | A | O | 71.1 | *Melissa officinalis* | A | O | 36.8 |
| *Elymus junceus* | A | R | 45.4 | *Melissa officinalis* | A | R | 53.7 |
| *Erigeron canadensis* | A | S | 35.7 | *Mentha piperita* | A | S | 57.7 |
| *Eruca vesicaria* | A | R | 59.9 | *Mentha pulegium* | A | S | 66.1 |
| *Fagopyrum esculentum* | A | V | 20.7 | *Mentha spicata* | A | S | 67.7 |
| *Fagopyrum tartaricum* | A | W | 30.3 | *Mentha suaveolens* | A | S | 51.8 |
| *Fagopyrum tartaricum* | A | O | 33.2 | *Momordica charantia* | A | R | 29.7 |
| *Festuca rubra* | A | R | 31.8 | *Momordica charantia* | A | S | 72.1 |
| *Foeniculum Vulgare* | A | W | 27.4 | *Nicotiana rustica* | A | O | 30.3 |
| *Foeniculum vulgare* | A | O | 50.6 | *Nicotiana rustica* | A | S | 59.1 |
| *Forsythia intermedia* | A | O | 100.0 | *Nicotiana tabacum* | A | S | 39.0 |
| *Fragaria x ananassa* | A | V | 30.0 | *Nicotiana tabacum* | A | W | 47.6 |
| *Fragaria x ananassa* | A | S | 36.3 | *Nicotiana tabacum* | A | O | 100.0 |
| *Galium odoratum* | A | R | 26.9 | *Nigella sativa* | A | R | 59.4 |
| *Gaultheria hispidula* | A | R | 28.4 | *Oenothera biennis* | A | O | 21.3 |
| *Gaultheria hispidula* | A | S | 40.7 | *Oenothera biennis* | A | O | 36.7 |
| *Gentiana lutea* | A | R | 34.7 | *Origanum vulgare* | A | W | 21.3 |
| *Glechoma hederacea* | A | S | 37.6 | *Origanum vulgare* | A | V | 42.7 |
| *Glycine max* | A | R | 38.1 | *Oryza sativa* | A | W | 56.5 |
| *Glycine Max* | A | O | 56.4 | *Oxyria digyna* | A | W | 35.1 |
| *Glycine max* | A | S | 71.4 | *Oxyria digyna* | A | V | 76.4 |
| *Glycyrrhiza glabra* | A | S | 62.6 | *Pastinaca sativa* | A | V | 20.3 |
| *Glycyrrhiza glabra* | A | W | 100.0 | *Pastinaca sativa* | A | W | 23.2 |
| *Guizotia abyssinica* | A | R | 91.9 | *Pastinaca sativa* | A | O | 42.1 |
| *Hamamelis virginiana* | A | S | 41.0 | *Pastinaca sativa* | A | R | 46.9 |
| *Hamamelis virginiana* | A | R | 74.6 | *Phalaris canariensis* | A | R | 20.3 |
| *Hedeoma pulegioides* | A | O | 22.0 | *Phalaris canariensis* | A | O | 80.5 |
| *Helianthus tuberosus* | A | W | 21.2 | *Phaseolus mungo* | A | O | 51.3 |
| *Helianthus tuberosus* | A | W | 51.5 | *Phaseolus mungo* | A | S | 74.1 |
| *Helichrysum angustifolium* | A | V | 21.0 | *Phaseolus vulgaris* | A | V | 23.0 |
| *Heliotropium arborescens* | A | S | 54.1 | *Phaseolus vulgaris* | A | O | 51.4 |
| *Helleborus niger* | A | S | 37.8 | *Phaseolus vulgaris* | A | S | 62.6 |
| *Hordeum hexastichon* | A | W | 38.0 | *Phlox paniculata* | A | O | 41.0 |
| *Hyssopus officinalis* | A | O | 25.1 | *Physalis alkekengi* | A | R | 31.6 |
| *Inula helenium* | A | S | 29.7 | *Physalis ixocarpa* | A | S | 45.2 |
| *Isatis tinctoria* | A | S | 41.5 | *Physalis ixocarpa* | A | O | 65.3 |
| *Lactuca serrila* | A | R | 41.3 | *Physalis Pruinosa* | A | O | 87.3 |
| *Lactuca serriola* | A | S | 46.6 | *Phytolacca americana* | A | S | 49.6 |
| *Laportea Canadensis* | A | S | 26.3 | *Phytolacca americana* | A | O | 89.8 |
| *Lathyrus sativus* | A | O | 22.2 | *Pimpinella anisum* | A | S | 100.0 |
| *Lathyrus sativus* | A | R | 50.2 | *Plantago coronopus* | A | S | 48.3 |
| *Lathyrus sylvestris* | A | V | 31.3 | *Plantago coronopus* | A | O | 89.3 |
| *Lathyrus sylvestris* | A | W | 31.8 | *Plantago major* | A | S | 21.8 |
| *Laurus nobilis* | A | S | 25.7 | *Poa compressa* | A | R | 22.4 |
| *Laurus nobilis* | A | V | 30.0 | *Poa compressa* | A | S | 49.3 |
| *Lavandula latifolia* | A | S | 40.3 | *Poa pratensis* | A | R | 22.4 |
| *Leonurus cardiac* | A | R | 27.0 | *Polygonum pensylvanicum* | A | S | 43.3 |
| *Lepidium sativum* | A | S | 41.8 | *Polygonum persicaria* | A | O | 21.6 |
| *Levisticum officinale* | A | S | 29.0 | *Sium Sisarum* | A | R | 32.6 |
| *Polygonum persicaria* | A | S | 38.5 | *Sium Sisarum* | A | O | 42.7 |
| *Potentilla anserine* | A | S | 26.3 | *Solanum dulcamara* | A | S | 43.3 |
| *Potentilla anserine* | A | O | 31.2 | *Solanum dulcamara* | A | O | 48.6 |

TABLE 4-continued

MMP-9

| Nom latin | Stress | extrait | Inhibition (%) | Nom latin | Stress | extrait | Inhibition (%) |
|---|---|---|---|---|---|---|---|
| *Poterium Sanquisorba* | A | S | 29.2 | *Solanum melanocerasum* | A | O | 21.3 |
| *Pteridium aquilinum* | A | S | 27.3 | *Solanum melongena* | A | R | 20.5 |
| *Raphanus sativus* | A | W | 22.7 | *Solanum melongena* | A | V | 35.6 |
| *Raphanus sativus* | A | R | 30.8 | *Solanum melongena* | A | O | 49.4 |
| *Raphanus sativus* | A | R | 40.2 | *Solanum melongena* | A | S | 65.2 |
| *Raphanus sativus* | A | S | 71.5 | *Solidago sp* | A | R | 32.7 |
| *Raphanus sativus* | A | O | 100.0 | *Spinacia oleracea* | A | S | 41.0 |
| *Rheum rhabarbarum* | A | S | 21.3 | *Stachys affinis* | A | R | 22.5 |
| *Rheum rhabarbarum* | A | V | 67.9 | *Stachys affinis* | A | S | 43.9 |
| *Rheum rhabarbarum* | A | W | 72.4 | *Stachys affinis* | A | O | 92.0 |
| *Ribes nidigrolaria* | A | W | 32.6 | *Symphytum officinale* | A | S | 28.0 |
| *Ribes nidigrolaria* | A | V | 64.6 | *Tanacetum cinerariifolium* | A | O | 20.3 |
| *Ribes nigrum* | A | W | 23.6 | *Tanacetum cinerariifolium* | A | R | 69.7 |
| *Ribes nigrum* | A | V | 27.2 | *Tanacetum vulgare* | A | O | 20.2 |
| *Ribes nigrum* | A | S | 41.0 | *Tanacetum vulgare* | A | S | 84.2 |
| *Ribes nigrum* | A | O | 65.8 | *Teucrium chamaedrys* | A | O | 20.4 |
| *Ribes Nigrum* | A | W | 100.0 | *Teucrium chamaedrys* | A | R | 20.4 |
| *Ribes Salivum* | A | R | 75.4 | *Thymus serpyllum* | A | W | 24.3 |
| *Ribes Sylvestre* | A | V | 27.7 | *Thymus vulgaris* | A | S | 42.5 |
| *Ribes Sylvestre* | A | W | 100.0 | *Thymus x citriodorus* | A | W | 27.4 |
| *ribes uva-crispa* | A | S | 24.4 | *Tragopogon porrifolius* | A | W | 21.9 |
| *Ribes Uva-crispa* | A | W | 36.6 | *Tragopogon porrifolius* | A | V | 26.2 |
| *Ricinus communis* | A | R | 21.6 | *Trifolium hybridum* | A | R | 30.9 |
| *Rosa rugose* | A | V | 30.6 | *Trifolium pannonicum* | A | R | 41.0 |
| *Rosa rugose* | A | S | 36.2 | *Trifolium repens* | A | R | 51.3 |
| *Rosa rugose* | A | W | 39.3 | *Trigonella foenum graecum* | A | S | 44.2 |
| *Rosmarinus officinalis* | A | W | 27.2 | *Triticum spelta* | A | S | 30.0 |
| *Rosmarinus officinalis* | A | R | 45.7 | *Triticum turgidum* | A | S | 31.3 |
| *Rubus alleghenensis* | A | S | 53.7 | *Typha latifolia* | A | S | 57.7 |
| *Rubus Canadensis* | A | V | 27.0 | *Urtica dioica* | A | O | 26.5 |
| *Rubus Canadensis* | A | S | 41.0 | *Urtica dioica* | A | S | 50.2 |
| *Rubus Canadensis* | A | W | 41.2 | *Vaccinium Corymbosum* | A | W | 39.9 |
| *Rubus Canadensis* | A | S | 45.1 | *Vaccinium Corymbosum* | A | S | 64.8 |
| *Rubus idaeus* | A | V | 24.3 | *Vaccinum augustifolium* | A | R | 44.8 |
| *Rubus idaeus* | A | S | 39.7 | *Vaccinum macrocarpon* | A | S | 100.0 |
| *Rubus idaeus* | A | W | 62.2 | *Veratrum virid* | A | S | 29.1 |
| *Rubus ideaus* | A | R | 37.0 | *Veratrum viride* | A | O | 31.8 |
| *Rumex acetosella* | A | V | 75.8 | *Verbascum thapsus* | A | S | 42.6 |
| *Rumex acotosa* | A | W | 25.5 | *Verbascum thapsus* | A | O | 75.2 |
| *Rumex crispus* | A | R | 73.3 | *Viburnum trilobum* | A | V | 97.4 |
| *Rumex crispus* | A | O | 60.5 | *Vicia sativa* | A | R | 53.3 |
| *Rumex patientia* | A | O | 49.4 | *Vicia villosa* | A | R | 48.9 |
| *Rumex patientia* | A | S | 65.8 | *Vigna unguiculata* | A | R | 27.0 |
| *Rumex Scutatus* | A | W | 25.5 | *Vigna unguiculata* | A | O | 44.8 |
| *Rumex Scutatus* | A | V | 61.9 | *Vigna unguiculata* | A | S | 55.5 |
| *Rumex Scutatus* | A | O | 93.8 | *Vinca minor* | A | S | 35.1 |
| *Ruta graveolens* | A | S | 25.8 | *Vitis sp.* | A | V | 52.2 |
| *Ruta graveolens* | A | W | 27.1 | *Vitis sp.* | A | S | 59.6 |
| *Salix purpurea* | A | S | 22.1 | *Vitis sp.* | A | R | 87.8 |
| *Salix purpurea* | A | R | 33.8 | *Xanthium sibiricum* | A | S | 57.1 |
| *Salvia elegans* | A | W | 23.7 | *Zea mays* | A | V | 26.1 |
| *Salvia officinalis* | A | V | 20.8 | *Zea mays* | A | W | 32.1 |
| *Salvia officinalis* | A | S | 31.4 | *Zea Mays* | A | O | 38.7 |
| *Salvia sclarea* | A | S | 28.0 | *Achillea millefolium* | G | S | 45.5 |
| *Satureja montana* | A | W | 21.7 | *Aconitum napellus* | G | S | 24.0 |
| *Scuttellaria lateriflora* | A | S | 54.1 | *Aconitum napellus* | G | O | 53.9 |
| *Secale cereale* | A | V | 22.6 | *Acorus calamus* | G | O | 87.6 |
| *Secale cereale* | A | S | 22.9 | *Acorus calamus* | G | S | 100.0 |
| *Secale cereale* | A | W | 26.9 | *Actinidia arguta* | G | S | 33.8 |
| *Sesamum indicum* | A | O | 21.2 | *Adiantum pedatum* | G | R | 31.6 |
| *Setaria italica* | A | O | 27.0 | *Brassica oleracea* | G | S | 76.1 |
| *Adiantum pedatum* | G | S | 31.7 | *Brassica oleracea* | G | O | 100.0 |
| *Ageratum conyzoides* | G | S | 23.1 | *Brassica rapa* | G | R | 21.1 |
| *Agropyron cristatum* | G | R | 64.1 | *Brassica rapa* | G | S | 64.0 |
| *Agropyron repens* | G | S | 29.2 | *Brassica rapa* | G | O | 100.0 |
| *Agropyron repens* | G | O | 32.6 | *Bromus inermis* | G | R | 36.7 |
| *Agrostis Stolonifera* | G | R | 34.4 | *Campanula rapunculus* | G | O | 59.9 |
| *Alcea rosea* | G | S | 22.7 | *Canna edulis* | G | O | 20.8 |
| *Alchemilla mollis* | G | S | 30.5 | *Canna edulis* | G | O | 83.1 |
| *Alchemilla mollis* | G | W | 33.2 | *Capsicum annuum* | G | R | 20.2 |
| *Allium ampeloprasum* | G | O | 53.4 | *Capsicum annuum* | G | S | 29.6 |
| *Allium cepa* | G | S | 22.5 | *Capsicum annuum* | G | O | 51.5 |
| *Allium cepa* | G | O | 60.7 | *Capsicum annuum* | G | S | 60.8 |
| *Allium schoenoprasum* | G | S | 21.1 | *Capsicum frutescens* | G | S | 32.8 |
| *Allium schoenoprasum* | G | O | 60.4 | *Carthamus tinctorius* | G | R | 29.8 |

TABLE 4-continued

MMP-9

| Nom latin | Stress | extrait | Inhibition (%) | Nom latin | Stress | extrait | Inhibition (%) |
|---|---|---|---|---|---|---|---|
| *Allium tuberosum* | G | S | 38.8 | *Carum carvi* | G | S | 30.4 |
| *Allium tuberosum* | G | O | 74.4 | *Chelidonium majus* | G | O | 39.9 |
| *Althaea officianalis* | G | S | 54.9 | *Chenopodium bonus-henricus* | G | O | 63.0 |
| *Amaranthus caudathus* | G | O | 42.6 | *Chenopodium quinoa* | G | O | 34.1 |
| *Amaranthus caudathus* | G | W | 27.1 | *Chenopodium quinoa* | G | W | 42.8 |
| *Amaranthus gangeticus* | G | S | 56.8 | *Chenopodium quinoa* | G | V | 46.1 |
| *Amaranthus gangeticus* | G | S | 74.4 | *Chichorium endivia* subsp *endivia* | G | W | 22.0 |
| *Ambrosia artemisiifolia* | G | R | 49.0 | *Chichorium endivia* subsp *endivia* | G | S | 22.9 |
| *Amelanchier sanguinea* | G | W | 45.2 | *Chrysanthemum coronarium* | G | R | 23.2 |
| *Angelica archangelica* | G | S | 20.9 | *Chrysanthemum coronarium* | G | S | 68.4 |
| *Anthemis nobilis* | G | R | 58.9 | *Chrysanthemum leucanthemum* | G | R | 20.5 |
| *Apium graveolens* | G | O | 30.4 | *Cicer arietinum* | G | S | 25.7 |
| *Apium graveolens* | G | S | 36.4 | *Cichorium intybus* | G | W | 51.1 |
| *Apium graveolens* | G | R | 60.6 | *Cichorium intybus* | G | S | 53.4 |
| *Arachis hypogaea* | G | W | 26.0 | *Citrullus lanatus* | G | S | 36.5 |
| *Aralia cordata* | G | S | 66.0 | *Citrullus lanatus* | G | O | 71.5 |
| *Arctium minus* | G | O | 26.6 | *Coix Lacryma-Jobi* | G | O | 21.0 |
| *Arctium minus* | G | R | 30.8 | *Cornus canadensis* | G | S | 34.8 |
| *Arctostaphylos uva-ursi* | G | S | 29.3 | *Crataegus* sp | G | W | 54.0 |
| *Arctostaphylos uva-ursi* | G | 0 | 38.8 | *Crataegus submollis* | G | S | 31.3 |
| *Arctostaphylos uva-ursi* | G | R | 80.2 | *Cryptotaenia canadensis* | G | W | 32.1 |
| *Armoracia rusticana* | G | S | 62.7 | *Cucumis anguria* | G | S | 27.3 |
| *Aronia melanocarpa* | G | O | 26.7 | *Cucumis anguria* | G | O | 32.5 |
| *Aronia melanocarpa* | G | V | 100.0 | *Cucumis sativus* | G | O | 39.4 |
| *Aronia melanocarpa* | G | R | 100.0 | *Cucumis sativus* | G | S | 69.4 |
| *Aronia melanocarpa* (Michx.) Ell. | G | W | 39.1 | *Cucurbita maxima* | G | O | 34.1 |
| *Artemisia dracunculus* | G | O | 44.3 | *Cucurbita maxima* | G | S | 42.6 |
| *Artemisia dracunculus* | G | S | 65.4 | *Cucurbita moschata* | G | S | 32.0 |
| *Asclepias incarnata* | G | R | 20.3 | *Cucurbita moschata* | G | O | 39.2 |
| *Asparagus officinalis* | G | O | 22.3 | *Cucurbita pepo* | G | S | 28.8 |
| *Asparagus officinalis* | G | S | 26.6 | *Cucurbita pepo* | G | O | 32.6 |
| *Asparagus officinalis* | G | W | 28.7 | *Curcuma zedoaria* | G | O | 23.3 |
| *Aster* sp | G | O | 34.3 | *Curcuma zedoaria* | G | S | 57.6 |
| *Aster* sp | G | R | 62.6 | *Cymbopogon citratus* | G | O | 70.1 |
| *Atropa belladonna* | G | S | 34.9 | *Cynara scolymus* | G | S | 20.2 |
| *Beta vulgaris* | G | R | 28.3 | *Cynara scolymus* | G | O | 37.5 |
| *Beta vulgaris* | G | R | 42.2 | *Cynara scolymus* | G | R | 88.7 |
| *Beta vulgaris* | G | O | 47.0 | *Cyperus esculentus* | G | S | 66.7 |
| *Beta vulgaris* spp. *Maritima* | G | O | 46.7 | *Datura metel* | G | S | 29.2 |
| *Brassica cepticepa* | G | R | 26.7 | *Datura stramonium* | G | O | 27.6 |
| *Brassica cepticepa* | G | S | 68.3 | *Daucus carota* | G | O | 24.2 |
| *Brassica juncea* | G | O | 45.0 | *Daucus carota* | G | R | 29.3 |
| *Brassica juncea* | G | S | 66.1 | *Dipsacus sativus* | G | S | 48.7 |
| *Brassica Napus* | G | S | 27.5 | *Dirca palustris* | G | O | 29.9 |
| *Brassica Napus* | G | R | 37.6 | *Dirca palustris* | G | S | 36.4 |
| *Brassica napus* | G | O | 94.8 | *Dolichos Lablab* | G | S | 35.8 |
| *Brassica nigra* | G | S | 36.4 | *Dolichos Lablab* | G | R | 74.5 |
| *Brassica oleracea* | G | R | 38.7 | *Diyopteris filix-mas* | G | S | 27.9 |
| *Brassica oleracea* | G | W | 39.0 | *Diyopteris filix-mas* | G | R | 42.6 |
| *Brassica oleracea* | G | R | 49.4 | *Leonurus cardiaca* | G | O | 22.6 |
| *Echinochloa frumentacea* | G | O | 68.4 | *Lepidium sativum* | G | S | 23.3 |
| *Eleusine coracana* | G | O | 47.8 | *Levisticum officinale* | G | S | 23.1 |
| *Elymus junceus* | G | R | 42.7 | *Levisticum officinale* | G | W | 27.5 |
| *Erigeron canadensis* | G | S | 37.8 | *Levisticum officinale* | G | O | 41.3 |
| *Erigeron speciosus* | G | R | 34.6 | *Linum usitatissimum* | G | R | 21.4 |
| *Errhenatherum elatius* | G | R | 34.4 | *Lolium perenne* | G | R | 32.7 |
| *Fagopyrum tartaricum* | G | W | 31.4 | *Lotus corniculatus* | G | R | 54.2 |
| *Foeniculum vulgare* | G | W | 28.0 | *Malus hupehensis* | G | R | 26.4 |
| *Foeniculum vulgare* | G | S | 44.6 | *Malva verticillata* | G | R | 37.9 |
| *Foeniculum vulgare* | G | O | 68.9 | *Matricaria recutita* | G | O | 50.3 |
| *Foeniculum Vulgare* | G | R | 100.0 | *Medicago sativa* | G | W | 29.1 |
| *Forsythia intermedia* | G | O | 100.0 | *Melilotus albus* | G | R | 52.1 |
| *Forsythia x Intermedia* | G | O | 79.5 | *Melissa officinalis* | G | O | 22.7 |
| *Galium odoratum* | G | S | 32.4 | *Melissa officinalis* | G | S | 35.9 |
| *Galium odoratum* | G | R | 100.0 | *Melissa officinalis* | G | R | 38.6 |
| *Gaultheria hispidula* | G | R | 48.4 | *Mentha piperita* | G | S | 64.4 |
| *Gaultheria hispidula* | G | S | 80.4 | *Mentha suaveolens* | G | W | 22.5 |
| *Gaultheria hispidula* | G | O | 100.0 | *Momordica charantia* | G | R | 29.3 |
| *Gaultheria procumbens* | G | S | 26.9 | *Momordica charantia* | G | S | 90.6 |
| *Gaultheria procumbens* | G | W | 54.3 | *Nepeta cataria* | G | R | 50.5 |
| *Glechoma hederacea* | G | S | 26.6 | *Nicotiana rustica* | G | O | 35.3 |
| *Glycine max* | G | R | 52.5 | *Nicotiana rustica* | G | S | 100.0 |
| *Glycine max* | G | O | 67.9 | *Nicotiana tabacum* | G | S | 31.6 |
| *Glycine max* | G | O | 75.8 | *Nicotiana tabacum* | G | O | 100.0 |

TABLE 4-continued

| MMP-9 | | | | | | | |
|---|---|---|---|---|---|---|---|
| Nom latin | Stress | extrait | Inhibition (%) | Nom latin | Stress | extrait | Inhibition (%) |
| Glycyrrhiza glabra | G | R | 21.4 | Nigella sativa | G | R | 24.2 |
| Glycyrrhiza glabra | G | V | 21.6 | Ocimum basilicum | G | S | 30.6 |
| Glycyrrhiza glabra | G | W | 100.0 | Oenothera biennis | G | O | 48.0 |
| Guizotia abyssinica | G | R | 91.4 | Oenothera biennis | G | R | 76.6 |
| Hamamelis virginiana | G | O | 39.8 | Origanum vulgare | G | V | 41.3 |
| Hamamelis virginiana | G | R | 78.8 | Oryza Saliva | G | O | 22.1 |
| Hamamelis virginiana | G | S | 96.6 | Oxyria digyna | G | O | 26.5 |
| Hedeoma pulegioides | G | S | 45.4 | Oxyria digyna | G | V | 70.3 |
| Helenium hoopesii | G | S | 22.6 | Panicum miliaceum | G | O | 94.4 |
| Helenium hoopesii | G | O | 52.8 | Pastinaca sativa | G | R | 29.4 |
| Helianthus annuus | G | R | 22.0 | Pastinaca sativa | G | S | 79.2 |
| Helianthus annuus | G | S | 31.6 | Pennisetum alopecuroides | G | O | 22.0 |
| Helianthus strumosus | G | R | 30.5 | Petasites japonicus | G | S | 29.2 |
| Helianthus strumosus | G | O | 71.7 | Peucedanum oreaselinum | G | O | 21.3 |
| Helianthus tuberosus | G | W | 21.2 | Phacelia tanacetifolia | G | R | 23.5 |
| Helianthus tuberosus | G | S | 50.7 | Phalaris arundinacea | G | R | 47.5 |
| Helianthus tuberosus L. | G | R | 24.9 | Phalaris canariensis | G | R | 23.1 |
| Heliotropium arborescens | G | S | 40.0 | Phalaris canariensis | G | O | 100.0 |
| Heliotropium arborescens | G | O | 45.6 | Phaseolus coccineus | G | O | 37.0 |
| Helleborus niger | G | S | 38.0 | Phaseolus coccineus | G | R | 74.1 |
| Hordeum vulgare | G | S | 21.5 | Phaseolus mungo | G | O | 42.2 |
| Humulus lupulus | G | O | 35.1 | Phaseolus mungo | G | S | 52.2 |
| Hypericum sp | G | W | 26.1 | Phaseolus vulgaris | G | V | 35.5 |
| Hyssopus officinalis | G | S | 74.5 | Phaseolus vulgaris | G | S | 48.0 |
| Iberis amara | G | O | 20.9 | Phaseolus vulgaris | G | O | 58.1 |
| Iberis amara | G | S | 21.7 | Phlox paniculata | G | S | 32.2 |
| Inula helenium | G | S | 27.6 | Phlox paniculata | G | O | 40.1 |
| Ipomoea batatas | G | S | 37.5 | Physalis ixocarpa | G | O | 20.6 |
| Isatis tinctoria | G | S | 48.0 | Physalis pruinosa | G | O | 80.0 |
| Lachica serrola | G | R | 53.0 | Phytolacca americana | G | S | 62.0 |
| Lactuca sativa | G | W | 24.5 | Phytolacca americana | G | O | 100.0 |
| Laportea canadensis | G | S | 36.0 | Pimpinella anisum | G | S | 37.3 |
| Laportea canadensis | G | O | 81.7 | Pisum sativum | G | W | 34.4 |
| Lathyrus sativus | G | W | 37.8 | Pisum sativum | G | O | 63.3 |
| Lathyrus sylvestris | G | R | 40.7 | Plantago coronopus | G | O | 42.7 |
| Lathyrus sylvestris | G | O | 79.1 | Plantago coronopus | G | S | 46.4 |
| Laurus nobilis | G | S | 22.7 | Plantago major | G | O | 28.3 |
| Lavandula angustifolia | G | S | 31.7 | Plantago major | G | S | 41.4 |
| Lavandula latifolia | G | O | 27.2 | Plectranthus sp. | G | S | 29.3 |
| Ledum groenlandicum | G | S | 61.1 | solanum melongena | G | S | 36.6 |
| Poa compressa | G | R | 22.1 | solanum melongena | G | O | 40.1 |
| Poa compressa | G | S | 45.5 | solanum melongena | G | V | 50.0 |
| Poa pratensis | G | R | 35.7 | solanum melongena | G | S | 74.9 |
| Polygonum pensylvanicum | G | S | 38.3 | Solanum tuberosum | G | S | 39.1 |
| Polygonum persicaria | G | S | 31.0 | Solanum tuberosum | G | O | 39.2 |
| Potentilla anserina | G | O | 46.8 | Solidago sp | G | R | 30.7 |
| Poterium sanquisorba | G | S | 24.7 | Sorghum caffrorum | G | O | 87.9 |
| Poterium sanquisorba | G | W | 30.6 | Sorghum dochna | G | W | 20.6 |
| Prunus cerasifera | G | R | 45.9 | Sorghum dochna | G | O | 20.6 |
| Pteridium aquilinum | G | S | 22.4 | Sorghum dochna | G | S | 34.1 |
| Raphanus Raphanistrum | G | S | 36.5 | Sorghum dochna | G | O | 97.0 |
| Raphanus Raphanistrum | G | O | 75.0 | Sorghum durra | G | O | 30.6 |
| Raphanus sativus | G | R | 20.8 | sorghum durra | G | S | 30.6 |
| Raphanus sativus | G | R | 27.5 | sorghum durra | G | O | 48.0 |
| Raphanus sativus | G | S | 35.4 | Sorghum sudanense | G | S | 21.7 |
| Rheum rhabarbarum | G | S | 27.0 | Sorghum sudanense | G | O | 24.6 |
| Ribes Grossularia | G | W | 33.7 | Sorghum sudanense | G | V | 32.1 |
| Ribes nidigrolaria | G | S | 30.7 | Spinacia oleracea | G | S | 53.2 |
| Ribes nidigrolaria | G | V | 40.5 | Stachys Affinis | G | S | 25.0 |
| Ribes nigrum | G | V | 35.9 | Stachys Affinis | G | R | 27.8 |
| Ribes nigrum | G | W | 58.6 | Stachys Affinis | G | O | 100.0 |
| Ribes Silvestris | G | V | 26.9 | Symphytum officinale | G | W | 21.7 |
| Ribes Silvestris | G | W | 100.0 | Symphytum officinale | G | O | 25.2 |
| Ricinus communis | G | R | 21.8 | Symphytum officinale | G | S | 34.6 |
| Rosmarinus officinalis | G | S | 24.7 | Tanacetum cinerariifolium | G | R | 52.4 |
| Rosmarinus officinalis | G | W | 30.9 | Tanacetum vulgare | G | R | 27.1 |
| Rosmarinus officinalis | G | R | 60.3 | Tanacetum vulgare | G | S | 72.7 |
| Rubus ideaus | G | O | 32.5 | Teucrium chamaedrys | G | R | 24.6 |
| Rubus ideaus | G | S | 47.0 | Teucrium chamaedrys | G | O | 52.8 |
| Rubus occidentalis | G | S | 39.4 | Thymus fragantissumus | G | R | 100.0 |
| Rubus occidentalis | G | R | 74.1 | Thymus vulgaris | G | V | 24.2 |
| Rumex acetosa | G | W | 45.6 | Thymus x citriodorus | G | S | 23.7 |
| Rumex acetosella | G | W | 22.8 | Tiarella cordifolia | G | S | 20.8 |
| Rumex acetosella | G | V | 31.5 | Tiarella cordifolia | G | O | 30.8 |
| Rumex crispus | G | O | 25.9 | Tragopogon porrifolius | G | O | 22.8 |

TABLE 4-continued

MMP-9

| Nom latin | Stress | extrait | Inhibition (%) | Nom latin | Stress | extrait | Inhibition (%) |
|---|---|---|---|---|---|---|---|
| *Rumex crispus* | G | R | 70.3 | *Trifolium hybridum* | G | R | 24.7 |
| *Rumex patientia* | G | O | 39.8 | *Trifolium pannonicum* | G | R | 65.5 |
| *Rumex patientia* | G | S | 54.2 | *Trifolium repens* | G | R | 57.5 |
| *Rumex scutatus* | G | W | 23.8 | *Trigonella foenumgraecum* | G | S | 37.6 |
| *Rumex scutatus* | G | V | 69.9 | *Triticum furgidum* | G | S | 56.5 |
| *Rumex scutatus* | G | O | 78.8 | *Triticum spelta* | G | S | 40.8 |
| *Ruta graveolens* | G | R | 30.7 | *Tropaeolum majus* | G | O | 76.1 |
| *Ruta graveolens* | G | S | 61.5 | *Typha latifolia* | G | S | 43.3 |
| *Salvia elagens* | G | W | 25.4 | *Urtica dioica* | G | S | 40.3 |
| *Salvia elegans* | G | S | 31.1 | *Vaccinium angustifolium* | G | S | 42.4 |
| *Sambucus canadensis* | G | W | 80.6 | *Vaccinium corymbosum* | G | S | 61.5 |
| *Sambucus ebulus* | G | W | 26.1 | *Vaccinium macrocarpon* | G | S | 43.7 |
| *Sambucus ebulus* | G | V | 34.4 | *Vaccinum angustifolium* | G | R | 23.1 |
| *Sambucus ebulus* | G | S | 37.8 | *Veratrum viride* | G | S | 43.6 |
| *Sanguisorba officinalis* | G | R | 100.0 | *Verbascum thapsus* | G | S | 37.8 |
| *Santolina chamaecyparissus* | G | R | 21.7 | *Verbascum thapsus* | G | O | 87.0 |
| *Santolina chamaecyparissus* | G | S | 25.2 | *Veronica officinalis* | G | S | 30.5 |
| *Satureja montana* | G | O | 21.2 | *Viburnum trilobum* | G | S | 49.4 |
| *Scuttellaria lateriflora* | G | S | 37.0 | *Viburnum trilobum* | G | R | 100.0 |
| *Secale cereale* | G | S | 26.7 | *Viburnum trilobum* | G | V | 100.0 |
| *Secale cereale* | G | W | 27.3 | *Vicia faba* | G | R | 50.5 |
| *Serratula tinctoria* | G | S | 36.2 | *Vicia sativa* | G | R | 42.4 |
| *Serratula tinctoria* | G | O | 70.3 | *Vicia villosa* | G | R | 89.2 |
| *Sesamum indicum* | G | O | 27.6 | *Vigna angularia* | G | R | 28.1 |
| *Sesamum indicum* | G | S | 44.3 | *Vigna angularia* | G | S | 71.5 |
| *Silybum marianum* | G | S | 34.7 | *Vigna unguiculata* | G | R | 21.0 |
| *Sium sisarum* | G | O | 79.0 | *Vigna unguiculata* | G | O | 38.7 |
| *Solanum dulcamara* | G | R | 25.2 | *Vigna unguiculata* | G | S | 61.1 |
| *Solatium dulcamara* | G | S | 64.6 | *Apium graveolens* | T | W | 32.4 |
| *Vinca minor* | G | O | 33.6 | *Apium graveolens* | T | R | 56.6 |
| *Vinca minor* | G | S | 34.3 | *Aralia cordata* | T | R | 29.2 |
| *Vitis* sp. | G | O | 29.0 | *Aralia cordata* | T | S | 45.0 |
| *Vitis* sp. | G | W | 50.2 | *Arctium minus* | T | R | 25.8 |
| *Vitis* sp. | G | S | 53.3 | *Arctostaphylos uva-ursi* | T | O | 31.0 |
| *Vitis* sp. | G | V | 63.0 | *Arctostaphylos uva-ursi* | T | S | 35.2 |
| *Vitis* sp. | G | R | 86.6 | *Arctostaphylos uva-ursi* | T | R | 58.6 |
| *Withania somnifera* | G | S | 20.3 | *Armoracia rusticana* | T | W | 24.9 |
| *Xanthium sibiricum* | G | S | 34.7 | *Armoracia rusticana* | T | S | 52.9 |
| *Xanthium strumarium* | G | S | 23.2 | *Aronia melanocarpa* | T | W | 40.0 |
| *Zea mays* | G | V | 20.1 | *Aronia melanocarpa* | T | V | 91.9 |
| *Zea mays* | G | S | 45.9 | *Aronia prunifolia* | T | W | 100.0 |
| *Zea mays* | G | O | 97.5 | *Arrhenatherum elatius* | T | R | 22.8 |
| *Abelmochus esculentus* | T | S | 24.8 | *Artemisia draculus* | T | S | 74.9 |
| *Abies lasiocarpa* | T | W | 44.7 | *Artemisia dracunculus* | T | S | 47.8 |
| *Achillea millefolium* | T | O | 24.1 | *Asclepias incarnate* | T | R | 20.5 |
| *Achillea millefolium* | T | S | 59.2 | *Asctinidia chinensis* | T | V | 43.4 |
| *Aconitum napellus* | T | S | 40.6 | *Asctinidia chinensis* | T | O | 66.4 |
| *Aconitum napellus* | T | O | 41.6 | *Asparagus officinalis* | T | O | 91.3 |
| *Acorus calamus* | T | O | 47.1 | *Asparagus officiralis* | T | R | 23.3 |
| *Actinidia arguta* | T | S | 21.8 | *Asparagus officiralis* | T | S | 44.7 |
| *Adiantum pedatum* | T | S | 26.8 | *Aster* Linne | T | S | 47.5 |
| *Adiantum pedatum* | T | O | 45.8 | *Aster* sp | T | R | 62.0 |
| *Adiantum pedatum* | T | R | 86.0 | *Atriplex hortensis* | T | R | 54.6 |
| *Agaricus bisporus* | T | S | 26.3 | *Atropa belladonna* | T | R | 20.1 |
| *Agaricus bisporus* | T | O | 29.8 | *Atropa belladonna* | T | S | 51.0 |
| *Agaricus bisporus* | T | W | 36.9 | *Avena sativa* | T | R | 24.8 |
| *Agaricus bisporus* | T | W | 44.0 | *Avena sativa* | T | W | 26.4 |
| *Agaricus bisporus* | T | S | 46.0 | *Averrhoa carambola* | T | W | 23.4 |
| *Agastache foeniculum* | T | S | 70.0 | *Ayperus esculentus* | T | S | 46.2 |
| *Ageratum conyzoides* | T | S | 31.7 | *Beta vulgaris* | T | R | 28.2 |
| *Agropyron cristatum* | T | R | 86.9 | *Beta vulgaris* | T | S | 30.4 |
| *Agropyron repens* | T | O | 49.6 | *Beta vulgaris* | T | O | 56.8 |
| *Agrostis alba* | T | R | 21.9 | *Beta vulgaris* spp. *Maritima* | T | R | 23.6 |
| *Agrostis Stolonifera* | T | R | 35.8 | *Betula glandulosa* | T | O | 22.2 |
| *Alcea rosea* | T | S | 35.2 | *Betula glandulosa* | T | V | 22.2 |
| *Alchemilla mollis* | T | S | 37.9 | *Betula glandulosa* | T | S | 25.7 |
| *Allium ampeloprasum* | T | O | 48.0 | *Betula glandulosa* | T | W | 32.9 |
| *Allium ascalonicum* | T | S | 26.2 | *Boletus edulis* | T | S | 36.2 |
| *Allium ascalonicum* | T | O | 77.2 | *Boletus edulis* | T | O | 90.2 |
| *Allium cepa* | T | O | 92.6 | *Borago officinalis* | T | S | 27.9 |
| *Allium grande* | T | R | 60.4 | *Borago officinalis* | T | O | 76.1 |
| *Allium schoenoporasum* | T | O | 65.8 | *Brassica cepticepa* | T | O | 65.4 |
| *Allium schoenoprasum* | T | W | 31.0 | *Brassica cepticepa* | T | S | 71.5 |
| *Allium tuberosum* | T | S | 22.8 | *Brassica Chineusis* | T | R | 27.1 |
| *Allium tuberosum* | T | O | 99.7 | *Brassica juncea* | T | O | 51.0 |

TABLE 4-continued

| MMP-9 | | | | | | |
|---|---|---|---|---|---|---|
| Nom latin | Stress | extrait | Inhibition (%) | Nom latin | Stress | extrait | Inhibition (%) |
| Althaea officianalis | T | S | 22.8 | Brassica juncea | T | R | 66.0 |
| Althaea officinalis | T | O | 22.1 | Brassica juncea | T | S | 74.1 |
| Amaranthus candathus | T | W | 43.9 | Brassica Napus | T | S | 22.0 |
| Amaranthus gangeticus | T | O | 30.3 | Brassica Napus | T | R | 34.0 |
| Amaranthus gangeticus | T | S | 66.0 | Brassica Napus | T | O | 100.0 |
| Ambrosia artemisiifolia | T | R | 58.7 | Brassica nigra | T | S | 26.7 |
| Amelanchier alnitolia | T | R | 70.5 | Brassica nigra | T | O | 27.4 |
| Amelanchier sanguinea | T | W | 37.3 | Brassica nigra | T | R | 82.5 |
| Ananas comosus | T | W | 23.8 | Brassica oleracea | T | O | 21.2 |
| Ananas comosus | T | V | 95.0 | Brassica oleracea | T | S | 22.1 |
| Ananas comosus | T | O | 99.6 | Brassica oleracea | T | W | 26.2 |
| angelica archangelica | T | S | 30.5 | Brassica oleracea | T | R | 27.2 |
| angelica archangelica | T | R | 38.9 | Brassica oleracea | T | O | 31.3 |
| Anthemis nobilis | T | O | 41.4 | Brassica oleracea | T | W | 46.5 |
| Anthemis nobilis | T | R | 72.8 | Brassica oleracea | T | S | 71.2 |
| Anthemis tinctorium | T | S | 27.3 | Brassica oleracea | T | O | 93.5 |
| Anthriscus cerefolium | T | W | 35.8 | Brassica rapa | T | R | 25.6 |
| Apium graveolens | T | S | 31.7 | Cucumis melo | T | O | 46.2 |
| Brassica rapa | T | R | 33.9 | Cucumis metuliferus | T | W | 32.0 |
| Brassica rapa | T | R | 56.0 | Cucumis sativus Fanfare | T | O | 40.3 |
| Brassica rapa | T | S | 69.7 | Cucurbita maxima | T | S | 23.6 |
| Brassica rapa | T | O | 100.0 | Cucurbita maxima | T | S | 33.1 |
| Bromus inermis | T | R | 57.3 | Cucurbita maxima | T | O | 55.2 |
| Campanula rapunculus | T | O | 77.5 | Cucurbita moschata | T | S | 20.1 |
| Canna edulis | T | O | 75.6 | Cucurbita moschata | T | S | 26.7 |
| Cantharellus ciparium | T | O | 52.5 | Cucurbita moschata | T | O | 41.7 |
| Capsella bursa-pastoris | T | O | 35.9 | Cucurbita pepo | T | S | 41.9 |
| Capsicum annus | T | S | 43.9 | Cucurbita pepo | T | O | 82.9 |
| Capsicum annuum | T | S | 50.1 | Curcuma zedoaria | T | S | 100.0 |
| Capsicum frutescens | T | S | 28.9 | Cydonia oblonga | T | W | 42.9 |
| Carica papaya | T | W | 31.1 | Cynara scolymus | T | R | 51.6 |
| Carthamus tinctorius | T | R | 37.3 | Cynara scolymus | T | S | 60.9 |
| Carum carvi | T | S | 30.1 | Dactilis Glomerata | T | R | 25.7 |
| Castanea spp. | T | W | 21.7 | Datura stramonium | T | R | 21.9 |
| Chaerophyllum bulbosum | T | S | 46.0 | Daucus carota | T | R | 25.9 |
| Chamaemelum nobile | T | W | 36.8 | Dioscorea batatas | T | O | 47.6 |
| Chamaemelum nobile | T | W | 48.4 | Dioscorea batatas | T | O | 83.1 |
| Chelidonium majus | T | O | 46.6 | Diospiros Kaki | T | W | 34.9 |
| Chenapodium bonus-henricus | T | R | 22.4 | Dirca palustris | T | S | 27.6 |
| Chenopodium bonus-henricus | T | S | 57.6 | Dirca palustris | T | O | 90.4 |
| Chenopodium quinoa | T | V | 35.5 | Dolichus lablab | T | R | 66.4 |
| Chenopodium quinoa | T | W | 54.4 | Dolichus lablab | T | O | 85.3 |
| Chrysanthemum leucanthemum | T | R | 26.5 | Diyopteris filix-mas | T | S | 21.9 |
| Chrysanthemun coronarium (Chp suey) | T | R | 48.4 | Diyopteris filix-mas | T | R | 77.9 |
| Chrysanthemum coronarium | T | R | 38.2 | Echinacea purpurea | T | S | 48.6 |
| Chrysanthemum coronarium | T | S | 63.9 | Eleusine coracana | T | O | 45.2 |
| Cicer arietinum | T | S | 20.0 | Elymus junceus | T | R | 41.0 |
| Cichorium endivia | T | S | 25.6 | Erigeron canadensis | T | S | 31.4 |
| Cichorium endivia crispa | T | O | 38.4 | Eriobotrya japonica | T | W | 28.3 |
| Cichorium intybus | T | S | 30.2 | Eruca vesicaria | T | R | 44.9 |
| Cimicifuga racemosa | T | S | 33.7 | Fagopyrum esculentum | T | W | 76.7 |
| Citrullus colocynthus | T | S | 20.4 | Fagopyrum tartaricum | T | W | 42.6 |
| Citrullus lanatus | T | O | 68.3 | Festuca rubra | T | R | 29.6 |
| Citrullus lanatus | T | S | 31.9 | Festuca rubra | T | S | 42.9 |
| Citrus limettoides | T | W | 20.4 | Foeniculum vulgare | T | V | 22.1 |
| Citrus limettoides | T | V | 37.5 | Foericulum vulgare | T | S | 21.6 |
| Citrus limon | T | V | 47.7 | Foericulum vulgare | T | O | 84.8 |
| Citrus limon | T | O | 72.4 | Forsythia intermedia | T | O | 70.8 |
| Citrus paradisi | T | W | 23.8 | Forsythia x intermedia | T | O | 60.2 |
| Citrus paradisi | T | V | 33.4 | Fortunella spp | T | S | 35.7 |
| Citrus reticulata | T | V | 20.4 | Fortunella spp | T | W | 50.7 |
| Citrus reticulata | T | V | 20.9 | Fortunella spp | T | O | 74.5 |
| Citrus reticulata | T | W | 26.0 | Fragaria | T | W | 24.8 |
| Citrus reticulata | T | S | 40.4 | Fragaria | T | V | 52.4 |
| Citrus reticulata | T | O | 50.0 | Fragaria | T | O | 100.0 |
| Citrus reticulata | T | O | 79.2 | Fragaria x ananassa | T | S | 29.3 |
| Citrus sinensis | T | W | 25.3 | Galium odoratum | T | R | 26.0 |
| Citrus sinensis | T | V | 59.8 | Gaultheria hispidula | T | W | 40.3 |
| Coix Laciyma-Tobi | T | W | 20.0 | Ginkgo biloba | T | V | 27.0 |
| Corchorus olitorius | T | S | 38.9 | Ginkgo biloba | T | W | 68.9 |
| Cornus canadensis | T | S | 35.6 | Glechoma hederacea | T | R | 20.4 |
| Cosmos sulphureus | T | S | 51.4 | Glechoma hederacea | T | S | 30.4 |
| Cratagus sp | T | V | 28.0 | Glycine max | T | O | 26.6 |

TABLE 4-continued

| MMP-9 | | | | | | | |
|---|---|---|---|---|---|---|---|
| Nom latin | Stress | extrait | Inhibition (%) | Nom latin | Stress | extrait | Inhibition (%) |
| Crataegus sp | T | R | 60.9 | Glycine max | T | R | 47.4 |
| Crataegus submollis | T | O | 25.5 | Glycine max | T | S | 82.0 |
| Crithmum maritima | T | S | 50.6 | Glycyrrhiza glabra | T | S | 35.4 |
| Cryptotaenia canadensis | T | O | 21.2 | Glycyrrhiza glabra | T | O | 40.5 |
| Cryptotaenia canadensis | T | W | 26.0 | Glycyrrhiza glabra | T | W | 100.0 |
| Cryptotaenia canadensis | T | V | 40.0 | Gossypium herbaceum | T | S | 36.1 |
| Cucumis anguria | T | S | 38.7 | Guizotia abyssinica | T | R | 28.9 |
| Cucumis anguria | T | O | 46.6 | Guizotia abyssinica | T | S | 40.4 |
| Cucumis melo | T | S | 30.3 | Malus | T | V | 44.4 |
| Hamamelis virginiana | T | O | 52.4 | Malus hupehensis (Pamp.) Rehd. | T | R | 26.3 |
| Hamamelis virginiana | T | S | 67.5 | Malus hupehensis (Pamp.) Rehd. | T | S | 67.0 |
| Hamamelis virginiana | T | R | 84.1 | Malus sp. | T | R | 65.3 |
| Hedeoma pulegiodes | T | S | 57.4 | Malva moschata | T | S | 41.1 |
| Helenium hoopesii | T | O | 33.7 | Malva sylvestris | T | S | 36.4 |
| Helenium hoopesii | T | S | 49.0 | Malva sylvestris | T | O | 47.4 |
| Helianthus annus | T | S | 53.4 | Malva verticillata | T | R | 42.7 |
| Helianthus strumosus | T | R | 20.3 | Mangifera indica | T | O | 30.5 |
| Helianthus strumosus | T | O | 71.7 | Manihot esculenta syn. M. utilissima | T | W | 38.3 |
| Helianthus tuberosa | T | W | 22.8 | Manihot esculenta syn. M. utilissima | T | S | 50.4 |
| Helianthus tuberosus L. | T | V | 22.6 | Manihot esculenta syn. M. utilissima | T | O | 86.5 |
| Helianthus tuberosus L. | T | S | 55.0 | Melilotus alba | T | R | 30.4 |
| Helichrysum angustifolium | T | S | 67.0 | Melilotus officinalis | T | R | 68.1 |
| Heliotropium arborescens | T | S | 58.9 | Melissa officinalis | T | S | 33.7 |
| Helleborus niger | T | S | 31.9 | Melissa officinalis | T | O | 34.7 |
| Hibiscus cannabinus | T | S | 48.9 | mentha arvensis | T | R | 53.7 |
| Hordeum vulgare | T | S | 29.2 | Mentha suaveolens | T | S | 26.8 |
| Humulus lupulus | T | W | 22.4 | Menyanthes trifoliata | T | S | 32.8 |
| Humulus lupulus | T | R | 39.1 | Miscanthus sinensis Andress | T | R | 22.7 |
| Humulus lupulus | T | O | 63.1 | Momordica charantia | T | S | 55.5 |
| Humulus lupulus | T | S | 100.0 | Monarda didyma | T | S | 26.8 |
| Hydrastis canadensis | T | S | 20.2 | Monarda fistulosa | T | S | 21.5 |
| Hydrastis canadensis | T | W | 31.0 | Montia perfoliata | T | R | 26.6 |
| Hyoscyamus niger | T | O | 56.8 | Musa paradisiaca | T | W | 29.0 |
| Hypericum henryi | T | O | 48.8 | nasturtium officinale | T | S | 35.4 |
| Hypericum perforatum | T | S | 48.1 | Nepeta cataria | T | W | 26.5 |
| Hypericum perforatum | T | O | 63.7 | Nepeta cataria | T | O | 27.5 |
| Hypomyces lactiflorum | T | S | 44.8 | Nepeta cataria | T | S | 41.9 |
| Hypomyces lactiflorum | T | O | 60.9 | Nephelium longana ou Euphoria longana | T | W | 43.4 |
| Hyssops officinalis | T | W | 22.9 | Nicotiana rustica | T | O | 26.0 |
| Inula helenium | T | S | 24.6 | Nicotiana rustica | T | S | 32.7 |
| Juniperus communis | T | S | 33.0 | Nicotiana tabacum | T | S | 25.1 |
| Juniperus communis | T | O | 38.2 | Nicotiana tabacum | T | O | 77.7 |
| Lactuca sativa | T | S | 44.5 | Nigella sativa | T | R | 59.3 |
| Lactuca sativa | T | R | 50.7 | Nigella sativa | T | R | 100.0 |
| Laportea canadensis | T | S | 30.2 | Ocimum Basilicum | T | W | 20.2 |
| Lathyrus Sativus | T | O | 20.4 | Ocimum Basilicum | T | V | 20.2 |
| Lathyrus Sativus | T | R | 52.5 | Ocimum Basilicum | T | S | 32.8 |
| Lathyrus sylvestris | T | W | 27.7 | Oenothera biennis linne | T | R | 100.0 |
| Lathyrus sylvestris | T | O | 36.8 | Onobrychis viciafolia | T | R | 45.0 |
| Laurus nobilis | T | S | 52.0 | Optunia sp. | T | W | 33.4 |
| Lavendula angustifolia | T | W | 26.4 | Origanum marjonara | T | O | 20.5 |
| Lavendula angustifolia | T | S | 53.2 | Origanum vulgare | T | O | 20.8 |
| Lavendula latifolia | T | S | 51.3 | Origanum vulgare | T | W | 21.6 |
| Ledum groenlandicum | T | S | 44.4 | Oryza sativa | T | W | 42.4 |
| Lentinus edodes | T | W | 42.1 | oxyria digyna | T | O | 57.0 |
| Lentinus edodes | T | O | 100.0 | oxyria digyna | T | V | 77.9 |
| Lepidium sativum | T | S | 44.2 | Panax quinquefolius L. | T | O | 23.5 |
| Levisticum officinale | T | S | 20.8 | Panicum miliaceum | T | W | 36.5 |
| Levisticum officinale | T | O | 39.4 | Passiflora spp | T | S | 35.8 |
| Linum usitatissimum | T | R | 42.3 | Passiflora spp | T | V | 38.3 |
| Litchi chinensis | T | W | 25.7 | Passiflora spp | T | W | 46.2 |
| Lolium multiflorum | T | S | 20.6 | Passiflora spp | T | O | 100.0 |
| Lolium perenne | T | R | 28.7 | Pastinaca sativa | T | O | 21.7 |
| Lonicera ramosissima | T | S | 26.3 | Pastinaca sativa | T | R | 38.6 |
| Lonicera ramosissima | T | O | 40.4 | Pastinaca sativa | T | S | 39.2 |
| Lonicera ramosissima | T | W | 53.2 | Persea americana | T | V | 32.5 |
| Lonicera syringantha | T | W | 95.8 | Persea americana | T | O | 38.6 |
| Lotus comiculatus | T | R | 100.0 | Petasites Japonicus | T | S | 26.2 |
| Lotus tetragonolubus | T | S | 65.4 | Phalaris canariensis | T | O | 80.0 |
| Lunaria annua | T | O | 55.7 | Phaseolus coccineus | T | S | 44.4 |
| Lunaria annua | T | S | 67.3 | Phaseolus coccineus | T | R | 79.1 |
| Lycopersicon esculentum | T | R | 37.6 | Phaseolus mungo | T | S | 27.0 |
| Malus | T | W | 31.8 | Raphanus sativus | T | W | 38.1 |
| Phaseolus mungo | T | O | 37.9 | Raphanus sativus | T | S | 63.6 |

TABLE 4-continued

| MMP-9 | | | | | | |
|---|---|---|---|---|---|---|
| Nom latin | Stress | extrait | Inhibition (%) | Nom latin | Stress | extrait | Inhibition (%) |
| *Phaseolus vulgaris* | T | R | 20.1 | *Raphanus sativus* | T | O | 93.4 |
| *Phaseolus vulgaris* | T | S | 51.9 | *Reseda luteola* | T | S | 22.5 |
| *Phaseolus vulgaris* | T | O | 61.7 | *Rhamnus frangula* | T | S | 34.2 |
| *Phlox paniculata* | T | S | 22.9 | *Rhamnus frangula* | T | R | 39.5 |
| *Phlox paniculata* | T | O | 44.5 | *Rheum officinale* | T | S | 100.0 |
| *Phoenix dactylifera* | T | O | 29.6 | *Rheum palmatum* | T | W | 20.2 |
| *Physalis alkekengi* | T | R | 32.9 | *Rheum rhabarbarum* | T | S | 33.8 |
| *Physalis ixocarpa* | T | R | 26.6 | *Rianus communis* | T | S | 20.9 |
| *Physalis ixocarpa* | T | O | 28.3 | *Ribes nidigrolaria* | T | W | 44.5 |
| *Physalis pruinosa* | T | S | 27.3 | *Ribes nidigrolaria* | T | V | 53.1 |
| *Physalis pruinosa* | T | R | 47.8 | *Ribes nigrum* | T | S | 40.7 |
| *Physalis pruinosa* | T | O | 93.1 | *Ribes nigrum* L. | T | W | 50.0 |
| *Physalis* sp | T | W | 39.1 | *Ribes nigrum* L. | T | V | 60.1 |
| *Physalis* sp | T | V | 60.8 | *Ribes sativam* syme | T | W | 47.9 |
| *Phytolacca americana* | T | S | 41.8 | *Ribes Sativum* | T | R | 48.2 |
| *Phytolacca americana* | T | O | 100.0 | *Ribes Silvestre* | T | V | 26.3 |
| *Phytolacca decandra* syn. *P. americana* | T | O | 85.9 | *Ribes Silvestre* | T | W | 100.0 |
| *Pimpinella anisum* | T | S | 20.2 | *Ribes uva-crispa* | T | O | 57.5 |
| *Pimpinella anisum* | T | O | 68.4 | *Rosa rugosa* | T | S | 27.8 |
| *Pisum sativum* | T | W | 20.1 | *Rosa rugosa thunb.* | T | W | 37.5 |
| *Pisum sativum* | T | S | 25.8 | *Rosa rugosa thunb.* | T | V | 45.7 |
| *Pisum sativum* | T | V | 27.0 | *Rosmarinum officinalis* | T | R | 44.2 |
| *Pisum sativum* | T | O | 51.8 | *Rosmarinum officinalis* | T | W | 65.9 |
| *Plantago coronopus* | T | R | 21.9 | *Rubus canadensis* | T | S | 45.5 |
| *Plantago coronopus* | T | O | 48.6 | *Rubus idaeus* | T | W | 31.4 |
| *Plantago coronopus* | T | S | 66.8 | *Rubus idaeus* | T | V | 57.2 |
| *Plantago major* | T | S | 35.1 | *Rubus ideaus* | T | S | 28.5 |
| *Pleurotus* spp | T | W | 25.3 | *Rubus ideaus* | T | O | 38.0 |
| *Pleurotus* spp | T | S | 59.3 | *Rubus occidentalis* | T | O | 21.4 |
| *Pleurotus* spp | T | O | 85.2 | *Rubus occidentalis* | T | S | 36.5 |
| *Poa compressa* | T | R | 26.2 | *Rubus occidentalis* | T | R | 60.2 |
| *Poa pratensis* | T | O | 21.5 | *Rumes scutatus* | T | O | 84.5 |
| *Poa pratensis* | T | R | 30.0 | *Rumex crispus* linne | T | O | 52.5 |
| *Podophyllum peltatum* | T | O | 33.9 | *Rumex crispus* linne | T | R | 100.0 |
| *Podophyllum peltatum* | T | S | 50.2 | *Rumex patientia* | T | O | 23.1 |
| *Polygonum aviculare* linne | T | R | 31.0 | *Rumex patientia* | T | S | 65.8 |
| *Polygonum pennsylvanicum* | T | S | 56.6 | *Ruta graveolens* | T | S | 37.2 |
| *Polygonum persicaria* | T | S | 20.1 | *Sabal serrulata* syn. *Serenoa repens* | T | V | 34.4 |
| *Populus incrassata* | T | W | 54.9 | *Sabal serrulata* syn. *Serenoa repens* | T | S | 44.6 |
| *Populus Tremula* | T | W | 31.0 | *Salix purpurea* | T | R | 67.8 |
| *Populus* x *petrowskyana* | T | W | 100.0 | *Salvia* (elegens) | T | O | 51.1 |
| *Potentilla anserina* | T | S | 22.1 | *Sambucus canadensis* | T | S | 44.8 |
| *Potentilla anserina* | T | O | 41.1 | *Sambucus canadensis* | T | O | 72.4 |
| *Prunus cerasus* | T | V | 30.1 | *Sambucus canadensis* L. | T | W | 67.8 |
| *Prunus persica* | T | W | 26.6 | *Sambucus ebulus* | T | V | 44.3 |
| *Prunus persica* | T | V | 38.5 | *Sanguisorba officinalis* | T | R | 100.0 |
| *Prunus* spp | T | S | 24.0 | *Santolina* | T | R | 37.9 |
| *Prunus* spp | T | V | 49.1 | *Satureja montana* | T | S | 20.0 |
| *Psidium guajaba* | T | V | 22.5 | *Satureja montana* | T | O | 21.3 |
| *Psidium guajaba* | T | W | 44.3 | *Satureja repandra* | T | S | 36.3 |
| *Psidium guajaba* | T | O | 95.4 | *Scorzorera hipanica* | T | R | 27.1 |
| *Psidium* spp | T | S | 36.6 | *Scorzorera hipanica* | T | S | 31.7 |
| *Psidium* spp | T | W | 47.6 | *Scuttellaria lateriflora* | T | S | 44.3 |
| *Psidium* spp | T | O | 87.6 | *Secale cereale* | T | S | 24.2 |
| *Pteridium aquilinum* | T | R | 22.0 | *Secale cereale* | T | W | 31.1 |
| *Punica granatum* | T | V | 52.1 | *Sechium edule* | T | S | 37.8 |
| *Pyrus communis* | T | V | 39.5 | *Sesamum indicum* | T | S | 59.2 |
| *Pyrus pyrifolia* | T | W | 33.7 | *Setaria italica* | T | W | 33.0 |
| *Raphanus raphanistrum* | T | O | 24.5 | *Silybum marianum* | T | O | 92.4 |
| *Raphanus raphanistrum* | T | S | 44.8 | *Slum sisarum* | T | O | 32.7 |
| *Raphanus raphanistrum* | T | S | 46.1 | *Slum sisarum* | T | S | 33.1 |
| *Raphanus sativus* | T | V | 25.4 | *Sium sisarum* | T | O | 81.3 |
| *Raphanus sativus* | T | R | 32.1 | *Vaccinium angustifolium* | T | R | 34.6 |
| | | | | *Vaccinium angustifolium* | T | O | 59.6 |
| *Solanum melogena* | T | O | 21.9 | *Vaccinium angustifolium* | T | R | 65.7 |
| *solanum melogena* | T | V | 26.1 | *Vaccinium macrocarpon* | T | O | 30.2 |
| *Solanum melogena* | T | R | 34.0 | *Vaccinium macrocarpon* | T | S | 39.0 |
| *Solanum melogena* | T | S | 67.1 | *Vaccinium macrocarpon* | T | S | 56.9 |
| *Solanum Tuberosum* | T | O | 68.6 | *Vaccinum macrocarpon* | T | V | 39.2 |
| *Solidago canadensis* | T | S | 48.4 | *Vaccinum macrocarpon* | T | W | 42.3 |
| *Solidago* sp | T | R | 31.4 | *Veratrum viride* | T | O | 20.5 |
| *Solidago virgaurea* | T | S | 56.2 | *Veratrum viride* | T | S | 33.1 |
| *Sorghum caffrorum* | T | O | 23.3 | *Verbascum thapsus* | T | S | 43.1 |

TABLE 4-continued

MMP-9

| Nom latin | Stress | extrait | Inhibition (%) | Nom latin | Stress | extrait | Inhibition (%) |
|---|---|---|---|---|---|---|---|
| *Sorghum dochna bicolor* gr *technicum* | T | W | 20.8 | *Verbascum thapsus* | T | O | 70.2 |
| *Sorghum dochna Snowdrew* | T | S | 21.4 | *Veronica officinalis* | T | O | 20.5 |
| *Sorghum dochna Snowdrew* | T | O | 27.7 | *Viburnum trilobum* Marsh. | T | S | 40.6 |
| *Spinacia oleracea* | T | V | 25.0 | *Vicia faba* | T | R | 61.5 |
| *Spinacia oleracea* | T | W | 32.1 | *Vicia sativa* | T | R | 30.1 |
| *Spinacia oleracea* | T | S | 47.6 | *Vigna angularia* | T | R | 32.6 |
| *Spinacia oleracea* | T | O | 63.1 | *Vigna angularia* | T | S | 64.2 |
| *Stachys affinis* | T | R | 31.7 | *Vigna unguiculata* | T | R | 32.4 |
| *Stachys affinis* | T | O | 100.0 | *Vigna unguiculata* | T | O | 47.4 |
| *Stachys byzantina* | T | W | 30.9 | *Vigna unguiculata* | T | S | 51.0 |
| *Stipa capiliata* L. | T | R | 20.1 | *Vinca minor* | T | S | 21.3 |
| *Symphytum officinale* | T | S | 24.1 | *Vitis* sp. | T | V | 28.3 |
| *Tanacetum cinerarifolium* | T | O | 24.2 | *Vitis* sp. | T | O | 29.4 |
| *Tanacetum cinerarifolium* | T | R | 84.4 | *Vitis* sp. | T | S | 45.4 |
| *Tanacetum vulgare* | T | R | 25.7 | *Vitis* sp. | T | V | 50.7 |
| *Tanacetum vulgare* | T | S | 75.6 | *Vitis* sp. | T | W | 61.6 |
| *Taraxacum officinale* (Red ribe) | T | S | 21.1 | *Vitis* sp. | T | R | 100.0 |
|  |  |  |  | *Weigela coracensis* | T | W | 35.5 |
| *Tepary* | T | R | 56.7 | *Withania somnifera* | T | S | 35.5 |
| *Teucrium chamaedrys* L. | T | R | 27.3 | *Xanthium sibiricum* | T | S | 38.6 |
| *Thalpsi arvense* | T | S | 61.4 | *Xanthium strumarium* | T | S | 33.5 |
| *Thymus fragantissumus* | T | R | 100.0 | *Zea mays* | T | S | 37.1 |
| *Thymus herba-barona* | T | W | 22.0 | *Zea mays* | T | O | 65.5 |
| *Thymus pseudolanuginosus* | T | R | 36.8 | *Zingiber officinale* | T | S | 20.1 |
| *Thymus pseudolanuginosus* | T | S | 37.1 | *Zingiber officinale* | T | W | 58.9 |
| *Thymus serpyllum* | T | S | 26.0 | *Zingiber officinale* | T | O | 75.9 |
| *Thymus serpyllum* | T | W | 42.7 |  |  |  |  |
| *Thymus x citriodorus* | T | O | 22.7 |  |  |  |  |
| *Tiarella cordifolia* | T | R | 100.0 |  |  |  |  |
| *Tragopogon porrifolius* | T | V | 26.8 |  |  |  |  |
| *Tragopogon porrifolius* | T | O | 28.4 |  |  |  |  |
| *Tragopogon porrifolius* | T | S | 42.1 |  |  |  |  |
| *Tragopogon* sp. | T | O | 20.3 |  |  |  |  |
| *Tragopogon* sp. | T | S | 32.0 |  |  |  |  |
| *Tragopogon* sp. | T | W | 66.3 |  |  |  |  |
| *Trichosanthes kirilowii* | T | O | 66.5 |  |  |  |  |
| *Trifolium incarnatum* | T | R | 47.9 |  |  |  |  |
| *Trifolium repens* | T | R | 81.7 |  |  |  |  |
| *Trigonella foenum graecum* | T | S | 39.6 |  |  |  |  |
| *Triticale* sp. | T | O | 64.1 |  |  |  |  |
| *Triticum aestivum* | T | W | 24.5 |  |  |  |  |
| *Triticum aestivum* | T | S | 29.4 |  |  |  |  |
| *Triticum furgidumm* | T | S | 35.8 |  |  |  |  |
| *Triticum spelta* | T | S | 34.7 |  |  |  |  |
| *Tropaeolum majus* | T | O | 90.3 |  |  |  |  |
| *Tropaeolum malus* | T | W | 20.1 |  |  |  |  |
| *Tsuga canOadensis* | T | O | 21.5 |  |  |  |  |
| *Tsuga canOadensis* | T | W | 64.4 |  |  |  |  |
| *Tsuga diversifolia* | T | O | 45.9 |  |  |  |  |
| *Tsuga diversifolia* | T | W | 100.0 |  |  |  |  |
| *Tsuga F. macrophylla* | T | W | 28.1 |  |  |  |  |
| *Typha latifolia* L. | T | S | 30.6 |  |  |  |  |
| *Urtica dioica* | T | O | 31.4 |  |  |  |  |
| *Urtica dioica* | T | R | 36.9 |  |  |  |  |
| *Urtica dioica* | T | S | 41.7 |  |  |  |  |
| *Vaccinium angustifolium* | T | V | 25.2 |  |  |  |  |

TABLE 5

Cath B

| Nom latin | Stress | extrait | Inhibition (%) | Nom latin | Stress | extrait | Inhibition (%) |
|---|---|---|---|---|---|---|---|
| *Achillea millefolium* | A | O | 61.9 | *Cichorium intybus* | A | R | 100.0 |
| *Achillea tomentosa* | A | O | 60.8 | *Citrullus lanatus* | A | O | 24.4 |
| *Aconitum* | A | O | 38.6 |  |  |  |  |
| *Aconitum napellus* | A | O | 61.1 | *Convallaria maialis* | A | O | 57.0 |
| *Alchemilla mollis* | A | R | 26.7 |  |  |  |  |
| *Allium* | A | R | 43.0 | *Coriandrum* | A | R | 20.8 |

TABLE 5-continued

Cath B

| Nom latin | Stress | extrait | Inhibition (%) | Nom latin | Stress | extrait | Inhibition (%) |
|---|---|---|---|---|---|---|---|
| Allium cepa gr. Cepa | A | O | 49.9 | sativum Cryptotaenia canadensis | A | O | 20.4 |
| Allium cepa gr. Cepa | A | O | 70.1 | Cucumis Anguria | A | O | 26.8 |
| Allium cepa gr. Cepa | A | R | 45.8 | Cucumis sativus | A | R | 45.6 |
| Allium sativum | A | O | 25.6 | Curburbita pepo | A | O | 30.8 |
| Allium Tuberosum | A | O | 91.5 | Daucus carota | A | R | 68.8 |
| Allium Tuberosum | A | O | 75.0 | Daucus carota | A | O | 20.3 |
| Allium victorialis | A | O | 31.1 | Daucus carota | A | R | 72.5 |
| Amaranthus gangeticus | A | O | 26.1 | Daucus carota | A | O | 22.6 |
| Amaranthus gangeticus | A | O | 29.0 | Daucus carota | A | O | 25.6 |
| Amelanchier canadensis | A | R | 28.7 | Daucus carota | A | R | 65.9 |
| Anthemis tinctoria | A | O | 26.8 | Daucus carota | A | R | 77.3 |
| Anthemis tinctoria | A | R | 32.4 | Daucus carota | A | R | 41.6 |
| Anthoxanthum odoratum | A | O | 24.9 | Dirca palustris | A | R | 100.0 |
| Apium graveolens | A | O | 31.1 | Eruca vesicaria | A | O | 41.4 |
| Apium graveolens | A | O | 20.6 | Filipendula rubra | A | R | 65.0 |
| Aralia cordata | A | R | 52.3 | Forsythia intermedia | A | R | 100.0 |
| Arctium lappa | A | O | 33.7 | Forsythia x intermedia | A | R | 100.0 |
| Arctium lappa | A | R | 33.0 | Geum rivale | A | O | 26.4 |
| Aronia melanocarpa (Michx.) Ell. | A | R | 41.2 | Glycyrrhiza glabra | A | R | 86.8 |
| Aronia melanocarpa (Michx.) Ell. | A | O | 21.6 | Heliotropium arborescens | A | O | 29.5 |
| Asarum europaeum | A | O | 24.9 | Humulus Lupulus | A | O | 65.4 |
| Athaea officinalis | A | O | 57.7 | Humulus Lupulus | A | R | 100.0 |
| Athyrium asperum | A | O | 27.3 | Hylotelephium | A | R | 23.7 |
| Atropa belladonna | A | O | 37.7 | Hypericum henryl | A | R | 44.4 |
| Begonia convolvulacea | A | O | 26.0 | Iberis sempervirens | A | O | 84.6 |
| Begonia eminii | A | O | 34.2 | Jeffersonia diphylla | A | O | 35.4 |
| Begonia glabra | A | O | 38.9 | Ligularia dentata | A | O | 30.3 |
| Begonia Hannii | A | O | 52.9 | Lonicera ramosissima | A | R | 48.7 |
| Begonia polygonoides | A | O | 67.3 | Miscanthus sacchariflorus | A | O | 50.9 |
| Berberis vulgaris | A | O | 54.6 | Nicotiana tabacum | A | O | 40.0 |
| Beta vulgaris | A | R | 39.9 | Nicotiana tabacum | A | O | 56.8 |
| Beta vulgaris | A | R | 30.4 | Nicotiana tabacum | A | O | 55.2 |
| Beta vulgaris | A | O | 61.9 | Nigella sativa | A | O | 40.3 |
| Beta vulgaris | A | O | 43.0 | Origanum majorana | A | O | 49.7 |
| Beta vulgaris | A | R | 91.0 | Origanum vulgare | A | O | 67.0 |
| Beta vulgaris | A | O | 46.7 | Origanum vulgare | A | O | 39.9 |
| Beta vulgaris | A | R | 65.3 | Panax quinquefolius L. | A | O | 24.0 |
| Beta vulgaris | A | R | 33.4 | Pastinaca sativa | A | R | 33.5 |
| Beta vulgaris | A | O | 54.3 | Petroselinum crispum | A | O | 70.2 |
| Beta vulgaris | A | O | 38.2 | Peucedanum cervaria | A | O | 21.5 |
| Beta vulgaris | A | R | 55.9 | Phaseolus Vulgaris | A | O | 67.9 |
| Beta vulgaris | A | R | 28.5 | Philadelphus coronarius | A | O | 24.0 |
| Beta vulgaris | A | O | 40.1 | Physostegia virginiana | A | O | 56.9 |
| Beta vulgaris spp. Maritima | A | O | 33.4 | Phytolacca | A | O | 100.0 |
| Brassica juncea | A | O | 21.3 | Plantago major | A | O | 31.2 |
| Brassica Oleracea | A | O | 27.5 | | | | |
| Brassica Oleracea | A | O | 48.2 | | | | |
| Brassica rapa | A | O | 20.8 | | | | |
| Calendula officinalis | A | O | 35.6 | | | | |
| Camellia sinensis syn. Thea sinensis | A | R | 24.4 | | | | |
| Cana edulis | A | R | 100.0 | | | | |
| Capsicum annuum | A | O | 25.0 | | | | |
| Capsicum frutescens | A | O | 29.6 | | | | |
| Chrysanthemum balsamita | A | O | 89.3 | | | | |
| Chrysanthemun balsamina | A | O | 55.0 | | | | |

TABLE 5-continued

| Cath B | | | | | | |
|---|---|---|---|---|---|---|
| Nom latin | Stress | extrait | Inhibition (%) | Nom latin | Stress | extrait | Inhibition (%) |
| Chrysanthemun coronarium (Chp Suey) | A | O | 30.1 | Plectranthus fruticosus | A | O | 32.1 |
| Chrysanthemun coronarium (Chp Suey) | A | O | 36.4 | Polygonum pennsylvanicum | A | R | 70.1 |
| Salvia sclarea | A | O | 21.5 | Pulmonaria saccharata | A | O | 31.1 |
| Saponaria officinalis | A | O | 68.5 | Raphanus sativus | A | O | 21.5 |
| Satureja montana | A | O | 47.6 | Raphanus sativus | A | O | 50.5 |
| Scorzonera hispanica | A | O | 29.9 | Raphanus sativus | A | O | 58.9 |
| Sesamum indicum | A | O | 84.8 | Ribes nigrum L. | A | O | 53.1 |
| Solanum dulcamara | A | O | 51.3 | Rubus Allegheniensis | A | O | 56.7 |
| Solidago canadensis | A | O | 95.3 | Rubus ideaus | A | R | 89.0 |
| Solidago hybrida | A | O | 94.5 | Rumex crispus linné | A | R | 65.2 |
| Solidago hybrida | A | O | 99.5 | Salvia elegens | A | O | 32.6 |
| Solidago sp ? | A | O | 60.9 | Salvia nemorosa | A | O | 26.2 |
| Stellaria graminea linné | A | O | 40.2 | Salvia officianalis | A | O | 26.3 |
| Tamarindus indica | A | O | 59.2 | Salvia sclarea | A | R | 51.6 |
| Taraxacum officinale | A | O | 88.6 | Daucus carota | G | O | 27.2 |
| Thalictrum aquilegiifolium | A | O | 65.2 | Dirca palustris | G | R | 100.0 |
| Thalictrum Aquilegiifolium | A | O | 44.5 | Echinacea purpurea | G | O | 22.9 |
| Thuja occidentalis | A | O | 50.6 | Equisetum hyemale | G | O | 100.0 |
| Thymus praecox subsp arctitus | A | O | 23.9 | Erigeron canadensis | G | O | 73.3 |
| Tiarella | A | R | 34.4 | Erigeron speciosus (Lindl.) D.C. | G | O | 22.9 |
| Vaccinum augustifolium | A | R | 67.2 | | | | |
| Vaccinum macrocarpon | A | R | 37.1 | Eruca vesicaria | G | O | 29.2 |
| Vitia sp. | A | R | 93.7 | Erysimum perofskianum | G | O | 89.8 |
| Xanthium strumarium | A | O | 83.2 | Fish. S. Fenouil bronze | G | R | 23.7 |
| Yucca filamentosa | A | O | 34.5 | Filipendula rubra | G | R | 93.2 |
| Zea mays | A | O | 29.7 | Filipendula rubra | G | R | 100.0 |
| Zea mays | A | O | 93.2 | Filipendula ulmaria | G | O | 20.5 |
| Achillea tomentosa | G | O | 41.0 | Filipendula vulgaris | G | O | 26.2 |
| Adiantum tenerum | G | R | 30.2 | | | | |
| Alcea rosea | G | O | 37.7 | | | | |
| Alchemilla mollis | G | R | 32.8 | | | | |
| Allium schoenoporasum | G | O | 49.3 | Forsythia intermedia | G | R | 100.0 |
| Allium tuberosum | G | O | 79.1 | Forsythia x intermedia | G | R | 100.0 |
| Allium tuberosum | G | O | 77.4 | | | | |
| Allium victorialis | G | O | 45.5 | | | | |
| Althaea officinalis | G | O | 67.2 | Galium odoratum | G | O | 21.0 |
| amaranthus gangeticus | G | O | 23.5 | Gaultheria hispidula (L.) Muhl | G | R | 39.3 |
| Anaphalis margaritacea | G | R | 34.7 | | | | |
| Angelica dahurica | G | R | 27.9 | Gaultheria procumbens | G | R | 43.4 |
| Anthemis nobilis | G | O | 42.3 | | | | |
| Apium graveolens | G | O | 25.7 | Geum rivale | G | O | 21.7 |
| Apium graveolens | G | O | 27.4 | Glycine max | G | O | 64.2 |
| Arctostaphylos uva-ursi | G | R | 94.5 | Glycyrrhiza glabra | G | R | 53.4 |
| Aronia melanocarpa | G | R | 74.5 | Hamamelis virginiana | G | R | 88.4 |
| Aronia melanocarpa | G | 0 | 21.3 | Heliotropium arborescens | G | O | 23.0 |
| Aronia melanocarpa (Michx.) Ell. | G | R | 79.9 | Humulus lupulus | G | R | 100.0 |
| Aronia melanocarpa (Michx.) Ell. | G | R | 28.3 | Humulus lupulus | G | O | 90.2 |
| | | | | Hydrastis canadensis | G | O | 30.9 |
| Asarum europaeum | G | O | 55.4 | Hylotelephium | G | R | 43.8 |
| | | | | Hypericum | G | R | 50.3 |

TABLE 5-continued

Cath B

| Nom latin | Stress | extrait | Inhibition (%) | Nom latin | Stress | extrait | Inhibition (%) |
|---|---|---|---|---|---|---|---|
| *Atropa belladonna* | G | O | 58.9 | *henryi* | | | |
| *Begonia eminii* | G | O | 24.7 | *Iberis sempervirens* | G | O | 87.7 |
| *Begonia glabra* | G | O | 42.9 | | | | |
| *Begonia manii* | G | O | 32.1 | *Lathyrus sativus* | G | R | 25.9 |
| *Begonia polygonoides* | G | O | 38.2 | *Ligularia dentata* | G | O | 31.5 |
| *Berberis vulgaris* | G | O | 42.3 | | | | |
| *Beta vulgaris* | G | R | 75.3 | *Lunaria annua* | G | O | 59.7 |
| *Beta vulgaris* | G | O | 28.7 | *Lythrum salicaire* | G | R | 33.1 |
| *Beta vulgaris* | G | O | 21.7 | | | | |
| *Beta vulgaris* | G | R | 40.0 | *Melissa officinalis* | G | O | 27.6 |
| *Beta vulgaris* spp. Maritima | G | O | 31.4 | *Miscanthus sacchariflorus* | G | O | 30.7 |
| *Betula glandulosa* | G | R | 38.5 | | | | |
| *Calendula officinalis* | G | O | 36.2 | *Nicotiana rustica* | G | O | 54.8 |
| *Capsicum annus* | G | O | 49.9 | *Nicotiana tabacum* | G | O | 36.2 |
| *Chrysanthemum balsamita* | G | O | 100.0 | *Nigella sativa* | G | O | 40.3 |
| *Chrysanthemum balsamina* | G | O | 33.1 | *Origan* | G | O | 98.8 |
| | | | | *Origanum majorana* | G | O | 48.9 |
| *Cynara scolymus* | G | O | 51.9 | | | | |
| *Daucus carota* | G | O | 81.3 | *Panax quinquefolius* L. | G | O | 21.1 |
| *Silene vulgaris* | G | O | 35.5 | | | | |
| *Solanum dulcamara* | G | O | 56.9 | *Panicum miliaceum* | G | R | 100.0 |
| *Solidago canadensis* | G | O | 99.8 | *Passiflora caerula* | G | | 66.2 |
| *Solidago canadensis* | G | O | 100.0 | *Petroselinum crispum* | G | | 65.0 |
| *Solidago* sp ? | G | O | 71.8 | *Phaseolus vulgaris* | G | R | 40.3 |
| *Sorghum caffrorum* | G | O | 34.5 | *Physostegia virginiana* | G | O | 74.0 |
| *Tamarindus indica* | G | O | 65.4 | | | | |
| *Taraxacum officinale* | G | O | 82.7 | *Phytolacca americana* | G | O | 100.0 |
| *taraxacum officinale* | G | O | 42.7 | *Plantago major* | G | O | 60.9 |
| | | | | *Plectranthus fruticosus* | G | O | 29.2 |
| *Tetradenia riparia* | G | O | 32.5 | | | | |
| *Thalictrum aquilegiifolium* | G | O | 62.1 | *Polygonum aviculare linné* | G | R | 45.6 |
| *Thuja occidentalis* | G | O | 57.7 | *Pongamia pinnata* | G | O | 41.7 |
| *Thymus vulgaris* "Argenteus" | G | O | 40.7 | *Pulmonaria officinalis* | G | O | 36.9 |
| *Tiarella* | G | R | 39.0 | | | | |
| *Tropaeolum majus* | G | O | 36.6 | *Pulmonaria saccharata* | G | O | 24.7 |
| *Tussilago farfara* | G | O | 26.8 | | | | |
| *Vaccinium angustifolium* | G | R | 26.4 | *Raphanus sativus* | G | O | 38.9 |
| *Vaccinium angustifolium* | G | R | 89.1 | *Raphanus sativus* | G | O | 86.4 |
| *Vaccinum macrocarpon* | G | R | 33.9 | *Rhus aromatica* | G | O | 49.1 |
| | | | | *Ribes nigrum* L. | G | O | 20.6 |
| *Vitia* sp. | G | R | 100.0 | *Rubus ideaus* | G | R | 56.9 |
| *Vitia* sp. | G | R | 90.9 | *Rubus occidentalis* | G | R | 61.3 |
| *Vitis* sp. | G | O | 37.1 | | | | |
| *Achillea millefolium* | T | O | 44.1 | *Saponaria officinalis* | G | O | 48.3 |
| *Aconitum napelius* | T | O | 27.4 | *Sarriette vivace* | G | O | 44.6 |
| *Aesculus hippocastanum* | T | R | 84.2 | *Satureja repandra* | G | O | 72.3 |
| *Aesculus hippocastanum* | T | O | 47.3 | *Sesamum indicum* | G | O | 46.8 |
| *Alcea rosea* "Nigra" | T | O | 24.3 | *Sidalcea* | G | O | 55.2 |
| | | | | *Aubepine, hawthorne* | T | R | 72.7 |
| *Alchemilla mollis* | T | R | 24.9 | | | | |
| *Allium ascalonicum* | T | O | 31.1 | *Begonia convolvulacea* | T | O | 32.1 |
| *Allium cepa* gr. Cepa | T | O | 39.4 | *Begonia eminii* | T | O | 40.4 |
| | | | | *Begonia glabra* | T | O | 84.3 |
| *Allium cepa* gr. Cepa | T | R | 23.2 | *Begonia manii* | T | O | 64.2 |
| | | | | *Berberus vulgaris* | T | O | 35.4 |
| *Allium cepa* gr. Cepa | T | O | 45.5 | | | | |
| | | | | *Beta vulgaris* | T | O | 34.1 |
| *Allium fistulosum* | T | O | 21.9 | *Beta vulgaris* | T | R | 86.7 |

TABLE 5-continued

| Cath B | | | | | | |
|---|---|---|---|---|---|---|
| Nom latin | Stress | extrait | Inhibition (%) | Nom latin | Stress | extrait | Inhibition (%) |
| *Allium grande* | T | O | 39.5 | *Beta vulgaris* | T | O | 23.8 |
| *Allium tuberosum* | T | O | 26.6 | *Beta vulgaris* | T | R | 79.4 |
| *Allium tuberosum* | T | O | 33.1 | *Beta vulgaris* | T | O | 34.2 |
| *Allium tuberosum* | T | O | 72.3 | *Beta vulgaris* | T | R | 20.8 |
| *Allium tuberosum* | T | R | 22.6 | *Beta vulgaris* | T | R | 37.0 |
| *Allium victorialis* | T | O | 42.3 | *Beta vulgaris* | T | R | 83.6 |
| *Alpinia oficinarum* | T | O | 57.4 | spp. *Maritima* | | | |
| *Alpinia oficinarum* | T | R | 88.9 | *Betula glandulosa* | T | R | 62.5 |
| *Althacea officinalis* | T | O | 51.5 | *Borago officinalis* | T | O | 23.5 |
| *Althaea* | T | O | 25.2 | | | | |
| *Amelanchier canadensis* | T | O | 20.8 | *Brassica Napus* | T | O | 27.6 |
| | | | | *Brassica oleracea* | T | O | 21.8 |
| *Amelanchier canadensis* | T | R | 42.1 | *Brassica oleracea* | T | O | 22.3 |
| *Amsonia tabernaemontana* | T | O | 30.2 | *Butomus umbellatus* | T | O | 20.8 |
| *Ananas comosus* | T | R | 36.2 | | | | |
| *Anaphalis margaritacea* | T | R | 33.9 | *Canna edulis* | T | R | 100.0 |
| | | | | cannelle | T | R | 99.5 |
| *Angelica dahurica* | T | R | 40.7 | *Carica papaya* | T | R | 100.0 |
| *Angelica sinensis* syn. *A. polymorpha* | T | O | 91.0 | *Chrysanthemum balsamita* | T | O | 89.3 |
| | | | | *Chrysanthemum parthenium* | T | R | 44.6 |
| *Anthriscus cerefolium* | T | R | 23.3 | *chrysanthemun coronarium* (Chp Suey) | T | O | 28.7 |
| *Anthriscus cerefolium* | T | O | 21.7 | | | | |
| *Aralia cordata* | T | R | 44.1 | *chrysanthemun coronarium* (Chp Suey) | T | O | 59.2 |
| *Aronia melanocarpa* | T | R | 33.1 | | | | |
| *Aronia melanocarpa* | T | R | 100.0 | *Citrus paradisi* | T | R | 100.0 |
| | | | | *Citrus sinensis* | T | R | 100.0 |
| *Aronia melanocarpa* (Michx.) Ell. | T | R | 35.0 | *Cocos nucifera* | T | R | 100.0 |
| | | | | *Cocos nucifera* | T | O | 71.9 |
| | | | | *Convallaria majalis* | T | O | 67.1 |
| *Aronia prunifolia* | T | R | 50.4 | | | | |
| *Artemisia draculus* | T | O | 42.5 | *Corchorus olitorius* | T | R | 26.0 |
| *Asarum europaeum* | T | O | 39.4 | | | | |
| | | | | *Crataegus sanguinea* | T | O | 33.1 |
| *Asclepias incarnata* L. | T | O | 48.7 | *Cryptotaenia canadensis* | T | R | 23.1 |
| *Asclepias tuberosa* | T | O | 21.5 | | | | |
| *Asctinidia chinensis* | T | O | 24.9 | *Cucumis anguria* | T | O | 26.4 |
| *Atriplex hortensis* | T | O | 22.4 | *Cucumis sativus* (Fanfare) | T | O | 25.7 |
| *Atropa belladonna* | T | O | 94.1 | | | | |
| *Iberis sempervirens* | T | O | 90.8 | *Cydonia oblonga* | T | R | 23.6 |
| *Jeffersonia diphylla* | T | O | 43.0 | *Datura stramonium* | T | O | 61.4 |
| *Juglans nigra* | T | R | 66.7 | *Daucus carota* | T | R | 21.1 |
| *Kochia scoparia* (L.) Schrad. | T | O | 38.4 | *Diospiros Kaki* | T | R | 100.0 |
| | | | | *Echinacea purpurea* | T | O | 27.8 |
| *Krameria Triandra* | T | R | 63.6 | *Eriobotrya japonica* | T | R | 25.2 |
| *Lentinus edodes* | T | R | 100.0 | | | | |
| *Lentinus edodes* | T | R | 26.2 | *Eruca vesicaria* | T | O | 34.5 |
| *Ligularia dentata* | T | O | 34.9 | *Erysimum perofskianum* | T | O | 91.0 |
| *Ligustrum vulgare* | T | O | 29.5 | | | | |
| *Lunaria annua* | T | O | 72.3 | Fish. S. | | | |
| *Lunaria annua* | T | R | 51.1 | *Fragaria x ananassa* | T | R | 37.5 |
| *Lupinus polyphyllus lind* L. | T | O | 47.4 | *Fucus vesiculosis* | T | R | 87.1 |
| *Lychnis chalcedonica* | T | O | 34.4 | *Fumaria officianalis officinalis* | T | O | 44.4 |
| *Lythrum salicaire* | T | R | 53.8 | | | | |
| *Mangifera indica* | T | R | 100.0 | | | | |
| *Mangifera indica* | T | O | 29.3 | *Gaultheria procumbens* | T | R | 74.8 |
| *Nigella sativa* | T | O | 26.1 | | | | |
| Nil | T | O | 73.6 | *Gentiana macrophylla* | T | O | 44.5 |
| Nil | T | R | 25.4 | | | | |
| Nil | T | R | 24.6 | *Glyceria maxima* | T | O | 37.6 |
| Nil | T | R | 49.8 | | | | |
| Nil | T | O | 43.6 | *Glycine max* | T | O | 40.3 |

TABLE 5-continued

Cath B

| Nom latin | Stress | extrait | Inhibition (%) | Nom latin | Stress | extrait | Inhibition (%) |
|---|---|---|---|---|---|---|---|
| Nil | T | R | 28.4 | Envy | | | |
| Optunia sp. | T | R | 100.0 | Glycyrrhiza glabra | T | R | 37.7 |
| Panax quinquefolius L. | T | O | 27.4 | Hamamelis virginiana | T | R | 78.3 |
| Passiflora caerula | T | O | 39.8 | | | | |
| Pastinaca sativa | T | O | 20.5 | Helichrysum angustifolium | T | R | 21.8 |
| Perroselinum crispum | T | O | 60.9 | Heliotropium arborescens | T | O | 26.8 |
| Phaseolus vulgaris | T | O | 37.5 | | | | |
| Physostegia virginiana | T | O | 64.2 | Humulus lupulus | T | R | 84.7 |
| Phytolacca americana | T | O | 51.9 | Humulus lupulus | T | O | 39.2 |
| Phytolacca americana | T | O | 100.0 | Humulus lupulus | T | O | 100.0 |
| Plectranthus fruticosus | T | O | 23.4 | Humulus lupulus | T | R | 100.0 |
| Polygonatum odoratum | T | O | 100.0 | Hydrastis canadensis | T | 1 | 42.7 |
| Polygonium chinense | T | R | 33.6 | Hypericum henryi | T | R | 51.8 |
| Pontederia cordata | T | O | 26.2 | Hypericum perforatum | T | O | 52.3 |
| Portulacea oleracea | T | O | 20.7 | Hypomyces lactiflorum | T | O | 30.1 |
| Primula veris | T | O | 58.2 | Silene vulgaris | T | O | 51.3 |
| Prunus persica | T | R | 100.0 | Solidago | T | O | 92.8 |
| Prunus persica (hybride de la peche) | T | R | 100.0 | hybrida Solidago Hybrida | T | O | 100.0 |
| Pulmonaria officinalis | T | O | 22.8 | Solidago Hybrida | T | R | 100.0 |
| Punica granatum | T | R | 100.0 | Solidago sp ? | T | O | 39.6 |
| Pyrus pyrifolia | T | R | 22.4 | Tamarindus indica | T | O | 64.2 |
| Radix Paeonia rubra | T | O | 39.8 | Tanacetum balsamila | T | O | 100.0 |
| Rahmnus frangula | T | R | 25.3 | | | | |
| Raphanus sativus | T | O | 45.8 | Tanacetum vulgare | T | O | 23.3 |
| Rhus trilobata | T | O | 20.2 | | | | |
| Ribes uva-crispa | T | R | 34.2 | Taraxacum officinale | T | O | 90.9 |
| Rosa Rugosa "Alba" | T | O | 45.4 | Taraxacum officinale (Red ribe) | T | O | 34.5 |
| Rubus idaeus | T | R | 31.2 | | | | |
| Rubus idaeus L. | T | O | 42.7 | | | | |
| Rubus ideaus | T | R | 74.2 | Thuja occidentalis | T | O | 37.6 |
| Rubus occidentalis | T | R | 68.1 | | | | |
| Rumex crispus linné | T | R | 37.9 | Thymus serpyllum | T | O | 20.6 |
| Salvia nemorosa | T | O | 38.2 | Tiarella | T | R | 35.6 |
| Sambucus canadensis | T | O | 27.5 | Tragopogon sp. | T | R | 21.1 |
| | | | | Trigonella foenum graecum | T | R | 97.3 |
| Sambucus nigra | T | O | 30.8 | | | | |
| Sanguisorba minor | T | R | 78.3 | | | | |
| Saponaria officinalis | T | O | 68.7 | Tropaeolum majus | T | O | 58.8 |
| Saponaria officinalis L. | T | O | 44.2 | Tropaeolum majus | T | R | 28.6 |
| Satureja hortensis | T | O | 62.1 | Tropaeolum majus | T | O | 36.7 |
| Sechium edule | T | O | 34.4 | | | | |
| Sesamum indicum | T | O | 78.6 | Tsuga diversifolia | T | R | 64.0 |
| Sidalcea | T | O | 42.9 | | | | |
| | | | | Vaccinium angustifolium | T | R | 72.2 |
| | | | | Vaccinium angustifolium | T | R | 50.7 |
| | | | | Vaccinium macrocarpon | T | R | 52.6 |
| | | | | Vitia sp. | T | O | 35.1 |
| | | | | Vitia sp. | T | R | 98.9 |
| | | | | Vitis sp. | T | R | 32.6 |
| | | | | Weigela coracensis | T | R | 24.6 |
| | | | | Zea mays | T | R | 100.0 |
| | | | | Zea mays | T | R | 48.1 |

TABLE 6

Cath D

| Nom latin | Stress | extrait | Inhibition (%) | Nom latin | Stress | extrait | Inhibition (%) |
|---|---|---|---|---|---|---|---|
| *Agastache foeniculum* | A | O | 91.6 | *Citrullus lanatus* | A | R | 35.9 |
| *Agropyron cristatum* | A | O | 24.5 | *Citrullus lanatus* | A | O | 76.5 |
| *Agropyron repens* | A | O | 75.2 | *Coix Lacryma-Jobi* | A | O | 20.9 |
| *Agrostis Stofonifera* | A | O | 94.7 | *Coix Lacryma-Jobi* | A | O | 93.2 |
| *Alchemilla mollis* | A | O | 39.0 | *Cornus canadensis* | A | O | 30.9 |
| *Allium sativum* | A | R | 100.0 | *Cuburbita pepo* | A | O | 21.9 |
| *Allium schoenoprasum* | A | R | 40.0 | *Cucumis melo* | A | O | 44.1 |
| *Althaea officinalis* | A | O | 96.5 | *Cucumis sativus* | A | O | 21.3 |
| *Amaranthus gangeticus* | A | R | 67.4 | *Cucumis sativus* | A | R | 33.3 |
| *Amaranthus gangeticus* | A | O | 74.3 | *Cucurbita Maxima* | A | R | 100.0 |
| *Amaranthus retroflexus* | A | O | 100.0 | *Cucurbita moschata* | A | R | 20.5 |
| *Ambrosia artemisiifolia* | A | O | 75.4 | *Cucurbita pepo* | A | O | 31.9 |
| *Anethum graveolens* | A | O | 48.7 | *Cucurbita pepo* | A | R | 40.9 |
| *Angelica archangelica* | A | O | 27.6 | *Cucurbita pepo* | A | O | 41.2 |
| *Anthemis nobilis* | A | O | 56.2 | *Curcuma zedoaria* | A | O | 26.3 |
| *Anthemis tinctoria* | A | S | 42.3 | *Cymbopogon martinii* | A | O | 77.8 |
| *Aralia cordata* | A | R | 100.0 | *Daucus carota* | A | O | 55.1 |
| *Aralia nudicaulis* | A | R | 44.9 | *Daucus carota* | A | R | 100.0 |
| *Arctium minus* | A | O | 93.2 | *Dipsacus sativus* | A | O | 21.1 |
| *Arctium minus* | A | O | 100.0 | *Elymus junceus* | A | O | 27.7 |
| *Aronia melanocarpa* | A | O | 22.8 | *Eschscholzia califomica* | A | O | 44.4 |
| *Artemisia abrotanum* | A | O | 31.3 | *Foeniculum vulgare* | A | O | 81.8 |
| *Artemisia abrotanum* | A | O | 43.6 | *Forsythia intermedia* | A | O | 40.4 |
| *Artemisia absinthium* | A | O | 58.3 | *Forsythia intermedia* | A | R | 100.0 |
| *Artemisia Absinthium* | A | O | 71.4 | *Fragaria x ananassa* | A | R | 38.5 |
| *Artemisia dracunculus* | A | O | 70.5 | *Galinsoga ciliata* | A | O | 46.7 |
| *Artemisis Ludoviciana* | A | O | 74.4 | *Galium odoratum* | A | O | 21.6 |
| *Artemisis Ludoviciana* | A | O | 100.0 | *Galium odoratum* | A | R | 22.7 |
| *Asparagus officinalis* | A | O | 61.9 | *Gaultheria hispidula* | A | R | 71.9 |
| *Aster sp* | A | O | 100.0 | *Gaultheria hispidula* | A | O | 90.2 |
| *Aster sp* | A | O | 100.0 | *Gentiana lutea* | A | R | 100.0 |
| *Atropa belladonna* | A | O | 100.0 | *Glechoma hederacea* | A | O | 32.7 |
| *Beckmannia eruciformis* | A | R | 22.1 | *Glycine max* | A | S | 55.1 |
| *Beckmannia eruciformis* | A | O | 48.3 | *Glycine max* | A | R | 100.0 |
| *Beta vulgaris* | A | R | 21.2 | *Glycyrrhiza glabra* | A | R | 100.0 |
| *Beta vulgaris* | A | R | 100.0 | *Guizotia abyssinica* | A | O | 73.8 |
| *Beta vulgaris* spp. *Maritima* | A | O | 30.8 | *Hedeoma pulegioides* | A | O | 100.0 |
| *Betta vulgaris* | A | O | 100.0 | *Helianthus tuberosus* | A | O | 37.2 |
| *Brassica napus* | A | R | 63.6 | *Hordeum hexastichon* | A | R | 34.6 |
| *Brassica oleracea* | A | R | 33.3 | *Hordeum hexastichon* | A | O | 63.6 |
| *Brassica rapa* | A | R | 23.8 | *Hordeum vulgare* | A | O | 66.7 |
| *Brassica rapa* | A | O | 26.1 | *Hordeum vulgare* subsp. *Vulgare* | A | O | 33.3 |
| *Bromus inermis* | A | O | 59.6 | *Hypericum henryi* | A | O | 66.7 |
| *Calamintha nepeta* | A | R | 24.0 | *Hyssopus officinalis* | A | O | 100.0 |
| *Campanula rapunculus* | A | O | 41.6 | *Ipomoea Batatas* | A | O | 55.1 |
| *Canna edulis* | A | O | 100.0 | *Iris versicolor* | A | R | 24.1 |
| *Capsella bursa-pastoris* | A | O | 36.7 | *Iris versicolor* | A | O | 30.8 |
| *Capsicum annuum* | A | R | 25.8 | *Lathyrus sativus* | A | O | 20.6 |
| *Capsicum annuum* | A | R | 28.2 | *Laurus nobilis* | A | O | 33.3 |
| *Capsicum annuum* | A | O | 64.7 | *Levisticum officinale* | A | O | 87.6 |
| *Capsicum annuum* | A | R | 76.9 | *Linum usitatissimum* | A | R | 21.4 |
| *Capsicum frutescens* | A | O | 44.1 | *Linum usitatissimum* | A | O | 44.4 |
| *Carthamus tinctorius* | A | O | 42.9 | *Lolium perenne* | A | O | 30.9 |
| *Carum carvi* | A | R | 28.6 | *Lotus corniculatus* | A | O | 23.4 |
| *Chaerophyllum bulbosom* | A | O | 100.0 | *Lycopersicon esculentum* | A | R | 40.0 |
| *Chelidonium majus* | A | R | 100.0 | *Matricaria recutita* | A | S | 56.4 |
| *chenopodium bonus-henricus* | A | O | 54.3 | *Medicago sativa* | A | R | 20.5 |
| *Chenopodium quinoa* | A | R | 22.2 | *Melissa officinalis* | A | O | 100.0 |
| *Chrysanthemum coronarium* | A | O | 96.8 | *Mentha piperita* | A | O | 22.7 |
| *Cichorium endivia* susp. *Endivia* | A | R | 36.0 | *Mentha piperita* | A | R | 100.0 |
| *Cichorium endivia* susp. *Endivia* | A | O | 78.4 | *Mentha suaveolens* | A | O | 53.2 |
| *Cichorium intybus* | A | O | 100.0 | *Nepeta cataria* | A | O | 100.0 |
| *Citrullus lanatus* | A | O | 22.7 | *Nicotiana tabacum* | A | O | 37.7 |
| *Citrullus lanatus* | A | R | 26.7 | *Solanum melanocerasum* | A | S | 44.6 |
| *Nicotiana tabacum* | A | R | 44.3 | *Solanum melanocerasum* | A | R | 60.0 |
| *Oenothera biennis* | A | O | 23.8 | *Solanum tuberosum* | A | O | 29.2 |
| *Oenothera biennis* | A | O | 40.0 | *Solidago sp* | A | O | 98.4 |
| *Oenothera biennis* | A | R | 100.0 | *Spinacia oleracea* | A | O | 40.5 |
| *Origanum vulgare* | A | O | 94.7 | *Spinacia oleracea* | A | S | 57.7 |
| *Panax quinquefolius* | A | O | 29.8 | *Stachys affinis* | A | O | 23.8 |
| *Panax quinquefolius* | A | O | 35.1 | *Stachys byzantina* | A | O | 96.1 |
| *Panax quinquefolius* | A | O | 40.4 | *Stellaria graminea* | A | O | 34.4 |
| *Pastinaca sativa* | A | O | 74.4 | *Stellaria media* | A | O | 24.6 |
| *Perilla frutescens* | A | O | 86.7 | *Symphytum officinale* | A | O | 87.7 |
| *Perilla frutescens* | A | R | 100.0 | *Symphytum officinale* | A | O | 100.0 |

TABLE 6-continued

Cath D

| Nom latin | Stress | extrait | Inhibition (%) | Nom latin | Stress | extrait | Inhibition (%) |
|---|---|---|---|---|---|---|---|
| Petasites japonicus | A | O | 43.5 | Tanacetum cinerariifolium | A | O | 70.7 |
| Petroselinum crispum | A | O | 100.0 | Tanacetum parthenium | A | R | 40.0 |
| Phalaris arundinacea | A | O | 21.3 | Tanacetum parthenium | A | O | 74.7 |
| Phalaris canariensis | A | O | 22.0 | Tanacetum parthenium | A | R | 100.0 |
| Phaseolus coccineus | A | O | 68.8 | Tanacetum vulgare | A | O | 26.7 |
| Phaseolus mungo | A | S | 58.5 | Tanacetum vulgare | A | R | 32.7 |
| Phaseolus mungo | A | O | 100.0 | Tanacetum vulgare | A | O | 98.4 |
| Phaseolus vulgaris | A | O | 33.3 | Tanacetum vulgare | A | O | 100.0 |
| Phaseolus vulgaris | A | O | 80.3 | Taraxacum officinale | A | R | 22.7 |
| Phleum pratense | A | O | 20.2 | Taraxacum officinale | A | O | 100.0 |
| Physalis ixocarpa | A | R | 100.0 | Teucrium chamaedrys | A | O | 100.0 |
| Pimpinella anisum | A | O | 86.7 | Thymus praecox subsp arcticus | A | O | 75.6 |
| Plantago major | A | O | 99.0 | Thymus praecox subsp arcticus | A | O | 100.0 |
| Plectranthus sp. | A | R | 50.0 | Thymus serpyllum | A | O | 78.1 |
| Plectranthus sp. | A | O | 64.0 | Thymus vulgaris | A | O | 90.9 |
| Polygonum aviculare | A | O | 55.7 | Trichosanthes kirilowii | A | O | 100.0 |
| Poterium sanguisorba | A | R | 100.0 | Trifolium incarnatum | A | S | 76.9 |
| Poterium Sanquisorba | A | O | 23.4 | Trifolium pannonicum | A | O | 72.6 |
| Prunus Tomentosa | A | O | 27.6 | Trifolium pratense | A | O | 100.0 |
| Raphanus Sativus | A | O | 36.8 | Trifolium repens | A | O | 100.0 |
| Raphanus sativus | A | R | 100.0 | Triticum durum | A | R | 22.7 |
| Rheun rhabarbarum | A | R | 33.0 | Triticum spelta | A | R | 24.0 |
| Ribes nigrum | A | R | 21.1 | Triticum spelta | A | O | 32.4 |
| Ribes nigrum | A | O | 32.6 | Typha latifolia | A | O | 52.1 |
| Ribes rubrum | A | O | 24.5 | Vaccinium Corymbosum | A | R | 53.3 |
| Ribes Sylvestre | A | O | 21.1 | Vaccinium macrocarpon | A | R | 44.3 |
| Ribes Sylvestre | A | R | 30.3 | Valeriana officinalis | A | O | 23.1 |
| Rosa rugosa | A | R | 21.1 | Verbascum thapsus | A | O | 65.6 |
| Rosa rugosa | A | O | 36.6 | Vitis sp. | A | O | 33.7 |
| Rosa rugosa | A | O | 40.2 | Vitis sp. | A | R | 93.3 |
| Rosmarinus officinalis | A | O | 95.7 | Zea mays | A | R | 25.0 |
| Rubus canadensis | A | R | 25.8 | Zea mays | A | R | 50.0 |
| Rubus canadensis | A | O | 31.7 | Achillea millefolium | G | O | 47.7 |
| Rubus idaeus | A | O | 85.9 | Agropyron repens | G | O | 93.3 |
| Rubus ideaus | A | R | 66.7 | Alchemilla mollis | G | O | 32.1 |
| Rumex acetosella | A | O | 27.4 | Allium ascalonicum | G | O | 29.7 |
| Rumex crispus | A | O | 25.0 | Allium sativum | G | R | 100.0 |
| Rumex Scutatus | A | O | 21.3 | Allium schoenoprasum | G | R | 100.0 |
| Salvia officinalis | A | O | 21.3 | Allium tuberosum | G | R | 100.0 |
| Salvia officinalis | A | O | 85.1 | Althaea officinalis | G | O | 95.6 |
| Salvia officinalis | A | R | 100.0 | Amaranthus caudathus | G | O | 95.3 |
| Salvia sclarea | A | O | 29.9 | Amaranthus gangeticus | G | O | 45.7 |
| Sanguisorba officinalis | A | O | 23.1 | Amaranthus retroflexus | G | O | 78.3 |
| Sanguisorba officinalis | A | R | 48.3 | Ambrosia artemisiifolia | G | O | 73.8 |
| Santolina chamaecyparissus | A | O | 52.9 | Amelanchier alnifolius | G | O | 50.5 |
| Satureja montana | A | O | 87.4 | Anethum graveolens | G | O | 100.0 |
| Scorzonera hispanica | A | O | 30.8 | Anthemis nobilis | G | O | 94.3 |
| Secale cereale | A | R | 21.2 | Apium graveolens | G | O | 21.9 |
| Senecio vulgaris | A | O | 42.6 | Arctium minus | G | O | 65.9 |
| Sesamum indicum | A | O | 27.3 | Arctium minus | G | O | 71.7 |
| Silybum marianum | A | O | 25.2 | Arctostaphylos uva-ursi | G | O | 84.8 |
| Sium sisarum | A | O | 34.4 | Aronia melanocarpa | G | O | 31.5 |
| Solanum dulcamara | A | R | 21.4 | Foeniculum vulgare | G | O | 100.0 |
| Arrhenatherum elatius | G | S | 50.8 | Forsythia intermedia | G | R | 100.0 |
| Artemisia abrotanum | G | O | 52.1 | Forsythia x intermedia | G | O | 42.1 |
| Artemisia absinthium | G | O | 59.7 | Galium odoratum | G | R | 63.6 |
| Artemisia absinthium | G | O | 72.9 | Galium odoratum | G | O | 64.7 |
| Artemisia Ludoviciana | G | O | 64.1 | Gaultheria hispidula | G | R | 63.4 |
| Artemisia Ludoviciana | G | O | 90.7 | Gaultheria hispidula | G | O | 69.6 |
| Artemisia vulgaris | G | O | 55.2 | Glechoma hederacea | G | O | 50.5 |
| Artemisia vulgaris | G | O | 83.3 | Glechoma hederacea | G | R | 100.0 |
| Asclepias incarnata | G | O | 38.9 | Glycine max | G | O | 27.9 |
| Asclepias incarnata | G | O | 75.6 | Glycine max | G | R | 100.0 |
| Asparagus officinalis | G | R | 27.8 | Guizotia abyssinica | G | R | 33.3 |
| Aster sp | G | O | 33.3 | Guizotia abyssinica | G | O | 83.6 |
| Atropa belladonna | G | O | 96.6 | Helianthus annuus | G | R | 100.0 |
| Beta vulgaris | G | O | 92.1 | Helianthus strumosus | G | R | 28.9 |
| Beta vulgaris | G | R | 100.0 | Helianthus strumosus | G | O | 52.2 |
| Beta vulgaris spp. Maritima | G | R | 100.0 | Helianthus tuberosus | G | O | 29.3 |
| Borago officinalis | G | O | 100.0 | Helianthus tuberosus | G | O | 54.9 |
| Brassica napus | G | R | 40.9 | Helichrysum thianschanicum | G | O | 30.5 |
| Brassica oleracea | G | R | 66.7 | Heliotropium arborescens | G | R | 29.1 |
| Bromus inermis | G | O | 38.3 | Hysopus officinalis | G | O | 100.0 |
| Calamintha nepeta | G | R | 25.3 | Ipomoea batatas | G | O | 45.8 |
| Campanula rapunculus | G | S | 50.8 | Lactuca sativa | G | O | 26.6 |

TABLE 6-continued

Cath D

| Nom latin | Stress | extrait | Inhibition (%) | Nom latin | Stress | extrait | Inhibition (%) |
|---|---|---|---|---|---|---|---|
| *Campanula rapunculus* | G | O | 68.8 | *Lathyrus sativus* | G | O | 72.7 |
| *Campanula rapunculus* | G | O | 69.9 | *Lathyrus sylvestris* | G | O | 33.3 |
| *Canna edulis* | G | S | 50.8 | *Lathyrus sylvestris* | G | R | 56.8 |
| *Capsella bursa-pastoris* | G | O | 30.0 | *Lavandula angustifolia* | G | R | 100.0 |
| *Capsicum annuum* | G | O | 27.9 | *Lavandula angustifolia* | G | O | 100.0 |
| *Capsicum annuum* | G | R | 33.3 | *Lavandula latifolia* | G | O | 100.0 |
| *Capsicum annuum* | G | R | 35.9 | *Leonurus cardiaca* | G | O | 100.0 |
| *Capsicum annuum* | G | R | 41.0 | *Levisticum officinale* | G | O | 98.1 |
| *Capsicum annuum* | G | S | 43.1 | *Levisticum officinale* | G | R | 100.0 |
| *Capsicum annuum* | G | O | 56.9 | *Linum usitatissimum* | G | O | 42.9 |
| *Capsicum frutescens* | G | O | 60.8 | *Lolium perenne* | G | O | 25.5 |
| *Carthamus tinctorius* | G | O | 30.2 | *Lotus tetragonolobus* | G | R | 49.2 |
| *Carum carvi* | G | O | 28.6 | *Lupinus polyphyllus* | G | O | 33.3 |
| *Chaerophyllum bulbosum* | G | O | 88.9 | *Lycopersicon esculentum* | G | O | 29.5 |
| *Chrysanthemum coronarium* | G | O | 82.5 | *Lycopersicon esculentum* | G | R | 43.3 |
| *Cicer arietinum* | G | R | 31.8 | *Lycopersicon pimpinellifolium* | G | R | 100.0 |
| *Cichorium endivia* subsp *endivia* | G | O | 100.0 | *Malva moschata* | G | O | 100.0 |
| *Cichorium intybus* | G | O | 100.0 | *Medicago sativa* | G | O | 32.6 |
| *Circium arvense* | G | S | 53.8 | *Melissa officinalis* | G | O | 100.0 |
| *Circium arvense* | G | O | 63.3 | *Mentha piperita* | G | O | 40.3 |
| *Citrullus lanatus* | G | O | 40.9 | *Mentha suaveolens* | G | O | 79.2 |
| *Citrullus lanatus* | G | O | 56.9 | *Monarda didyma* | G | R | 100.0 |
| *Coix Lacryma-Jobi* | G | O | 100.0 | *Nepeta cataria* | G | O | 100.0 |
| *Cornus canadensis* | G | O | 20.2 | *Ocimum basilicum* | G | O | 80.5 |
| *Cornus canadensis* | G | O | 35.1 | *Oenothera biennis* | G | O | 41.7 |
| *Cucumis anguria* | G | R | 40.0 | *Oenothera biennis* | G | R | 100.0 |
| *Cucurbita maxima* | G | O | 31.4 | *Origanum majorana* | G | O | 67.4 |
| *Cucurbita maxima* | G | R | 40.9 | *Origanum vulgare* | G | O | 100.0 |
| *Cucurbita moschata* | G | O | 23.0 | *Oxalis Deppei* | G | O | 22.2 |
| *Cucurbita moschata* | G | R | 31.8 | *Oxalis Deppei* | G | S | 44.6 |
| *Cucurbita moschata* | G | S | 47.7 | *Oxyria digyna* | G | O | 21.3 |
| *Cucurbita pepo* | G | O | 29.8 | *Panax quinquefolius* | G | O | 25.5 |
| *Cucurbita pepo* | G | R | 53.3 | *Panax quinquefolius* | G | O | 38.3 |
| *Cymbopogon martinii* | G | O | 100.0 | *Panicum miliaceum* | G | R | 83.3 |
| *Cynara scolymus* | G | O | 27.3 | *Pennisetum alopecuroides* | G | R | 21.5 |
| *Datura metel* | G | O | 54.1 | *Petasites japonicus* | G | O | 40.6 |
| *Daucus carota* | G | O | 28.6 | *Petroselinum crispum* | G | O | 100.0 |
| *Daucus carota* | G | R | 100.0 | *Peucedanum cervaria* | G | O | 42.9 |
| *Digitalis purpurea* | G | R | 100.0 | *Phaseolus mungo* | G | O | 100.0 |
| *Dirca palustris* | G | R | 24.5 | *Phaseolus vulgaris* | G | O | 54.8 |
| *Elymus junceus* | G | O | 38.3 | *Phaseolus vulgaris* | G | O | 67.2 |
| *Erigeron speciosus* | G | O | 73.7 | *Thymus praecox* subsp *arcticus* | G | O | 100.0 |
| *Plantago major* | G | O | 95.2 | *Thymus serpyllum* | G | O | 100.0 |
| *Plectranthus* sp. | G | R | 100.0 | *Thymus vulgaris* | G | O | 64.4 |
| *Plectranthus* sp. | G | O | 100.0 | *Thymus x citriodorus* | G | O | 72.7 |
| *Poa compressa* | G | O | 20.2 | *Tiarella cordifolia* | G | O | 92.4 |
| *Portulaca oleracera* | G | O | 60.0 | *Trifolium hybridum* | G | O | 29.5 |
| *Potentilla anserina* | G | R | 100.0 | *Trifolium pannonicum* | G | O | 54.7 |
| *Poterium sanguisorba* | G | O | 21.3 | *Trifolium pratense* | G | O | 92.9 |
| *Poterium sanguisorba* | G | R | 100.0 | *Trifolium repens* | G | O | 100.0 |
| *Prunella vulgaris* | G | O | 70.3 | *Triticum spelta* | G | R | 37.3 |
| *Raphanus Raphanistrum* | G | O | 33.3 | *Triticum turgidum* | G | O | 59.5 |
| *Raphanus Raphanistrum* | G | R | 80.0 | *Typha latifolia* | G | O | 23.4 |
| *Raphanus sativus* | G | O | 52.6 | *Vaccinium corymbosum* | G | O | 26.5 |
| *Raphanus sativus* | G | R | 100.0 | *Vaccinum angustifolium* | G | O | 27.7 |
| *Ribes nigrum* | G | O | 42.1 | *Vaccinum macrocarpon* | G | R | 33.0 |
| *Ribes Sylvestre* | G | R | 32.0 | *Valeriana officinalis* | G | R | 27.6 |
| *Ricinus communis* | G | R | 100.0 | *Valeriana officinalis* | G | O | 51.3 |
| *Rosa rugosa* | G | O | 52.4 | *Verbascum thapsus* | G | O | 21.3 |
| *Rosa rugosa* | G | O | 90.2 | *Vinca minor* | G | O | 28.6 |
| *Rosmarinus officinalis* | G | O | 100.0 | *Vitis* sp. | G | R | 40.0 |
| *Rubus ideaus* | G | O | 34.8 | *Vitis* sp. | G | O | 42.6 |
| *Rubus occidentalis* | G | R | 60.0 | *Zea mays* | G | R | 26.9 |
| *Rubus occidentalis* | G | O | 65.3 | *Zea mays* | G | R | 100.0 |
| *Rumex crispus* | G | O | 43.3 | *Perilla frutescens* | T | O | 96.0 |
| *Ruta graveolens* | G | O | 23.0 | *Perilla frutescens* | T | R | 100.0 |
| *Salvia officinalis* | G | O | 100.0 | *Abies lasiocarpa* | T | O | 25.6 |
| *Salvia officinalis* | G | R | 100.0 | *Agastache foeniculum* | T | O | 100.0 |
| *Sambucus canadensis* | G | O | 80.6 | *Agropyron cristatum* | T | O | 20.2 |
| *Sambucus ebulus* | G | R | 21.1 | *Agrostis alba* | T | O | 24.5 |
| *Sambucus ebulus* | G | O | 36.8 | *Alchemilla mollis* | T | O | 33.3 |
| *Sanguisorba officinalis* | G | O | 43.6 | *Alchemilla mollis* | T | S | 49.2 |
| *Santolina chamaecyparissus* | G | O | 50.6 | *Alchemilla mollis* | T | O | 66.2 |
| *Saponaria officinalis* | G | O | 85.6 | *Allium ampeloprasum* | T | O | 100.0 |
| *Satureja hortensis* | G | R | 36.8 | *Allium ascalonicum* | T | O | 29.7 |

TABLE 6-continued

Cath D

| Nom latin | Stress | extrait | Inhibition (%) | Nom latin | Stress | extrait | Inhibition (%) |
|---|---|---|---|---|---|---|---|
| *Satureja hortensis* | G | O | 68.4 | *Allium ascalonicum* | T | R | 38.7 |
| *Senecio vulgaris* | G | O | 31.1 | *Allium cepa* | T | R | 100.0 |
| *Sesamum indicum* | G | O | 27.3 | *Allium tuberosum* | T | R | 100.0 |
| *Sium sisarum* | G | O | 20.8 | *Alpinia officinarum* | T | R | 50.0 |
| *Sium sisarum* | G | O | 47.8 | *Althaea officinalis* | T | O | 58.6 |
| *Solanum melanocerasum* | G | O | 23.5 | *Amaranthus candathus* | T | R | 22.9 |
| *Solanum melongens* | G | O | 28.6 | *Amaranthus candatus* | T | O | 93.2 |
| *solanum melongens* | G | R | 41.2 | *Amaranthus caudathus* | T | O | 100.0 |
| *Solidago* sp | G | O | 72.1 | *Amaranthus gangeticus* | T | O | 57.1 |
| *Sonchus oleraceus* | G | O | 95.1 | *Amaranthus retroflexus* | T | O | 100.0 |
| *Stachys Affinis* | G | O | 38.1 | *Ambrosia artemisiifolia* | T | O | 86.9 |
| *Stachys byzantina* | G | O | 28.6 | *Amelanchier alnifolia* | T | O | 50.5 |
| *Stellaria graminea* | G | O | 39.3 | *Anthemis nobilis* | T | O | 100.0 |
| *Stellaria media* | G | O | 21.3 | *Anthriscus cerefolium* | T | O | 100.0 |
| *Symphytum officinale* | G | R | 37.8 | *Aralia cordata* | T | R | 100.0 |
| *Symphytum officinale* | G | S | 43.1 | *Arctium minus* | T | O | 68.3 |
| *Symphytum officinale* | G | O | 92.6 | *Aronia melanocarpa* | T | O | 50.0 |
| *Symphytum officinale* | G | O | 100.0 | *Aronia prunifolia* | T | O | 44.7 |
| *Tanacetum cinerariifolium* | G | O | 91.3 | *Arrhenatherum elatius* | T | O | 78.7 |
| *Tanacetum parthenium* | G | R | 60.0 | *Artemisia absinthium* | T | O | 58.4 |
| *Tanacetum parthenium* | G | O | 86.7 | *Artemisia dracunculus* | T | R | 28.6 |
| *Tanacetum vulgare* | G | O | 44.4 | *Artemisia dracunculus* | T | O | 86.3 |
| *Tanacetum vulgare* | G | O | 67.9 | *Artemisia Ludoviciana* | T | O | 48.8 |
| *Tanacetum vulgare* | G | O | 85.7 | *Artemisia vulgaris* | T | O | 50.0 |
| *taraxacum officinale* | G | R | 40.9 | *Artemisia vulgaris* | T | O | 82.8 |
| *taraxacum officinale* | G | O | 100.0 | *Asclepias incarnata* | T | O | 72.9 |
| *Teucrium chamaedrys* | G | R | 33.3 | *Asparagus officinalis* | T | O | 69.8 |
| *Teucrium chamaedrys* | G | O | 66.7 | *Aster* sp | T | O | 35.0 |
| *Thymus fragantissimus* | G | O | 24.1 | *Avena sativa* | T | O | 31.8 |
| *Thymus praecox* subsp *arcticus* | G | R | 25.0 | *Baptisia tinctoria* | T | O | 33.8 |
| *Thymus praecox* subsp *arcticus* | G | O | 92.7 | *Dioscorea batatas* | T | S | 41.5 |
| *Beta vulgaris* | T | O | 25.5 | *Dipsacus sativus* | T | O | 73.7 |
| *Beta vulgaris* | T | O | 28.6 | *Dirca palustris* | T | O | 88.5 |
| *Beta vulgaris* | T | R | 34.6 | *Eleusine coracana* | T | S | 49.2 |
| *Beta vulgaris* | T | S | 43.6 | *Elymus junceus* | T | O | 35.1 |
| *Beta vulgaris* | T | O | 54.5 | *Erigeron speciosus* | T | O | 67.8 |
| *Beta vulgaris* | T | R | 100.0 | *Fagopyrum esculentum* | T | O | 27.3 |
| *Beta vulgaris* spp. *Maritima* | T | R | 100.0 | *Foeniculum vulgare* | T | R | 80.0 |
| *Brassica nigra* | T | R | 45.5 | *Forsythia intermedia* | T | O | 50.9 |
| *Brassica oleracea* | T | O | 50.0 | *Forsythia x intermedia* | T | O | 57.9 |
| *Brassica oleracea* | T | R | 100.0 | *Fucus vesiculosus* | T | O | 83.7 |
| *Bromus inermis* | T | O | 30.9 | *Fucus vesiculosus* | T | R | 100.0 |
| *Calamagrostis arundiflora* | T | O | 85.6 | *Galinsoga ciliata* | T | O | 56.7 |
| *Calendula officinalis* | T | O | 23.7 | *Galium aparine* | T | O | 60.5 |
| *Campanula rapunculus* | T | O | 25.0 | *Galium odoratum* | T | R | 31.8 |
| *Canna edulis* | T | O | 26.3 | *Gaultheria hispidula* | T | O | 33.7 |
| *Capsella bursa-pastoris* | T | O | 21.7 | *Gaultheria procumbens* | T | O | 25.0 |
| *Capsicum annum* | T | O | 46.1 | *Gentiana lutea* | T | O | 98.1 |
| *Capsicum annuum* | T | R | 20.5 | *Gentiana macrophylla* | T | O | 100.0 |
| *Capsicum annuum* | T | O | 23.3 | *Glechoma hederacea* | T | O | 62.6 |
| *Capsicum annuum* | T | R | 41.0 | *Glycine max* | T | O | 26.2 |
| *Capsicum frutescens* | T | O | 58.8 | *Glycyrrhiza glabra* | T | R | 50.0 |
| *Carthamus tinctorius* | T | O | 36.5 | *Glycyrrhiza glabra* | T | S | 51.3 |
| *Carum carvi* | T | O | 88.6 | *Guizotia abyssinica* | T | O | 39.3 |
| *Chaerophyllum bulbosum* | T | O | 25.0 | *Guizotia abyssinica* | T | R | 100.0 |
| *Chaerophyllum bulbosum* | T | O | 95.2 | *Hedeoma pulegioides* | T | O | 100.0 |
| *Chelidonium majus* | T | O | 27.1 | *Helianthus annus* | T | O | 75.8 |
| *Chelidonium majus* | T | R | 50.0 | *Helianthus strumosus* | T | R | 55.6 |
| *Chenopodium bonus-henricus* | T | O | 60.0 | *Helianthus tuberosus* | T | O | 22.1 |
| *Chenopodium quinoa* | T | R | 31.5 | *Helichrysum angustifolium* | T | O | 96.1 |
| *Chenopodium quinoa* | T | O | 50.0 | *Helichrysum thianschanicum* | T | O | 70.5 |
| *Chrysanthemum coronarium* | T | R | 65.5 | *Heliotropium arborescens* | T | O | 83.2 |
| *Chrysanthemum coronarium* | T | O | 100.0 | *Helleborus niger* | T | O | 24.1 |
| *Cicer arietinum* | T | R | 27.3 | *Herba Schizonepetae* | T | O | 60.5 |
| *Cichorium endivia* subsp *endivia* | T | R | 27.3 | *Hibiscus cannabinus* | T | S | 52.6 |
| *Cichorium endivia* subsp *endivia* | T | O | 97.3 | *Hordeum vulgare* | T | O | 77.8 |
| *Cichorium intybus* | T | O | 100.0 | *Hydrastis canadensis* | T | O | 64.9 |
| *Cimicifuga racemosa* | T | R | 22.2 | *Hypericum henryl* | T | O | 100.0 |
| *Circium arvense* | T | O | 78.3 | *Hypericum perforatum* | T | R | 31.0 |
| *Citrullus lanatus* | T | R | 26.7 | *Hyssopus officinalis* | T | O | 100.0 |
| *Citrullus lanatus* | T | O | 45.5 | *Inula helenium* | T | O | 100.0 |
| *Citrullus lanatus* | T | O | 62.7 | *Ipomoea batalas* | T | O | 91.5 |
| *Coix Lacryma-Jobi* | T | O | 77.3 | *Iris versicolor* | T | O | 35.9 |
| *Coriandrum sativum* | T | O | 90.0 | *Juniperus communis* | T | O | 83.8 |
| *Cornus canadensis* | T | O | 29.3 | *Krameria Triandra* | T | O | 25.6 |

TABLE 6-continued

Cath D

| Nom latin | Stress | extrait | Inhibition (%) | Nom latin | Stress | extrait | Inhibition (%) |
|---|---|---|---|---|---|---|---|
| *Cucumis anguria* | T | R | 50.0 | *Lactuca sativa* | T | O | 100.0 |
| *Cucumis anguria* | T | O | 70.1 | *Lathyrus Sativus* | T | R | 27.3 |
| *Cucumis melo* | T | R | 20.5 | *Lathyrus Sativus* | T | O | 33.3 |
| *Cucumis melo* | T | O | 51.0 | *Lathyrus sylvestris* | T | O | 20.3 |
| *Cucumis sativus* | T | O | 23.4 | *Lathyrus sylvestris* | T | R | 100.0 |
| *Cucurbita maxima* | T | O | 50.0 | *Laurus nobilis* | T | R | 23.8 |
| *Cucurbita moschata* | T | O | 84.9 | *Laurus nobilis* | T | O | 26.0 |
| *Cucurbita pepo* | T | R | 20.5 | *Lavandula latifolia* | T | R | 100.0 |
| *Cucurbita pepo* | T | O | 39.2 | *Lavandula latifolia* | T | O | 100.0 |
| *Cucurbita pepo* | T | S | 53.8 | *Lens culinaris* subsp *culinaris* | T | O | 21.3 |
| *Curcuma zedoaria* | T | O | 24.6 | *Leonorus cardiaca* | T | O | 57.9 |
| *Cymbopogon citratus* | T | O | 100.0 | *Lepidium sativum* | T | O | 31.6 |
| *Cynara scolymus* | T | R | 33.3 | *Levisticum officinale* | T | O | 90.5 |
| *Dactilis Glomerata* | T | O | 20.2 | *Levisticum officinale* | T | R | 100.0 |
| *Datura metel* | T | O | 37.8 | *Linum usitatissimum* | T | O | 23.8 |
| *Datura stramonium* | T | R | 50.0 | *Lonicera syringantha* | T | O | 79.5 |
| *Daucus carota* | T | R | 21.1 | *Lotus corniculatus* | T | R | 46.7 |
| *Daucus carota* | T | O | 30.3 | *Lupinus polyphyllus* lindl. | T | O | 36.6 |
| *Daucus carota* | T | O | 49.3 | *Lycopersicon esculentum* | T | R | 60.0 |
| *Daucus carota* | T | S | 52.3 | *Rumex scutatus* | T | O | 23.0 |
| *Lycopersicon pimpinellifollum* | T | R | 100.0 | *Ruta graveolens* | T | O | 62.1 |
| *Malus hupehensis* | T | R | 100.0 | *Saccharum officinarum* | T | O | 27.0 |
| *Malva sylvestris* | T | O | 100.0 | *Salvia officinalis* | T | O | 92.0 |
| *Matricaria* spp. | T | O | 100.0 | *Salvia officinalis* | T | O | 93.3 |
| *Medicago sativa* | T | O | 27.7 | *Sambucus canadensis* | T | O | 42.9 |
| *Melissa officinalis* | T | O | 100.0 | *Sanguisorba officinalis* | T | O | 68.6 |
| *Menyanthes trifoliata* | T | O | 44.9 | *Santolina chamaecyparissus* | T | O | 66.7 |
| *Menyanthes trifoliata* | T | R | 50.0 | *Saponaria officinalis* | T | O | 36.6 |
| *Miscanthus sinensis* | T | R | 23.5 | *Saponaria officinalis* | T | O | 84.7 |
| *Miscanthus sinensis* | T | O | 24.6 | *Satureja montana* | T | O | 80.5 |
| *Nepeta cataria* | T | O | 78.9 | *Satureja repandra* | T | O | 47.1 |
| *Ocimum Basilicum* | T | R | 35.7 | *Senecio vulgaris* | T | O | 44.3 |
| *Ocimum Basilicum* | T | O | 100.0 | *Setaria italica* | T | O | 27.9 |
| *Oenothera biennis* | T | R | 100.0 | *Silybum marianum* | T | O | 31.0 |
| *Origanum vulgare* | T | O | 94.7 | *Sium sisarum* | T | O | 24.8 |
| *Origanum vulgare* | T | R | 100.0 | *Sium sisarum* | T | R | 25.5 |
| *Oxalis Deppei* | T | O | 21.1 | *Solanum dulcamara* | T | R | 21.4 |
| *oxyria digyna* | T | O | 24.6 | *Solanum melongena* | T | R | 25.8 |
| *Panax quinquefolius* | T | O | 39.4 | *Solanum melongena* | T | O | 34.9 |
| *Panicum miliaceum* | T | R | 20.8 | *Solanum tuberosum* | T | O | 38.1 |
| *Pastinaca sativa* | T | O | 21.3 | *Solidago canadensis* | T | O | 100.0 |
| *Pastinaca sativa* | T | R | 25.0 | *Solidago* sp | T | O | 73.8 |
| *Pastinaca sativa* | T | R | 25.0 | *Sonchus oleraceus* | T | O | 100.0 |
| *Pastinaca sativa* | T | O | 79.4 | *Sorghum durra* | T | O | 23.8 |
| *Pastinaca sativa* | T | O | 100.0 | *Spinacia oleracea* | T | R | 29.3 |
| *Petasites Japonicus* | T | O | 29.0 | *Stachys affinis* | T | R | 23.6 |
| *Petroselinum crispum* | T | R | 40.0 | *Stachys affinis* | T | O | 23.9 |
| *Peucedanum oreaselinum* | T | S | 55.1 | *Stachys affinis* | T | O | 50.0 |
| *Pfaffia paniculata* | T | R | 100.0 | *Stachys byzantina* | T | O | 41.6 |
| *Phaseolus mungo* | T | O | 70.2 | *Stellaria graminea* | T | O | 62.3 |
| *Phaseolus vulgaris* | T | O | 71.4 | *Stipa capillata* | T | O | 27.1 |
| *Phaseolus vulgaris* | T | O | 100.0 | *Symphytum officinale* | T | R | 28.9 |
| *Phaseolus vulgaris* | T | R | 100.0 | *Symphytum officinale* | T | O | 87.7 |
| *Physalis ixocarpa* | T | O | 25.5 | *Symphytum officinale* | T | O | 97.8 |
| *Pimpinella anisum* | T | R | 100.0 | *Tanacetum cinerarlifolium* | T | O | 62.7 |
| *Pimpinella anisum* | T | O | 100.0 | *Tanacetum parthenium* | T | O | 94.7 |
| *Pisum sativum* | T | O | 37.5 | *Tanacetum vulgare* | T | R | 28.9 |
| *Plantago major* | T | O | 100.0 | *Tanacetum vulgare* | T | S | 47.7 |
| *Plectranthus* sp. | T | O | 36.0 | *Tanacetum vulgare* | T | O | 75.6 |
| *Plectranthus* sp. | T | R | 80.0 | *Tanacetum vulgare* | T | O | 95.2 |
| *Poa pratensis* | T | O | 38.3 | *Tanacetum vulgare* | T | O | 100.0 |
| *Populus* x *petrowskyana* | T | O | 25.5 | *Taraxacum officinale* | T | O | 95.3 |
| *Prunella vulgaris* | T | O | 23.3 | *Thymus praecox* subsp *arcticus* | T | R | 24.4 |
| *Prunella vulgaris* | T | O | 88.1 | *Thymus praecox* subsp *arcticus* | T | O | 60.0 |
| *Raphanus raphanistrum* | T | O | 73.7 | *Thymus praecox* subsp *arcticus* | T | O | 90.0 |
| *Raphanus raphanistrum* | T | R | 100.0 | *Thymus pseudolanuginosus* | T | O | 83.9 |
| *Raphanus sativus* | T | S | 60.3 | *Thymus serpyllum* | T | O | 100.0 |
| *Raphanus sativus* | T | R | 100.0 | *Tiarella cordifolia* | T | O | 93.3 |
| *Reseda luteola* | T | O | 100.0 | *Tragopogon porrifolius* | T | O | 34.4 |
| *Rheum officinale* | T | O | 36.8 | *Tragopogon porrifolius* | T | O | 58.0 |
| *Ribes sativum* | T | O | 20.4 | *Trichosanthes kirilowii* | T | R | 25.3 |
| *Ribes Sylvestre* | T | R | 44.3 | *Trifolium pannonicum* | T | O | 61.1 |
| *Ricinus communis* | T | R | 100.0 | *Trifolium pratense* | T | O | 92.9 |
| *Rosmarinus officinalis* | T | R | 60.0 | *Trifolium repens* | T | O | 100.0 |
| *Rosmarinus officinalis* | T | O | 100.0 | *Triticum aestivum* | T | O | 29.5 |

TABLE 6-continued

Cath D

| Nom latin | Stress | extrait | Inhibition (%) | Nom latin | Stress | extrait | Inhibition (%) |
|---|---|---|---|---|---|---|---|
| *Rubus canadensis* | T | R | 32.0 | *Triticum durum* | T | O | 100.0 |
| *Rubus canadensis* | T | O | 34.7 | *Triticum turgidum* | T | O | 29.7 |
| *Rubus idaeus* | T | O | 93.5 | *Ulmus americana* | T | O | 76.9 |
| *Rubus idaeus* | T | R | 100.0 | *Ulmus americana* | T | O | 81.0 |
| *Rubus occidentalis* | T | O | 38.6 | *Urtica dioica* | T | R | 40.9 |
| *Rubus occidentalis* | T | S | 52.3 | *Vaccinium angustifolium* | T | R | 26.3 |
| *Rubus occidentalis* | T | R | 100.0 | *Vaccinium angustifolium* | T | O | 28.3 |
| *Rumex acetosella* | T | O | 26.3 | *Vaccinium angustifolium* | T | O | 47.6 |
| *Rumex crispus* | T | O | 30.0 | | | | |
| *Vaccinium angustifolium* | T | R | 100.0 | | | | |
| *Vaccinium corymbosum* | T | O | 21.4 | | | | |
| *Vaccinium macrocarpon* | T | R | 80.0 | | | | |
| *Valeriana officinalis* | T | O | 43.6 | | | | |
| *Vicia sativa* | T | S | 43.1 | | | | |
| *Vitiis* sp. | T | O | 26.7 | | | | |
| *Vitiis* sp. | T | R | 93.3 | | | | |
| *Zea mays* | T | R | 21.2 | | | | |
| *Zea mays* | T | R | 100.0 | | | | |

TABLE 7

Cath G

| Nom latin | Stress | extrait | Inhibition (%) | Nom latin | Stress | extrait | Inhibition (%) |
|---|---|---|---|---|---|---|---|
| *Achillea millefolium* | A | V | 40.1 | *Echinacea purpurea* | A | W | 100.0 |
| *Achillea millefolium* | A | O | 29.5 | *Filipendula rubra* | A | O | 20.2 |
| *Acorus calamus* | A | R | 68.6 | *Filipendula rubra* | A | S | 77.6 |
| *Adiantum pedatum* | A | R | 29.7 | *Foeniculum vulgare* | A | R | 23.3 |
| *Agastache foeniculum* | A | O | 36.8 | *Fragaria x ananassa* | A | O | 32.3 |
| *Agastache foeniculum* | A | S | 22.4 | *Fragaria x ananassa* | A | W | 100.0 |
| *Agropyron rupens* | A | S | 24.5 | *Fragaria x ananassa* | A | S | 100.0 |
| *Alchemilla mollis* | A | W | 100.0 | *Fragaria x ananassa* | A | S | 100.0 |
| *Alchemilla mollis* | A | S | 81.1 | *Frangoria x ananassa* | A | W | 100.0 |
| *Alchemilla mollis* | A | O | 51.5 | *Frangoria x ananassa* | A | V | 100.0 |
| *Alchemilla mollis* | A | S | 78.6 | *Galinsoga ciliata* (Rofiresque) Blake | A | R | 21.2 |
| *Alchemilla mollis* | A | O | 82.9 | *Gaultheria hispidula* (L.) Muhl. | A | R | 85.3 |
| *Alchemilla mollis* | A | S | 35.6 | *Gaultheria hispidula* (L.) Muhl. | A | R | 100.0 |
| *Alkanna tinctoria* | A | O | 51.6 | *Gaultheria procumbens* | A | W | 56.1 |
| *Alkanna tinctoria* | A | R | 100.0 | *Glycine Max* | A | S | 36.0 |
| *Allium Tuberosum* | A | S | 20.6 | *Glycine max* | A | S | 38.7 |
| *Althaea officinalis* | A | R | 21.6 | *Glycyrrhiza glabra* | A | W | 46.2 |
| *Althaea officinalis* | A | S | 39.6 | *Glycyrrhiza glabra* | A | S | 35.5 |
| *Ambrosia artemisiifolia* linné | A | O | 47.6 | *Glycyrrhiza glabra* | A | R | 100.0 |
| *Ambrosia artemisiifolia* linné | A | R | 38.2 | *Hamamelis virginiana* | A | R | 100.0 |
| *Amelanchier sanguinea* (Pursh) DC. | A | W | 29.7 | *Helianthus tuberosus* | A | W | 22.6 |
| *Angelica archangelica* | A | S | 68.1 | *Helichrysum angustifolium* | A | V | 82.6 |
| *Anthemis tinctoria* | A | O | 26.0 | *Heliotropium arborescens* | A | O | 57.3 |
| *Anthemis tinctoria* | A | V | 28.4 | *Heliotropium arborescens* | A | R | 57.2 |
| *Anthemis tinctorium* | A | O | 46.9 | *Hordeum vulgare* | A | O | 34.3 |
| *Arachis hypogaea* | A | V | 84.5 | *Hypericum henryi* | A | O | 30.4 |
| *Aralia nudicaulis* | A | S | 61.9 | *Hypericum perforatum* | A | R | 100.0 |
| *Arctostaphylos uva-ursi* | A | O | 25.0 | *Inula helenium* | A | S | 64.0 |
| *Arctostaphylos uva-ursi* | A | R | 100.0 | *Isatis tinctoria* | A | O | 94.0 |
| *Arctostaphylos uva-ursi* | A | S | 38.4 | *Laurus nobilis* | A | S | 49.9 |
| *Aronia melanocarpa* (Michx.) Ell. | A | O | 24.4 | *Lavendula latifolia* | A | W | 100.0 |
| *Aronia melanocarpa* (Michx.) Ell. | A | R | 27.3 | *Lavendula latifolia* | A | V | 48.7 |
| *Aronia melanocarpa* (Michx.) Ell. | A | W | 47.8 | *Leonorus cardiaca* | A | R | 100.0 |
| *Artemisia dracunculus sativa* | A | W | 32.2 | *Levisecum officinale* | A | V | 46.8 |
| *Artemisis Ludoviciana* | A | O | 88.8 | *Lolium multiflorum* | A | O | 34.1 |
| *Aster* sp ? | A | O | 47.2 | *Melissa officinalis* | A | O | 54.1 |
| *Aster* sp ? | A | R | 100.0 | *Melissa officinalis* | A | W | 100.0 |
| *Beta vulgaris* | A | R | 23.9 | *Melissa officinalis* | A | V | 80.7 |
| *Brassica napus* | A | R | 22.3 | *Melissa officinalis* | A | O | 100.0 |
| *Brassica napus* | A | S | 22.8 | *Mentha pulegium* | A | O | 29.1 |
| *Brassica nigra* | A | S | 47.2 | *Mentha spicata* | A | V | 47.0 |
| *Brassica rapa* | A | S | 46.0 | *Nepeta cataria* | A | V | 57.6 |
| *Capsella bursa-pastoris* (linné) médicus | A | R | 43.4 | *Ocrothera biennis* | A | S | 33.1 |
| *Chaerophyllum bulbosom* | A | V | 90.7 | *Oenothera biennis* linné | A | O | 47.4 |
| *Chaerophyllum bulbosom* | A | W | 57.4 | *Oenothera biennis* linné | A | R | 100.0 |
| *chenopodium bonus-henricus* | A | R | 23.7 | *Origanum majorana* | A | S | 34.6 |

TABLE 7-continued

Cath G

| Nom latin | Stress | extrait | Inhibition (%) | Nom latin | Stress | extrait | Inhibition (%) |
|---|---|---|---|---|---|---|---|
| Chichorium endivia | A | O | 53.0 | Origanum vulgare | A | V | 65.9 |
| Chrysanthemum leucanthemum linné | A | O | 55.5 | Origanum vulgare | A | W | 48.2 |
| Cicer arietinum | A | R | 26.2 | Origanum vulgare | A | V | 70.0 |
| Cichorium intybus | A | O | 100.0 | Origanum vulgare | A | W | 62.9 |
| Cichorium intybus | A | V | 83.6 | Origanum vulgare | A | O | 68.4 |
| Cichorium intybus | A | O | 51.0 | Origanum vulgare | A | V | 81.9 |
| Crataegus sp ? | A | O | 100.0 | Origanum vulgare | A | W | 61.3 |
| Crataegus sp ? | A | R | 81.6 | Origanum vulgare | A | S | 21.7 |
| Cymbopogan citratus | A | S | 33.9 | Oxyria digyna | A | V | 40.1 |
| Datisca cannabina | A | S | 20.2 | Perilla frutescens | A | V | 65.0 |
| Daucus carota | A | O | 62.0 | Perilla frutescens | A | W | 51.9 |
| Daucus carota | A | W | 99.4 | Peucedanum cervaria | A | R | 28.3 |
| Dirca palustris | A | R | 24.9 | Peucedanum cervaria | A | R | 45.1 |
| Dirca palustris | A | S | 47.0 | Phaseolus Vulgaris | A | S | 38.4 |
| Diyopteris filix-mas | A | O | 24.1 | Phaseolus Vulgaris | A | S | 26.3 |
| Diyopteris filix-mas | A | R | 95.7 | Tanacetum vulgare "Goldsticks" | A | V | 51.9 |
| Echinacea purpurea | A | V | 80.7 | Taraxacum officinale | A | W | 28.5 |
| Phytolacca americana | A | S | 27.8 | Taraxacum officinale | A | V | 82.3 |
| Plantago coronopus | A | O | 22.7 | Thymus praecox subsp arctitus | A | O | 43.4 |
| Polygonum aviculare linné | A | R | 76.0 | Thymus pseudolanuginosus | A | V | 29.7 |
| Poterium sanguisorba | A | O | 20.1 | Thymus serpyllum | A | O | 100.0 |
| Poterium sanguisorba | A | R | 93.1 | Thymus serpyllum | A | W | 73.6 |
| Poterium sanguisorba | A | V | 47.7 | Thymus serpyllum | A | V | 74.9 |
| Poterium sanguisorba | A | S | 36.1 | Thymus vulgaris | A | O | 35.6 |
| Pteridium aquilinum | A | O | 25.7 | Thymus vulgaris | A | R | 66.5 |
| Pteridium aquilinum | A | R | 100.0 | Thymus vulgaris "Argenteus" | A | V | 73.9 |
| Ribes nidigrolaria | A | W | 51.8 | Triticum furgidum?? | A | O | 21.6 |
| Ribes Nigrum | A | W | 100.0 | Vaccinum augustifolium | A | S | 26.1 |
| Ribes nigrum | A | S | 33.6 | Vaccinum Corymbosum | A | W | 95.7 |
| Ribes nigrum L. | A | W | 58.8 | Vaccinum macrocarpon | A | W | 46.1 |
| Ribes nigrum L. | A | O | 21.5 | Valerianella locusta | A | S | 96.0 |
| Ribes Salivum | A | R | 21.4 | Veronica officinalis | A | S | 26.4 |
| Ricinus communis | A | R | 100.0 | Viburnum trilobum Marsh. | A | W | 25.0 |
| Rosa rugosa thunb. | A | W | 20.1 | Vida sativa | A | O | 28.2 |
| Rosa rugosa thunb. | A | W | 100.0 | Vicia villosa | A | O | 34.5 |
| Rosa rugosa thunb. | A | R | 100.0 | Vitia sp. | A | W | 26.0 |
| Rosmarinus officinalis | A | O | 100.0 | Vitia sp. | A | S | 41.6 |
| Rosmarinus officinalis | A | R | 64.0 | Vitia sp. | A | W | 100.0 |
| Rosmarinus officinalis | A | W | 55.6 | Vitia sp. | A | S | 30.8 |
| Rosmarinus officinalis | A | V | 76.7 | Vitia sp. | A | O | 22.3 |
| Rubus alleghaniensis | A | S | 32.1 | Vitia sp. | A | S | 28.5 |
| Rubus canadensis | A | W | 94.5 | Zea Mays | A | S | 32.3 |
| Rubus canadensis | A | S | 64.2 | Zea Mays | A | S | 34.5 |
| Rubus idaeus | A | S | 86.0 | Achillea millefolium | G | W | 30.6 |
| Rubus idaeus | A | O | 29.5 | Achillea millefolium | G | V | 71.1 |
| Rubus idaeus | A | W | 38.7 | Aconitum napellus | G | R | 100.0 |
| Rubus idaeus | A | S | 41.0 | Acorus calamus | G | R | 27.8 |
| Rubus idaeus | A | W | 100.0 | Adiantum pedatum | G | R | 100.0 |
| Rubus idaeus L. | A | V | 30.2 | Agastache toeniculum "Snow Pike" | G | V | 46.9 |
| Rubus idaeus L. | A | W | 29.4 | Agastache toeniculum "Snow Pike" | G | W | 71.5 |
| Rubus idaeus L. | A | S | 100.0 | Alchemilla mollis | G | W | 100.0 |
| Rubus ideaus | A | R | 100.0 | Alchemilla mollis | G | O | 52.6 |
| Rubus ideaus | A | S | 67.1 | Alchemilla mollis | G | S | 80.7 |
| Rubus occidentalis | A | S | 100.0 | Alchemilla mollis | G | O | 33.4 |
| Rumex crispus linné | A | R | 100.0 | Alchemilla mollis | G | S | 38.7 |
| Salvia elegens | A | W | 69.7 | althaea officinalis | G | R | 27.5 |
| Salvia officinalis | A | W | 100.0 | althaea officinalis | G | S | 36.9 |
| Salvia officinalis | A | V | 58.0 | Ambrosia artemisiifolia linné | G | O | 48.4 |
| Salvia officinalis | A | O | 100.0 | Ambrosia artemisiifolia linné | G | R | 36.0 |
| Salvia officinalis | A | R | 39.9 | Amelanchier sanguinea (Pursh) DC. | G | W | 46.5 |
| Salvia officinalis | A | V | 45.7 | Angelica archangelica | G | S | 39.1 |
| Salvia officinalis | A | W | 65.4 | Arachis hypogaea | G | V | 81.8 |
| Salvia sclarea | A | W | 29.1 | Aralia nudicaulis | G | S | 44.9 |
| Santolina | A | W | 65.5 | Arctium minus (Hill) Bernhardi | G | O | 35.6 |
| Satureja montana | A | V | 72.2 | Arctostaphylos uva-ursi | G | S | 59.9 |
| Satureja montana | A | W | 100.0 | Aronia melanocarpa (Michx.) Ell. | G | W | 28.4 |
| Satureja montana | A | O | 90.5 | Artemisia Ludoviciana | G | O | 66.0 |
| Satureja montana | A | V | 28.9 | Aster sp ? | G | O | 51.8 |
| Scuttellaria lateriflora | A | S | 23.7 | Aster sp ? | G | R | 100.0 |
| Sonchus oleraceus L. | A | O | 25.9 | Beta vulgaris | G | O | 26.5 |
| Sorghum dochna bicolor | A | O | 25.6 | Brassica napus | G | R | 32.9 |
| Sorghum durra (Stapif) | A | O | 46.9 | Brassica napus | G | S | 33.5 |
| Symphytum officinale | A | O | 99.4 | Brassica oleracea | G | S | 100.0 |
| Symphytum officinale | A | O | 97.8 | Calamintha nepeta | G | V | 51.5 |
| Tanacetum cinerarifolium | A | W | 28.2 | Calendula officinalis L. | G | O | 26.7 |

TABLE 7-continued

Cath G

| Nom latin | Stress | extrait | Inhibition (%) | Nom latin | Stress | extrait | Inhibition (%) |
|---|---|---|---|---|---|---|---|
| *Tanacetum parthenium* | A | W | 34.8 | *Canna edulis* | G | O | 20.6 |
| *Tanacetum vulgare* | A | W | 80.0 | *Chaerophyllum bulbosum* | G | O | 37.0 |
| *Tanacetum vulgare* | A | V | 53.8 | *Chaerophyllum bulbosum* | G | V | 88.6 |
| *Tanacetum vulgare* | A | O | 35.9 | N | G | R | 34.8 |
| *Tanacetum vulgare* | A | R | 68.8 | *Nepeta cataria* | G | V | 38.4 |
| *Chaerophyllum bulbosum* | G | W | 26.5 | *Ocimum basilicum* | G | W | 20.4 |
| *Chichorium endivia* | G | S | 25.2 | *Ocimum basilicum* | G | O | 89.9 |
| *Chrysanthemum leucanthemum* linné | G | O | 44.2 | *Ocimum basilicum* | G | V | 31.3 |
| *Cicer arietinum* | G | R | 26.1 | *Ocimum basilicum* | G | W | 82.3 |
| *Cichorium endivia* | G | O | 23.7 | *Oenothera biennis* linné | G | O | 62.8 |
| *Cichorium intybus* | G | O | 100.0 | *Oenothera biennis* linné | G | R | 100.0 |
| *Cichorium intybus* | G | V | 79.2 | *Oenothera biennis* linné | G | R | 100.0 |
| *Cichorium intybus* | G | O | 82.5 | *Oenothera biennis* Linne | G | S | 100.0 |
| *Crataegus* sp ? | G | W | 27.9 | *Origanum vulgare* | G | V | 67.1 |
| *Cynara scolymus* | G | O | 66.3 | *Origanum vulgare* | G | V | 65.5 |
| *Dirca palustris* | G | R | 28.8 | *Origanum vulgare* | G | W | 58.1 |
| *Dirca palustris* | G | S | 85.2 | *Origanum vulgare* | G | V | 70.5 |
| *Diyopteris filix-mas* | G | R | 100.0 | *Origanum vulgare* | G | W | 34.5 |
| *Echinacea purpurea* | G | V | 84.2 | *Origanum vulgare* | G | V | 60.1 |
| *Echinacea purpurea* | G | O | 83.2 | *Origanum vulgare* | G | O | 100.0 |
| *Erigeron speciosus* (Lindl.) D.C. | G | O | 46.1 | *Origanum vulgare* | G | S | 28.5 |
| *Fagopyrum esculentum* | G | O | 27.5 | *Origanum vulgare* | G | O | 83.7 |
| *Filipendula rubra* | G | S | 59.6 | *Origanum vulgare* | G | S | 22.1 |
| *Galinsoga ciliata* (Rofiresque) Blake | G | R | 20.5 | *Oxyria digyna* | G | V | 57.7 |
| *Galium odoratum* | G | R | 56.8 | *Perilla frutescens* | G | V | 75.8 |
| *Gaultheria hispidula* (L.) Muhl | G | O | 100.0 | *Peucedanum cervaria* | G | R | 37.5 |
| *Glycine max* | G | O | 22.8 | *Peucedanum cervaria* | G | R | 25.3 |
| *Glycyrrhiza glabra* | G | S | 28.4 | *Plantago major* | G | O | 31.7 |
| *Hamamelis virginiana* | G | O | 33.8 | *Plectranthus* sp. | G | V | 28.5 |
| *Hamamelis virginiana* | G | R | 100.0 | *Portulaca oleracera* linné | G | O | 37.8 |
| *Helianthus annus* | G | R | 26.5 | *Potentilla anserina* | G | S | 21.1 |
| *Helianthus strumosus* | G | O | 21.2 | *Poterium sanguisorba* | G | V | 72.1 |
| *Helianthus tuberosus* L. | G | W | 48.4 | *Poterium sanguisorba* | G | S | 65.9 |
| *Helichrysum angustifolium* | G | W | 38.1 | *Poterium sanguisorba* | G | O | 63.6 |
| *Helichrysum angustifolium* | G | V | 83.8 | *Poterium sanquisorba* | G | W | 28.7 |
| *Helichrysum thianschanicum* Regel | G | O | 61.3 | *Prunella vulgaris* | G | O | 40.7 |
| *Heliotropium arborescens* | G | O | 56.2 | *Pteridium aquilinum* | G | O | 25.7 |
| *Heliotropium arborescens* | G | R | 54.9 | *Pteridium aquilinum* | G | R | 100.0 |
| *Humulus lupulus* | G | V | 70.5 | *Raphanus Raphanistrum* | G | R | 42.7 |
| *Humulus lupulus* | G | S | 43.0 | *Ribes nidigrolaria* | G | W | 45.9 |
| *Hypericum henryi* | G | O | 31.0 | *Ribes nigrum* | G | W | 35.9 |
| *Hypericum perforatum* | G | R | 100.0 | *Ribes Silvestris* | G | W | 34.9 |
| *Inula helenium* | G | W | 85.3 | *Ribes Uva-crispa* | G | S | 30.5 |
| *Inula helenium* | G | V | 74.7 | *Ricinus communis* | G | R | 95.0 |
| *Inula helenium* | G | S | 37.4 | *Ricinus communis* | G | S | 48.3 |
| *Ipomea batatas* | G | O | 39.0 | *Rosa rugosa* thunb. | G | W | 40.3 |
| *Isatis tinctoria* | G | O | 100.0 | *Rosa rugosa* thunb. | G | S | 97.8 |
| *Laportea canadensis* | G | O | 26.9 | *Rosmarinus officinalis* | G | O | 100.0 |
| *Laurus nobilis* | G | W | 51.5 | *Rosmarinus officinalis* | G | R | 54.1 |
| *Laurus nobilis* | G | S | 100.0 | *Rosmarinus officinalis* | G | W | 77.7 |
| *Lavendula angustifolia* | G | V | 44.4 | *Rosmarinus officinalis* | G | V | 72.2 |
| *Lavendula latifolia* | G | V | 44.8 | *Rubus canadensis* | G | S | 25.3 |
| *Ledum groenlandicum* | G | S | 100.0 | *Rubus idaeus* L. | G | W | 31.1 |
| *Levistecum officinale* | G | W | 39.6 | *Rubus ideaus* | G | S | 100.0 |
| *Matricaria recutita* | G | O | 100.0 | *Rubus ideaus* | G | R | 37.6 |
| *Melissa officinalis* | G | W | 98.0 | *Rubus ideaus* | G | O | 34.8 |
| *Melissa officinalis* | G | V | 76.3 | *Rubus occidentalis* | G | S | 93.3 |
| *Melissa officinalis* | G | R | 36.6 | *Rubus occidentalis* | G | O | 22.7 |
| *Melissa officinalis* | G | O | 80.6 | *Rubus occidentalis* | G | S | 21.6 |
| *Mentha arvensis* | G | O | 83.5 | *Rumex crispus* linné | G | R | 100.0 |
| *Mentha piperita* | G | O | 79.0 | *Rumex crispus* linné | G | R | 100.0 |
| *Mentha piperita vulgaris* | G | V | 45.9 | *Salvia elegens* | G | V | 41.3 |
| *Mentha pulegium* | G | O | 47.0 | *Salvia elegens* | G | W | 62.9 |
| *Mentha spicata* | G | V | 73.9 | *Salvia officinalis* | G | R | 43.3 |
| *Mentha spicata* | G | O | 81.3 | *Salvia officinalis* | G | O | 55.1 |
| *Mentha spicata* | G | O | 93.0 | *Salvia officinalis* | G | W | 100.0 |
| *Monarda didyma* | G | S | 35.8 | *Alchemilla mollis* | T | S | 98.8 |
| N | G | R | 100.0 | *Alchemilla mollis* | T | O | 24.3 |
| *Salvia officinalis* | G | V | 52.5 | *Alchemilla mollis* | T | S | 83.7 |
| *Salvia officinalis* | G | O | 100.0 | *Alchemilla mollis* | T | O | 80.0 |
| *Salvia officinalis* | G | R | 38.8 | *Althaea officinalis* | T | S | 34.1 |
| *Salvia officinalis* | G | V | 49.5 | *Althaea officinalis* | T | S | 34.3 |
| *Salvia officinalis* | G | W | 95.3 | *Althaea officinalis* | T | S | 30.8 |
| *Salvia officinalis* | G | W | 41.3 | *Ambrosia artemisiifolia* linné | T | O | 61.6 |
| *Salvia sclarea* | G | W | 31.1 | *Ambrosia artemisiifolia* linné | T | R | 52.1 |

TABLE 7-continued

Cath G

| Nom latin | Stress | extrait | Inhibition (%) | Nom latin | Stress | extrait | Inhibition (%) |
|---|---|---|---|---|---|---|---|
| *Sarriette commune* | G | O | 59.7 | *Amelanchier sanguinea* x *A. laevis* | T | S | 38.6 |
| *Sarriette vivace* | G | O | 72.3 | *angelica archangelica* | T | S | 54.8 |
| *Sarriette vivace* | G | S | 26.0 | *Anthemis tinctorium* | T | O | 67.7 |
| *Satureja montana* | G | V | 78.5 | *Arachis hypogaea* | T | V | 85.1 |
| *Satureja montana* | G | W | 100.0 | *Aralia nudicaulis* | T | S | 74.2 |
| *Solanum tuberosum* | G | O | 35.8 | *Arctostaphylos uva-ursi* | T | R | 98.8 |
| *Sonchus oleraceus* L. | G | O | 41.0 | *Arctostaphylos uva-ursi* | T | S | 82.4 |
| *Sorghum dochna* | G | S | 100.0 | *Aronia prunifolia* | T | W | 27.3 |
| *Sorghum sudanense* | G | O | 32.6 | *Artemisia draculus* | T | S | 20.2 |
| *Sorghum sudanense* | G | W | 39.7 | *Artemisia dracunlus* | T | S | 37.2 |
| *Symphytum officinale* | G | V | 79.4 | *Artemisia Ludoviciana* | T | O | 54.8 |
| *Symphytum officinale* | G | O | 74.6 | *Aster* sp ? | T | O | 43.4 |
| *Tanacetum parthenium* | G | V | 23.1 | *Aster* sp ? | T | R | 99.9 |
| *Tanacetum parthenium* | G | W | 24.3 | *Ayperus esculentus* | T | W | 46.9 |
| *Tanacetum vulgare* | G | W | 20.8 | *Beta vulgaris* | T | R | 81.4 |
| *Tanacetum vulgare* | G | O | 32.0 | *Beta vulgaris* | T | O | 30.6 |
| *Tanacetum vulgare* | G | O | 58.5 | *Betula glandulosa* | T | W | 58.2 |
| *Tanacetum vulgare* "Goldsticks" | G | V | 44.8 | *Borago officinalis* | T | O | 20.2 |
| *Taraxacum officinale* | G | V | 58.2 | *Brassica juncea* | T | R | 56.6 |
| *Thymus fragantissumus* | G | R | 39.9 | *Brassica napus* | T | R | 34.1 |
| *Thymus herba-barona* | G | W | 26.6 | *Brassica nigra* | T | S | 32.3 |
| *Thymus herba-barona* | G | V | 35.7 | *Brassica rapa* | T | R | 21.4 |
| *Thymus praecox* subsp *arctitus* | G | O | 78.0 | *Calamintha nepeta* | T | V | 71.4 |
| *Thymus serpyllum* | G | V | 47.4 | *Calamintha nepeta* | T | W | 30.3 |
| *Thymus serpyllum* | G | O | 100.0 | *Canna edulis* | T | O | 31.9 |
| *Thymus serpyllum* | G | W | 22.6 | *Canneberge* | T | R | 66.3 |
| *Thymus serpyllum* | G | V | 70.2 | *Capsella bursa-pastoris* (linné) médicus | T | R | 37.1 |
| *Thymus vulgaris* | G | O | 40.8 | *Carya cordiformis* | T | W | 100.0 |
| *Thymus vulgaris* | G | W | 37.3 | *Chaerophyllum bulbosum* | T | V | 86.0 |
| *Thymus vulgaris* "Argenteus" | G | V | 87.7 | *Chrysanthemum leucanthemum* linné | T | O | 45.4 |
| *Thymus x citriodorus* | G | W | 27.2 | *Cichorium intybus* | T | V | 74.8 |
| *Vaccinum angustifolium* | G | S | 41.7 | *Cichorium intybus* | T | W | 23.8 |
| *Vaccinum macrocarpon* | G | W | 63.5 | *Cichorium intybus* | T | O | 38.9 |
| *Viburnum trilobum* Marsh. | G | R | 67.7 | *Cimicifuga racemosa* | T | W | 65.1 |
| *Viburnum trilobum* Marsh. | G | W | 23.6 | *Citrullus colocynthus* | T | S | 50.2 |
| *Vica sativa* | G | O | 38.5 | *Citrus limettoides* | T | O | 45.1 |
| *Vica villosa* | G | O | 25.2 | *Citrus limettoides* | T | V | 28.9 |
| *Vitia* sp. | G | S | 24.8 | *Citrus limon* | T | O | 25.9 |
| *Vitia* sp. | G | W | 100.0 | *Citrus limon* | T | V | 43.3 |
| *Vitia* sp. | G | R | 100.0 | *Coix Laciyma-Jobi* | T | O | 22.1 |
| *Vitia* sp. | G | S | 20.8 | *Coriandrum sativum* | T | W | 62.0 |
| *Zea mays* | G | O | 53.7 | *Crataegus* sp ? | T | R | 44.0 |
| *Perilla frutescens* | T | O | 100.0 | *Crataegus submollis* | T | S | 40.7 |
| *Perilla frutescens* | T | W | 61.7 | *Crataegus submollis* | T | S | 29.3 |
| *Perilla frutescens* | T | V | 75.6 | *Curcuma longa* syn. *C. domestica* | T | O | 22.2 |
| *Achillea millefolium* | T | W | 41.8 | *Cynara scolymus* | T | R | 42.2 |
| *Achillea millefolium* | T | V | 31.5 | *Dioscorea batatas* | T | O | 29.1 |
| *Acorus calamus* | T | R | 68.4 | *Dioscorea batatas* | T | O | 28.9 |
| *Acorus calamus* | T | S | 39.2 | *Diospiros Kaki* | T | V | 57.8 |
| *Adiantum pedatum* | T | R | 100.0 | *Dirca palustris* | T | S | 39.2 |
| *Agastache foeniculum* | T | O | 78.0 | *Dolichus lablab* | T | R | 42.9 |
| *Agastache foeniculum* "Snow Pike" | T | W | 34.5 | *Dryopteris filix-mas* | T | O | 24.9 |
| *Agastache foeniculum* "Snow Pike" | T | V | 54.3 | *Dryopteris filix-mas* | T | R | 100.0 |
| *Agrimonia eupatoria* | T | W | 100.0 | *Echinacea purpurea* | T | V | 78.9 |
| *Alchemilla mollis* | T | V | 37.1 | *Melissa officinalis* | T | V | 36.0 |
| *Alchemilla mollis* | T | W | 100.0 | *Melissa officinalis* | T | W | 36.8 |
| *Echinacea purpurea* | T | W | 95.8 | *Melissa officinalis* | T | O | 100.0 |
| *Echinacea purpurea* | T | O | 53.7 | *Melissa officinalis* | T | R | 30.3 |
| *Erigeron speciosus* (Lindl.) D.C. | T | O | 96.2 | *mentha arvensis* | T | R | 67.2 |
| *Fragaria* | T | O | 42.7 | *Mentha piperita* | T | S | 20.8 |
| *Fragaria* x *ananassa* | T | S | 100.0 | *Mentha piperita* | T | O | 100.0 |
| *Fragaria* x *ananassa* | T | S | 100.0 | *Mentha piperita* | T | S | 26.9 |
| *Fruit de la passion* | T | O | 30.2 | *Mentha piperita* | T | O | 97.8 |
| *Fucus vesiculosis* | T | O | 93.3 | *Mentha piperita vulgaris* | T | W | 20.2 |
| *Galinsoga ciliata* (Rofiresque) Blake. | T | R | 33.0 | *Mentha piperita vulgaris* | T | V | 42.5 |
| *Galium odoratum* | T | R | 27.0 | *Mentha pulegium* | T | O | 100.0 |
| *Gaultheria hispidula* (L.) Muhl | T | W | 100.0 | *Mentha spicata* | T | W | 51.6 |
| *Gaultheria procumbens* | T | W | 30.0 | *Mentha spicata* | T | V | 81.8 |
| *Gaultheria procumbens* | T | S | 100.0 | *Mentha spicata* | T | O | 100.0 |
| *Glycine max* Envy | T | O | 20.1 | *Mentha spicata* | T | O | 100.0 |
| *Glycyrrhiza glabra* | T | W | 47.9 | *Mentha spicata* | T | S | 23.2 |
| *Guizotia abyssinica* | T | R | 74.1 | *Nepeta cataria* | T | V | 62.8 |
| *Guizotia abyssinica* | T | S | 22.7 | *Ocimum Basilicum* | T | V | 41.1 |
| *Hamamelis virginiana* | T | O | 100.0 | *Ocimum Basilicum* | T | W | 40.0 |
| *Hamamelis virginiana* | T | R | 100.0 | *Ocimum Basilicum* | T | O | 28.4 |

TABLE 7-continued

Cath G

| Nom latin | Stress | extrait | Inhibition (%) | Nom latin | Stress | extrait | Inhibition (%) |
|---|---|---|---|---|---|---|---|
| *Helenium hoopesii* | T | O | 21.7 | *Oenothera biennis* linné | T | O | 67.3 |
| *Helenium hoopesii* | T | S | 24.6 | *Oenothera biennis* linné | T | R | 100.0 |
| *Helianthus annus* | T | O | 21.0 | *Onobrychis viciafolia* | T | O | 34.0 |
| *Helianthus strumosus* | T | O | 85.6 | *Origanum marjonara* | T | O | 29.5 |
| *Helianthus tuberosa* | T | V | 64.5 | *Origanum vulgare* | T | V | 55.5 |
| *Helianthus tuberosa* | T | W | 100.0 | *Origanum vulgare* | T | W | 67.7 |
| *Helichrysum angustifolium* | T | O | 100.0 | *Origanum vulgare* | T | W | 46.4 |
| *Helichrysum angustifolium* | T | W | 87.0 | *Origanum vulgare* | T | V | 68.6 |
| *Helichrysum angustifolium* | T | V | 84.4 | *Origanum vulgare* | T | W | 99.9 |
| *Helichrysum angustifolium* | T | S | 92.3 | *Origanum vulgare* | T | V | 42.0 |
| *Helichrysum thianschanicum* Regel | T | O | 59.5 | *Origanum Vulgare* | T | V | 28.8 |
| *Heliotropium arborescens* | T | O | 85.1 | *Origanum Vulgare* | T | W | 46.7 |
| *Hibiscus cannabinus* | T | O | 25.0 | *Origanum vulgare* | T | O | 100.0 |
| *Humulus lupulus* | T | S | 21.4 | *Origanum vulgare* | T | W | 51.7 |
| *Humulus lupulus* | T | S | 21.5 | *Origanum vulgare* | T | S | 30.8 |
| *Humulus lupulus* | T | R | 88.4 | *Origanum vulgare* | T | O | 25.4 |
| *Humulus lupulus* | T | S | 22.5 | *Origanum vulgare* | T | S | 38.2 |
| *Hypericum perforatum* | T | R | 100.0 | *oxyria digyna* | T | V | 23.1 |
| *Inula helenium* | T | V | 97.1 | *Pastinaca sativa* | T | O | 33.1 |
| *Inula helenium* | T | W | 69.0 | *Pastinaca sativa* | T | R | 22.2 |
| *Inula helenium* | T | S | 29.3 | *Petroselinum crispum* Nyman ex. A. W Hill | T | W | 24.8 |
| *Ipomea batalas* | T | O | 27.0 | *Peucedanum cervaria* | T | R | 53.0 |
| *Iris versicolor* | T | R | 22.9 | *Peucedanum cervaria* | T | R | 35.9 |
| *Juniperus communis* | T | R | 100.0 | *Plaffia paniculata* | T | O | 85.9 |
| *Krameria Triandra* | T | O | 52.6 | *Phaseolus vulgaris* | T | O | 35.7 |
| *Lathyrus sylvestris* | T | R | 32.5 | *Phytolacca americana* | T | S | 28.6 |
| *Laurus nobilis* | T | S | 100.0 | *Phytolacca decandra* syn. *P. americana* | T | O | 31.6 |
| *Lavendula angustifolia* | T | V | 74.8 | *Plectranthus* sp. | T | V | 66.0 |
| *Lavendula angustifolia* | T | W | 70.2 | *Polygonium chinense Polygonum* | T | S | 33.2 |
| *Lavendula latifolia* | T | W | 85.6 | *Polygonium aviculare* linné | T | R | 100.0 |
| *Lavendula latifolia* | T | V | 63.3 | *Populus x petrowskyana* | T | O | 25.4 |
| *Lavendula latifolia* | T | O | 20.2 | *Potentilla anserina* | T | S | 55.8 |
| *Ledum groenlandicum* | T | R | 100.0 | *Poterium sanguisorba* | T | W | 100.0 |
| *Ledum groenlandicum* | T | S | 94.1 | *Poterium sanguisorba* | T | V | 82.3 |
| *Lepidium sativum* | T | O | 20.5 | *Prunella vulgaris* | T | O | 52.6 |
| *Litchi chinensis* | T | S | 100.0 | *Psoralea corylifolia* | T | O | 21.3 |
| *Lolium multiflorum* | T | O | 22.7 | *Psoralea corylifolia* | T | S | 26.0 |
| *Lonicera ramosissima* | T | S | 30.9 | *Psoralea corylifolia* | T | S | 27.4 |
| *Lotus corniculatus* | T | R | 60.2 | *Pteridium aquilinum* | T | R | 100.0 |
| *Malus* | T | V | 23.1 | *Punica granatum* | T | V | 21.3 |
| *Malva moschata* | T | S | 31.4 | *Punica granatum* | T | W | 77.1 |
| *Melissa officinalis* | T | V | 81.4 | *Punica granatum* | T | S | 43.9 |
| *Melissa officinalis* | T | W | 87.5 | *Satureja repandra* | T | R | 35.8 |
| *Melissa officinalis* | T | O | 100.0 | *Satureja repandra* | T | W | 100.0 |
| *Radix Rehmannia* | T | O | 23.9 | *Satureja repandra* | T | V | 75.0 |
| *Raphanus raphanistrum* | T | R | 36.5 | *Solanum Tuberosum* | T | O | 30.9 |
| *Raphanus raphanistrum* | T | R | 30.5 | *Solidago canadensis* | T | R | 91.8 |
| *Rhamnus frangula* | T | R | 100.0 | *Sonchus oleraceus* L. | T | O | 45.9 |
| *Rheum palmatum* | T | W | 100.0 | *Sorghum dochna* Snowdrew | T | O | 31.5 |
| *Rianus communis* | T | R | 100.0 | *Sorghum sudanense* | T | O | 33.6 |
| *Rianus communis* | T | S | 100.0 | *Stipa capillata* L. | T | O | 33.0 |
| *Rianus communis* | T | S | 68.2 | *Symphytum officinale* | T | O | 94.1 |
| *Ribes Grossularia* L. | T | W | 61.1 | *Symphytum officinale* | T | O | 42.8 |
| *Ribes nidigrolaria* | T | W | 32.1 | *Tanacetum parthenium* | T | W | 40.1 |
| *Ribes nigrum* | T | O | 90.2 | *Tanacetum parthenium* | T | V | 33.6 |
| *Ribes nigrum* | T | S | 20.3 | *Tanacetum vulgare* | T | V | 36.5 |
| *Ribes nigrum* L. | T | W | 21.1 | *Tanacetum vulgare* | T | W | 51.2 |
| *Ribes nigrum* L. | T | W | 51.6 | *Tanacetum vulgare* | T | O | 95.6 |
| *Ribes sativam syme* | T | W | 20.9 | *Tanacetum vulgare* | T | O | 38.4 |
| *Ribes uva-crispa* | T | S | 41.8 | *Tanacetum vulgare* | T | R | 27.4 |
| *Rosa rugosa* | T | S | 100.0 | *Tanacetum vulgare* "Goldsticks" | T | V | 37.9 |
| *Rosa rugosa* thumb. | T | W | 94.1 | *Taraxacum officinale* | T | V | 57.8 |
| *Rosmarinum officinalis* | T | O | 100.0 | *Thymus fragantissumus* | T | R | 34.0 |
| *Rosmarinum officinalis* | T | R | 40.0 | *Thymus fragantissumus* | T | W | 72.7 |
| *Rosmarinum officinalis* | T | V | 76.9 | *Thymus fragantissumus* | T | V | 71.0 |
| *Rubus canadensis* | T | S | 31.3 | *Thymus praecox* subsp *arctitus* | T | O | 59.2 |
| *Rubus canadensis* | T | V | 22.8 | *Thymus pseudolanuginosus* | T | V | 85.7 |
| *Rubus canadensis* | T | W | 100.0 | *Thymus pseudolanuginosus* | T | W | 20.9 |
| *Rubus idaeus* | T | V | 25.0 | *Thymus serpyllum* | T | O | 94.8 |
| *Rubus idaeus* L. | T | S | 100.0 | *Thymus serpyllum* | T | W | 38.4 |
| *Rubus ideaus* | T | S | 46.1 | *Thymus vulgaris* | T | O | 100.0 |
| *Rubus ideaus* | T | R | 32.0 | *Thymus vulgaris* "Argenteus" | T | V | 80.4 |
| *Rubus ideaus* | T | O | 28.5 | *Thymus x citriodorus* | T | O | 100.0 |
| *Rubus occidentalis* | T | R | 100.0 | *Tiarella cordifolia* | T | R | 100.0 |
| *Rubus occidentalis* | T | O | 23.5 | *Trichosanthes kirilowii* | T | O | 100.0 |

TABLE 7-continued

Cath G

| Nom latin | Stress | extrait | Inhibition (%) | Nom latin | Stress | extrait | Inhibition (%) |
|---|---|---|---|---|---|---|---|
| *Rumes scutatus* | T | O | 27.1 | *Triticale* sp. | T | O | 24.4 |
| *Rumex acetosella* linné | T | O | 23.0 | *Tropaeolum majus* | T | O | 20.6 |
| *Rumex crispus* linné | T | R | 100.0 | *Ulmus americana* | T | O | 43.7 |
| *Rumex crispus* linné | T | R | 100.0 | *Urtica dioica* | T | R | 28.9 |
| *Salvia (elegens)* | T | O | 100.0 | *Vaccinium angustifolium* | T | S | 43.2 |
| *Salvia elegens* | T | W | 63.5 | *Vaccinium angustifolium* | T | S | 42.4 |
| *Salvia officinalis* | T | O | 34.0 | *Vaccinium macrocarpon* | T | W | 59.2 |
| *Salvia officinalis* | T | R | 41.7 | *Vaccinium macrocarpon* | T | S | 27.2 |
| *Salvia officinalis* | T | V | 64.3 | *Vaccinium macrocarpon* | T | S | 21.6 |
| *Salvia officinalis* | T | W | 100.0 | *Vaccinum macrocarpon* | T | V | 62.6 |
| *Salvia officinalis* | T | R | 38.8 | *Veronica officinalis* | T | S | 52.6 |
| *Salvia officinalis* | T | O | 73.4 | *Viburnum trilobum* Marsh. | T | R | 100.0 |
| *Salvia officinalis* | T | W | 95.3 | *Vida villosa* | T | O | 36.6 |
| *Salvia officinalis* | T | V | 56.8 | *Vitia* sp. | T | W | 58.9 |
| *Salvia officinalis* | T | W | 25.1 | *Vitis* sp | T | S | 24.7 |
| *Salvia sclarea* | T | W | 28.6 | *Vitis* sp. | T | S | 22.8 |
| *Sambucus canadensis* | T | S | 40.1 | *Vitis* sp. | T | S | 21.7 |
| *Sambucus canadensis* L. | T | O | 50.2 | *Zea mays* | T | S | 20.5 |
| *Sambucus canadensis* | T | S | 29.7 | | | | |
| *Sanguisorba minor* | T | V | 32.0 | | | | |
| *Sanguisorba minor* | T | W | 59.5 | | | | |
| *Sanguisorba minor* | T | S | 58.5 | | | | |
| *Sanguisorba minor* | T | S | 68.5 | | | | |
| *Satureja hortensis* | T | O | 66.5 | | | | |
| *Satureja hortensis* | T | S | 20.1 | | | | |
| *Satureja montana* | T | O | 43.3 | | | | |
| *Satureja montana* | T | R | 36.7 | | | | |
| *Satureja montana* | T | W | 100.0 | | | | |
| *Satureja montana* | T | V | 81.1 | | | | |
| *Satureja montana* | T | S | 40.6 | | | | |
| *Satureja montana* | T | V | 54.0 | | | | |
| *Satureja montana* | T | O | 90.1 | | | | |

TABLE 8

Cath L

| Nom latin | Stress | extrait | Inhibition (%) | Nom latin | Stress | extrait | Inhibition (%) |
|---|---|---|---|---|---|---|---|
| *Actinidia arguta* | A | R | 63.3 | *Capsella bursa-pastoris* | A | O | 47.0 |
| *Actinidia arguta* | A | O | 46.3 | *Capsicum annuum* | A | R | 29.1 |
| *Achillea millefolium* | A | O | 32.4 | *Carum carvi* | A | O | 60.4 |
| *Achillea millefolium* | A | R | 26.3 | *Chaerophyllum bulbosum* | A | O | 48.6 |
| *Aconitum napellus* | A | O | 30.0 | *Chaerophyllum bulbosum* | A | R | 48.2 |
| *Acorus calamus* | A | R | 25.9 | *Chelidonium majus* | A | O | 35.5 |
| *Adiantum pedatum* | A | O | 20.2 | *Chelidonium majus* | A | R | 23.1 |
| *Adiantum pedatum* | A | R | 22.2 | *Chenopodium bonus-henricus* | A | O | 65.9 |
| *Agropyron repens* | A | O | 98.6 | *Chenopodium quinoa* | A | R | 62.3 |
| *Agropyron repens* | A | R | 61.8 | *Chenopodium quinoa* | A | O | 90.0 |
| *Alchemilla mollis* | A | O | 75.7 | *Cicer arietinum* | A | O | 82.4 |
| *Alchemilla mollis* | A | R | 36.5 | *Cichorium intybus* | A | R | 58.0 |
| *Allium porrum* | A | R | 39.7 | *Cichorium intybus* | A | O | 81.7 |
| *Allium porrum* | A | O | 58.2 | *Coix Lacryma-Jobi* | A | R | 32.6 |
| *Allium cepa* | A | O | 51.0 | *Coix Lacryma-Jobi* | A | O | 43.4 |
| *Allium sativum* | A | O | 53.8 | *Coriandrum sativum* | A | R | 26.9 |
| *Allium schoenoprasum* | A | O | 74.6 | *Coriandrum sativum* | A | O | 65.0 |
| *Allium Tuberosum* | A | O | 69.5 | *Cornus canadensis* | A | R | 99.7 |
| *Aloe vera* | A | R | 44.7 | *Cornus canadensis* | A | O | 60.6 |
| *Aloe vera* | A | O | 55.6 | *Crataegus* sp | A | R | 25.9 |
| *Althaea officinalis* | A | O | 95.0 | *Crataegus* sp | A | O | 28.2 |
| *Althaea officinalis* | A | R | 33.4 | *Cryptotaenia canadensis* | A | O | 73.3 |

TABLE 8-continued

Cath L

| Nom latin | Stress | extrait | Inhibition (%) | Nom latin | Stress | extrait | Inhibition (%) |
|---|---|---|---|---|---|---|---|
| Amaranthus retroflexus | A | R | 74.5 | Cryptotaenia canadensis | A | R | 36.1 |
| Amaranthus retroflexus | A | O | 98.4 | Cymbopogon citratus | A | O | 32.7 |
| Anethum graveolens | A | R | 37.4 | Daucus carota | A | R | 63.6 |
| Anethum graveolens | A | O | 58.7 | Daucus carota | A | O | 43.4 |
| Angelica archangelica | A | O | 79.1 | Dirca palustris | A | O | 61.1 |
| Apium graveolens | A | R | 27.9 | Dirca palustris | A | R | 46.6 |
| Apium graveolens | A | O | 46.5 | Echinacea purpurea | A | O | 54.8 |
| Aralia nudicaulis | A | O | 89.3 | Eleusine coracana | A | O | 36.4 |
| Aralia nudicaulis | A | R | 55.4 | Fagopyrum esculentum | A | R | 37.9 |
| Arctium lappa | A | R | 32.8 | Fagopyrum esculentum | A | O | 43.3 |
| Arctium minus | A | R | 72.5 | Fagopyrum tataricum | A | R | 28.4 |
| Arctium minus | A | O | 61.3 | Fagopyrum tataricum | A | O | 32.8 |
| Armoracia rusticana | A | O | 95.8 | Foeniculum vulgare | A | O | 48.8 |
| Aronia melanocarpa | A | R | 39.8 | Fragaria x ananassa | A | R | 46.3 |
| Aronia melanocarpa | A | O | 28.2 | Fragaria x ananassa | A | O | 78.8 |
| Artemisia Absinthium | A | R | 51.7 | Galinsoga ciliata | A | O | 46.0 |
| Artemisia Absinthium | A | O | 63.7 | Galium odoratum | A | R | 59.8 |
| Artemisia dracunculus | A | O | 45.4 | Galium odoratum | A | O | 79.5 |
| Aster sp | A | R | 41.8 | Gaultheria hispidula | A | R | 53.4 |
| Aster sp | A | O | 91.5 | Gaultheria hispidula | A | O | 54.3 |
| Atropa belladonna | A | O | 47.3 | Glechoma hederacea | A | O | 23.4 |
| Atropa belladonna | A | R | 31.7 | Glechoma hederacea | A | R | 26.9 |
| Cyperus esculentus | A | R | 41.3 | Glycine max | A | R | 20.5 |
| Cyperus esculentus | A | O | 33.8 | Glycine max | A | O | 73.8 |
| Beckmannia eruciformis | A | O | 60.8 | Glycyrrhiza glabra | A | O | 57.7 |
| Beckmannia eruciformis | A | O | 60.8 | Glycyrrhiza glabra | A | R | 53.8 |
| Beta vulgaris | A | R | 66.1 | Guizotia abyssinica | A | R | 29.6 |
| Beta vulgaris | A | O | 79.5 | Guizotia abyssinica | A | O | 78.6 |
| Beta vulgaris spp. Maritima | A | O | 63.3 | Hamamelis virginiana | A | R | 41.2 |
| Beta vulgaris spp. Maritima | A | R | 59.1 | Hedeoma pulegioides | A | O | 26.3 |
| Borago officinalis | A | O | 40.9 | Helleborus niger | A | O | 36.9 |
| Brassica napus | A | O | 64.6 | Helleborus niger | A | R | 35.4 |
| Brassica napus | A | R | 21.1 | Hordeum hexastichon | A | R | 31.1 |
| Brassica oleracea | A | R | 66.6 | Hyssopus officinalis | A | R | 84.8 |
| Brassica oleracea | A | O | 68.6 | Hyssopus officinalis | A | O | 85.8 |
| Brassica rapa | A | O | 99.0 | Inula helenium | A | O | 58.4 |
| Brassica rapa | A | R | 99.3 | Inula helenium | A | R | 32.7 |
| Campanula rapunculus | A | R | 59.0 | Ipomoea Batatas | A | O | 29.6 |
| Campanula rapunculus | A | O | 50.6 | Lathyrus sativus | A | R | 31.7 |
| Canna edulis | A | O | 23.9 | Lathyrus sativus | A | O | 71.1 |
| Capsella bursa-pastoris | A | R | 49.0 | Lathyrus sylvestris | A | R | 65.3 |
| Lathyrus sylvestris | A | O | 66.4 | Rosa rugosa | A | O | 35.9 |
| Laurus nobilis | A | R | 43.1 | Rosmarinus officinalis | A | O | 78.2 |
| Laurus nobilis | A | O | 46.1 | Rubus alleghensis | A | O | 76.8 |

TABLE 8-continued

Cath L

| Nom latin | Stress | extrait | Inhibition (%) | Nom latin | Stress | extrait | Inhibition (%) |
|---|---|---|---|---|---|---|---|
| Leonurus cardiaca | A | O | 63.3 | Rubus canadensis | A | R | 40.7 |
| Leonurus cardiaca | A | R | 24.5 | Rubus canadensis | A | O | 72.6 |
| Levisticum officinale | A | R | 20.9 | Rubus idaeus | A | R | 35.5 |
| Levisticum officinale | A | O | 43.8 | Rubus idaeus | A | O | 97.9 |
| Lotus corniculatus | A | R | 59.0 | Rumex Acetosa | A | O | 32.0 |
| Lotus corniculatus | A | O | 87.4 | Rumex acetosella | A | R | 73.2 |
| Lycopersicon esculentum | A | R | 28.0 | Rumex acetosella | A | O | 56.9 |
| Malva sylvestris | A | O | 23.1 | Rumex crispus | A | R | 49.7 |
| Medicago sativa | A | R | 63.8 | Rumex crispus | A | O | 37.5 |
| Medicago sativa | A | O | 53.6 | Rumex Scutatus | A | O | 53.1 |
| Melilotus albus | A | O | 93.7 | Rumex Scutatus | A | R | 25.9 |
| Melilotus albus | A | R | 80.1 | Ruta graveolens | A | O | 56.2 |
| Melissa officinalis | A | R | 40.8 | Salix purpurea | A | R | 71.4 |
| Melissa officinalis | A | O | 69.5 | Salix purpurea | A | O | 24.7 |
| Mentha piperita | A | R | 61.0 | Salvia elegans | A | O | 67.6 |
| Mentha piperita | A | O | 73.2 | Salvia officinalis | A | O | 70.5 |
| Mentha pulegium | A | O | 69.0 | Salvia officinalis | A | R | 56.6 |
| Mentha spicata | A | O | 94.6 | Salvia sclarea | A | O | 70.1 |
| Mentha suaveolens | A | O | 55.2 | Santolina chamaecyparissus | A | R | 59.5 |
| Nepeta cataria | A | R | 45.9 | Santolina chamaecyparissus | A | O | 59.2 |
| Nepeta cataria | A | O | 66.3 | Satureja montana | A | O | 71.7 |
| Nicotiana tabacum | A | R | 46.8 | Scorzonera hispanica | A | O | 21.9 |
| Oenothera biennis | A | R | 69.8 | Secale cereale | A | R | 33.3 |
| Oenothera biennis | A | O | 47.3 | Senecio vulgaris | A | R | 47.5 |
| Origanum majorana | A | O | 38.5 | Senecio vulgaris | A | O | 20.8 |
| Origanum vulgare | A | R | 43.3 | Setaria italica | A | R | 48.6 |
| Origanum vulgare | A | O | 68.2 | Setaria italica | A | O | 37.1 |
| Panax quinquefolius | A | R | 41.7 | Sium Sisarum | A | O | 33.8 |
| Panax quinquefolius | A | O | 83.7 | Sium Sisarum | A | O | 62.5 |
| Pastinaca sativa | A | O | 62.8 | Solanum tuberosum | A | O | 53.6 |
| Pastinaca sativa | A | R | 44.2 | Solidago sp | A | R | 54.0 |
| Perilla frutescens | A | O | 66.2 | Solidago sp | A | O | 95.1 |
| Petasites japonicus | A | R | 22.6 | Sonchus oleraceus | A | R | 59.4 |
| Petasites japonicus | A | O | 25.5 | Sonchus oleraceus | A | O | 69.2 |
| Petroselinum crispum | A | O | 79.1 | Sorghum dochna | A | R | 33.9 |
| Petroselinum crispum | A | R | 32.3 | Sorghum dochna | A | O | 55.3 |
| Phalaris canariensis | A | R | 45.4 | Sorghum durra | A | R | 61.3 |
| Phaseolus vulgaris | A | R | 31.0 | Sorghum durra | A | O | 83.9 |
| Phaseolus Vulgaris | A | O | 61.8 | Stachys byzantina | A | R | 61.6 |
| Pimpinella anisum | A | O | 38.1 | Stachys byzantina | A | O | 73.8 |
| Plantago major | A | O | 95.1 | Stellaria graminea | A | R | 40.1 |
| Plectranthus sp. | A | R | 76.9 | Stellaria graminea | A | O | 55.8 |
| Plectranthus sp. | A | O | 58.0 | Stellaria media | A | R | 70.9 |
| Polygonum aviculare | A | R | 28.0 | Stellaria media | A | O | 51.4 |
| Polygonum aviculare | A | O | 49.7 | Tanacetum cinerariifolium | A | O | 67.7 |
| Potentilla anserina | A | R | 26.6 | Tanacetum parthenium | A | R | 50.8 |
| Poterium Sanquisorba | A | O | 58.0 | Tanacetum parthenium | A | O | 81.9 |
| Pteridium aquilinum | A | R | 32.9 | Tanacetum vulgare | A | R | 56.2 |
| Raphanus raphanistrum | A | R | 70.7 | Tanacetum vulgare | A | O | 51.9 |
| Raphanus raphanistrum | A | O | 83.2 | Taraxacum officinale | A | O | 98.7 |
| Raphanus salivus | A | R | 90.9 | Taraxacum officinale | A | R | 82.1 |

TABLE 8-continued

| Cath L | | | | | | | |
|---|---|---|---|---|---|---|---|
| Nom latin | Stress | extrait | Inhibition (%) | Nom latin | Stress | extrait | Inhibition (%) |
| Raphanus sativus | A | O | 95.4 | Teucrium chamaedrys | A | O | 62.2 |
| Rheum rhabarbarum | A | R | 26.0 | Thymus praecox subsp arcticus | A | R | 42.0 |
| Rheum rhabarbarum | A | O | 62.9 | Thymus praecox subsp arcticus | A | O | 54.2 |
| Ribes nigrum | A | O | 62.9 | Thymus serpyllum | A | O | 93.4 |
| Ribes Sylvestre | A | R | 34.5 | Thymus serpyllum | A | R | 57.5 |
| Ribes Sylvestre | A | O | 80.3 | Thymus vulgaris | A | R | 68.7 |
| Ricinus communis | A | R | 89.9 | Thymus vulgaris | A | O | 55.8 |
| Ricinus communis | A | O | 81.0 | Thymus x citriodorus | A | O | 72.8 |
| Rosa rugosa | A | R | 32.9 | Thymus x citriodorus | A | R | 31.9 |
| Tragopogon porrifolius | A | O | 67.2 | Asparagus officinalis | G | O | 86.3 |
| Tragopogon porrifolius | A | R | 37.0 | Aster Linne | G | O | 57.5 |
| Tropaeolum malus | A | O | 62.8 | Aster sp | G | R | 48.7 |
| Typha latifolia | A | R | 77.5 | Aster sp | G | O | 94.5 |
| Typha latifolia | A | O | 70.6 | Atropa belladonna | G | R | 29.2 |
| Vaccinium Corymbosum | A | O | 74.7 | Beckmannia eruciformis | G | O | 32.9 |
| Vaccinium Corymbosum | A | R | 69.5 | Beta vulgaris | G | R | 47.9 |
| Vaccinium macrocarpon | A | R | 71.4 | Beta vulgaris | G | O | 61.9 |
| Vaccinum macrocarpon | A | O | 78.9 | Borago officinalis | G | O | 51.9 |
| Verbascum thapsus | A | O | 76.8 | Brassica Napus | G | O | 92.1 |
| Verbascum thapsus | A | R | 62.0 | Brassica napus | G | R | 30.2 |
| Vicia sativa | A | R | 79.2 | Brassica oleracea | G | R | 79.0 |
| Vicia sativa | A | O | 88.7 | Brassica oleracea | G | O | 85.4 |
| Vicia villosa | A | O | 74.5 | Brassica rapa | G | O | 81.7 |
| Vicia villosa | A | R | 61.0 | Calamagrostis arundiflora | G | R | 59.7 |
| Vinca minor | A | O | 46.7 | Campanula rapunculus | G | R | 65.4 |
| Vinca minor | A | R | 31.9 | Campanula rapunculus | G | O | 54.8 |
| Vitiis sp. | A | R | 89.5 | Canna edulis | G | O | 30.0 |
| Vitiis sp. | A | O | 54.6 | Capsella bursa-pastoris | G | R | 48.1 |
| Zea mays | A | R | 52.0 | Capsella bursa-pastoris | G | O | 50.9 |
| Zea mays | A | O | 93.8 | Tropaeolum majus | G | R | 22.2 |
| Achillea millefolium | G | O | 45.8 | Tropaeolum majus | G | O | 59.1 |
| Achillea millefolium | G | R | 24.6 | Carum carvi | G | O | 62.4 |
| Aconitum napellus | G | R | 28.7 | Cerastium tomentosum | G | R | 45.1 |
| Acorus calamus | G | R | 37.5 | Chaerophyllum bulbosum | G | O | 30.0 |
| Acorus calamus | G | O | 32.8 | Chaerophyllum bulbosum | G | R | 54.5 |
| Actinidia arguta | G | R | 47.8 | Chelidonium majus | G | O | 43.2 |
| Actinidia arguta | G | O | 78.4 | Chelidonium majus | G | R | 30.7 |
| Adiantum pedatum | G | O | 45.9 | Chichorium endivia | G | O | 64.2 |
| Adiantum pedatum subsp endivia | G | R | 27.0 | Chichorium endivia | G | R | 48.3 |
| Agropyron repens subsp endivia | G | O | 83.0 | Chichorium endivia | G | O | 67.0 |
| Agropyron repens | G | R | 31.9 | Cichorium intybus | G | O | 78.3 |
| Alchemilla mollis | G | O | 71.0 | Cichorium intybus | G | R | 87.8 |
| Allium ampeloprasum | G | R | 36.8 | Circium arvense | G | R | 94.1 |
| Allium ampeloprasum | G | O | 62.2 | Circium arvense | G | O | 58.7 |
| Allium cepa | G | R | 56.1 | Coix Lamyma-Tobi | G | R | 35.7 |
| Allium cepa | G | O | 64.4 | Coix Lamyma-Tobi | G | O | 31.4 |
| Allium sativum | G | O | 65.2 | Cornus canadensis | G | R | 61.3 |

TABLE 8-continued

| Cath L | | | | | | |
|---|---|---|---|---|---|---|
| Nom latin | Stress | extrait | Inhibition (%) | Nom latin | Stress | extrait | Inhibition (%) |
| *Allium schoenoporasum* | G | O | 78.4 | *Cornus canadensis* | G | O | 80.6 |
| *Allium tuberosum* | G | O | 46.6 | *Crataegus submollis* | G | R | 21.0 |
| *Aloe vera* | G | O | 45.7 | *Crataegus submollis* | G | O | 44.4 |
| *Althaea officianalis* | G | O | 50.0 | *Cymbopogon citratus* | G | R | 39.6 |
| *althaea officinalis* | G | R | 42.2 | *Cyperus esculentus* | G | R | 62.4 |
| *Amaranthus retroflexus* | G | R | 41.7 | *Cyperus esculentus* | G | O | 49.6 |
| *Amaranthus retroflexus* | G | O | 90.3 | *Daucus carota* | G | O | 36.3 |
| *Anethum graveolens* | G | R | 31.3 | *Daucus carota* | G | R | 44.3 |
| *Anethum graveolens* | G | O | 60.5 | *Dirca palustris* | G | O | 85.1 |
| *Angelica archangelica* | G | O | 64.3 | *Dirca palustris* | G | R | 47.1 |
| *Angelica archangelica* | G | R | 63.3 | *Echinacea purpurea* | G | O | 36.4 |
| *Apium graveolens* | G | O | 57.0 | *Eleusine coracana* | G | O | 65.4 |
| *Apium graveolens* | G | R | 28.4 | *Eleusine coracana* | G | R | 36.8 |
| *Aralia nudicaulis* | G | O | 71.8 | *Erigeron speciosus* | G | R | 39.1 |
| *Aralia nudicaulis* | G | R | 38.2 | *Erysimum perofskianum* | G | R | 58.7 |
| *Arctium minus* | G | R | 42.4 | *Erysimum perofskianum* | G | O | 93.1 |
| *Arctium minus* | G | O | 41.5 | *Fagopyrum esculentum* | G | R | 36.4 |
| *Armoracia rusticana* | G | O | 67.1 | *Fagopyrum esculentum* | G | O | 41.0 |
| *Aronia melanocarpa* | G | R | 32.0 | *Fagopyrum tataricum* | G | R | 43.3 |
| *Aronia melanocarpa* | G | O | 70.0 | *Fagopyrum tataricum* | G | O | 29.1 |
| *Artemisia absinthium* | G | R | 63.1 | *Galinsoga ciliata* | G | R | 49.8 |
| *Artemisia absinthium* | G | O | 61.1 | *Galinsoga ciliata* | G | O | 58.0 |
| *Asclepias incarnata* | G | R | 58.4 | *Galium odoratum* | G | R | 65.1 |
| *Asclepias incarnata* | G | O | 63.3 | *Galium odoratum* | G | O | 94.2 |
| *Asparagus officinalis* | G | R | 61.2 | *Gaultheria hispidula* | G | R | 55.7 |
| *Gaultheria hispidula* | G | O | 50.6 | *Oenothera biennis* | G | O | 44.3 |
| *Gaultheria procumbens* | G | R | 53.3 | *Origanum majorana* | G | O | 44.7 |
| *Gaultheria procumbens* | G | O | 67.7 | *Origanum vulgare* | G | O | 58.1 |
| *Glechoma hederacea* | G | O | 70.9 | *Origanum vulgare* | G | R | 22.9 |
| *Glechoma hederacea* | G | R | 25.3 | *Oryza Sativa* | G | R | 71.8 |
| *Glycine max* | G | R | 78.6 | *Oryza Sativa* | G | O | 39.8 |
| *Glycine max* | G | O | 85.9 | *Oxalis Deppei* | G | R | 80.1 |
| *Glycyrrhiza glabra* | G | R | 59.1 | *Oxalis Deppei* | G | O | 28.8 |
| *Glycyrrhiza glabra* | G | O | 60.6 | *Oxyria digyna* | G | R | 51.8 |
| *Guizotia abyssinica* | G | R | 41.8 | *Oxyria digyna* | G | O | 36.2 |
| *Guizotia abyssinica* | G | O | 74.3 | *Panax quinquefolius* | G | R | 72.1 |
| *Hamamelis virginiana* | G | R | 44.2 | *Panax quinquefolius* | G | O | 81.6 |
| *Helianthus strumosus* | G | O | 40.6 | *Panicum miliaceum* | G | O | 93.4 |
| *Helianthus strumosus* | G | R | 61.4 | *Passiflora caerula* | G | R | 33.2 |
| *Helianthus tuberosus* | G | O | 75.1 | *Passiflora caerula* | G | O | 63.2 |

TABLE 8-continued

| Cath L | | | | | | |
|---|---|---|---|---|---|---|
| Nom latin | Stress | extrait | Inhibition (%) | Nom latin | Stress | extrait | Inhibition (%) |
| Helianthus tuberosus | G | R | 30.1 | Pastinaca sativa | G | O | 54.0 |
| Helichrysum thianschanicum | G | R | 56.3 | Pennisetum alopecuroides | G | R | 61.0 |
| Helichrysum thianschanicum | G | O | 84.0 | Petasites japonicus | G | O | 50.0 |
| Helleborus niger | G | O | 38.8 | Petroselinum crispum | G | R | 49.1 |
| Helleborus niger | G | R | 25.9 | Petroselinum crispum | G | O | 52.2 |
| Hordeum hexastichon | G | O | 62.3 | Phalaris canariensis | G | O | 72.1 |
| Hordeum hexastichon | G | R | 29.4 | Phaseolus vulgaris | G | R | 21.8 |
| Hyssopus officinalis | G | R | 64.7 | Pimpinella anisum | G | O | 86.2 |
| Hyssopus officinalis | G | O | 71.9 | Pisum sativum | G | O | 61.6 |
| Inula helenium | G | O | 29.4 | Pisum sativum | G | R | 57.5 |
| Inula helenium | G | R | 25.7 | Plantago major | G | O | 91.9 |
| Ipomoea batatas | G | O | 36.9 | Plectranthus sp. | G | R | 53.0 |
| Lactuca sativa | G | O | 70.4 | Plectranthus sp. | G | O | 73.0 |
| Lactuca sativa | G | R | 49.9 | Polygonum aviculare | G | R | 32.2 |
| Lathyrus sativus | G | O | 62.8 | Polygonum aviculare | G | O | 36.4 |
| Lathyrus sativus | G | R | 29.0 | Portulaca oleracea | G | R | 82.1 |
| Lathyrus sylvestris | G | R | 52.1 | Portulaca oleracea | G | O | 63.3 |
| Lathyrus sylvestris | G | O | 52.5 | Potentilla anserina | G | R | 26.3 |
| Laurus nobilis | G | R | 27.1 | Poterium sanquisorba | G | O | 79.9 |
| Laurus nobilis | G | O | 61.0 | Prunella vulgaris | G | R | 68.8 |
| Lavandula angustifolia | G | R | 51.9 | Prunella vulgaris | G | O | 57.4 |
| Lavandula angustifolia | G | O | 57.0 | Raphanus Raphanistrum | G | R | 91.9 |
| Ledum groenlandicum | G | O | 73.4 | Raphanus Raphanistrum | G | O | 55.2 |
| Ledum groenlandicum | G | R | 52.6 | Rhaphanus sativus | G | R | 55.7 |
| Leonurus cardiaca | G | O | 88.8 | Rhaphanus sativus | G | O | 78.4 |
| Leonurus cardiaca | G | R | 38.5 | Rheum rhabarbarum | G | R | 27.1 |
| Levistecum officinale | G | R | 51.2 | Rheum rhabarbarum | G | O | 56.8 |
| Levistecum officinale | G | O | 78.3 | Ribes nidigrolaria | G | O | 70.7 |
| Lotus comiculatus | G | O | 86.8 | Ribes nigrum | G | R | 37.9 |
| Lotus comiculatus | G | R | 50.3 | Ribes nigrum | G | O | 98.9 |
| Lupinus polyphyllus | G | R | 78.9 | Ribes Sylvestris | G | R | 25.2 |
| Lupinus polyphyllus | G | O | 66.7 | Ribes Sylvestris | G | O | 65.7 |
| Malus hupehensis | G | R | 52.7 | Ricinus communis | G | R | 39.3 |
| Malus hupehensis | G | O | 64.1 | Ricinus communis | G | O | 84.3 |
| Malva sylvestris officinalis | G | R | 26.2 | Rosmarinus | G | O | 68.6 |
| Medicago sativa | G | R | 43.4 | Rubus idaeus | G | O | 26.3 |
| Medicago sativa | G | O | 92.5 | Rumex crispus | G | R | 54.2 |
| Melilotus albus | G | R | 75.5 | Rumex crispus | G | O | 62.0 |
| Melilotus albus | G | O | 70.0 | Rumex scutatus | G | O | 38.1 |
| Melissa officinalis | G | O | 81.1 | Ruta graveolens | G | O | 85.0 |
| Mentha piperita | G | O | 54.4 | Salix purpurea | G | R | 74.7 |
| Mentha pulegium | G | O | 59.4 | Salix purpurea | G | O | 38.5 |
| Mentha spicata | G | R | 38.8 | Salvia elegans | G | O | 54.8 |
| Mentha spicata | G | O | 83.0 | Salvia officinalis | G | R | 89.7 |
| Mentha suaveolens | G | O | 56.5 | Salvia officinalis | G | O | 84.9 |
| Nepeta cataria | G | O | 56.2 | Salvia sclarea | G | O | 61.8 |
| Ocimum basilicum | G | O | 60.3 | Sambucus ebulus | G | R | 48.2 |
| Oenothera biennis | G | R | 39.2 | Sambucus ebulus | G | O | 98.2 |
| Santolina chamaecyparissus | G | R | 61.3 | Vaccinium macrocarpon | G | O | 76.7 |
| Santolina chamaecyparissus | G | O | 88.2 | Veratrum viride | G | O | 35.4 |

TABLE 8-continued

| Cath L | | | | | | |
|---|---|---|---|---|---|---|
| Nom latin | Stress | extrait | Inhibition (%) | Nom latin | Stress | extrait | Inhibition (%) |
| Saponaria officinalis | G | R | 52.9 | Verbascum thapsus | G | O | 72.9 |
| Saponaria officinalis | G | O | 71.8 | Verbascum thapsus | G | R | 60.5 |
| Satureja hortensis | G | O | 44.9 | Viburnum trilobum | G | R | 52.6 |
| Satureja montana | G | O | 76.8 | Vicia sativa | G | R | 36.6 |
| Scorzonera hispanica | G | R | 32.9 | Vicia sativa | G | O | 83.2 |
| Scuttellaria lateriflora | G | O | 49.8 | Vicia villosa | G | O | 77.3 |
| Scuttellaria lateriflora | G | R | 39.6 | Vicia villosa | G | R | 46.8 |
| Secale cereale | G | R | 37.0 | Vinca minor | G | O | 63.0 |
| Senecio vulgaris | G | R | 31.0 | Vinca minor | G | R | 30.8 |
| Senecio vulgaris | G | O | 47.0 | Vitis sp. | G | R | 52.7 |
| Setaria italica | G | R | 44.9 | Vitis sp. | G | O | 99.2 |
| Setaria italica | G | O | 42.0 | Zea mays | G | R | 45.1 |
| Silene vulgaris | G | R | 76.8 | Zea mays | G | O | 55.3 |
| Silene vulgaris | G | O | 92.2 | Perilla frutescens | T | R | 68.0 |
| Sium sisarum | G | O | 58.9 | Perilla frutescens | T | O | 74.4 |
| Sium sisarum | G | R | 66.6 | Achillea millefolium | T | O | 46.0 |
| solanum melongena | G | R | 66.8 | Achillea millefolium | T | R | 32.9 |
| Solanum tuberosum | G | O | 47.4 | Aconitum napellus | T | O | 35.2 |
| Solidago sp | G | R | 53.6 | Aconitum napellus | T | R | 31.9 |
| Solidago sp | G | O | 88.3 | Acorus calamus | T | O | 40.6 |
| Sonchus oleraceus | G | R | 62.5 | Acorus calamus | T | R | 26.9 |
| Sonchus oleraceus | G | O | 55.5 | Actinidia arguta | T | R | 80.0 |
| Sorghum dochna | G | R | 67.4 | Actinidia arguta | T | O | 66.3 |
| Sorghum dochna | G | O | 73.7 | Adiantum pedatum | T | O | 43.4 |
| sorghum durra eupatoria | G | R | 24.8 | Agrimonia | T | O | 37.5 |
| sorghum durra | G | O | 42.3 | Agropyron repens | T | O | 75.0 |
| Sorghum sudanense | G | R | 35.5 | Agropyron repens | T | R | 50.0 |
| Sorghum sudanense | G | O | 66.3 | Alchemilla mollis | T | O | 71.6 |
| Stachys byzantina | G | R | 75.5 | Alchemilla mollis | T | R | 81.1 |
| Stachys byzantina | G | O | 66.7 | Allium ampeloprasum | T | O | 84.4 |
| Stellaria graminea | G | R | 36.9 | Allium cepa | T | O | 49.2 |
| Stellaria graminea | G | O | 40.1 | Allium cepa | T | R | 30.1 |
| Stellaria media | G | R | 31.2 | Allium sativum | T | O | 63.8 |
| Stellaria media | G | O | 51.1 | Allium schoenoprasum | T | O | 79.6 |
| Symphytum officinale | G | R | 90.2 | Allium tuberosum | T | O | 55.8 |
| Symphytum officinale | G | O | 90.8 | Allium tuberosum | T | R | 29.6 |
| Tanacetum cinerariifolium | G | O | 76.1 | Aloe vera | T | R | 30.3 |
| Tanacetum parthenium | G | R | 70.1 | Aloe vera | T | O | 42.7 |
| Tanacetum parthenium | G | O | 62.4 | Althaea officinalis | T | R | 42.5 |
| Tanacetum vulgare | G | R | 36.2 | Althaea officinalis | T | O | 46.3 |
| Tanacetum vulgare | G | O | 72.5 | Amaranthus candatus | T | R | 37.3 |
| Taraxacum officinale | G | O | 100.0 | Amaranthus candatus | T | O | 60.0 |
| Taraxacum officinale | G | R | 78.6 | Amaranthus retroflexus | T | R | 33.2 |
| Teucrium chamaedrys | G | O | 50.5 | Amaranthus retroflexus | T | O | 94.3 |
| Teucrium chamaedrys | G | R | 40.1 | angelica archangelica | T | O | 37.4 |
| Thymus fragantissimus | G | R | 81.4 | angelica archangelica | T | R | 55.7 |
| Thymus fragantissimus | G | O | 58.4 | Anthriscus cerefolium | T | O | 86.5 |
| Thymus praecox subsp arcticus | G | R | 49.2 | Anthriscus cerefolium | T | R | 69.6 |

TABLE 8-continued

| Cath L | | | | | | |
|---|---|---|---|---|---|---|
| Nom latin | Stress | extrait | Inhibition (%) | Nom latin | Stress | extrait | Inhibition (%) |
| Thymus praecox subsp arcticus | G | O | 62.4 | Apium graveolens | T | R | 22.0 |
| Thymus serpyllum | G | O | 70.4 | Aralia nudicaulis | T | O | 77.5 |
| Thymus serpyllum | G | R | 54.9 | Aralia nudicaulis | T | R | 28.4 |
| Thymus vulgaris | G | R | 55.1 | Arctium minus | T | R | 54.4 |
| Thymus x citriodorus | G | O | 47.1 | Arctium minus | T | O | 89.5 |
| Tiarella cordifolia | G | O | 52.8 | Armoracia rusticana | T | O | 84.9 |
| Typha latifolia | G | R | 65.1 | Aronia melanocarpa | T | R | 61.9 |
| Typha latifolia | G | O | 46.9 | Aronia melanocarpa | T | O | 84.5 |
| Vaccinium corymbosum | G | O | 54.5 | Artemisia absinthium | T | R | 29.0 |
| Vaccinium corymbosum | G | R | 82.9 | Artemisia absinthium | T | O | 55.9 |
| Vaccinium angustifolium | G | R | 27.9 | Artemisia dracunculus | T | O | 96.7 |
| Vaccinium angustifolium | G | O | 66.8 | Artium lappa | T | O | 26.0 |
| Vaccinium macrocarpon | G | R | 40.7 | Asclepias incarnata | T | R | 58.5 |
| Asclepias incarnata | T | O | 66.8 | Fagopyrum tataricum | T | O | 25.6 |
| Aster spp | T | R | 40.5 | Foeniculum vulgare | T | O | 79.0 |
| Aster spp | T | O | 86.7 | Fragaria x ananassa | T | O | 26.0 |
| Atropa belladonna | T | O | 61.4 | Galinsoga ciliata | T | R | 34.6 |
| Atropa belladonna | T | R | 30.4 | Galinsoga ciliata | T | O | 60.3 |
| Avena sativa | T | R | 38.0 | Galium odoratum | T | R | 98.8 |
| Cyperus esculentus | T | O | 47.6 | Galium odoratum | T | O | 96.1 |
| Cyperus esculentus | T | R | 49.5 | Gaultheria hispidula | T | O | 33.1 |
| Beta vulgaris | T | O | 62.2 | Gaultheria procumbens | T | O | 84.2 |
| Borago officinalis | T | O | 39.1 | Glechoma hederacea | T | O | 70.1 |
| Brassica Napus | T | O | 89.3 | Glechoma hederacea | T | R | 38.5 |
| Brassica nigra | T | R | 26.9 | Glycine max | T | O | 54.8 |
| Brassica oleracea | T | O | 63.9 | Glycine max | T | R | 38.0 |
| Brassica oleracea | T | R | 76.2 | Glycine max | T | O | 88.7 |
| Brassica oleracea | T | O | 69.9 | Glycyrrhiza glabra | T | O | 65.5 |
| Bromus inermis | T | R | 79.8 | Glycyrrhiza glabra | T | R | 40.5 |
| Bromus inermis | T | O | 88.1 | Guizotia abyssinica | T | R | 48.1 |
| Calamagrostis arundifloram | T | R | 62.8 | Guizotia abyssinica | T | O | 84.1 |
| Calendula officinalis | T | R | 64.6 | Hamamelis virginiana | T | R | 35.9 |
| Canna edulis | T | O | 47.5 | Hedeoma pulegioides | T | R | 24.8 |
| Capsella bursa-pastoris | T | R | 48.7 | Helianthus strumosus | T | O | 32.9 |
| Capsella bursa-pastoris | T | O | 40.9 | Helianthus strumosus | T | R | 31.0 |
| Carex morrowii | T | R | 45.7 | Helianthus tuberosus | T | R | 42.8 |
| Carex morrowii | T | O | 70.3 | Helianthus tuberosus | T | O | 72.1 |
| Carum carvi | T | R | 22.7 | Helichrysum angustifolium | T | R | 69.6 |
| Cerastium tomentosum | T | R | 46.8 | Helichrysum angustifolium | T | O | 84.9 |
| Chaerophyllum bulbosum | T | R | 22.9 | Helichrysum thianschanicum | T | R | 96.2 |
| Chaerophyllum bulbosum | T | O | 40.9 | Helichrysum thianschanicum | T | O | 80.7 |
| Chelidonium majus | T | O | 60.7 | Humulus lupulus | T | O | 71.3 |
| Chelidonium majus | T | R | 24.0 | Humulus lupulus | T | R | 60.6 |
| Chenopodium quinoa | T | R | 41.5 | Hyoscyamus niger | T | O | 68.0 |

TABLE 8-continued

Cath L

| Nom latin | Stress | extrait | Inhibition (%) | Nom latin | Stress | extrait | Inhibition (%) |
|---|---|---|---|---|---|---|---|
| Chenopodium quinoa | T | O | 86.7 | Hyssopus officinalis | T | R | 73.3 |
| Cicer arietinum | T | R | 20.4 | Hyssopus officinalis | T | O | 76.9 |
| Cicer arietinum | T | O | 84.2 | Inula helenium | T | O | 93.3 |
| Cichorium endivia | T | O | 76.3 | Inula helenium | T | R | 63.5 |
| Cichorium intybus | T | O | 81.7 | Ipomoea batalas | T | O | 99.9 |
| Cichorium intybus | T | R | 73.3 | Juniperus communis | T | R | 26.9 |
| Circium arvense | T | R | 50.0 | Kochia scoparia. | T | O | 76.7 |
| Circium arvense | T | O | 74.8 | Koeleria glauca | T | R | 89.1 |
| Citrullus colocynthus | T | O | 62.5 | Koeleria glauca | T | O | 67.7 |
| Citrullus colocynthis | T | R | 57.3 | Lactuca sativa | T | O | 75.2 |
| Coix Lacryma-Jobi | T | R | 33.7 | Lactuca sativa | T | R | 55.3 |
| Coriandrum sativum | T | O | 59.2 | Lathyrus Sativus | T | R | 23.3 |
| Coriandrum sativum | T | R | 37.1 | Lathyrus Sativus | T | O | 70.6 |
| Cornus canadensis | T | R | 82.6 | Lathyrus sylvestris | T | R | 77.1 |
| Cornus canadensis | T | O | 47.7 | Lathyrus sylvestris | T | O | 53.0 |
| Crataegus sp | T | O | 33.9 | Laurus nobilis | T | R | 61.6 |
| Crataegus submollis | T | O | 64.3 | Laurus nobilis | T | O | 92.7 |
| Cryptotaenia canadensis | T | O | 60.9 | Lavandula angustifolia | T | R | 54.1 |
| Cryptotaenia canadensis | T | R | 41.5 | Lavandula angustifolia | T | O | 84.4 |
| Cymbopogon citratus | T | R | 65.2 | Lavandula latifolia | T | R | 55.4 |
| Cymbopogon citratus | T | O | 65.6 | Lavandula latifolia | T | O | 82.9 |
| Daucus carota | T | R | 27.5 | Ledum groenlandicum | T | O | 96.1 |
| Dioscorea batatas | T | O | 42.3 | Ledum groenlandicum | T | R | 74.0 |
| Dirca palustris subsp culinaris | T | O | 57.4 | Lens culinaris | T | R | 36.4 |
| Dirca palustris subsp culinaris | T | R | 29.5 | Lens culinaris | T | O | 100.0 |
| Echinacea purpurea | T | O | 83.0 | Levisticum officinale | T | R | 38.8 |
| Eleusine coracana | T | O | 70.3 | Levisticum officinale | T | O | 73.4 |
| Erysimum perofskianum | T | R | 90.4 | Lotus corniculatus | T | O | 81.6 |
| Erysimum perofskianum | T | O | 92.2 | Lotus corniculatus | T | R | 52.0 |
| Fagopyrum esculentum | T | R | 61.6 | Lupinus polyphyllus | T | R | 53.3 |
| Fagopyrum esculentum | T | O | 39.0 | Lupinus polyphyllus | T | O | 64.4 |
| Fagopyrum tataricum | T | R | 36.7 | Luzula sylvatica | T | R | 62.6 |
| Malus | T | O | 70.9 | Ribes Sylvestre | T | O | 87.9 |
| Malus hupehensis | T | R | 77.6 | Ribes Siylvestre | T | R | 40.2 |
| Malus hupehensis | T | O | 72.4 | Ribes Siylvestre | T | O | 45.2 |
| Medicago sativa | T | R | 41.0 | Rosmarinus officinalis | T | O | 69.6 |
| Medicago sativa | T | O | 94.1 | Rubus canadensis | T | R | 37.2 |
| Melilotus officinalis | T | R | 44.0 | Rubus canadensis | T | O | 57.9 |
| Melilotus officinalis | T | O | 90.8 | Rubus idaeus | T | R | 64.9 |
| Mentha piperita | T | O | 20.6 | Rubus idaeus | T | O | 94.9 |
| Menyanthes trifoliata | T | R | 20.8 | Rumes scutatus | T | O | 74.9 |
| Miscanthus sinensis | T | R | 89.0 | Rumes scutatus | T | R | 20.7 |
| Miscanthus sinensis | T | O | 73.7 | Rumex acetosella | T | R | 40.1 |
| Nepeta cataria | T | R | 25.3 | Rumex acetosella | T | O | 42.0 |
| Ocimum Basilicum | T | O | 65.7 | Rumex crispus | T | R | 40.7 |
| Oenothera biennis | T | R | 40.2 | Rumex crispus | T | O | 51.2 |

TABLE 8-continued

| Cath L | | | | | | |
|---|---|---|---|---|---|---|
| Nom latin | Stress | extrait | Inhibition (%) | Nom latin | Stress | extrait | Inhibition (%) |
| Oenothera biennis | T | O | 49.2 | Ruta graveolens | T | O | 91.2 |
| Onobrychis viciiafolia | T | R | 53.2 | Salix purpurea | T | R | 55.5 |
| Onobrychis viciiafolia | T | O | 49.2 | Salix purpurea | T | O | 51.2 |
| Origanum vulgare | T | R | 50.6 | Salvia officinalis | T | R | 64.7 |
| Origanum vulgare | T | O | 45.1 | Salvia officinalis | T | O | 66.6 |
| Oryza sativa canadensis | T | R | 40.3 | Sambucus | T | O | 92.5 |
| Oryza sativa | T | O | 28.6 | Sambucus canadensis | T | R | 64.0 |
| Oxalis Deppei | T | R | 35.2 | Sanguisorba minor | T | O | 68.4 |
| Oxalis Deppei | T | O | 42.1 | Santolina chamaecyparissus | T | R | 84.4 |
| oxyria digyna | T | R | 42.8 | Santolina chamaecyparissus | T | O | 33.9 |
| oxyria digyna | T | O | 52.3 | Saponaria officinalis | T | R | 59.3 |
| Panax quinquefolius | T | O | 78.8 | Saponaria officinalis | T | O | 80.4 |
| Panicum miliaceum | T | R | 52.6 | Satureja hortensis | T | O | 26.5 |
| Passiflora caerulea | T | O | 77.5 | Satureja hortensis | T | R | 23.0 |
| Pastinaca sativa | T | R | 52.0 | Satureja montana | T | R | 57.2 |
| Pastinaca sativa | T | O | 31.8 | Satureja montana | T | O | 43.5 |
| Pennisetum alopecuroides | T | O | 73.4 | Satureja repandra | T | R | 47.1 |
| Pertoselinum crispum | T | R | 65.2 | Satureja repandra | T | O | 66.3 |
| Petasites Japonicus | T | R | 31.3 | Scuttellaria lateriflora | T | O | 20.3 |
| Petasites Japonicus | T | O | 24.6 | Scuttellaria lateriflora | T | R | 33.8 |
| Pertoselinum crispum | T | O | 45.2 | Secale cereale | T | R | 28.5 |
| Phalaris canariensis | T | R | 33.6 | Senecio vulgaris | T | R | 34.0 |
| Phalaris canariensis | T | O | 86.5 | Setaria italica | T | R | 40.7 |
| Phaseolus vulgaris | T | O | 57.0 | Silene vulgaris | T | R | 66.3 |
| Physalis pruinosa | T | O | 58.2 | Silene vulgaris | T | O | 99.7 |
| Pimpinella anisum | T | O | 95.9 | Sium sisarum | T | O | 90.7 |
| Pimpinella anisum | T | R | 91.7 | Sium sisarum | T | R | 39.6 |
| Pisum sativum | T | R | 30.5 | Solidago sp | T | R | 44.3 |
| Pisum sativum | T | O | 69.3 | Solidago sp | T | O | 73.6 |
| Plantago major | T | O | 93.8 | Sonchus oleraceus | T | R | 53.7 |
| Plantago major | T | R | 20.2 | Sonchus oleraceus | T | O | 36.9 |
| Plectranthus sp. | T | R | 44.4 | Sorghum caffrorum | T | R | 96.4 |
| Plectranthus sp. | T | O | 50.8 | Sorghum caffrorum | T | O | 80.1 |
| Polygonum aviculare | T | R | 47.9 | Sorghum dochna | T | R | 95.3 |
| Polygonum aviculare | T | O | 72.7 | Sorghum dochna | T | O | 70.3 |
| Potentilla anserina | T | R | 21.8 | Sorghum dochna | T | R | 98.5 |
| Prunella vulgaris | T | R | 84.3 | Sorghum dochna | T | O | 85.3 |
| Prunella vulgaris | T | O | 56.7 | Sorghum durra | T | R | 86.5 |
| Pteridium aquilinum | T | R | 32.6 | Sorghum durra | T | O | 81.7 |
| Raphanus raphanistrum | T | R | 68.6 | Sorghum sudanense | T | R | 34.7 |
| Raphanus raphanistrum | T | O | 77.0 | Stachys affinis | T | O | 75.7 |
| Raphanus sativus | T | R | 41.0 | Stachys affinis | T | R | 33.5 |
| Raphanus sativus | T | O | 63.1 | Stachys byzantina | T | R | 60.8 |
| Frangula alnus | T | O | 27.0 | Stachys byzantina | T | O | 77.5 |
| Frangula alnus | T | R | 45.3 | Stellaria graminea | T | R | 37.5 |
| Ricinus communis | T | R | 22.4 | Stellaria graminea | T | O | 54.7 |
| Ricinus communis | T | O | 72.0 | Stellaria media | T | R | 26.0 |
| Ribes nigrum | T | R | 50.5 | Stellaria media | T | O | 49.0 |
| Ribes nigrum | T | O | 70.1 | Stipa capillata | T | R | 43.4 |
| Symphytum officinale | T | R | 55.1 | Urtica dioica | T | R | 77.8 |

TABLE 8-continued

Cath L

| Nom latin | Stress | extrait | Inhibition (%) | Nom latin | Stress | extrait | Inhibition (%) |
|---|---|---|---|---|---|---|---|
| *Symphytum officinale* | T | O | 64.0 | *Urtica dioica* | T | O | 75.6 |
| *Tanacetum cinerariifolium* | T | O | 65.5 | *Vaccinium angustifolium* | T | O | 58.6 |
| *Tanacetum parthenium* | T | R | 45.2 | *Vaccinium macrocarpon* | T | R | 20.1 |
| *Tanacetum parthenium* | T | O | 54.7 | *Vaccinium macrocarpon* | T | O | 41.7 |
| *Tanacetum vulgare* | T | R | 59.8 | *Veratrum viride* | T | O | 57.1 |
| *Tanacetum vulgare* | T | O | 86.0 | *Veratrum viride* | T | R | 26.6 |
| *Taraxacum officinale* | T | O | 100.0 | *Verbascum thapsus* | T | O | 72.8 |
| *Taraxacum officinale* | T | R | 91.3 | *Verbascum thapsus* | T | R | 56.0 |
| *Teucrium chamaedrys* | T | O | 60.8 | *Vibumum trilobum* | T | R | 49.5 |
| *Teucrium chamaedrys* L. | T | R | 69.2 | *Viburnum trilobum* | T | O | 56.8 |
| *Thymus fragantissimus* | T | R | 97.8 | *Vicia sativa* | T | O | 73.9 |
| *Thymus fragantissimus* | T | O | 81.7 | *Vicia villosa* | T | R | 79.2 |
| *Thymus praecox subsp arcticus* | T | R | 36.1 | *Vicia villosa* | T | O | 70.9 |
| *Thymus praecox subsp arcticus* | T | O | 31.8 | *Vinca minor* | T | O | 21.5 |
| *Thymus pseudolanuginosus* | T | R | 33.9 | *Vitis* sp. | T | R | 79.7 |
| *Thymus pseudolanuginosus* | T | O | 43.7 | *Vitis* sp. | T | O | 97.4 |
| *Thymus serpyllum* | T | R | 39.2 | *Zea mays* | T | R | 83.5 |
| *Thymus serpyllum* | T | O | 68.6 | *Zea mays* | T | O | 58.2 |
| *Thymus x citriodorus* | T | O | 70.9 | | | | |
| *Thymus x citriodorus* | T | R | 46.1 | | | | |
| *Tiarella cordifolia* | T | O | 72.0 | | | | |
| *Tragopogon porrifolius* | T | O | 40.9 | | | | |
| *Tragopogon porrifolius* | T | R | 20.5 | | | | |
| *Triticosecala* spp. | T | O | 38.2 | | | | |
| *Triticum aestivum* | T | R | 31.4 | | | | |
| *Triticum aestivum* | T | O | 33.8 | | | | |
| *Tropaeolum majus* | T | R | 29.2 | | | | |
| *Tropaeolum majus* | T | O | 20.9 | | | | |
| *Typha latifolia* | T | R | 67.0 | | | | |
| *Typha latifolia* | T | O | 56.0 | | | | |

TABLE 9

Cath K

| Nom latin | Stress | extrait | Inhibition (%) | Nom latin | Stress | extrait | Inhibition (%) |
|---|---|---|---|---|---|---|---|
| *Achillea millefolium* | A | O | 27.6 | *Allium schoenoprasum* | A | O | 78.2 |
| *Aconitum napellus* | A | O | 74.0 | *Allium Tuberosum* | A | O | 99.6 |
| *Acorus calamus* | A | O | 74.8 | *Aloe vera* | A | R | 60.0 |
| *Actinidia arguta* | A | R | 28.1 | *Aloe vera* | A | O | 78.4 |
| *Actinidia arguta* | A | O | 96.6 | *Althaea officinalis* | A | O | 98.1 |
| *Agropyron repens* | A | O | 98.0 | *Amaranthus retroflexus* | A | R | 37.4 |
| *Alchemilla mollis* | A | O | 61.3 | *Amaranthus retroflexus* | A | O | 43.4 |
| *Alchemilla mollis* | A | R | 95.8 | *Anethum graveolens* | A | O | 33.7 |
| *Allium cepa* | A | O | 80.6 | *Angelica archangelica* | A | R | 36.0 |

TABLE 9-continued

Cath K

| Nom latin | Stress | extrait | Inhibition (%) | Nom latin | Stress | extrait | Inhibition (%) |
|---|---|---|---|---|---|---|---|
| *Allium porrum* | A | R | 30.9 | *Angelica archangelica* | A | O | 85.2 |
| *Allium porrum* | A | O | 87.5 | *Apium graveolens* | A | R | 46.7 |
| *Allium sativum* | A | O | 71.2 | *Apium graveolens* | A | O | 88.8 |
| *Aralia nudicaulis* | A | R | 79.0 | *Hordeum hexastichon* | A | R | 26.9 |
| *Aralia nudicaulis* | A | O | 98.5 | *Hyssopus officinalis* | A | R | 40.2 |
| *Arctium minus* | A | R | 24.6 | *Inula helenium* | A | O | 86.0 |
| *Arctium minus* | A | O | 67.9 | *Ipomoea Batatas* | A | R | 25.6 |
| *Arctostaphylos uva-ursi* | A | R | 75.1 | *Lathyrus sativus* | A | R | 26.9 |
| *Arctostaphylos uva-ursi* | A | O | 89.8 | *Lathyrus sativus* | A | O | 84.9 |
| *Armoracia rusticana* | A | O | 92.3 | *Lathyrus sylvestris* | A | R | 22.4 |
| *Aronia melanocarpa* | A | O | 60.1 | *Lathyrus sylvestris* | A | O | 93.4 |
| *Aronia melanocarpa* | A | R | 61.6 | *Laurus nobilis* | A | O | 64.2 |
| *Aronia melanocarpa* | A | O | 82.3 | *Laurus nobilis* | A | R | 64.6 |
| *Artemisia Absinthium* | A | R | 88.6 | *Leonurus cardiaca* | A | O | 90.0 |
| *Artemisia dracunculus* | A | O | 55.6 | *Levisticum officinale* | A | R | 49.4 |
| *Aster sp* | A | R | 50.7 | *Levisticum officinale* | A | O | 53.3 |
| *Atropa belladonna* | A | O | 89.4 | *Lotus corniculatus* | A | R | 67.4 |
| *Beckmannia eruciformis* | A | R | 86.0 | *Lotus corniculatus* | A | O | 98.8 |
| *Beckmannia eruciformis* | A | O | 96.2 | *Lycopersicon esculentum* | A | R | 30.1 |
| *Beta vulgaris* | A | R | 69.3 | *Malva sylvestris* | A | O | 82.3 |
| *Beta vulgaris* | A | O | 87.6 | *Medicago sativa* | A | R | 44.0 |
| *Beta vulgaris* spp. *Maritima* | A | R | 53.7 | *Medicago sativa* | A | O | 94.4 |
| *Beta vulgaris* spp. *Maritima* | A | O | 84.2 | *Melilotus albus* | A | R | 80.7 |
| *Borago officinalis* | A | O | 38.6 | *Chenopodium quinoa* | A | O | 84.3 |
| *Brassica napus* | A | R | 43.5 | *Cicer arietinum* | A | O | 91.1 |
| *Brassica napus* | A | O | 84.4 | *Cichorium intybus* | A | R | 21.0 |
| *Brassica oleracea* | A | O | 60.6 | *Cichorium intybus* | A | O | 94.8 |
| *Brassica rapa* | A | R | 62.1 | *Mentha piperita* | A | R | 60.8 |
| *Brassica rapa* | A | O | 98.9 | *Mentha pulegium* | A | O | 55.4 |
| *Campanula rapunculus* | A | O | 77.0 | *Mentha spicata* | A | O | 97.0 |
| *Canna edulis* | A | R | 32.0 | *Mentha suaveolens* | A | O | 46.8 |
| *Capsella bursa-pastoris* | A | R | 71.4 | *Nepeta cataria* | A | R | 32.6 |
| *Capsella bursa-pastoris* | A | O | 72.8 | *Nepeta cataria* | A | O | 67.2 |
| *Capsicum annuum* | A | R | 39.0 | *Nicotiana tabacum* | A | R | 34.1 |
| *Chaerophyllum bulbosum* | A | O | 86.6 | *Oenothera biennis* | A | R | 48.5 |
| *Chelidonium majus* | A | O | 90.3 | *Oenothera biennis* | A | O | 83.4 |
| *Chenopodium bonus-henricus* | A | O | 38.8 | *Origanum majorana* | A | O | 63.2 |
| *Chenopodium quinoa* | A | R | 42.3 | *Origanum vulgare* | A | R | 62.2 |
| *Coix Lacryma-Jobi* | A | O | 35.2 | *Origanum vulgare* | A | O | 90.0 |
| *Coriandrum sativum* | A | R | 63.6 | *Panax quinquefolius* | A | O | 32.3 |
| *Coriandrum sativum* | A | O | 84.4 | *Panax quinquefolius* | A | R | 75.9 |
| *Cornus canadensis* | A | O | 58.6 | *Panicum miliaceum* | A | R | 25.6 |
| *Cornus canadensis* | A | R | 99.4 | *Panicum miliaceum* | A | O | 45.1 |
| *Crataegus sp* | A | R | 22.7 | *Pastinaca sativa* | A | O | 100.0 |
| *Crataegus submollis* | A | O | 45.4 | *Petasites japonicus* | A | O | 82.7 |
| *Cryptotaenia canadensis* | A | R | 26.3 | *Petroselinum crispum* | A | R | 50.2 |
| *Cryptotaenia canadensis* | A | O | 29.1 | *Petroselinum crispum* | A | O | 85.7 |

TABLE 9-continued

| | | Cath K | | | | | |
|---|---|---|---|---|---|---|---|
| Nom latin | Stress | extrait | Inhibition (%) | Nom latin | Stress | extrait | Inhibition (%) |
| Cymbopogon citratus | A | O | 45.2 | Petroselinum crispum | A | O | 92.2 |
| Cyperus esculentus | A | O | 75.0 | Phalaris canariensis | A | R | 89.5 |
| Daucus carota | A | O | 92.9 | Phaseolus vulgaris | A | R | 22.1 |
| Dirca palustris | A | O | 84.7 | Phaseolus Vulgaris | A | O | 90.3 |
| Dirca palustris | A | R | 94.2 | Pimpinella anisum | A | O | 72.4 |
| Diyopteris filix-mas | A | O | 85.7 | Plantago major | A | R | 22.2 |
| Echinacea purpurea | A | O | 89.8 | Plantago major | A | O | 99.8 |
| Eleusine coracana | A | R | 50.6 | Plectranthus sp. | A | R | 73.5 |
| Eleusine coracana | A | O | 58.7 | Potentilla anserina | A | O | 92.9 |
| Fagopyrum esculentum | A | O | 68.0 | Pteridium aquilinum | A | O | 81.9 |
| Fagopyrum tataricum | A | O | 20.3 | Raphanus raphanistrum | A | O | 70.2 |
| Fagopyrum tataricum | A | R | 33.0 | Raphanus sativus | A | R | 28.4 |
| Foeniculum vulgare | A | O | 40.3 | Raphanus sativus | A | O | 99.0 |
| Fragaria x ananassa | A | R | 44.8 | Rheum rhabarbarum | A | R | 21.4 |
| Fragaria x ananassa | A | O | 92.3 | Rheum rhabarbarum | A | O | 95.6 |
| Galinsoga ciliata | A | O | 55.3 | Ribes nigrum | A | R | 59.3 |
| Galium odoratum | A | O | 88.4 | Ribes nigrum | A | O | 81.8 |
| Gaultheria hispidula | A | R | 61.6 | Ribes Sylvestre | A | O | 98.6 |
| Gaultheria hispidula | A | O | 87.1 | Ricinus communis | A | R | 78.5 |
| Glechoma hederacea | A | O | 96.2 | Ricinus communis | A | O | 90.2 |
| Glycine max | A | R | 41.6 | Rosa rugosa | A | R | 36.1 |
| Glycine max | A | O | 100.0 | Rubus allegheniensis | A | O | 59.3 |
| Glycyrrhiza glabra | A | R | 50.8 | Rubus canadensis | A | O | 94.4 |
| Glycyrrhiza glabra | A | O | 90.2 | Rubus idaeus | A | R | 58.4 |
| Guizotia abyssinica | A | R | 23.1 | Rubus idaeus | A | O | 97.4 |
| Guizotia abyssinica | A | O | 94.8 | Rumex Acetosa | A | O | 83.9 |
| Hamamelis virginiana | A | R | 91.8 | Rumex acetosella | A | R | 46.7 |
| Hedeoma pulegioides | A | O | 93.3 | Rumex acetosella | A | O | 90.9 |
| Helleborus niger | A | O | 82.9 | Rumex crispus | A | R | 32.9 |
| Rumex crispus | A | O | 91.8 | Allium schoenoporasum | G | O | 88.7 |
| Rumex Scutatus | A | O | 94.9 | Allium tuberosum | G | O | 80.3 |
| Ruta graveolens | A | O | 92.5 | Aloe vera | G | R | 28.8 |
| Salix purpurea | A | O | 44.8 | althaea officinalis | G | O | 94.5 |
| Salix purpurea | A | R | 68.1 | Amaranthus retroflexus | G | R | 35.3 |
| Salvia elegans | A | O | 64.2 | Amaranthus retroflexus | G | O | 73.8 |
| Melilotus albus | A | O | 98.9 | Anethum graveolens | G | O | 52.0 |
| Melissa officinalis | A | O | 89.4 | Angelica archangelica | G | R | 39.0 |
| Melissa officinalis | A | R | 93.6 | Angelica archangelica | G | O | 80.6 |
| Mentha piperita | A | O | 60.1 | Apium graveolens | G | R | 37.7 |
| Senecio vulgaris L. | A | R | 80.9 | Apium graveolens | G | O | 83.9 |
| Setaria italica | A | R | 30.0 | Aralia nudicaulis | G | O | 86.7 |
| Setaria italica | A | O | 66.2 | Aralia nudicaulis | G | R | 89.5 |
| Sium Sisarum | A | R | 30.0 | Arctium minus | G | R | 27.1 |
| Sium Sisarum | A | O | 93.3 | Arctium minus | G | O | 93.4 |
| Solanum tuberosum | A | R | 30.1 | Arctostaphylos uva-ursi | G | R | 73.3 |
| Solanum tuberosum | A | O | 79.8 | Armoracia rusticana | G | O | 53.8 |
| Solidago sp | A | R | 43.7 | Aronia melanocarpa | G | R | 73.2 |
| Solidago sp | A | O | 72.1 | Aronia melanocarpa | G | O | 81.2 |
| Sonchus oleraceus | A | R | 21.6 | Artemisia absinthium | G | R | 92.0 |
| Sonchus oleraceus | A | O | 92.4 | Artemisia dracunculus | G | R | 36.0 |

TABLE 9-continued

Cath K

| Nom latin | Stress | extrait | Inhibition (%) | Nom latin | Stress | extrait | Inhibition (%) |
|---|---|---|---|---|---|---|---|
| Sorghum dochna | A | O | 60.9 | Artemisia dracunculus | G | O | 72.7 |
| Sorghum durra | A | O | 89.3 | Asclepias incarnata | G | R | 67.4 |
| Stachys affinis | A | R | 29.3 | Asclepias incarnata | G | O | 87.0 |
| Stachys byzantina | A | R | 28.3 | Asparagus officinalis | G | O | 98.2 |
| Stellaria graminea | A | R | 49.9 | Aster | G | O | 37.4 |
| Stellaria graminea | A | O | 87.6 | Aster sp | G | R | 37.3 |
| Stellaria media | A | R | 25.7 | Aster sp | G | O | 81.3 |
| Stellaria media | A | O | 26.0 | Beckmannia eruciformis | G | O | 90.0 |
| Tanacetum parthenium | A | R | 64.6 | Beta vulgaris | G | O | 29.0 |
| Tanacetum vulgare | A | R | 36.0 | Beta vulgaris | G | R | 71.5 |
| Tanacetum vulgare | A | O | 85.7 | Borago officinalis | G | O | 36.4 |
| Taraxacum officinale | A | R | 36.9 | Brassica napus | G | R | 26.6 |
| Taraxacum officinale | A | O | 100.0 | Brassica napus | G | O | 98.8 |
| Teucrium chamaedrys | A | O | 92.5 | Brassica oleracea | G | O | 97.8 |
| Thymus praecox subsp arcticus | A | O | 50.1 | Brassica rapa | G | R | 25.3 |
| Thymus serpyllum | A | R | 27.3 | Brassica rapa | G | O | 67.8 |
| Thymus serpyllum | A | O | 88.9 | Calamagrostis arundiflora | G | R | 23.2 |
| Thymus vulgaris | A | R | 60.9 | Campanula rapunculus | G | O | 80.2 |
| Thymus vulgaris | A | O | 74.3 | Canna edulis | G | R | 31.6 |
| Thymus x citriodorus | A | O | 80.9 | Canna edulis | G | O | 44.2 |
| Tragopogon porrifolius | A | R | 43.2 | Capsella bursa-pastoris | G | R | 63.0 |
| Tragopogon porrifolius | A | O | 81.9 | Capsella bursa-pastoris | G | O | 69.5 |
| Tropaeolum majus | A | R | 42.6 | Carum carvi | G | O | 32.3 |
| Tropaeolum majus | A | O | 82.6 | Chaerophyllum bulbosum | G | R | 30.7 |
| Typha latifolia | A | O | 49.5 | Chaerophyllum bulbosum | G | O | 38.0 |
| Typha latifolia | A | R | 65.4 | Chelidonium majus | G | O | 91.3 |
| Vaccinium Corymbosum | A | O | 94.5 | Cicer arietinum | G | R | 44.7 |
| Vaccinium macrocarpon | A | O | 94.1 | Cicer arietinum | G | O | 92.7 |
| Veratrum viride subsp. Endivia | A | O | 78.4 | Cichorium endivia | G | O | 94.9 |
| Verbascum thapsus | A | O | 96.4 | Cichorium intybus | G | R | 25.8 |
| Vicia sativa | A | O | 98.7 | Agropyron repens | G | O | 98.2 |
| Vicia villosa | A | R | 29.0 | Alchemilla mollis | G | O | 65.5 |
| Vicia villosa | A | O | 97.6 | Alchemilla mollis | G | R | 88.9 |
| Vinca minor | A | O | 74.6 | Allium ampeloprasum | G | R | 39.0 |
| Vitis sp. | A | R | 82.1 | Allium ampeloprasum | G | O | 53.8 |
| Vitis sp. | A | O | 99.5 | Allium cepa | G | R | 35.6 |
| Zea mays | A | R | 24.4 | Allium cepa | G | O | 75.1 |
| Zea mays | A | O | 99.2 | Allium sativum | G | O | 82.4 |
| Achillea millefolium | G | O | 42.8 | Daucus carota | G | O | 57.3 |
| Aconitum napellus | G | O | 37.1 | Dirca palustris | G | R | 67.1 |
| Acorus calamus | G | O | 89.0 | Dirca palustris | G | O | 97.2 |
| Actinidia arguta | G | R | 35.5 | Diyopteris filix-mas | G | O | 52.2 |
| Actinidia arguta | G | O | 45.4 | Echinacea purpurea | G | O | 74.4 |
| Adiantum pedatum | G | O | 25.0 | Eleusine coracana | G | R | 38.7 |
| Salvia officinalis | A | O | 67.8 | Eleusine coracana | G | O | 76.8 |
| Salvia officinalis | A | R | 85.4 | Erigeron speciosus | G | R | 26.8 |
| Salvia sclarea | A | O | 61.0 | Erysimum perofskianum | G | R | 59.8 |
| Santolina chamaecyparissus | A | R | 54.1 | Erysimum perofskianum | G | O | 100.2 |
| Santolina chamaecyparissus | A | O | 63.1 | Fagopyrum esculentum | G | R | 37.6 |

TABLE 9-continued

| Cath K | | | | | | |
|---|---|---|---|---|---|---|
| Nom latin | Stress | extrait | Inhibition (%) | Nom latin | Stress | extrait | Inhibition (%) |
| Satureja montana | A | O | 75.6 | Fagopyrum tartaricum | G | O | 27.3 |
| Scorzonera hispanica | A | O | 62.7 | Fagopyrum tartaricum | G | R | 30.7 |
| Scutellaria lateriflora | A | O | 82.7 | Galinsoga ciliata | G | O | 30.9 |
| Galinsoga ciliata | G | R | 51.3 | Passiflora caerulae | G | R | 21.1 |
| Galium odoratum | G | O | 96.9 | Passiflora caerulae | G | O | 60.6 |
| Gaultheria hispidula | G | R | 70.9 | Pastinaca sativa | G | O | 72.8 |
| Gaultheria hispidula | G | O | 82.2 | Pennisetum alopecuroides | G | R | 30.6 |
| Gaultheria procumbens | G | O | 69.6 | Petasites japonicus | G | O | 81.6 |
| Glechoma hederacea | G | O | 94.0 | Petroselinum crispum | G | R | 62.9 |
| Glycine max | G | R | 76.1 | Petroselinum crispum | G | O | 76.3 |
| Glycine max | G | O | 100.0 | Phalaris canariensis | G | O | 22.0 |
| Glycyrrhiza glabra | G | R | 33.3 | Phalaris canariensis | G | R | 36.7 |
| Glycyrrhiza glabra | G | O | 94.5 | Phaseolus vulgaris | G | R | 65.5 |
| Guizotia abyssinica | G | R | 41.5 | Phaseolus vulgaris | G | O | 88.2 |
| Guizotia abyssinica | G | O | 95.4 | Pimpinella anisum | G | O | 46.2 |
| Hamamelis virginiana | G | O | 79.7 | Pisum sativum | G | O | 52.5 |
| Hamamelis virginiana | G | R | 90.8 | Plantago major | G | R | 29.0 |
| Helianthus strumosus | G | R | 31.7 | Plantago major | G | O | 96.3 |
| Helianthus strumosus | G | O | 39.4 | Plectranthus sp. | G | R | 54.5 |
| Helianthus tuberosus | G | R | 31.5 | Polygonum aviculare | G | O | 29.6 |
| Helianthus tuberosus | G | O | 70.6 | Portulaca oleracera | G | R | 50.9 |
| Helichrysum thianschanicum | G | R | 40.4 | Potentilla anserina | G | O | 92.5 |
| Helichrysum thianschanicum | G | O | 69.2 | Poterium sanquisorba | G | O | 74.2 |
| Helleborus niger | G | R | 43.8 | Prunella vulgaris | G | O | 77.1 |
| Helleborus niger | G | O | 90.6 | Prunella vulgaris | G | R | 91.8 |
| Hordeum hexastichon | G | R | 22.6 | Pteridium aquilinum | G | O | 87.5 |
| Hordeum hexastichon | G | O | 86.0 | Levisticum officinale | G | R | 75.1 |
| Hyssopus officinalis | G | R | 25.8 | Levisticum officinale | G | O | 92.5 |
| Inula helenium | G | O | 82.2 | Lotus corniculatus | G | R | 25.7 |
| Lactuca sativa | G | R | 28.5 | Lotus corniculatus | G | O | 98.5 |
| Lactuca sativa | G | O | 95.5 | Lupinus polyphyllus | G | O | 94.5 |
| Lathyrus sylvestris | G | R | 22.1 | Lupinus polyphyllus | G | R | 99.9 |
| Lathyrus sylvestris | G | O | 79.5 | Lycopersicon esculentum | G | R | 70.0 |
| Laurus nobilis | G | R | 49.6 | Lycopersicon esculentum | G | O | 90.2 |
| Laurus nobilis | G | O | 72.3 | Malus hupehensis | G | R | 44.8 |
| Lavandula angustifolia | G | O | 57.6 | Malus hupehensis | G | O | 82.9 |
| Lavandula angustifolia | G | R | 65.2 | Medicago sativa | G | R | 26.2 |
| Ledum groenlandicum | G | R | 35.1 | Medicago sativa | G | O | 99.2 |
| Ledum groenlandicum | G | O | 97.9 | Ruta graveolens | G | R | 46.4 |
| Leonurus cardiaca | G | O | 99.9 | Ruta graveolens | G | O | 84.6 |
| Cichorium intybus | G | O | 95.8 | Salix purpurea | G | O | 32.4 |
| Circium arvense | G | O | 73.0 | Salix purpurea | G | R | 95.3 |
| Circium arvense | G | R | 96.5 | Salvia elegans | G | O | 57.0 |
| Coix Lacryma-Jobi | G | O | 57.4 | Salvia officinalis | G | O | 65.8 |
| Cornus canadensis | G | O | 62.5 | Salvia officinalis | G | R | 94.9 |
| Cornus canadensis | G | R | 68.0 | Salvia sclarea | G | O | 58.5 |

TABLE 9-continued

| Cath K | | | | | | |
|---|---|---|---|---|---|---|
| Nom latin | Stress | extrait | Inhibition (%) | Nom latin | Stress | extrait | Inhibition (%) |
| *Crataegus submollis* | G | O | 58.3 | *Sambucus ebulus* | G | R | 32.1 |
| *Crataegus submollis* | G | R | 73.2 | *Sambucus ebulus* | G | O | 67.7 |
| *Cymbopogon citratus* | G | R | 65.5 | *Santolina chamaecyparissus* | G | R | 49.3 |
| *Cymbopogon citratus* | G | O | 70.9 | *Saponaria officinalis* | G | R | 22.3 |
| *Cyperus esculentus* | G | O | 85.0 | *Saponaria officinalis* | G | O | 88.5 |
| *Daucus carota* | G | R | 23.3 | *Satureja hortensis* | G | O | 73.3 |
| *Melilotus alba* | G | R | 96.9 | *Satureja montana* | G | O | 74.8 |
| *Melilotus alba* | G | O | 99.0 | *Scorzonera hispanica* | G | R | 43.1 |
| *Melissa officinalis* | G | O | 33.2 | *Scorzonera hispanica* | G | O | 52.1 |
| *Melissa officinalis* | G | R | 90.6 | *Scutellaria lateriflora* | G | O | 92.0 |
| *Mentha piperita* | G | O | 41.8 | *Secale cereale* | G | R | 23.7 |
| *Mentha pulegium* | G | O | 38.7 | *Senecio vulgaris* | G | R | 29.1 |
| *Mentha spicata* | G | R | 32.7 | *Setaria italica* | G | R | 21.9 |
| *Mentha spicata* | G | O | 80.1 | *Setaria italica* | G | O | 83.2 |
| *Mentha suaveolens* | G | O | 55.7 | *Silene vulgaris* | G | R | 24.1 |
| *Nepeta cataria* | G | R | 93.1 | *Stum sisarum* | G | R | 37.9 |
| *Ocimum basilicum* | G | O | 75.6 | *Sium sisarum* | G | O | 100.0 |
| *Oenothera biennis* | G | R | 42.9 | solanum melongena | G | R | 22.7 |
| *Oenothera biennis* | G | O | 86.1 | Solanum tuberosum | G | R | 50.2 |
| *Origanum majorana* | G | O | 65.8 | Solanum tuberosum | G | O | 73.3 |
| *Origanum vulgare* | G | O | 89.6 | *Solidago* sp | G | R | 32.8 |
| *Origanum vulgare* | G | R | 92.3 | *Solidago* sp | G | O | 87.3 |
| *Oryza Sativa* | G | O | 95.6 | *Sonchus oleraceus* | G | R | 37.8 |
| *Oxalis Deppei* | G | O | 86.3 | *Sonchus oleraceus* | G | O | 48.1 |
| *Oxalis Deppei* | G | R | 87.8 | *Sorghum dochna* | G | R | 43.1 |
| *Oxyria digyna* | G | R | 20.8 | *Sorghum dochna* | G | O | 91.3 |
| *Oxyria digyna* | G | O | 89.3 | sorghum durra | G | R | 56.4 |
| *Panax quinquefolius* | G | R | 52.7 | sorghum durra | G | O | 63.2 |
| *Panicum miliaceum* | G | R | 31.5 | *Sorghum sudanense* | G | R | 56.1 |
| *Panicum miliaceum* | G | O | 94.4 | *Sorghum sudanense* | G | O | 89.7 |
| *Stachys Affinis* | G | R | 27.9 | *Teucrium chamaedrys* | G | R | 61.7 |
| *Stachys byzantina* | G | R | 42.8 | *Teucrium chamaedrys* | G | O | 89.8 |
| *Stachys byzantina* | G | O | 72.1 | *Thymus fragantissimus* | G | O | 64.0 |
| *Stellaria graminea* | G | R | 39.7 | *Thymus fragantissimus* | G | R | 85.4 |
| *Stellaria media subsp arcticus* | G | R | 27.9 | *Thymus praecox* | G | R | 28.3 |
| *Stellaria media subsp arcticus* | G | O | 50.0 | *Thymus praecox* | G | O | 39.1 |
| *Symphytum officinale* | G | O | 43.5 | *Thymus serpyllum* | G | R | 28.4 |
| *Symphytum officinale* | G | R | 74.2 | *Thymus serpyllum* | G | O | 90.3 |
| *Tanacetum cinerariifolium* | G | O | 72.2 | *Thymus vulgaris* | G | R | 69.0 |
| *Rhaphanus sativus* | G | R | 24.0 | *Thymus vulgaris* | G | O | 70.6 |
| *Rhaphanus sativus* | G | O | 85.0 | *Thymus x citriodorus* | G | O | 70.7 |
| *Rheum rhabarbarum* | G | R | 22.9 | *Asclepias incarnata* | T | R | 86.7 |
| *Rheum rhabarbarum* | G | O | 85.5 | *Aster* | T | O | 34.1 |
| *Ribes nidrolaria* | G | O | 59.7 | *Aster* sp | T | R | 46.8 |
| *Ribes nigrum* | G | O | 80.4 | *Aster* sp | T | O | 49.7 |
| *Ribes nigrum* | G | R | 81.5 | *Atropa belladonna* | T | O | 71.7 |
| *Ribes Sylvestre* | G | O | 91.7 | *Avena sativa* | T | R | 40.4 |
| *Ricinus communis* | G | R | 27.0 | *Beta vulgaris* | T | O | 30.6 |
| *Ricinus communis* | G | O | 98.3 | *Beta vulgaris* | T | R | 41.7 |
| *Rosmarinus officinalis* | G | O | 27.5 | *Borago officinalis* | T | R | 59.2 |
| *Rubus idaeus* | G | R | 38.7 | *Borago officinalis* | T | O | 76.5 |
| *Rubus idaeus* | G | O | 51.2 | *Brassica napus* | T | R | 35.8 |
| *Rumex crispus* | G | R | 37.1 | *Brassica Napus* | T | O | 91.9 |

TABLE 9-continued

| Nom latin | Stress | extrait | Inhibition (%) | Nom latin | Stress | extrait | Inhibition (%) |
|---|---|---|---|---|---|---|---|
| Rumex crispus | G | O | 95.0 | Brassica nigra | T | R | 24.3 |
| Rumex scutatus | G | O | 88.5 | Brassica oleracea | T | O | 83.8 |
| Tiarella cordifolia | G | O | 88.4 | Bromus inermis | T | O | 69.6 |
| Tropaelum majus | G | O | 76.8 | Bromus inermis | T | R | 91.2 |
| Typha latifolia | G | O | 76.4 | Calendula officinalis | T | R | 34.5 |
| Typha latifolia | G | R | 82.9 | Canna edulis | T | R | 20.5 |
| Vaccinium corymbosum | G | R | 72.1 | Canna edulis | T | O | 73.5 |
| Vaccinium corymbosum | G | O | 95.4 | Capsella bursa-pastoris | T | R | 32.1 |
| Vaccinium macrocarpon | G | O | 95.3 | Capsella bursa-pastoris | T | O | 75.1 |
| Veratrum viride | G | O | 80.8 | Carex morrowii | T | R | 44.0 |
| Verbascum thapsus | G | R | 27.3 | Carex morrowii | T | O | 94.3 |
| Verbascum thapsus | G | O | 91.3 | Carum carvi | T | O | 20.5 |
| Viburnum trilobum | G | O | 68.5 | Cerastium tomentosum | T | R | 36.8 |
| Viburnum trilobum | G | R | 72.6 | Chaerophyllum bulbosum | T | R | 23.0 |
| Vicia sativa | G | R | 32.2 | Chaerophyllum bulbosum | T | O | 80.2 |
| Vicia sativa | G | O | 96.8 | Chelidonium majus | T | O | 94.3 |
| Vicia villosa | G | R | 29.7 | Chenopodium quinoa | T | O | 48.2 |
| Vicia villosa | G | O | 98.7 | Chenopodium quinoa | T | R | 48.3 |
| Vinca minor | G | O | 35.8 | Cicer arietinum | T | R | 25.6 |
| Vitis sp. | G | R | 77.5 | Cicer arietinum | T | O | 81.7 |
| Vitis sp. subsp endivia | G | O | 99.8 | Cichorium endivia | T | R | 20.8 |
| Zea mays subsp endivia | G | O | 54.2 | Cichorium endivia | T | O | 95.5 |
| Zea mays | G | R | 56.0 | Cichorium intybus | T | R | 20.4 |
| Perilla frutescens | T | R | 83.5 | Cichorium intybus | T | O | 96.0 |
| Achillea millefolium | T | O | 89.0 | Circium arvense | T | R | 58.3 |
| Aconitum napellus | T | O | 63.6 | Circium arvense | T | O | 79.6 |
| Acorus calamus | T | O | 94.2 | Citrullus colocynthis | T | R | 41.2 |
| Actinidia arguta | T | R | 52.4 | Citrullus colocynthis | T | O | 84.9 |
| Actinidia arguta | T | O | 84.8 | Coriandrum sativum | T | O | 38.4 |
| Adiantum pedatum | T | O | 92.2 | Coriandrum sativum | T | R | 48.8 |
| Agrimonia eupatoria | T | O | 39.2 | Cornus canadensis | T | O | 32.1 |
| Agropyron rupens | T | O | 97.3 | Amaranthus caudathus | T | R | 20.7 |
| Alchemilla mollis | T | O | 85.2 | Amaranthus caudathus | T | O | 69.3 |
| Alchemilla mollis | T | R | 96.8 | Amaranthus retroflexus | T | R | 32.4 |
| Allium ampeloprasum | T | R | 33.5 | angelica archangelica | T | R | 44.2 |
| Allium ampeloprasum | T | O | 94.1 | angelica archangelica | T | O | 55.7 |
| Allium cepa | T | R | 54.4 | Anthriscus cerefolium | T | O | 96.1 |
| Allium cepa | T | O | 100.0 | Apium graveolens | T | R | 30.3 |
| Allium sativum | T | O | 76.5 | Aralia nudicaulis | T | R | 68.2 |
| Allium schoenoprasum | T | O | 87.0 | Aralia nudicaulis | T | O | 97.8 |
| Allium tuberosum | T | R | 53.6 | Arctium minus | T | O | 92.9 |
| Allium tuberosum | T | O | 98.7 | Arctostaphylos uva-ursi | T | O | 72.0 |
| Aloe vera | T | R | 43.7 | Arctostaphylos uva-ursi | T | R | 79.8 |
| Aloe vera | T | O | 79.9 | Armoracia rusticana | T | O | 88.0 |
| Althaea officinalis | T | O | 95.8 | Aronia melanocarpa | T | R | 74.9 |
| Tanacetum parthenium | G | R | 67.9 | Aronia melanocarpa | T | O | 80.0 |
| Tanacetum vulgare | G | R | 49.5 | Artemisia absinthium | T | O | 41.7 |
| Tanacetum vulgare | G | O | 97.8 | Artemisia absinthium | T | R | 96.1 |
| Taraxacum officinale | G | R | 45.4 | Artemisia dracunculus | T | O | 96.2 |

TABLE 9-continued

Cath K

| Nom latin | Stress | extrait | Inhibition (%) | Nom latin | Stress | extrait | Inhibition (%) |
|---|---|---|---|---|---|---|---|
| taraxacum officinale | G | O | 100.0 | Artium lappa | T | O | 21.1 |
| Asclepias incarnata | T | O | 81.5 | Oxalis Deppei | T | O | 73.4 |
| Fragaria x ananassa | T | O | 44.3 | oxyria digyna | T | R | 23.6 |
| Galinsoga ciliata | T | R | 49.4 | oxyria digyna | T | O | 92.5 |
| Galinsoga ciliata | T | O | 56.9 | Panax quinquefolius | T | O | 24.8 |
| Galium odoratum | T | R | 59.4 | Panax quinquefolius | T | R | 36.6 |
| Galium odoratum | T | O | 95.3 | Panicum miliaceum | T | R | 26.9 |
| Gaultheria hispidula | T | R | 37.9 | Passiflora caerulea | T | R | 55.3 |
| Gaultheria hispidula | T | O | 78.5 | Passiflora caerulea | T | O | 77.6 |
| Gaultheria procumbens | T | O | 85.7 | Pastinaca sativa | T | O | 49.2 |
| Glechoma hederacea | T | O | 95.9 | Pastinaca sativa | T | O | 82.9 |
| Glycine max | T | O | 96.8 | Pennisetum alopecuroides | T | O | 74.9 |
| Glycine max | T | R | 32.8 | Petasites Japonicus | T | R | 22.9 |
| Glycine max | T | O | 100.0 | Petasites Japonicus | T | O | 79.5 |
| Glycyrrhiza glabra | T | R | 70.2 | Petroselinum crispum | T | O | 61.1 |
| Glycyrrhiza glabra | T | O | 90.3 | Petroselinum crispum | T | O | 83.7 |
| Guizotia abyssinica | T | R | 34.4 | Petroselinum crispum | T | R | 99.0 |
| Guizotia abyssinica | T | O | 97.9 | Phalaris canariensis | T | R | 29.5 |
| Hamamelis virginiana | T | R | 72.1 | Phalaris canariensis | T | O | 67.2 |
| Hamamelis virginiana | T | O | 77.1 | Phaseolus vulgaris | T | O | 93.1 |
| Hedeoma pulegioides | T | O | 34.7 | Physalis pruinosa | T | O | 64.2 |
| Helianthus strumosus | T | R | 20.6 | Pimpinella anisum | T | R | 59.0 |
| Helianthus strumosus | T | O | 57.2 | Pimpinella anisum | T | O | 88.5 |
| Helianthus tuberosa | T | O | 61.0 | Pisum sativum | T | O | 75.4 |
| Helianthus tuberosus | T | R | 46.9 | Plantago major | T | O | 99.6 |
| Helichrysum angustifolium | T | O | 23.5 | Plectranthus sp. | T | R | 49.4 |
| Helichrysum angustifolium | T | R | 94.5 | Podophyllum peltatum | T | O | 87.3 |
| Helichrysum thianschanicum | T | R | 98.1 | Laurus nobilis | T | R | 51.7 |
| Helleborus niger | T | O | 26.2 | Lauras nobilis | T | O | 87.2 |
| Humulus lupulus | T | R | 38.0 | Lavandula latifolia | T | R | 75.5 |
| Humulus lupulus | T | O | 93.8 | Lavendula angustifolia | T | R | 81.9 |
| Hyoscyamus niger | T | O | 41.5 | Ledum groenlandicum | T | R | 45.9 |
| Hyssopus officinalis | T | R | 44.6 | Ledum groenlandicum | T | O | 99.5 |
| Inula helenium Culinaris | T | O | 97.6 | Lens culinaris subsp. | T | R | 28.0 |
| Juniperus communis | T | R | 80.0 | Lens culinaris subsp. Culinaris | T | O | 97.6 |
| Koeleria glauca | T | O | 94.7 | Levisticum officinale | T | R | 51.4 |
| Koeleria glauca | T | R | 99.4 | Levisticum officinale | T | O | 87.8 |
| Lactuca sativa | T | O | 94.0 | Lotus corniculatus | T | R | 53.7 |
| Lathyrus Sativus | T | R | 24.0 | Lotus corniculatus | T | O | 97.4 |
| Lathyrus Sativus | T | O | 33.0 | Lupinus polyphyllus | T | O | 95.8 |
| Lathyrus sylvestris | T | O | 43.1 | Lupinus polyphyllus | T | R | 99.3 |
| Cornus canadensis | T | R | 80.2 | Luzula sylvatica | T | R | 29.5 |
| Crataegus sp | T | R | 22.9 | Malus hupehensis | T | R | 58.7 |
| Crataegus submollis | T | O | 81.5 | Malus hupehensis | T | O | 62.5 |
| Cryptotaenia canadensis | T | R | 20.9 | Malus spp. | T | O | 25.7 |

TABLE 9-continued

| Cath K | | | | | | | |
|---|---|---|---|---|---|---|---|
| Nom latin | Stress | extrait | Inhibition (%) | Nom latin | Stress | extrait | Inhibition (%) |
| Cymbopogon citratus | T | R | 40.5 | Malva sylvestris | T | O | 73.5 |
| Cymbopogon citratus | T | O | 77.0 | Medicago sativa | T | R | 46.2 |
| Cyperus esculentus | T | R | 20.9 | Medicago sativa | T | O | 94.9 |
| Cyperus esculentus | T | O | 72.0 | Melilotus officinalis | T | O | 99.4 |
| Dirca palustris | T | R | 67.1 | Melissa officinalis | T | R | 91.0 |
| Dirca palustris | T | O | 82.2 | Mentha piperita | T | O | 86.8 |
| Diyopteris filix-mas | T | O | 23.9 | Ruta graveolens | T | O | 68.5 |
| Echinacea purpurea | T | O | 92.2 | Salix purpurea | T | R | 37.1 |
| Eleusine coracana | T | R | 30.0 | Salix purpurea | T | O | 46.1 |
| Erysimum perofskianum | T | R | 81.7 | Salvia officinalis | T | O | 67.7 |
| Erysimum perofskianum | T | O | 98.8 | Salvia officinalis | T | R | 91.1 |
| Fagopyrum esculentum | T | O | 35.5 | Sambucus canadensis | T | R | 35.7 |
| Fagopyrum tararicum | T | O | 40.0 | Sambucus canadensis | T | O | 99.0 |
| Fagopyrum tataricum | T | R | 30.1 | Sanguisorba minor | T | O | 90.6 |
| Foeniculum vulgare | T | O | 21.0 | Santolina | T | O | 62.7 |
| Fpomoea batatas | T | O | 98.6 | Santolina | T | R | 73.4 |
| Menyanthes trifoliata | T | O | 64.3 | Saponaria officinalis | T | O | 93.2 |
| Miscanthus sinensis Andress | T | R | 36.1 | Satureja hortensis | T | R | 43.1 |
| Miscanthus sinensis Andress | T | O | 66.6 | Satureja hortensis | T | O | 87.9 |
| Nepeta cataria | T | O | 23.6 | Satureja montana | T | R | 55.1 |
| Ocimum Basilicum | T | O | 81.3 | Satureja montana | T | O | 79.2 |
| Oenothera biennis | T | R | 35.7 | Satureja repandra | T | R | 49.7 |
| Oenothera biennis | T | O | 75.6 | Satureja repandra | T | O | 73.3 |
| Onobrychis viciifolia | T | R | 44.5 | Scorzorera hipanica | T | O | 63.3 |
| Onobrychis viciifolia | T | O | 90.7 | Scuttellaria lateriflora | T | O | 29.3 |
| Origanum vulgare | T | R | 76.5 | Setaria italica | T | R | 20.8 |
| Origanum vulgare | T | O | 82.9 | Silene vulgaris | T | O | 96.8 |
| Oryza sativa | T | O | 51.4 | Sium sisarum | T | R | 27.4 |
| Oxalis Deppei | T | R | 48.4 | Slum sisarum | T | O | 88.8 |
| Solanum melongens | T | R | 21.9 | Teucrium chamaedrys | T | R | 40.0 |
| Solidago sp | T | R | 45.9 | Thymus fragantissimus | T | O | 93.7 |
| Solidago sp | T | O | 74.0 | Thymus fragantissimus | T | R | 97.3 |
| Sonchus oleraceus subsp arcticus | T | R | 22.7 | Thymus praecox | T | O | 46.0 |
| Sonchus oleraceus | T | O | 38.1 | Thymus pseudolanuginosus | T | R | 74.3 |
| Sorghum caffrorum | T | O | 57.0 | Thymus serpyllum | T | O | 88.6 |
| Sorghum caffrorum | T | R | 74.0 | Thymus x citriodorus | T | R | 66.4 |
| Sorghum dochna | T | O | 44.3 | Thymus x citriodorus | T | O | 97.8 |
| Sorghum dochna | T | O | 65.8 | Tiarella cordifolia | T | O | 94.9 |
| Sorghum dochna porrifolius | T | R | 70.7 | Tragopogon | T | R | 45.0 |
| Sorghum dochna porrifolius | T | R | 89.0 | Tragopogon | T | O | 72.0 |
| Sorghum durra | T | R | 39.6 | Triticosecale spp | T | R | 27.8 |
| Polygonum aviculare | T | R | 32.8 | Triticosecale spp | T | O | 87.8 |
| Polygonum aviculare | T | O | 53.9 | | | | |
| Potentilla anserina | T | O | 94.9 | | | | |
| Prunella vulgaris | T | O | 76.4 | | | | |
| Prunella vulgaris | T | R | 94.7 | | | | |

TABLE 9-continued

| Cath K | | | |
|---|---|---|---|
| Nom latin | Stress | extrait | Inhibition (%) |
| Pteridium aquilinum | T | O | 90.1 |
| Raphanus raphanistrum | T | R | 39.5 |
| Raphanus raphanistrum | T | O | 91.0 |
| Raphanus sativus | T | O | 79.1 |
| Ribes nigrum | T | R | 89.6 |
| Rites nigrum | T | O | 95.4 |
| Ribes Sylvestre | T | R | 20.1 |
| Ribes Sylvestre | T | O | 97.4 |
| Ricinus communis | T | R | 26.5 |
| Ricinus communis | T | O | 92.4 |
| Rosa rugosa | T | O | 41.6 |
| Rubus canadensis | T | O | 96.4 |
| Rubus idaeus | T | R | 44.8 |
| Rubus idaeus | T | O | 88.7 |
| Rumes scutatus | T | O | 88.7 |
| Rumex acetosella | T | R | 40.9 |
| Rumex acetosella | T | O | 90.9 |
| Rumex crispus | T | R | 33.4 |
| Rumex crispus | T | O | 89.3 |
| Triticum aestivum | T | R | 26.6 |
| Triticum aestivum | T | O | 42.6 |
| Tropaeolum majus | T | R | 21.4 |
| Tropaeolum majus | T | O | 81.5 |
| Typha latifolia | T | O | 44.8 |
| Typha latifolia | T | R | 72.5 |
| Urtica dioica | T | R | 35.2 |
| Urtica dioica | T | O | 62.9 |
| Vaccinium angustifolium | T | R | 27.4 |
| Vaccinium macrocarpon | T | R | 78.0 |
| Vaccinium macrocarpon | T | O | 87.8 |
| Veratrum viride | T | O | 90.2 |
| Verbascum thapsus | T | O | 84.3 |
| Viburnum trilobum | T | R | 45.2 |
| Viburnum trilobum | T | O | 70.0 |
| Vicia sativa | T | O | 99.0 |
| Vicia villosa | T | R | 44.2 |
| Vicia villosa | T | O | 98.3 |
| Vinca minor | T | O | 21.5 |
| Vitis sp. | T | O | 99.9 |
| Zea mays | T | R | 31.7 |
| Zea mays | T | O | 90.2 |
| Sorghum durra | T | O | 76.5 |
| Sorghum sudanense | T | O | 40.5 |
| Stachys affinis | T | R | 67.2 |
| Stachys affinis | T | O | 86.6 |
| Stachys byzantina | T | R | 85.7 |
| Stellaria graminea | T | O | 43.3 |
| Stellaria graminea linne | T | R | 39.2 |
| Stellaria media | T | R | 21.1 |
| Stipa capillata | T | R | 24.2 |
| Symphytum officinale | T | R | 64.4 |
| Tanacetum parthenium | T | R | 62.2 |
| Tanacetum vulgare | T | R | 42.5 |
| Tanacetum vulgare | T | O | 97.5 |
| Taraxacum officinale | T | R | 47.5 |
| Taraxacum officinale | T | O | 100.0 |

TABLE 10

HLE

| Nom latin | Stress | extrait | Inhibition (%) | Nom latin | Stress | extrait | Inhibition (%) |
|---|---|---|---|---|---|---|---|
| *Achillea millefolium* | A | O | 21.9 | *Cichorium intybus* | A | S | 32.1 |
| | | | | *Lolium multiflorum* | A | O | 31.0 |
| *Achillea millefolium* | A | S | 24.5 | | | | |
| | | | | *Lolium perenne* | A | O | 20.8 |
| *Aconitum napellus* | A | O | 25.8 | *Lolium perenne* | A | R | 21.7 |
| *Adiantum pedatum* | A | R | 27.6 | *Lolium perenne* | A | S | 22.1 |
| *Agrimonia eupatoria* | A | V | 26.0 | *Malva sylvestris* | A | S | 22.9 |
| | | | | *Matricaria recutita* | A | O | 28.5 |
| *Agropyron cristatum* | A | R | 21.0 | | | | |
| | | | | *Melaleuca alternifolia* | A | O | 21.9 |
| *Agropyron repens* | A | S | 23.4 | | | | |
| *Agropyron repens* | A | R | 28.2 | *Melissa officinalis* | A | S | 23.4 |
| *Agropyron repens* | A | S | 39.8 | *Mentha piperita* | A | O | 31.6 |
| *Agrostis Stofonifera* | A | O | 38.9 | *Mentha piperita* | A | W | 33.2 |
| | | | | *Mentha pulegium* | A | O | 42.2 |
| *Alchemilla mollis* | A | V | 27.9 | *Mentha pulegium* | A | V | 21.5 |
| *Alchemilla mollis* | A | O | 66.0 | *Mentha pulegium* | A | S | 33.8 |
| *Alchemilla mollis* | A | R | 100.0 | *Mentha spicata* | A | O | 24.3 |
| *Alchemilla mollis* | A | S | 23.5 | *Oenothera biennis* | A | O | 25.2 |
| *Alkanna tinctoria* | A | S | 26.2 | *Oenothera biennis* | A | R | 78.8 |
| *Allium Tuberosum* | A | S | 57.9 | *Origanum majorana* | A | V | 37.4 |
| *Aloe vera* | A | O | 20.5 | | | | |
| *Ambrosia artemisiifolia* | A | O | 29.1 | *Oxyria digyna* | A | V | 28.2 |
| | | | | *Panicum miliaceum* | A | oO | 33.3 |
| *Amelanchier sanguinea* | A | W | 96.5 | | | | |
| | | | | *Peucedanum cervaria* | A | R | 23.4 |
| *Amelanchier sanguinea* | A | V | 52.4 | | | | |
| | | | | *Phalaris arundinacea* | A | R | 22.4 |
| *Anethum graveolens* | A | O | 32.1 | | | | |
| | | | | *Phalaris canariensis* | A | O | 27.6 |
| *Anethum graveolens* | A | W | 22.8 | | | | |
| | | | | *Phaseolus coccineus* | A | S | 28.3 |
| *Angelica archangelica* | A | S | 39.2 | | | | |
| | | | | *Phaseolus mungo* | A | R | 37.8 |
| *Anthemis nobilis* | A | O | 37.6 | *Phaseolus vulgaris* | A | O | 24.3 |
| *Anthemis nobilis* | A | S | 26.4 | *Phaseolus Vulgaris* | A | S | 74.3 |
| *Anthemis tinctoria* | A | O | 31.9 | | | | |
| *Anthemis tinctoria* | A | S | 38.4 | *Phleum pratense* | A | R | 27.8 |
| *Apium graveolens* | A | S | 49.2 | *Physalis ixocarpa* | A | O | 21.5 |
| *Arctium minus* | A | O | 46.4 | *Physalis ixocarpa* | A | S | 26.5 |
| *Arctostaphylos uva-ursi* | A | R | 100.0 | *Physalis Pruinosa* | A | S | 60.2 |
| | | | | *Phytolacca americana* | A | S | 100.0 |
| *Aronia melanocarpa* | A | O | 21.9 | | | | |
| | | | | *Plantago coronopus* | A | O | 21.1 |
| *Aronia melanocarpa* | A | W | 78.4 | | | | |
| | | | | *Plantago coronopus* | A | S | 25.7 |
| *Aronia melanocarpa* | A | V | 100.0 | | | | |
| | | | | *Plantago major* | A | O | 26.0 |
| *Aronia melanocarpa* | A | R | 29.0 | *Plectranthus sp.* | A | O | 23.1 |
| | | | | *Poa pratensis* | A | O | 21.7 |
| *Aronia melanocarpa* | A | O | 33.6 | *Polygonum aviculare* | A | R | 79.7 |
| *Artemisia dracunculus* | A | W | 89.2 | *Portulaca olevcae* | A | O | 34.5 |
| | | | | *Poterium sanguisorba* | A | R | 25.8 |
| *Ludoviciana* | A | O | 33.4 | | | | |
| *Ludoviciana* | A | S | 20.7 | *Poterium sanguisorba* | A | O | 34.6 |
| *Aster sp* | A | R | 26.2 | | | | |
| *Beta vulgaris* | A | R | 100.0 | *Poterium sanguisorba* | A | W | 31.0 |
| *Beta vulgaris* spp. *Maritima* | A | R | 92.2 | | | | |
| | | | | *Pteridium aquilinum* | A | R | 54.4 |
| *Borago officinalis* | A | S | 22.6 | | | | |
| *Brassica napus* | A | S | 68.3 | *Raphanus sativus* | A | S | 66.4 |
| *Brassica napus* | A | R | 29.5 | *Raphanus sativus* | A | R | 81.8 |
| *Brassica nigra* | A | S | 32.6 | *Rheum officinale* | A | S | 37.9 |
| *Brassica oleracea* | A | O | 22.9 | *Ribes nigrum* | A | W | 100.0 |
| *Brassica oleracea* | A | V | 20.8 | *Ribes nigrum* | A | S | 47.6 |
| *Brassica oleracea* | A | R | 22.2 | *Ribes nigrum* | A | V | 27.5 |
| *Brassica rapa* | A | S | 23.2 | *Ribes rubrum* | A | R | 35.4 |
| *Brassica rapa* | A | R | 26.9 | *Ribes Sylvestre* | A | W | 100.0 |
| *Bromus inermis* | A | O | 34.1 | *Rosa rugosa* | A | W | 95.1 |
| *Bromus inermis* | A | R | 21.9 | *Rosa rugosa* | A | R | 24.6 |
| *Calamintha nepeta* | A | O | 35.4 | *Rosmarinus officinalis* | A | R | 58.4 |
| *Canna edulis* | A | O | 56.4 | *Rubus idaeus* | A | W | 27.6 |
| *Canna edulis* | A | R | 21.4 | *Rubus idaeus* | A | S | 33.0 |

TABLE 10-continued

HLE

| Nom latin | Stress | extrait | Inhibition (%) | Nom latin | Stress | extrait | Inhibition (%) |
|---|---|---|---|---|---|---|---|
| Carum carvi | A | O | 24.2 | Lavandula latifolia | A | S | 42.2 |
| Chaerophyllum bulbosum | A | O | 25.5 | Leonurus cardiaca | A | R | 100.0 |
| chenopodium bonus-henricus | A | R | 24.0 | Lepidium sativum | A | O | 100.0 |
| Chenopodium bonus-henricus | A | S | 85.8 | Saccharum officinarum | A | R | 23.8 |
| Citrullus lanatus | A | R | 26.3 | Salvia elegans | A | O | 100.0 |
| Coix Lacryma-Jobi | A | S | 86.1 | Salvia officinalis | A | O | 95.7 |
| | | | | Salvia officinalis | A | W | 77.9 |
| Cosmos sulphureus | A | O | 33.8 | Salvia officinalis | A | R | 83.7 |
| | | | | Salvia officinalis | A | S | 20.5 |
| | | | | Salvia sclarea | A | O | 100.0 |
| Cosmos sulphureus | A | S | 20.7 | Salvia sclarea | A | V | 28.6 |
| | | | | Santolina chamaecyparissus | A | O | 27.1 |
| Crataegus sp | A | O | 84.1 | | | | |
| Crataegus sp | A | R | 23.6 | Satureja montana | A | W | 23.2 |
| Crataegus sp | A | S | 21.7 | Satureja montana | A | S | 27.7 |
| Crataegus submollis | A | S | 34.0 | Scorzonera hispanica | A | R | 60.1 |
| Cryptotaenia canadensis | A | V | 22.1 | Scutellaria lateriflora | A | S | 45.9 |
| Cucumis anguria | A | O | 26.2 | Artemisia absinthium | G | O | 31.5 |
| Cucumis Anguria | A | R | 53.4 | | | | |
| Cucumis melo | A | S | 53.6 | Artemisia absinthium | G | V | 24.2 |
| Cucumis sativus | A | R | 53.3 | | | | |
| Curcuma zedoaria | A | O | 24.3 | Aster | G | S | 29.2 |
| Cymbopogon citratus | A | S | 91.2 | Beckmannia eruciformis | G | O | 22.7 |
| Datisca cannabina | A | S | 55.7 | Beta vulgaris | G | R | 100.0 |
| Daucus carota | A | R | 100.0 | Betula glandulosa | G | S | 26.7 |
| Daucus carota | A | V | 24.7 | Borago officinalis | G | O | 25.7 |
| Daucus carota | A | O | 37.9 | Brassica Napus | G | S | 50.4 |
| Digitalis purpurea | A | S | 34.0 | Brassica napus | G | R | 48.2 |
| Dirca palustris | A | R | 20.3 | Brassica nigra | G | S | 23.9 |
| Dirca palustris | A | S | 27.9 | Brassica oleracea | G | R | 28.1 |
| Dolichos Lablab | A | R | 21.5 | Brassica oleracea | G | S | 22.5 |
| Dryopteris filix-mas | A | R | 58.8 | Brassica rapa | G | R | 56.4 |
| | | | | Calamintha nepeta | G | V | 24.8 |
| Dryopteris filix-mas | A | S | 22.0 | Calamintha nepeta | G | O | 38.8 |
| | | | | Canna edulis | G | O | 66.3 |
| Echinacea purpurea | A | O | 38.2 | Capsella bursa-pastoris | G | R | 25.8 |
| Echinacea purpurea | A | S | 28.1 | Carthamus tinctorius | G | R | 22.2 |
| Eleusine coracana | A | S | 20.7 | Chelidonium majus | G | O | 31.6 |
| Erigeron canadensis | A | O | 29.6 | | | | |
| | | | | Chenopodium album | G | S | 21.3 |
| Fagopyrum esculentum | A | S | 29.3 | Cichorium endivia subsp. Endivia | G | S | 21.4 |
| Fagopyrum tataricum | A | S | 24.4 | Cicer arietinum | G | S | 50.7 |
| Foeniculum vulgare | A | O | 25.1 | Cichorium endivia subsp. Endivia | G | O | 48.5 |
| Fragaria x ananassa | A | O | 22.3 | Cichorium endivia subsp. Endivia | G | S | 27.9 |
| Fragaria x ananassa | A | W | 100.0 | Coix Lacryma-Jobi | G | O | 24.5 |
| Fragaria x ananassa | A | V | 21.4 | Cornus canadensis | G | S | 36.1 |
| | | | | Crataegus sp | G | W | 57.8 |
| Fragaria x ananassa | A | S | 29.4 | Cucurbita Pepo | G | R | 23.1 |
| | | | | Curcuma zedoaria | G | O | 24.0 |
| Fragaria x ananassa | A | V | 21.6 | Datura metel | G | O | 21.0 |
| | | | | Aconitum napellus | G | R | 97.7 |
| Galinsoga ciliata | A | R | 61.6 | Acorus calamus | G | S | 20.0 |
| Galium odoratum | A | R | 21.0 | Adiantum pedatum | G | R | 100.0 |
| Gaultheria hispidula | A | O | 33.7 | Agastache foeniculum | G | W | 25.3 |
| Gentiana lutea | A | R | 52.1 | Ageratum conyzoides | G | O | 28.5 |
| Glechoma hederacea | A | O | 21.8 | Agropyron cristatum | G | R | 37.3 |
| Glycine Max | A | S | 81.3 | | | | |
| Glycyrrhiza glabra | A | W | 100.0 | Agropyron repens | | R | 31.4 |
| | | | | Fagopyrum esculentum | G | S | 32.9 |
| Glycyrrhiza glabra | A | S | 63.3 | Fagopyrum | G | S | 41.2 |

TABLE 10-continued

HLE

| Nom latin | Stress | extrait | Inhibition (%) | Nom latin | Stress | extrait | Inhibition (%) |
|---|---|---|---|---|---|---|---|
| *Guizotia abyssinica* | A | R | 36.9 | *tataricum Foeniculum vulgare* | G | V | 25.7 |
| *Hamamelis virginiana* | A | R | 100.0 | *Foeniculum vulgare* | G | S | 42.5 |
| *Helianthus Tuberosus* | A | S | 32.1 | *Foeniculum Vulgare* | G | O | 24.1 |
| *Heliotropium arborescens* | A | R | 22.8 | *Galinsoga ciliata* | G | S | 25.0 |
| *Heliotropium arborescens* | A | S | 24.9 | *Galium odoratum* | G | R | 89.4 |
| *Helleborus niger* | A | S | 25.6 | *Gaultheria hispidula* | G | O | 35.1 |
| *Hordeum vulgare* | A | O | 58.1 | *Gaultheria hispidula* | G | R | 67.2 |
| *Hypericum perforatum* | A | S | 24.8 | *Gaultheria procumbens* | G | S | 74.7 |
| *Hyssopus officinalis* | A | O | 21.1 | *Glycine max* | G | R | 24.6 |
| *Hyssopus officinalis* | A | S | 93.6 | *Glycyrrhiza glabra* | G | W | 56.8 |
| *Lactuca serriola* | A | S | 34.3 | *Glycyrrhiza glabra* | G | V | 30.0 |
| *Laurus nobilis* | A | W | 100.0 | *Glycyrrhiza glabra* | G | R | 92.4 |
| *Lavandula latifolia* | A | W | 57.1 | *Glycyrrhiza glabra* | G | S | 28.6 |
| *Lavandula latifolia* | A | O | 43.7 | | | | |
| *Chenopodium quinoa* | A | S | 50.4 | *Hamamelis virginiana* | G | R | 100.0 |
| *Chrysanthemum coronarium* | A | O | 26.0 | *Hamamelis virginiana* | G | S | 29.3 |
| *Cicer arietinum* | A | S | 23.3 | *Hedeoma pulegioides* | G | O | 60.0 |
| *Senecio vulgaris* | A | R | 34.0 | | | | |
| *Sonchus oleraceus* | A | O | 29.1 | *Helenium hoopesii* | G | O | 37.3 |
| *Sorghum dochna* | A | O | 21.1 | *Helenium hoopesii* | G | S | 34.7 |
| *Sorghum dochna* | A | V | 24.4 | *Helianthus tuberosus* | G | V | 21.4 |
| *Sorghum durra* | A | O | 23.4 | | | | |
| *Sorghum durra* | A | V | 23.6 | *Helichrysum thianschanicum* | G | O | 43.0 |
| *Spinacia oleracea* | A | S | 26.8 | | | | |
| *Stellaria graminea* | A | O | 24.8 | *Helichrysum thianschanicum* | G | R | 39.2 |
| *Symphytum officinale* | A | O | 91.6 | *Heliotropium arborescens* | G | R | 22.8 |
| *Tanacetum cinerariifolium* | A | R | 28.3 | *Heliotropium arborescens* | G | S | 39.5 |
| *Tanacetum vulgare* | A | O | 46.3 | *Helleborus niger* | G | S | 34.2 |
| *Tanacetum vulgare* | A | S | 33.7 | *Hypericum henryi* | G | S | 23.7 |
| | | | | *Hypericum perforatum* | G | S | 23.8 |
| *Taraxacum officinale* | A | W | 26.4 | *Hyssopus officinalis* | G | W | 45.1 |
| *Taraxacum officinale* | A | V | 24.0 | *Hyssopus officinalis* | G | S | 24.2 |
| *Taraxacum officinale* | A | O | 21.0 | *Inula helenium* | G | W | 96.2 |
| *Teucrium chamaedrys* | A | O | 37.0 | *Ipomola batatas* | G | V | 21.9 |
| | | | | *Lactuca sativa* | G | W | 35.1 |
| *Thymus fragantissimus* | A | W | 20.2 | *Laportea canadensis* | G | O | 25.1 |
| *Thymus herba-barona* | A | W | 20.8 | *Laportea canadensis* | G | S | 26.5 |
| *Thymus vulgaris* | A | R | 77.9 | *Ricinus communis* | G | S | 46.0 |
| *Thymus vulgaris* | A | W | 23.6 | *Rosmarinus officinalis* | G | R | 60.4 |
| *Thymus x citriodorus* | A | W | 21.3 | *Rubus idaeus* | G | W | 28.2 |
| *Thymus x citriodorus* | A | S | 21.1 | *Rubus occidentalis* | G | R | 93.6 |
| | | | | *Mentha arvensis* | G | S | 65.5 |
| *Trichosanthes kirilowii* | A | O | 23.2 | *Mentha piperita* | G | O | 24.2 |
| | | | | *Mentha piperita* | G | S | 23.7 |
| *Trigonella foenum graecum* | A | S | 32.0 | *Mentha piperita* | G | V | 34.2 |
| | | | | *Mentha pulegium* | G | O | 63.3 |
| *Triticum durum* | A | S | 22.0 | *Mentha pulegium* | G | V | 30.2 |
| *Triticum turgidum* | A | O | 60.0 | *Mentha spicata* | G | S | 45.9 |
| *Triticum spelta* | A | S | 47.6 | *Monarda didyma* | G | S | 47.7 |
| *Urtica dioica* | A | O | 33.3 | *Nepeta cataria* | G | R | 100.0 |
| *Vaccinium augustifolium* | A | W | 42.6 | *Nicotiana tabacum* | G | O | 75.8 |
| | | | | *Hordeum vulgare* subsp. *Vulgare* | G | O | 33.4 |
| *Vaccinium Corymbosum* | A | W | 22.4 | *Sambucus ebulus* | G | R | 48.6 |

TABLE 10-continued

HLE

| Nom latin | Stress | extrait | Inhibition (%) | Nom latin | Stress | extrait | Inhibition (%) |
|---|---|---|---|---|---|---|---|
| *Vaccinium Corymbosum* | A | S | 21.6 | *Sanguisorba officinalis* | G | R | 100.0 |
| *Vaccinium macrocarpon* | A | W | 22.5 | *Santolina chamaecyparissus* | G | O | 100.0 |
| *Vaccinium macrocarpon* | A | S | 54.8 | *Serratula tinctoria* | G | S | 56.8 |
| | | | | *Satureja montana* | G | O | 34.1 |
| *Valerianella locusta* | A | O | 49.2 | *Scolymus hispanicus* | G | R | 37.9 |
| *Veronica officinalis* | A | O | 43.7 | *Scutellaria lateriflora* | G | S | 54.7 |
| *Viburnum trilobum* Marsh. | A | W | 75.4 | *Senecio vulgaris* | G | R | 35.3 |
| | | | | *Solidago* sp | G | S | 22.6 |
| *Vitis* | A | S | 33.8 | *Sonchus oleraceus* | G | O | 23.7 |
| *Vitis* | A | W | 100.0 | *Sorghum caffrorum* | G | V | 27.1 |
| *Vitis* | A | O | 21.0 | | | | |
| *Zea Mays* | A | S | 95.2 | *Sorghum dochna* | G | S | 40.7 |
| *Achillea millefolium* | G | O | 28.8 | *Sorghum dochna* | G | O | 21.4 |
| | | | | *Sorghum sudanense* | G | V | 23.3 |
| *Achillea millefolium* | G | S | 27.3 | | | | |
| | | | | *Sorghum sudanense* | G | W | 92.9 |
| *Aconitum napellus* | G | O | 23.1 | | | | |
| *Rubus idaeus* | A | R | 27.9 | *Stellaria graminea* | G | O | 25.4 |
| *Rubus idaeus* | A | O | 37.4 | *Stellaria media* | G | O | 30.4 |
| *Rumex Acetosa* | A | S | 45.2 | *Stellaria media* | G | R | 22.0 |
| *Rumex crispus* | A | O | 26.1 | *Tanacetum vulgare* | G | O | 57.3 |
| *Rumex crispus* | A | R | 100.0 | | | | |
| *Rumex Scutatus* | A | V | 43.8 | *Tanacetum vulgare* | G | W | 38.4 |
| *Ruta graveolens* | A | O | 28.7 | | | | |
| *Saccharum officinarum* | A | O | 29.6 | *Tanacetum vulgare* | G | O | 38.2 |
| *Alchemilla mollis* | G | W | 20.6 | *Tanacetum vulgare* | G | W | 26.3 |
| *Alchemilla mollis* | G | O | 56.1 | | | | |
| *Alchemilla mollis* | G | R | 28.1 | *Taraxacum officinale* | G | V | 20.0 |
| *Alchemilla mollis* | G | S | 25.3 | | | | |
| *Allium cepa* | G | O | 20.2 | *taraxacum officinale* | G | O | 28.0 |
| *Allium sativum* | G | O | 100.0 | | | | |
| *Allium tuberosum* | G | O | 100.0 | *Thymus fragantissimus* | G | R | 79.9 |
| *Althaea officinalis* | G | S | 30.8 | | | | |
| *Amaranthus caudatus* | G | S | 22.3 | *Thymus fragantissimus* | G | O | 26.2 |
| *Amelanchier sanguinea* | G | W | 88.3 | *Thymus herba-barona* | G | W | 20.2 |
| *Anethum graveolens* | G | O | 26.2 | *Thymus serpyllum* | G | V | 22.2 |
| | | | | *Triticosecale* spp. | G | S | 29.7 |
| *Angelica archangelica* | G | S | 43.2 | *Triticum durum* | G | S | 37.8 |
| | | | | *Triticum spelta* | G | O | 31.0 |
| *Anthemis nobilis* | G | S | 21.7 | *Triticum spelta* | G | S | 37.9 |
| *Arctostaphylos uva-ursi* | G | O | 33.1 | *Typha latifolia* | G | S | 27.5 |
| | | | | *Urtica dioica* | G | O | 60.3 |
| *Arctostaphylos uva-ursi* | G | R | 100.0 | *Vaccinium corymbosum* | G | S | 33.2 |
| *Arctostaphylos uva-ursi* | G | S | 23.4 | *Vaccinium angustifolium* | G | S | 43.7 |
| *Annoracia rusticana* | G | O | 22.5 | *Vaccinium macrocarpon* | G | W | 57.8 |
| *Aronia melanocarpa* | G | W | 79.0 | *Vaccinium macrocarpon* | G | S | 59.9 |
| *Aronia melanocarpa* | G | V | 100.0 | *Valerianella locusta* | G | O | 32.1 |
| *Aronia melanocarpa* | G | S | 22.7 | *Veratrum viride* | G | O | 22.1 |
| | | | | *Verbascum thapsus* | G | S | 33.8 |
| *Aronia melanocarpa* | G | O | 29.6 | | | | |
| | | | | *Viburnum trilobum* | G | V | 21.3 |
| *Laserpitium latifolium* | G | S | 22.1 | | | | |
| | | | | *Viburnum trilobum* | G | W | 73.0 |
| *Lathyrus sativus* | G | O | 29.9 | | | | |
| *Lathyrus sativus* | G | W | 27.8 | *Vicia faba* | G | S | 21.2 |
| *Lathyrus sativus* | G | S | 28.1 | *Vigna unguiculata* | G | R | 20.1 |
| *Laurus nobilis* | G | W | 100.0 | *Vitis* | G | V | 26.0 |
| *Lavandula angustifolia* | G | O | 65.7 | *Vitis* | G | W | 66.1 |
| | | | | *Vitis* | G | O | 41.7 |
| *Ledum groenlandicum* | G | O | 100.0 | *Rubus occidentalis* | G | O | 40.0 |
| | | | | *Rumex acetosella* | G | V | 24.3 |
| *Leonorus cardiaca* | G | R | 61.3 | *Rumex crispus* | G | R | 100.0 |
| *Lepidium sativum* | G | O | 100.0 | *Rumex patientia* | G | O | 32.0 |

TABLE 10-continued

HLE

| Nom latin | Stress | extrait | Inhibition (%) | Nom latin | Stress | extrait | Inhibition (%) |
|---|---|---|---|---|---|---|---|
| *Levisticum officinale* | G | W | 91.4 | *Rumex scutatus* | G | V | 28.6 |
|  |  |  |  | *Ruta graveolens* | G | S | 23.4 |
| *Lolium perenne* | G | O | 37.3 | *Saccharum officinarum* | G | O | 30.2 |
| *Lotus tetragonolobus* | G | S | 21.8 | *Salix purpurea* | G | S | 24.8 |
| *Lupinus polyphyllus* | G | O | 42.3 | *Salvia elegans* | G | O | 100.0 |
|  |  |  |  | *Corchorus olitorius* | T | O | 24.4 |
| *Malus hupehensis* | G | S | 25.9 |  |  |  |  |
| *Medicago sativa* | G | S | 32.1 | *Cornus canadensis* | T | S | 41.3 |
| *Melaleuca alternifolia* | G | O | 40.0 | *Crataegus* sp | T | S | 34.0 |
|  |  |  |  | *Crataegus submollis* | T | S | 39.6 |
| *Melissa officinalis* | G | S | 23.1 |  |  |  |  |
| *Daucus carota* | G | O | 32.3 | *Curcuma longa* | T | O | 55.3 |
| *Daucus carota* | G | R | 90.9 | *Curcuma zedoaria* | T | O | 24.4 |
| *Dipsacus sativus* | G | O | 32.7 | *Cydonia oblonga* | T | V | 35.2 |
| *Dirca palustris* | G | S | 33.5 | *Cynara scolymus* | T | O | 41.2 |
| *Dolichos Lablab* | G | R | 32.1 | *Cynara scolymus* | T | R | 36.8 |
| *Dryopteris filix-mas* | G | R | 80.9 | *Dactilis Glomerata* | T | O | 31.9 |
| *Echinacea purpurea* | G | S | 63.0 | *Datura stramonium* | T | S | 25.9 |
| *Elymus Junceus* | G | R | 25.9 | *Daucus carota* | T | R | 92.3 |
| *Erigeron canadensis* | G | O | 43.0 | *Daucus carota* | T | O | 31.0 |
|  |  |  |  | *Dipsacus sativus* | T | O | 100.0 |
| *Erigeron speciosus* | G | O | 22.8 | *Dirca palustris* | T | S | 31.4 |
|  |  |  |  | *Dolichos lablab* | T | O | 23.1 |
| *Erigeron speciosus* | G | S | 24.2 | *Dryopteris filix-mas* | T | R | 68.2 |
| *Erysimum perofskianum* | G | O | 20.8 | *Echinacea purpurea* | T | S | 38.2 |
| *Ocimum basilicum* | G | O | 40.1 | *Eleusine coracana* | T | O | 22.1 |
| *Ocimum basilicum* | G | S | 27.9 | *Elymus junceus* | T | R | 37.9 |
| *Oenothera biennis* | G | O | 26.3 | *Erigeron speciosus* | T | O | 35.0 |
| *Oenothera biennis* | G | R | 100.0 |  |  |  |  |
| *Oenothera biennis* | G | O | 49.6 | *Erysimum perofskianum* | T | O | 22.6 |
| *Oenothera biennis* | G | S | 54.0 |  |  |  |  |
| *Origanum vulgare* | G | W | 100.0 | *Erysimum perofskianum* | T | S | 23.2 |
| *Origanum vulgare* | G | O | 26.7 |  |  |  |  |
| *Origanum vulgare* | G | S | 21.3 | *Fagopyrum esculentum* | T | S | 24.7 |
| *Oryza Sativa* | G | S | 34.5 |  |  |  |  |
| *Oxalis Deppei Lodd.* | G | O | 27.4 | *Foeniculum vulgare* | T | O | 31.4 |
| *Panicum miliaceum* | G | O | 25.3 | *Foeniculum vulgare* | T | V | 69.1 |
| *Pastinaca sativa* | G | R | 95.0 | *Foeniculum vulgare* | T | S | 38.5 |
| *Petroselinum crispum* | G | R | 44.5 | *Fragaria x ananassa* | T | O | 50.4 |
| *Petroselinum crispum* | G | S | 26.5 | *Fragaria x ananassa* | T | V | 30.2 |
| *Peucedanum cervaria* | G | R | 25.1 | *Fragaria x ananassa* | T | S | 28.4 |
| *Phaseolus coccineus* | G | R | 30.9 |  |  |  |  |
|  |  |  |  | *Passiflora* spp. | T | O | 30.2 |
| *Phaseolus coccineus* | G | O | 27.5 | *Passiflora* spp. | T | V | 59.4 |
|  |  |  |  | *Passiflora* spp. | T | S | 24.4 |
| *Phaseolus mungo* | G | R | 24.3 | *Fucus vesiculosus* | T | O | 42.7 |
| *Phlox paniculata* | G | S | 37.9 | *Galinsoga ciliata* | T | R | 49.3 |
| *Physalis pruinosa* | G | S | 26.5 | *Gaultheria hispidula* | T | W | 36.9 |
| *Phytolacca americana* | G | S | 100.0 | *Gentiana macrophylla* | T | S | 26.1 |
| *Pimpinella anisum* | G | S | 23.7 |  |  |  |  |
| *Plantago coronopus* | G | O | 25.1 | *Bromus inermis* | T | O | 27.8 |
|  |  |  |  | *Canna edulis* | T | O | 40.3 |
| *Plantago major* | G | O | 25.0 | *Capsicum annuum* | T | S | 22.6 |
| *Plantago major* | G | R | 20.5 | *Carex morrowii* | T | O | 26.0 |
| *Plantago major* | G | S | 23.6 | *Carex morrowii* | T | R | 49.8 |
| *Poa compressa* | G | O | 28.5 | *Carya cordiformis* | T | S | 28.8 |
| *Poa pratensis* | G | O | 37.5 | *Carya cordiformis* | T | O | 21.0 |
| *Polygonum aviculare* | G | R | 25.4 | *Carya cordiformis* | T | W | 88.7 |
|  |  |  |  | *Clematis armandii* | T | O | 20.1 |
| *Polygonum pensylvanicum* | G | O | 21.3 | *Chaerophyllum bulbosum* | T | O | 22.8 |
| *Portulaca oleracea* | G | O | 28.0 | *Chaerophyllum bulbosum* | T | S | 24.3 |

TABLE 10-continued

HLE

| Nom latin | Stress | extrait | Inhibition (%) | Nom latin | Stress | extrait | Inhibition (%) |
|---|---|---|---|---|---|---|---|
| *Poterium sanguisorba* | G | O | 25.6 | *Agaricus bisporatus* | T | S | 25.4 |
| *Poterium sanguisorba* | G | V | 21.9 | *Chelidonium majus* | T | O | 39.0 |
| *Prunella vulgaris* | G | O | 23.4 | *Chenopodium bonus-henricus* | T | S | 44.3 |
| *Pteridium aquilinum* | G | R | 43.1 | *chrysanthemum coronarium* | T | O | 33.4 |
| *Reseda odorata* | G | O | 46.5 | | | | |
| *Rhaphanus sativus* | G | S | 32.6 | *chrysanthemum coronarium* | T | S | 23.9 |
| *Rheum x cultorum* | G | S | 20.9 | | | | |
| *Ribes nidrolaria* | G | W | 29.8 | *Cichorium endivia* subs. *Endivia* | T | O | 44.3 |
| *Ribes nidrolaria* | G | V | 53.7 | | | | |
| *Ribes nigrum* | G | V | 20.3 | *Cichorium endivia* subs. *Endivia* | T | S | 20.5 |
| *Ribes Silvestre* | G | W | 91.6 | | | | |
| *Salvia officinalis* | G | W | 52.4 | *Circium arvense* | T | R | 49.7 |
| *Salvia officinalis* | G | R | 100.0 | *Citrullus colocynthis* | T | R | 37.0 |
| *Salvia officinalis* | G | O | 100.0 | | | | |
| *Salvia sclarea* | G | O | 100.0 | *Hibiscus cannabinus* | T | O | 39.9 |
| *Salvia sclarea* | G | V | 23.0 | | | | |
| *Salvia sclarea* | G | W | 31.1 | *Hibiscus cannabinus* | T | S | 21.1 |
| *Sambucus ebulus* | G | O | 52.1 | | | | |
| *Alchemilla mollis* | T | S | 31.2 | *Humulus lupulus* | T | S | 54.8 |
| *Allium ascalonicum* | T | S | 42.9 | *Humulus lupulus* | T | R | 50.5 |
| | | | | *Hydrastis canadensis* | T | O | 20.5 |
| *Allium sativum* | T | O | 100.0 | | | | |
| *Allium tuberosum* | T | O | 100.0 | *Hypericum henryi* | T | O | 32.5 |
| *Alpinia officinarum* | T | O | 21.9 | *Hypericum perforatum* | T | S | 27.9 |
| *Alpinia officinarum* | T | S | 100.0 | *Hypericum* sp | T | W | 55.9 |
| | | | | *Hypomyces lactifluorum* | T | S | 42.7 |
| *Amaranthus candatus* | T | S | 36.0 | | | | |
| | | | | *Iberis amara* | T | S | 100.0 |
| *Amaranthus gangeticus* | T | S | 66.8 | *Inula helenium* | T | S | 30.1 |
| | | | | *Ipomola batatas* | T | V | 27.4 |
| *Ananas comosus* | T | O | 20.3 | *Ipomola batatas* | T | S | 44.9 |
| *Ananas comosus* | T | W | 23.8 | *Juniperus communis* | T | S | 57.8 |
| *Anethum graveolens* | T | O | 35.8 | | | | |
| | | | | *Laportea canadensis* | T | S | 63.5 |
| *angelica archangelica* | T | R | 53.5 | | | | |
| | | | | *Populus x petrowskyana* | T | W | 72.0 |
| *Anthemis nobilis* | T | O | 45.3 | | | | |
| *Anthemis tinctorium* | T | S | 47.5 | *Portulaca oleracera* | T | O | 33.7 |
| *Anthriscus cerefolium* | T | O | 20.5 | *Poterium sanguisorba* | T | W | 100.0 |
| *Arctium minus* | T | O | 54.1 | *Prunus* spp. | T | S | 39.6 |
| *Arctostaphylos uva-ursi* | T | O | 28.1 | *Prunus persica* | T | O | 21.4 |
| | | | | *Prunus persica* | T | V | 26.6 |
| *Arctostaphylos uva-ursi* | T | R | 100.0 | *Psidium guajava* | T | V | 37.7 |
| | | | | *Psoralea corylifolia* | T | S | 51.5 |
| *Aronia melanocarpa* | T | V | 100.0 | | | | |
| | | | | *Pteridium aquilinum* | T | R | 76.2 |
| *Aronia melanocarpa* | T | W | 42.7 | | | | |
| | | | | *Pteridium aquilinum* | T | S | 27.9 |
| *Aronia prunifolia* | T | W | 39.0 | | | | |
| *Artemisia absinthium* | T | O | 25.6 | *Punica granatum* | T | W | 66.4 |
| | | | | *mentha arvensis* | T | R | 34.0 |
| *Artemisia dracunulus* | T | O | 31.3 | *Mentha piperita* | T | S | 60.1 |
| | | | | *Mentha pulegium* | T | V | 24.5 |
| *Artemisia dracunulus* | T | S | 22.3 | *Mentha pulegium* | T | W | 24.8 |
| | | | | *Mentha spicata* | T | O | 24.4 |
| *Aster* | T | S | 20.9 | *Mentha suaveolens* | T | S | 28.9 |
| *Avena sativa* | T | S | 100.0 | | | | |
| *Averrhoa carambola* | T | O | 25.8 | *Monarda didyma* | T | O | 54.7 |
| | | | | *Musa paradisiaca* | T | O | 21.4 |
| *Beta vulgaris* | T | R | 100.0 | *Musa paradisiaca* | T | W | 32.8 |
| *Beta vulgaris* | T | O | 59.3 | *nasturtium officinale* | T | O | 100.0 |
| *Beta vulgaris* | T | S | 41.4 | | | | |
| *Betula glandulosa* | T | S | 61.8 | *Nepeta cataria* | T | O | 60.1 |
| *Boesenbergia rotunda* | T | O | 36.9 | *Nepeta cataria* | T | S | 23.4 |
| | | | | *Nigella sativa* | T | S | 23.2 |
| *Boesenbergia rotunda* | T | S | 42.5 | *Agaricus bisporatus* | T | S | 25.8 |
| *Boletus edulis* | T | S | 43.1 | *Psidium* spp. | T | S | 28.3 |
| *Borago officinalis* | T | S | 36.3 | *Pleurotus* spp. | T | S | 31.6 |

TABLE 10-continued

HLE

| Nom latin | Stress | extrait | Inhibition (%) | Nom latin | Stress | extrait | Inhibition (%) |
|---|---|---|---|---|---|---|---|
| *Brassica hirta* | T | S | 30.2 | *Citrus reticulata* | T | V | 32.7 |
| *Brassica juncea* | T | R | 41.4 | *Citrus reticulata* | T | S | 29.4 |
| *Brassica Napus* | T | S | 29.9 | *Ocimum Basilicum* | T | V | 30.7 |
| *Brassica napus* | T | R | 22.9 | *Ocimum Basilicum* | T | W | 30.9 |
| *Brassica oleracea* | T | R | 25.6 | *Ocimum Basilicum* | T | O | 39.1 |
| *Brassica oleracea* | T | V | 27.0 | *Oenothera biennis* | T | S | 29.6 |
| *Brassica oleracea* | T | R | 26.5 | *Oenothera biennis* | T | O | 24.2 |
| *Brassica rapa* | T | R | 24.8 | *Oenothera biennis* | T | R | 58.6 |
| *Vitis* | G | S | 30.7 | *Rubus occidentalis* | T | R | 93.2 |
| *Xanthium sibiricum* | G | O | 22.1 | *Rubus occidentalis* | T | O | 42.1 |
| | | | | *Rubus occidentalis* | T | S | 20.5 |
| *Zea mays* | G | S | 20.3 | *Rumex acetosella* | T | V | 44.9 |
| *Abies lasiocarpa* | T | S | 22.4 | *Rumex crispus* | T | O | 31.3 |
| *Achillea millefolium* | T | S | 21.1 | *Rumex crispus* | T | R | 100.0 |
| | | | | *Rumex crispus* | T | S | 20.8 |
| *Aconitum napellus* | T | O | 100.0 | *Ruta graveolens* | T | O | 24.1 |
| *Acorus calamus* | T | S | 21.0 | *Serenoa repens* | T | S | 28.5 |
| *Ageratum conyzoides* | T | O | 20.1 | *Salvia officinalis* | T | R | 66.5 |
| | | | | *Salvia officinalis* | T | O | 54.0 |
| *Agrimonia eupatoria* | T | W | 59.6 | *Salvia officinalis* | T | W | 47.2 |
| | | | | *Sambucus canadensis* | T | S | 23.2 |
| *Agropyron cristatum* | T | R | 53.4 | | | | |
| | | | | *Sambucus canadensis* | T | O | 35.0 |
| *Agropyron repens* | T | S | 22.6 | | | | |
| *Agrostis alba* | T | O | 25.3 | *Sambucus canadensis* | T | R | 32.6 |
| *Alchemilla mollis* | T | W | 88.7 | | | | |
| *Alchemilla mollis* | T | O | 42.6 | *Sambucus canadensis* | T | W | 54.0 |
| *Alchemilla mollis* | T | R | 70.4 | | | | |
| *Citrullus colocynthis* | T | S | 35.5 | *Sanguisorba minor* | T | W | 50.0 |
| *Citrus limettoides* | T | O | 47.1 | *Santolina chamaecyparissus* | T | O | 75.8 |
| *Citrus limon* | T | S | 26.2 | | | | |
| *Citrus limon* | T | O | 73.5 | *Santolina chamaecyparissus* | T | R | 33.3 |
| *Citrus sinensis* | T | V | 25.2 | | | | |
| *Coix Lacryma-Jobi* | T | O | 32.7 | *Serratula tinctoria* | T | S | 36.3 |
| | | | | *Datura metel* | T | O | 36.9 |
| *Coix Lacryma-Jobi* | T | S | 31.4 | *Datura metel* | T | S | 21.4 |
| | | | | *Satureja montana* | T | O | 100.0 |
| *Laurus nobilis* | T | W | 73.6 | *Satureja montana* | T | R | 66.8 |
| *Laurus nobilis* | T | S | 21.2 | *Satureja repandra* | T | R | 87.4 |
| *Lavandula angustifolia* | T | O | 22.7 | *Scorzorera hispanica* | T | R | 42.3 |
| *Lavandula angustifolia* | T | S | 25.1 | *Scorzorera hispanica* | T | S | 20.8 |
| *Lavandula latifolia* | T | O | 100.0 | *Scutellaria lateriflora* | T | S | 36.0 |
| *Lavandula latifolia* | T | S | 28.5 | *Slum sisarum* | T | O | 22.1 |
| | | | | *Solanum melongena* | T | O | 22.4 |
| *Ledum groenlandicum* | T | O | 54.3 | *Solidago sp* | T | S | 22.6 |
| *Lentinus edodes* | T | S | 25.7 | *Sonchus oleraceus* | T | R | 41.8 |
| *Leonurus cardiaca* | T | R | 24.3 | *Sorghum caffrorum* | T | O | 23.0 |
| *Lepidium sativum* | T | O | 100.0 | | | | |
| *Levisticum officinale* | T | R | 41.2 | *Sorghum dochna* | T | O | 30.3 |
| | | | | *Sorghum dochna* | T | O | 53.5 |
| *Litchi chinensis* | T | S | 100.0 | *Rehmannia glutinosa* | T | O | 83.0 |
| *Lolium multiflorum* | T | O | 24.0 | *Frangula alnus* | T | S | 40.7 |
| *Lolium perenne* | T | O | 27.8 | *Thymus fragantissimus* | T | O | 100.0 |
| *Lonicera ramosissima* | T | S | 20.9 | *Thymus praecox subsp arcticus* | T | O | 38.7 |
| *Lupinus polyphyllus* | T | O | 35.1 | *Thymus pseudolanuginosus* | T | R | 21.5 |
| *Lupinus polyphyllus* | T | S | 20.5 | *Thymus vulgaris* | T | W | 20.0 |
| *Luzula sylvatica* | T | R | 22.6 | *Triticosecale spp.* | T | O | 26.0 |
| *Majorana hortensis* | T | V | 20.1 | *Triticum aestivum* | T | O | 20.9 |
| | | | | *Triticum turgidum* | T | O | 49.4 |
| *Malus* spp. | T | V | 37.8 | *Triticum spelta* | T | O | 35.0 |
| *Malus* spp. | T | S | 45.1 | *Tropaeolum majus* | T | S | 23.5 |
| *Malus hupehensis* | T | S | 24.4 | *Tsuga diversifolia* | T | S | 34.3 |
| *Melaleuca alternifolia* | T | O | 26.7 | *Tsuga mertensiana* | T | S | 32.8 |
| | | | | *Typha latifolia* | T | S | 36.1 |
| *Melissa officinalis* | T | S | 20.7 | *Urtica dioica* | T | O | 32.8 |
| *Ginkgo biloba* | T | V | 27.1 | *Achillea ptarmica* | A | O | 54.3 |

TABLE 10-continued

HLE

| Nom latin | Stress | extrait | Inhibition (%) | Nom latin | Stress | extrait | Inhibition (%) |
|---|---|---|---|---|---|---|---|
| *Glycyrrhiza glabra* | T | W | 58.1 | *Achillea ptarmica* | G | O | 64.3 |
| *Glycyrrhiza glabra* | T | S | 50.4 | *Geranium pratense* | T | R | 93.4 |
| *Glycyrrhiza glabra* | T | R | 25.1 | *Geranium pratense* | A | R | 98.5 |
| *Gossypium herbaceum* | T | O | 22.7 | *Geranium pratense* | G | R | 97.4 |
| *Gossypium herbaceum* | T | S | 27.3 | *Thalictrum aquilegiifolium* | T | O | 53.6 |
| *Guizotia abyssinica* | T | S | 38.5 | *Thalictrum aquilegiifolium* | G | O | 60.4 |
| *Hamamelis virginiana* | T | O | 37.1 | *Veronica spicata* | T | O | 55.9 |
| *Hamamelis virginiana* | T | R | 100.0 | *Veronica spicata* | A | O | 59.2 |
| *Hedeoma pulegioides* | T | O | 28.5 | *Veronica spicata* | G | O | 56.2 |
| *Hedeoma pulegioides* | T | S | 28.2 | *Helenium* spp. | T | O | 55.7 |
| *Helenium hoopesii* | T | O | 31.7 | *Salvia sylvestris* | T | O | 77.4 |
| *Helenium hoopesii* | T | S | 56.0 | *Salvia sylvestris* | A | O | 66.9 |
| *Helianthus tuberosus* | T | V | 23.7 | *Salvia sylvestris* | G | O | 55.0 |
| *Helichrysum thianschanicum* | T | O | 38.4 | *Salvia regeliana* | T | O | 62.6 |
| *Helichrysum thianschanicum* | T | R | 27.0 | *Crambe cordifolia* | G | R | 56.3 |
| *Helleborus niger* | T | S | 32.1 | *Crambe cordifolia* | G | O | 56.7 |
| *Schizonepeta tenuifolia* | T | O | 29.1 | *Rudbeckia maxima* | G | O | 68.4 |
| *Schizonepeta tenuifolia* | T | S | 21.1 | *Trollius x cultorum* | T | R | 97.6 |
| *Onobrychis viciifolia* | T | O | 42.6 | *Trollius x cultorum* | A | R | 93.2 |
| *Origanum vulgare* | T | S | 53.8 | *Trollius x cultorum* | G | R | 100.1 |
| *Oryza sativa* | T | S | 33.3 | *Amsonia tabernaemontana* | A | R | 53.2 |
| *Oxalis Deppei* | T | O | 30.8 | *Oenothera fruticosa* spp. | T | R | 109.8 |
| *Panicum miliaceum* | T | S | 21.2 | *Oenothera fruticosa* spp. | T | O | 61.3 |
| *Pastinaca sativa* | T | S | 53.9 | *Oenothera fruticosa* spp. | A | R | 97.5 |
| *Pastinaca sativa* | T | R | 20.8 | *Oenothera fruticosa* spp. | G | R | 105.9 |
| *Pastinaca sativa* | T | O | 26.9 | *Veronica austriaca* ssp *teucrium* | T | O | 68.6 |
| *Petroselinum crispum* | T | R | 58.2 | *Veronica austriaca* ssp *teucrium* | G | O | 58.1 |
| *Phaseolus coccineus* | T | S | 27.1 | *Veronica austriaca* ssp *teucrium* | T | R | 55.6 |
| *Phaseolus vulgaris* | T | W | 37.9 | *Coreopsis verticillata* | G | O | 70.4 |
| *Phaseolus vulgaris* | T | O | 22.2 | *Coreopsis verticillata* | T | R | 104.8 |
| *Phaseolus vulgaris* | T | S | 23.2 | *Coreopsis verticillata* | A | R | 99.4 |
| *Phlox paniculata* | T | S | 21.3 | *Potentilla fruticosa* | G | O | 56.2 |
| *Physalis pruinosa* | T | S | 35.2 | *Pteridium aquilinum Matteuccia pensylvanica* | T | R | 67.2 |
| *Phytolacca americana* | T | S | 100.0 | *Matteuccia pensylvanica* | A | R | 59.0 |
| *Plantago coronopus* | T | O | 21.2 | *Ocimum tenuiflorum* | T | O | 54.8 |
| *Plantago coronopus* | T | S | 48.2 | *Carthamus tinctorius* | A | R | 50.9 |
| *Poa pratensis* | T | O | 50.7 | *Carthamus tinctorius* | G | R | 69.0 |
| *Podophyllum peltatum* | T | S | 27.9 | *Ligustrum vulgare* | T | O | 87.0 |
| *Polygonum chinense* | T | S | 25.0 | *Ligustrum vulgare* | A | O | 76.2 |
| *Polygonum aviculare* | T | O | 26.0 | *Ligustrum vulgare* | G | O | 85.7 |
| *Polygonum aviculare* | T | R | 100.0 | *Malva verticillata* | T | R | 80.1 |
| *Polygonum pensylvanicum* | T | O | 42.3 | *Malva verticillata* | A | R | 82.8 |
| *Polygonum persicaria* | T | O | 28.8 | *Malva verticillata* | G | R | 82.4 |
| | | | | *Hamamelis virginiana* | T | R | 56.1 |
| | | | | *Arctostaphylos uva-ursi* | T | R | 74.8 |

TABLE 10-continued

HLE

| Nom latin | Stress | extrait | Inhibition (%) | Nom latin | Stress | extrait | Inhibition (%) |
|---|---|---|---|---|---|---|---|
| *Populus incrassata* | T | S | 100.0 | *Arctostaphylos uva-ursi* | G | R | 86.0 |
| *Populus Tremula* | T | S | 48.5 | *Vicia faba* | T | O | 84.6 |
| *Populus x petrowskyana* | T | S | 44.1 | *Sempervivum tectorum* | T | O | 57.3 |
| *Populus x petrowskyana* | T | O | 100.0 | *Sempervivum tectorum* | A | O | 74.8 |
| *Raphanus sativus* | T | R | 36.5 | *Sempervivum tectorum* | G | O | 52.3 |
| *Raphanus sativus* | T | S | 22.4 | | | | |
| *Reseda luteola* | T | S | 23.6 | *Ajuga reptans* | T | O | 55.3 |
| *Reseda odorata* | T | O | 20.3 | *Ajuga reptans* | A | O | 52.3 |
| *Frangula alnus* | T | R | 65.3 | *Ajuga reptans* | G | O | 72.1 |
| *Rheum officinale* | T | O | 100.0 | *Phlox paniculata* | T | O | 66.2 |
| *Rheum officinale* | T | S | 33.3 | *Ligularia dentata* | A | O | 52.1 |
| *Rheum x cultorum* | T | S | 34.0 | *Ligularia dentata* | G | R | 50.8 |
| *Ricinus communis* | T | S | 27.5 | *Onoclea sensibilis* | G | O | 54.7 |
| *Ribes Grossularia* | T | W | 24.8 | *Onoclea sensibilis* | G | R | 50.1 |
| *Ribes nidrigrolaria* | T | W | 24.4 | *Pinus cembra* | A | R | 83.2 |
| *Ribes nigrum* | T | S | 50.1 | *Pinus cembra* | G | R | 76.3 |
| *Ribes nigrum* | T | V | 23.8 | *Cornus sericea* | T | R | 104.0 |
| *Ribes nigrum* | T | W | 64.1 | *Cornus sericea* | A | O | 53.4 |
| *Ribes Sylvestre* | T | W | 32.4 | *Cornus sericea* | A | R | 91.8 |
| *Rosa rugosa* | T | W | 100.0 | *Cornus sericea* | G | O | 51.0 |
| *Rosmarinus officinalis* | T | R | 75.8 | *Cornus sericea* | G | R | 98.5 |
| | | | | *Hydrangea quercifolia* | T | R | 58.1 |
| *Rosmarinus officinalis* | T | W | 46.6 | | | | |
| | | | | *Solidago caesia* | T | R | 60.7 |
| *Rubus idaeus* | T | O | 27.6 | *Solidago caesia* | A | R | 60.5 |
| *Rubus idaeus* | T | S | 24.3 | *Cornus alba* | T | R | 98.9 |
| *Rubus idaeus* | T | O | 35.5 | *Cornus alba* | A | R | 106.7 |
| *Vaccinium angustifolium* | T | S | 33.7 | *Cornus alba* | G | R | 85.3 |
| | | | | *Carpinus caroliniana* | T | R | 95.4 |
| *Vaccinium macrocarpon* | T | V | 24.1 | | | | |
| | | | | *Carpinus caroliniana* | A | R | 86.2 |
| *Vaccinium macrocarpon* | T | W | 30.3 | | | | |
| | | | | *Carpinus caroliniana* | G | R | 94.5 |
| *Vaccinium macrocarpon* | T | S | 70.9 | | | | |
| | | | | *Astilbe chinensis* | T | R | 54.3 |
| *Vaccinium macrocarpon* | T | O | 57.2 | *Astilbe chinensis* | G | R | 50.3 |
| | | | | *Symphoricarpos albus* | G | R | 52.0 |
| *Valeriana officinalis* | T | O | 26.0 | | | | |
| | | | | *Euphorbia amygdaloides* | T | R | 103.8 |
| *Valerianella locusta* | T | O | 53.7 | | | | |
| | | | | *Euphorbia amygdaloides* | A | R | 75.2 |
| *Verbascum thapsus* | T | O | 22.8 | | | | |
| | | | | *Euphorbia amygdaloides* | G | R | 71.3 |
| *Verbascum thapsus* | T | S | 25.2 | | | | |
| | | | | *Viburnum plicatum* | A | R | 61.0 |
| *Veronica officinalis* | T | O | 29.9 | | | | |
| | | | | *Viburnum plicatum* | G | R | 57.9 |
| *Vitis* | T | S | 39.1 | | | | |
| *Vitis* | T | O | 40.0 | *Buxus microphylla* | T | R | 58.0 |
| *Vitis* | T | W | 23.5 | *Astilboides tabularis* | T | R | 104.2 |
| *Vitis* | T | S | 26.4 | | | | |
| *Weigela coraeensis* | T | S | 20.1 | *Astilboides tabularis* | A | R | 108.1 |
| *Weigela hortensis* | T | S | 25.3 | *Astilboides tabularis* | G | R | 100.3 |
| *Xanthium sibiricum* | T | O | 28.4 | | | | |
| | | | | *Staphylea trifolia* | A | R | 63.6 |
| *Zea mays* | T | S | 38.4 | *Bergenia x schmidtii* | T | R | 100.5 |
| *Oenothera biennis* | A | R | 80.3 | | | | |
| *Alchemilla mollis* | T | R | 96.0 | *Bergenia x schmidtii* | A | R | 113.7 |
| *Alchemilla mollis* | A | R | 87.2 | | | | |
| *Symphytum officinale* | A | O | 80.2 | *Bergenia x schmidtii* | G | R | 99.3 |
| *Fragaria x ananassa* | A | R | 97.9 | *Rodgersia podophylla* | T | R | 68.9 |
| *Fragaria x ananassa* | G | R | 93.8 | *Rodgersia podophylla* | A | R | 59.4 |
| *Vaccinium corymbosum* | G | R | 58.6 | *Rodgersia podophylla* | G | R | 56.5 |
| *Vaccinium augustifolium* | A | R | 71.8 | *Geranium phaeum* | T | R | 92.7 |
| | | | | *Geranium phaeum* | A | R | 84.3 |
| *Vaccinium augustifolium* | G | R | 53.6 | *Geranium phaeum* | G | R | 101.0 |
| | | | | *Rubus pubescens* | T | R | 71.5 |

TABLE 10-continued

HLE

| Nom latin | Stress | extrait | Inhibition (%) | Nom latin | Stress | extrait | Inhibition (%) |
|---|---|---|---|---|---|---|---|
| Vitis | A | R | 62.5 | Rubus pubescens | A | R | 76.2 |
| Vitis | G | R | 79.4 | Rubus pubescens | G | R | 82.8 |
| Petasites japonicus | A | R | 56.5 | Taxus x media | T | R | 60.1 |
|  |  |  |  | Taxus x media | A | R | 61.6 |
| Petasites japonicus | G | R | 53.0 | Taxus x media | G | R | 52.3 |
|  |  |  |  | Geranium x cantabrigiense | T | R | 106.1 |
| Nicotiana rustica | G | O | 61.1 |  |  |  |  |
| Pysalis ixocarpa | A | R | 53.8 | Geranium x cantabrigiense | A | R | 94.2 |
| Pteridium aquilinum | T | O | 69.2 |  |  |  |  |
|  |  |  |  | Geranium x cantabrigiense | G | R | 95.9 |
| Pteridium aquilinum | A | R | 66.2 |  |  |  |  |
|  |  |  |  | Fuchia magellanica | T | R | 100.2 |
| Pteridium aquilinum | G | R | 56.3 |  |  |  |  |
|  |  |  |  | Fuchia magellanica | A | R | 91.9 |
| Sorghum durra | T | V | 21.6 |  |  |  |  |
| Sorghum sudanense | T | V | 23.7 | Fuchia magellanica | G | R | 102.2 |
| Stachys byzantina | T | O | 25.3 | Microbiata decussata | A | R | 51.5 |
| Stellaria graminea | T | O | 27.6 |  |  |  |  |
| Stellaria graminea | T | S | 36.7 | Microbiata decussata | G | R | 51.9 |
| Stellaria media | T | O | 22.6 |  |  |  |  |
| Stipa capillata | T | O | 36.7 | Rhododendron spp. | G | R | 51.2 |
| Symphytum officinale | T | O | 20.6 |  |  |  |  |
|  |  |  |  | Stephanandra incisa | T | R | 102.5 |
| Symphytum officinale | T | V | 25.0 |  |  |  |  |
|  |  |  |  | Stephanandra incisa | A | R | 104.6 |
| Tanacetum cinerariifolium | T | R | 24.9 |  |  |  |  |
|  |  |  |  | Stephanandra incisa | G | R | 99.1 |
| Tanacetum vulgare | T | O | 46.4 |  |  |  |  |
|  |  |  |  | Corylus maxima | A | R | 50.8 |
| Tanacetum vulgare | T | S | 32.0 | Corylus maxima | G | R | 57.1 |
|  |  |  |  | Cyperus altemifolius | G | R | 58.2 |
| Taraxacum oficinale | T | O | 63.1 |  |  |  |  |
|  |  |  |  | Soleirolia soleirolii | A | R | 51.2 |
| Thlaspi arvense | T | O | 32.5 |  |  |  |  |
| Thymus fragantissimus | T | R | 36.7 | Soleirolia soleirolii | G | R | 68.0 |
| Ligularia dentata | G | O | 52.6 | Strelitzia reginae | T | R | 106.5 |
| Achillea ptarmica | T | O | 50.9 | Strelitzia reginae | A | R | 94.3 |
| Potentilla fruticosa | G | R | 98.6 | Strelitzia reginae | G | R | 111.7 |
|  |  |  |  | Hedychium coronarium | T | R | 53.5 |
| Vemonia gigantea | A | R | 50.4 |  |  |  |  |
| Vemonia gigantea | A | O | 62.3 | Hedychium coronarium | A | R | 86.9 |
| Vemonia gigantea | G | R | 51.2 |  |  |  |  |
| Vemonia gigantea | G | O | 50.7 | Hedychium coronarium | G | R | 74.6 |
| Penstemon digitalis | T | R | 64.5 |  |  |  |  |
|  |  |  |  | Strelitzia reginae | T | R | 78.6 |
| Penstemon digitalis | A | R | 63.5 | Strelitzia reginae | A | R | 78.0 |
|  |  |  |  | Strelitzia reginae | G | R | 107.3 |
| Penstemon digitalis | A | O | 57.3 |  |  |  |  |
| Penstemon digitalis | G | R | 63.4 |  |  |  |  |
| Penstemon digitalis | G | O | 67.8 |  |  |  |  |
| Malus spp. | T | R | 56.1 |  |  |  |  |
| Malus spp. | T | O | 56.7 |  |  |  |  |
| Malus spp. | A | R | 50.8 |  |  |  |  |
| Malus spp. | G | R | 51.2 |  |  |  |  |
| Hosta sieboldiana | G | O | 50.9 |  |  |  |  |
| Hamamelis mollis | T | R | 99.1 |  |  |  |  |
| Hamamelis mollis | A | R | 94.1 |  |  |  |  |
| Hamamelis mollis | G | R | 89.4 |  |  |  |  |
| Chaenomeles x superba | T | R | 56.2 |  |  |  |  |
| Chaenomeles x superba | A | R | 71.9 |  |  |  |  |
| Chaenomeles x superba | G | R | 66.6 |  |  |  |  |
| Chaenomeles x superba | G | O | 52.0 |  |  |  |  |
| Centaurea dealbata | T | R | 50.9 |  |  |  |  |
| Centaurea dealbata | A | R | 74.1 |  |  |  |  |

TABLE 10-continued

| | HLE | | | | | | |
|---|---|---|---|---|---|---|---|
| Nom latin | Stress | extrait | Inhibition (%) | Nom latin | Stress | extrait | Inhibition (%) |
| *Paeonia* spp. | T | R | 79.8 | | | | |
| *Paeonia* spp. | T | O | 58.6 | | | | |
| *Paeonia* spp. | A | R | 79.6 | | | | |
| *Paeonia* spp. | A | O | 58.5 | | | | |
| *Paeonia* spp. | G | R | 82.0 | | | | |
| *Paeonia* spp. | G | O | 60.0 | | | | |
| *Lysimachia clethroides* | T | R | 83.3 | | | | |
| *Lysimachia clethroides* | T | O | 64.3 | | | | |
| *Lysimachia clethroides* | G | R | 85.8 | | | | |
| *Lysimachia clethroides* | G | O | 67.8 | | | | |
| *Magnolia x loebneri* | T | R | 61.4 | | | | |
| *Iberis sempervirens* | T | O | 62.4 | | | | |
| *Iberis sempervirens* | G | O | 63.8 | | | | |
| *Filipendula vulgaris* | T | R | 98.3 | | | | |
| *Filipendula vulgaris* | A | R | 94.5 | | | | |
| *Filipendula vulgaris* | G | R | 96.3 | | | | |
| *Geranium sanguineum* | T | R | 89.4 | | | | |
| *Geranium sanguineum* | T | O | 63.3 | | | | |
| *Geranium sanguineum* | A | R | 82.6 | | | | |
| *Geranium sanguineum* | A | O | 53.2 | | | | |
| *Garanium sanguineum* | G | R | 88.8 | | | | |
| *Garanium sanguineum* | G | O | 57.7 | | | | |
| *Philadelphus coronarius* | A | O | 55.5 | | | | |
| *paeonia suffruticosa* | T | R | 58.9 | | | | |
| *paeonia suffruticosa* | T | O | 52.1 | | | | |
| *Paeonia suffruticosa* | A | R | 73.8 | | | | |
| *Paeonia suffruticosa* | A | O | 52.2 | | | | |
| *Paeonia suffruticosa* | G | R | 58.7 | | | | |
| *Paeonia suffruticosa* | G | O | 50.4 | | | | |
| *Dahlia* spp. | T | R | 77.4 | | | | |
| *Begonia convolvulacea* | T | O | 69.8 | | | | |
| *Begonia convolvulacea* | A | O | 67.5 | | | | |
| *Begonia convolvulacea* | G | O | 72.6 | | | | |
| *Begonia eminii* | T | O | 72.8 | | | | |
| *Begonia eminii* | A | O | 77.2 | | | | |
| *Begonia eminii* | G | O | 75.4 | | | | |
| *Begonia glabra* | T | O | 82.3 | | | | |
| *Begonia mannii* | A | O | 82.5 | | | | |
| *Begonia mannii* | G | O | 72.8 | | | | |
| *Begonia polygonoides* | T | O | 79.0 | | | | |
| *Begonia polygonoides* | A | O | 74.8 | | | | |
| *Begonia polygonoides* | G | O | 73.2 | | | | |
| *Fushia* spp. | T | R | 76.6 | | | | |
| *Fushia* spp. | A | R | 70.7 | | | | |
| *Fushia* spp. | G | R | 76.9 | | | | |

TABLE 10-continued

HLE

| Nom latin | Stress | extrait | Inhibition (%) | Nom latin | Stress | extrait | Inhibition (%) |
|---|---|---|---|---|---|---|---|
| Butomus umbellatus | A | O | 58.8 | | | | |
| Symphoricarpos orbiculatus | G | R | 58.7 | | | | |
| Rodgersia spp. | A | R | 59.5 | | | | |
| Rodgersia spp. | G | R | 59.0 | | | | |
| Lamiastrum galeobdolon | T | R | 91.5 | | | | |
| Astilbe x arendsii | A | R | 84.5 | | | | |
| Clematis alpina | A | R | 54.4 | | | | |
| Stewartia pseudocamellia | T | R | 75.5 | | | | |
| Stewartia pseudocamellia | A | R | 84.1 | | | | |
| Stewartia pseudocamellia | G | R | 81.3 | | | | |
| Pinus mugo | T | R | 58.9 | | | | |
| Pinus mugo | A | R | 53.7 | | | | |
| Pinus mugo | G | R | 61.7 | | | | |
| Rubus thibelanus | T | R | 97.6 | | | | |
| Rubus thibelanus | A | R | 97.9 | | | | |
| Rubus thibetanus | G | R | 95.4 | | | | |
| Rubus arcticus | T | R | 89.3 | | | | |
| Rubus arcticus | A | R | 85.5 | | | | |
| Rubus arcticus | G | R | 93.2 | | | | |
| ribes americanum | T | R | 70.4 | | | | |
| Passiflora spp. | T | O | 62.4 | | | | |
| Rubus occidentalis | T | R | 70.9 | | | | |
| Nicotiana tabacum | G | O | 60.9 | | | | |
| Beta vulgaris | T | O | 71.3 | | | | |

TABLE 11

Clostripain

| Nom latin | Stress | extrait | Inhibition (%) | Nom latin | Stress | extrait | Inhibition (%) |
|---|---|---|---|---|---|---|---|
| Achidinia arguta | A | R | 34.1 | Campanula rapunculus | G | S | 24.5 |
| Anthoxanthum odoratum | A | R | 35.0 | Cirsium arvense | G | R | 30.0 |
| Apocynum cannabinum | A | R | 47.6 | Cissus discolor | G | O | 40.8 |
| | | | | Coccoloba caracasana | G | R | 24.9 |
| Arctium minus (Hill) | A | R | 34.5 | Convallaria majalis | G | R | 28.5 |
| Bemhardi | | | | Cucurbita pepo | G | O | 20.9 |
| Beckmannia erucaeformis | A | O | 47.3 | Cucurbita pepo | G | S | 42.5 |
| | | | | Errhenatherum elatius | G | S | 21.6 |
| Beta vulgaris | A | O | 37.2 | | | | |
| Brassica rapa | A | O | 24.6 | Filipendula rubra | G | R | 44.3 |
| Buddlej a davidii | A | R | 27.6 | Galium odoratum | G | O | 31.2 |
| Bupleurum falcatum | A | O | 34.6 | Glycyrrhiza glabra | G | O | 27.6 |
| | | | | Hedychium sp. | G | O | 35.6 |
| Capsicum annuum | A | S | 36.8 | Houttuynia cordata | G | O | 30.2 |
| Capsicum annuum | A | R | 24.9 | Lactuca sativa | G | O | 28.8 |
| Cotinus cossysria | A | R | 21.0 | Lactuca sativa | G | O | 21.6 |
| Kolkwitzia amabilis | A | R | 27.9 | Lotus tetragonolobus | G | S | 42.9 |
| Laserpitium latifolium | A | R | 20.4 | Lycopersicon esculentum | G | R | 32.3 |
| Lindera benzoin | A | R | 38.6 | Lysimachia clethroides | G | R | 22.7 |
| Lolium perenne | A | S | 34.7 | | | | |
| Miscanthus sacchariflorus | A | O | 39.9 | Magnolia stellata | G | R | 23.6 |
| | | | | Microlepia platyphylla | G | O | 21.0 |
| Ophiopogon iaponicus | A | R | 20.5 | | | | |
| | | | | Miscanthus sacchariflorus | G | R | 25.6 |
| Phaseolus mungo | A | S | 30.0 | | | | |
| Phaseolus Vulgaris | A | O | 36.4 | pastinaca sativa | G | S | 44.7 |
| | | | | Phaseolus vulgaris | G | O | 36.7 |
| Phaseolus Vulgaris | A | R | 23.4 | Pteridium aquilinum | G | O | 22.2 |

TABLE 11-continued

| Clostripain ||||||||
|---|---|---|---|---|---|---|---|
| Nom latin | Stress | extrait | Inhibition (%) | Nom latin | Stress | extrait | Inhibition (%) |
| *Plumbago zeylanica* | A | O | 26.5 | *Solidago* sp ? | G | S | 40.8 |
| *Portulacea oleracea* | A | O | 22.2 | *Symphytum officinale* | G | S | 22.7 |
|  |  |  |  | *Tanacetum vulgare* | G | S | 31.4 |
| *Salixpurpurea F. Gracilis* | A | R | 38.6 | *Thymus fragantissumus* | G | O | 20.1 |
| *Solanum melanocerasum* | A | S | 26.0 | *Urtica dioica* | G | O | 32.6 |
|  |  |  |  | *Zea mays* | G | O | 22.4 |
| *Stellaria media* (linne) Cyrillo | A | O | 31.6 | *Abies balsamea* | T | O | 38.6 |
|  |  |  |  | *Allium ampeloprasum* | T | S | 30.3 |
| *Tanacetum vulgare* | A | S | 35.3 | *Allium sativum* | T | O | 55.5 |
| *Tanacetum vulgare* | A | O | 35.4 | *Amaranthus gangeticus* | T | R | 75.4 |
| *Trifolium incamatum* | A | S | 22.0 | *Apium graveolens* | T | R | 21.7 |
|  |  |  |  | *Aralia cordata* | T | S | 48.2 |
| *Vaccinum augustifolium* | A | O | 34.0 | *Asclepias tuberosa* | T | O | 20.2 |
|  |  |  |  | *Asctinidia chinensis* | T | O | 47.7 |
| *Zea Mays* | A | O | 21.9 |  |  |  |  |
| *Aframomum melegueta* | G | O | 27.9 | *Baptisla tinctoria* | T | O | 50.4 |
|  |  |  |  | *Betula alleghaniensis* | T | R | 24.9 |
| *Allium sativum* | G | O | 35.3 |  |  |  |  |
| *Anthemis nobilis* | G | O | 35.8 | *Brassica oleracea* | T | R | 21.4 |
| *Anthurium guildingii* | G | O | 55.2 | *Brassica rapa* | T | R | 30.5 |
|  |  |  |  | *Caladium* sp. | T | O | 39.8 |
| *Astilbe x arendsii* | G | R | 25.6 | *Carica papaya* | T | R | 23.8 |
| *Beta vulgaris* | G | R | 28.0 | *Chaerophyllum bulbosum* | T | R | 24.3 |
| *Vaccinum macrocarpon* | T | O | 39.2 | *Chrysanthenum coronarium* | T | O | 32.7 |
| *Verbena officinalis* | T | R | 46.2 | *Clematis chiisanensis* | T | R | 21.6 |
| *Zea mays* | T | R | 32.5 |  |  |  |  |
| *Myrica pensylvanica* | G | O | 22.7 | *Coccoloba caracasana* | T | O | 40.1 |
| N | G | O | 24.4 | *Cocos nucifera* | T | R | 22.5 |
| *Nicotiana tabacum* | G | R | 22.8 | *Comus mas* | T | R | 34.2 |
| *Paeonia* | G | R | 31.3 | *Cucurbita pepo* | T | S | 24.9 |
| *pastinaca sativa* | G | R | 29.2 | *Cymbopogon citratus* | T | O | 20.4 |
|  |  |  |  | *Forsythia x intermedia* | T | S | 44.0 |
|  |  |  |  | *Heliotropium arborescens* | T | O | 27.1 |
|  |  |  |  | *Lonicera ramosissima* | T | O | 34.9 |
|  |  |  |  | *Malus pranifolia* | T | R | 23.6 |
|  |  |  |  | *Marrubium vulgare* | T | R | 49.3 |
|  |  |  |  | *Miscanthus sinensis Anchess* | T | R | 26.9 |
|  |  |  |  | *Nephelium longana ou Euphoria longana* | T | O | 42.6 |
|  |  |  |  | *Psoralea corylifolia* | T | S | 54.0 |
|  |  |  |  | *Raphanus sativus* | T | O | 21.4 |
|  |  |  |  | *Ribes Nigrum* | T | R | 40.9 |
|  |  |  |  | *Rubus thibetanus* | T | R | 24.2 |
|  |  |  |  | *Rumex acetosella* linne | T | O | 35.2 |
|  |  |  |  | *Sechium edule* | T | R | 25.6 |
|  |  |  |  | *Stachys macrantha* | T | O | 25.9 |
|  |  |  |  | *Tepary* | T | R | 34.9 |
|  |  |  |  | *Thymus vulgaris* "Argenteus" | T | O | 25.3 |
|  |  |  |  | *Trifolium pratense* | T | R | 31.3 |
|  |  |  |  | *Trollius x cultorum* | T | R | 26.5 |
|  |  |  |  | *Uvularia perfoliata* | T | R | 38.3 |

TABLE 12

| Nom latin | Stress | extrait | Inhibition (%) |
|---|---|---|---|
| Actaea racemosa | A | O | 20.6 |
| Alchemilla mollis | A | S | 23.5 |
| Borago officinalis | A | S | 20.5 |
| Capsicum annuum | A | S | 24.7 |
| Cornus canadensis L. | A | S | 22.6 |
| Genista multibracteata | A | R | 21.3 |
| Glycine max | A | S | 26.0 |
| Lolium perenne | A | S | 75.9 |
| Matricaria recutita | A | S | 23.2 |
| Phaseolus Vulgaris | A | O | 34.7 |
| Prunus Tomentosa | A | R | 20.4 |
| Scuttellaria lateriflora | A | O | 33.5 |
| Solidago canadensis | A | O | 42.0 |
| Spinacia oleracea | A | S | 100.0 |
| Tanacetum vulgare | A | S | 42.4 |
| Tanacetum vulgare | A | O | 26.7 |
| Typha latifolia L. | A | O | 24.9 |
| Zea mays | A | S | 20.9 |
| Zea Mays | A | O | 34.7 |
| Adiantum pedatum | G | S | 22.4 |
| Cichorium endivia | G | S | 26.7 |
| Cucurbita pepo | G | O | 20.8 |
| Echinacea purpurea | G | O | 27.6 |
| Lactuca sativa | G | O | 36.4 |
| pastinaca sativa | G | S | 52.1 |
| Pastinaca sativa | G | S | 20.1 |
| Ribes nigrum | G | O | 41.2 |
| Symphytum officinale | G | O | 30.0 |
| Urtica dioica | G | O | 38.2 |
| Vitis sp. | G | S | 22.3 |
| Alchemilla mollis | T | S | 22.6 |
| Althacea officinalis | T | O | 33.5 |
| Althaea officinalis | T | S | 53.5 |
| Aralia cordata | T | S | 21.0 |
| Asctinidia chinensis | T | O | 38.6 |
| Astilboides tabularis | T | O | 41.0 |
| Averrhoa carambola | T | S | 20.9 |
| Baptisia tinctoria | T | O | 25.5 |
| Beta vulgaris | T | S | 24.2 |
| Convallaria majalis | T | O | 48.2 |
| Datura stramonium | T | O | 27.3 |
| Dioscorea batatas | T | S | 36.4 |
| Eleusine coracana | T | S | 26.2 |
| Fragaria x ananassa | T | O | 39.5 |
| Ginkgo biloba | T | O | 98.8 |
| Heliotropium arborescens | T | O | 35.2 |
| Hibiscus cannabinus | T | S | 25.2 |
| Hypericum perforatum | T | O | 30.3 |
| Ipomea batalas | T | S | 22.1 |
| Lathyrus sylvestris | T | S | 21.8 |
| Lonicera ramosissima | T | O | 29.6 |
| Lonicera ramosissima | T | S | 39.9 |
| Lonicera syringantha | T | R | 31.1 |
| Madia sativa | T | O | 27.5 |
| Monarda | T | O | 28.2 |
| Ocimum Basilicum | T | S | 27.2 |
| Peucedanum oreaselinum | T | S | 29.2 |
| Psoralea corylifolia | T | S | 20.9 |
| Rahmnus frangula | T | O | 26.4 |
| Raphanus sativus | T | S | 25.5 |
| Rheum rhabarbarum | T | S | 21.6 |
| Ribes Nigrum | T | R | 28.9 |
| Rubus occidentalis | T | S | 22.8 |
| Rumes scutatus | T | S | 21.4 |
| Solidago Hybrida | T | O | 34.5 |
| Tanacetum balsamila | T | O | 33.9 |
| Vaccinum macrocarpon | T | O | 81.2 |
| Xanthium sibiricum | T | S | 31.7 |
| Zea mays | T | S | 28.3 |

The invention claimed is:

1. A method of inhibiting a cathepsin, comprising: contacting said cathepsin with a plant extract that is capable of inhibiting activity of said cathepsin, wherein said plant extract is prepared by extraction of plant material from *Polygonum aviculare* with a solvent mixture of 85% ethanol:15% methanol.

2. The method of claim 1, wherein said inhibition of cathepsin is greater than about 20%.

3. The method of claim 1, wherein said cathepsin is cathepsin G.

* * * * *